US00RE39590E

(19) United States
(12) Reissued Patent
Gupta et al.

(10) Patent Number: US RE39,590 E
(45) **Date of Reissued Patent: *Apr. 24, 2007**

(54) SUBSTITUTED BENZENE COMPOUNDS, PROCESS FOR THEIR PREPARATION, AND HERBICIDAL AND DEFOLIANT COMPOSITIONS CONTAINING THEM

(75) Inventors: Sandeep Gupta, Concord, OH (US); Shao-Yong Wu, Cupertino, CA (US); Masamitsu Tsukamoto, Moriyama (JP); David A. Pulman, Mentor, OH (US); Bai-Ping Ying, Fishers, IN (US)

(73) Assignee: ISK Americas Incorporated, Concord, OH (US)

( * ) Notice: This patent is subject to a terminal disclaimer.

(21) Appl. No.: 10/797,936

(22) PCT Filed: Apr. 27, 2000

(86) PCT No.: PCT/US98/17197

§ 371 (c)(1), (2), (4) Date: Apr. 27, 2000

(87) PCT Pub. No.: WO99/21837

PCT Pub. Date: May 6, 1999

Related U.S. Patent Documents

Reissue of:
(64) Patent No.: 6,355,799
Issued: Mar. 12, 2002
Appl. No.: 09/530,373
Filed: Apr. 27, 2000

U.S. Applications:

(63) Continuation-in-part of application No. 08/958,313, filed on Oct. 27, 1997, now abandoned.

(51) Int. Cl.
*C07D 239/54* (2006.01)
*A01N 43/54* (2006.01)

(52) U.S. Cl. ..... 504/240; 504/241; 504/243; 544/242; 544/309; 544/311; 544/312

(58) Field of Classification Search ..... 544/309, 544/311, 242, 312; 504/243, 240, 241
See application file for complete search history.

(56) References Cited

U.S. PATENT DOCUMENTS

| | | | | |
|---|---|---|---|---|
| 4,746,352 | A | * | 5/1988 | Wenger et al. |
| 4,859,229 | A | * | 8/1989 | Wenger et al. |
| 4,881,967 | A | * | 11/1989 | Semple |
| 4,927,451 | A | * | 5/1990 | Brouwer et al. |
| 5,084,085 | A | * | 1/1992 | Theodoridis |
| 5,116,404 | A | * | 5/1992 | Ishii et al. |
| 5,169,431 | A | * | 12/1992 | Enomoto et al. |
| 5,281,571 | A | * | 1/1994 | Woodard et al. |
| 5,281,574 | A | * | 1/1994 | Enomoto et al. |
| 5,356,863 | A | * | 10/1994 | Satow et al. |
| 5,441,925 | A | * | 8/1995 | Theodoridis |
| 5,476,834 | A | * | 12/1995 | Takemura et al. |
| 5,602,077 | A | * | 2/1997 | Amuti et al. |
| 5,759,957 | A | * | 6/1998 | Andree et al. |
| 6,077,812 | A | * | 6/2000 | Crawford et al. ..... 504/243 |
| 6,602,826 | B1 | | 8/2003 | Andree et al. |

FOREIGN PATENT DOCUMENTS

| | | | |
|---|---|---|---|
| EP | 705829 | * | 10/1996 |
| JP | 03215476 | * | 9/1991 |
| JP | 9-315006 | * | 9/1997 |
| JP | 09301973 | * | 11/1997 |
| WO | WO 8501939 | * | 5/1985 |
| WO | WO 9100278 | * | 1/1995 |
| WO | WO 95/02580 | * | 1/1995 |
| WO | WO 95/23509 | * | 9/1995 |
| WO | WO 97/06150 | * | 2/1997 |
| WO | WO 97/07104 | * | 2/1997 |
| WO | WO 97/08170 | * | 3/1997 |
| WO | WO 97/08171 | * | 3/1997 |
| WO | WO 97/09319 | | 3/1997 |
| WO | WO 97/11060 | * | 3/1997 |
| WO | WO 97/12883 | * | 4/1997 |
| WO | WO 97/12886 | * | 4/1997 |
| WO | WO 97/28127 | * | 8/1997 |
| WO | WO 9729105 | * | 8/1997 |
| WO | WO 9742188 | * | 11/1997 |
| WO | WO 98/39304 | | 9/1998 |

OTHER PUBLICATIONS

Sato et al., CAPLUS Abstract 128:108494, 1997.*

Chemical Abstracts, vol. 96, No. 24, Jun. 14, 1982, p. 43, column 1, Abstract No. 200709g,, Chernikov, A.Y. et al. Thermostable Composition. FR 2,476,068, Aug. 21, 1981.*

Chemical Abstract, vol. 69, No. 23, Dec. 2, 1968, p. 8993, column 1, Abstract No. 9620v, Agripat, S.A. "2–Nitro–3(and5)–phenoxy(and phenylthio)anilines and their 0–phenylenediamine derivatives." FR 1,499,717, Oct. 27, 1967.*

(Continued)

*Primary Examiner*—Deepak Rao
(74) *Attorney, Agent, or Firm*—Sughrue Mion, PLLC

(57) ABSTRACT

Novel herbicidal and defoliant substituted aniline derived compounds represented by general structure (I)

(I)

are described. W, X, Y, Z, and Q are as defined in the disclosure. Also described are the processes for the manufacture of these compounds and agriculturally suitable compositions containing these as active ingredients which are useful as herbicides for general or selective pre-emergent or post-emergent control of undesired plant species and defoliants at very low concentrations of these biologically active compounds.

14 Claims, No Drawings

OTHER PUBLICATIONS

Chemical Abstracts, vol. 45, No. 16, Aug. 25, 1951, p. 1951 column 1, Abstract No. 7033, Finger, G.C. et al., "Aromatic Fluorine compounds. II. 1,2,4,5–Tetrafluorobenzene and related compounds" J. Am. Chem. Soc., 1951, 73, 145–9.

Hall et al. "Formation of cis, cis–1, 4–Dicyano–1,3–butadiences by Thermal Decomposition of 1,2–Diazidobenzenes", Journal of the American Chemical Societ, Nov. 8, 1967, vol. 89, No. 23, pp. 5856–5861.*

Wittek, P.J. "Synthetic Studies of the Anitumor Antibiotic Stretonigrin. 3 synthesis of the C–D Ring of Strepoigrin by an Unsymmetrical Ullmann Reaction", Journal of Organic Chemistry, Mar. 1979, vol. 44, No. 5 pp. 870–872.*

Meegalla SK et al., "Synthesis and Pharmacological Evaluation of Isoindolo[1,2–b]quinazolinone and Isoindolo[2,1–α]benzimidazole Derivatives Related to the Antitumor Agent Batracylin", Journal of Medicinal Chemistry, Sep. 30, 1994, vol. 37, No. 20, pp. 3434–3439.*

Kato S. et al., "Synthesis of 4–Chloro–7–ethoxy–2(3H)–benzoxazolone–6–carboxylic Acid", Journal of Heterocyclic Chemistry, Jul.–Aug. 1996, vol. 33, No. 4, pp. 1171–1178.*

* cited by examiner

SUBSTITUTED BENZENE COMPOUNDS, PROCESS FOR THEIR PREPARATION, AND HERBICIDAL AND DEFOLIANT COMPOSITIONS CONTAINING THEM

Matter enclosed in heavy brackets [ ] appears in the original patent but forms no part of this reissue specification; matter printed in italics indicates the additions made by reissue.

RELATION TO OTHER APPLICATIONS

This application is the U.S. national stage entry of PCT application No. PCT/US98/17197, filed Aug. 21, 1998, and is a continuation-in-part application of U.S. Ser. No. 08/958,313, filed Oct. 27, 1997.

The present invention relates to substituted benzene compounds, process for their preparation, and herbicidal and defoliant compositions containing them.

BACKGROUND OF THE INVENTION

Use of uracils as herbicides has previously been reported. For example, U.S. Pat. Nos. 4,859,229 and 4,746,352 describe 3-phenyl uracil derivatives as herbicides. However the phenyl ring in the described compounds carry only four substituents. U.S. Pat. No. 4,927,451 describes herbicidal compounds carrying five substituents on the phenyl ring with a dihydrouracil ring. EP Patent 0705829 describes uracil herbicides caring pentasubstituted phenyl ring with a carbon linked substituent at position 2 of the phenyl ring. U.S. Pat. No. 5,346,881, 5,441,925, 5,169,431, 5,476,834, 5,602,077, and WO Patents 97/08170, 08171, 12886 and 42188 described uracil herbicides carrying a fused pentasubstituted phenyl ring where the 2 position of the phenyl ring is substituted either with a carbon, oxygen or nitrogen. U.S. Pat. No. 5,116,404 and JP Patent 05025144 describe uracil compounds with a 3-phenyl group which may be pentasubstituted but none of these Patents appears to make obvious the compounds of the present invention which carry a nitrogen linked substituent at position 2 of the phenyl ring alongwith substituents at positions 3, 4, and 6 and there appears to be no indication as to the criticality of the substitution pattern of the phenyl moiety in order to introduce the high herbicidal activity in combination with selectivity towards crops. Similarly use of pyrazole, tetrahydrophthalimide, triazolinone, tetrazolinone, and triazolidine derivatives are herbicides has been described before such as U.S. Pat. Nos. 5,281,571, 4,881,967, 5,084,085, WO Patent 85/01939, and Japanese Pat. No. 1-121290 respectively. Pyridazinones, pyridyls, bicyclic hydantoins, phthalimides, pyrimidinones, pyrazinones, and pyridinones have also been described as herbicides such as WO Patent 97107104, 95102580, 95123509, EP Patent 0786453, WO Patent 97/06150, 97/11060, and 97/28127. However, despite the broad coverage of these Patents, the general structure of the present invention has not been described.

SUMMARY OF THE INVENTION

This invention delineates a method for the control of undesired vegetation in a plantation crop by the application to the locus of the crop an effective amount of a compound described herein. The herbicidal and defoliant compounds of the present invention are described by the following general formula I or its salts:

I

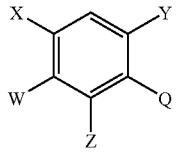

wherein X is hydrogen, halogen, nitro, amino, NMR, $N(R)_2$, amide, thioamide, cyano, alkylcarbonyl, alkoxycarbonyl, alkylsulfonamide, unsubstituted or substituted alkyl, haloalkyl, alkoxy, haloalkoxy, alkoxycarbonylalkoxy, benzyloxy, aryloxy, or heteroaiyloxy;

Y is hydrogen, halogen, or nitro;

W is hydrogen, OR, SR, NH, $N(R)_2$, $CH_2R$, $CH(R)_2$, or $C(R)_3$, halogen, nitro, or cyano, where multiple R groups represent any possible combination of substituents described by R; R is hydrogen, alkyl, alkenyl, alkynyl, cycloalkyl, aryl, heteroaryl, alkoxy, cycloalkyloxy, aryloxy, heteroaryloxy, alkylsulfonyl, benzyl, alkylcarbonyl, alkenylcarbonyl, alkynylcarbonyl, arylcaibonyl, heteroarylcarbonyl, alkoxycarbonyl, aryloxycarbonyl, or heteroaryloxycarbonyl, where any of these groups may be unsubstituted or substituted with any of the functional groups represented by one or more of the following: halogen, cyano, nitro, amino, carboxyl; alkyl, haloalkyl, alkylsilyl, alkylcarbonyl, haloalkylcarbonyl, alkoxy, alkoxycarbonyl, haloalkoxy, haloalkoxycarbonyl, alkylsulfonyl, haloalkylsulfonyl, aryl, heteroaryl, or cycloalkyl;

Q is a heterocycle, examples of which are as follows:

Q1

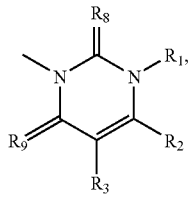

Q2

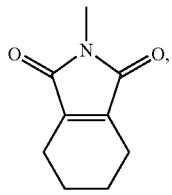

Q3

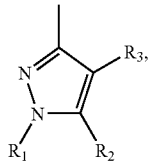

Q4

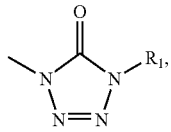

-continued

Q5

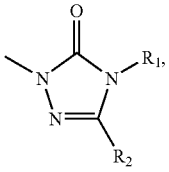

Q6

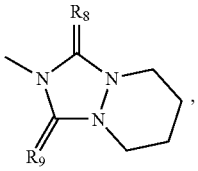

Q7

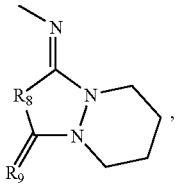

Q8

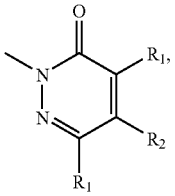

Q10

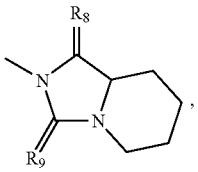

Q11

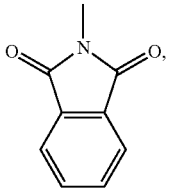

Q12

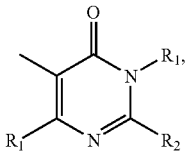

Q13

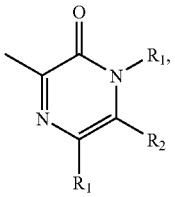

-continued

Q14

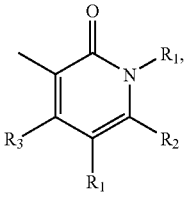

or

Q15

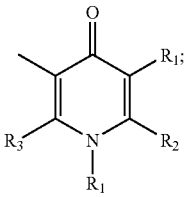

wherein $R_1$ is hydrogen, alkyl, haloalkyl, alkenyl, alkynyl, amino, alkoxyalkyl, acetyl, alkoxycarbonylamino, alkylcarbonylamino, or alkoxycarbonyl;

$R_2$ is alkyl or haloalkyl;

$R_1$ and $R_2$ could combine to form a five- or six-membered heterocyclic ring;

$R_3$ is hydrogen, halogen, nitro, amino, alkylamino, haloalkylamino, cyano, or amide;

$R_8$ and $R_9$ are independently oxygen, sulfur, or imino group;

Q6, Q7, and Q10 may optionally be unsaturated containing one or two double bonds in the 6-membered ring;

Z is amino, hydroxyl, thiol, formyl, carboxyl, cyano, alkylcarbonyl, arylcarbonyl, azido, or one of the following:

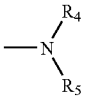

wherein $R_4$ is alkyl, alkenyl, alkynyl, amino, cycloalkyl, heterocycloalkyl, alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heteroarylcarbonyl, alkoxycarbonyl, alkylithiocarbonyl, cycloalkyloxycarbonyl, aryloxycarbonyl, arylthio-carbonyl, aryl-thiocarbonyl, heteroaryloxycarbonyl, aminocarbonyl, alkylaminocarbonyl, arylaminocarbonyl, heteroarylaminocarbonyl, alkoxyabonylcarbonyl or arylcarbonylcarbonyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl or methylenedioxy, wherein the alkyl moiety or aryl moiety may be substituted with halogen, cyano, nitro, alkyl, alkoxy, haloalkyl, haloalkoxy, alkoxycarbonyl, cycloalkyl, aryl, or heterocycloalkyl; and $R_5$ is hydrogen or any one of the groups represented by $R_4$; or $R_4$ and $R_5$ could combine to form a 4–8 membered heterocyclic ring;

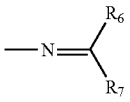

wherein $R_6$ represents alkyl, haloalkyl, dialkylamino, unsubstituted or substituted aryl and heteroaryl; and $R_7$ represents hydrogen, halogen or any of the groups represented by $R_6$;

—$OR_4$,

—$SR_4$,

—$CH_2R_{10}$,

—$CH(R_{10})_2$,

—$C(R_{10})_3$, or

—$CH{=}CHR_{10}$ wherein $R_{10}$ is carboxyl, alkyl, alkenyl, anyl, amino, cycloalkyl, heterocycloalkyl, alkylsulfonyl, arylsulfonyl, benzyl, aryl, heteroaryl, alkylcarbonyl, alkenylcarbonyl, alknykarbonyl, cycloalkylcarbonyl, atylcarbonyl, heteroarylcarbonyl, alkoxycarbonyl, alkyliiocarbonyl, cycloalkyloxycarbonyl, aryloxycarbonyl, arylthio-carbonyl, aryl-thiocarbonyl, heteroaryloxycarbonyl, aminocarbonyl, alkylaminocarbonyl, arylaminocaibonyl, heteroarylaminocarbonyl, alkoxycarbonylcarbonyl or arylcarbonylcarbonyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl or methylenedioxy, wherein the alkyl moiety or aryl moiety may be substituted with halogen, cyano, nitro, alkyl, alkoxy, haloalkyl, haloalkoxy, alkoxycarbonyl, cycloalkyl, aryl, or heterocycloalkyl; provided that (1) Z is not alkyl, alkoxy, haloalkyl, haloalkoxy, alkylthio, haloalkylthio, alklenyl, haloalkenyl, amino, monoalkylamino, dialkylamino, alkoxyalkoxy or cyano, when Q is Q1 and $R_2$ is haloalkyl, (2) Z is not amino when Q is Q3, and (3) Z is not hydroxyl, alkoxy, alkenyloxy, alkynyloxy, haloalkoxy, haloalkenyloxy, or —$NR_4R_5$, wherein $R_4$ is alkyl, alkenyl, alkynyl, cycloalkyl, haloalkyl, haloalkenyl, alkylsulfonyl, alkylcarbonyl, alkoxycatbonyl, or cycloalkylalkyl, and $R_5$ is alkyl, alkenyl, alkynyl, cycloalkyl, haloalkyl, haloalkenyl, alkylcarbonyl, alkoxycarbonyl, or cycloalkylalkyl, when Q is Q14 or Q15.

DETAILED DESCRIPTION OF THE INVENTION

In the above definitions, the term alkyl used either alone or in compound words such as haloalkyl indicates either straight chain or branched alkyls containing 1–8 carbon atoms. Alkenyl and alkynyl include straight chain or branched alkenes and alkynes respectively containing 2–8 carbon atoms. The term halogen either alone or in the compound words such as haloalkyl indicates fluorine, chlorine, bromine, or iodine. Further a haloalkyl is represented by an alkyl partially or fully substituted with halogen atoms which may be same or different. A cycloalkyl group implies a saturated or unsaturated carbocycle containing 3–8 carbon atoms. A heterocycloalkyl group is a cycloalkyl group carrying 1–4 heteroatoms which are represented by oxygen, nitrogen, or sulfur atoms. An aryl group signifies an aromatic carbocycle containing 4–10 carbon atoms, and may be phenyl or naphthyl. A heteroaryl group is an aromatic ring containing 1–4 heteroatoms which are represented by oxygen, nitrogen, or sulfur atoms, and may for example be furanyl, pyridyl, thienyl, pyrimidinyl, benzofuranyl, quinolyl, benzothienyl or quinoxalyl.

The compound of the formula I may form a salt with an acidic substance or a basic substance. The salt with an acidic substance may be an inorganic acid salt such as a hydrochloride, a hydrobromide, a phosphate, a sulfate or a nitrate. The salt with a basic substance may be a salt of an inorganic or organic base such as a sodium salt, a potassium salt, a calcium salt, a quaternary ammonium salt such as ammonium salt or a dimethylamine salt.

The compound of the formula I may exist as geometrical or optical isomers and the present invention includes all of these isomeric forms.

Preferred compounds for the reasons of ease of synthesis or greater herbicidal efficacy are represented by the formula I wherein (1) Z is —$NR_4$, or —$CH_2R_{10}$, (2) X is halogen or cyano; Y is halogen; W is —OR; and R is alkyl, alkenyl, or alkynyl, where any of these groups may be unsubstituted or substituted with any of the functional groups represented by one or more of the following: halogen, cyano, nitro, amino, or carboxyl, or (3) Q is Q1 or Q6; $R_1$ is alkyl, amino or haloalkyl; $R_2$ is haloalkyl; $R_3$ is hydrogen; and $R_8$ and $R_9$ are independently oxygen, sulfur, or imino group, Still more preferred compounds for the reasons of greater herbicidal efficacy are represented by formula I wherein X is halogen; Y is fluorine; W is OR; R is alkyl, alkenyl, or alkynyl, where any of these groups may be unsubstituted or substituted with halogen or cyano; Q is Q1 or Q6; $R_1$ is alkyl, amino, or haloalkyl; $R_2$ is haloalkyl; $R_3$ is hydrogen; and $R_8$ and $R_9$ are independently oxygen, sulfur, or imino group; Z is —$NR_4R_5$; $R_4$ is alkylcarbonyl, alkenylcarbonyl, alkynylcarbonyl, cycloalkylcarbonyl, arylcarbonyl, heteroarylcarbonyl, alkoxycarbonyl, alkylthiocarbonyl, cycloalkyloxycarbonyl, aryloxycarbonyl, arylthio-carbonyl, aryl-thiocarbonyl, heteroaryloxycarbonyl, aminocarbonyl, alkylaminocarbonyl, arylaminocarbonyl, heteroarylaminocarbonyl, alkoxycarbonylcarbonyl, arylcarbonylcarbonyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl, or methylenedioxy, wherein the alkyl moiety or aryl moiety may be substituted with halogen, cyano, nitro, alkyl, alkoxy, haloalkyl, haloalkoxy, alkoxycarbonyl, cycloalkyl, aryl, or heterocycloalkyl; and $R_5$ is hydrogen; or Z is —$CH_2R_{10}$; $R_{10}$ is carboxyl alkyl, alkenyl or alkynyl, where any of these groups may be unsubstituted or substituted with any of the functional groups represented by one or more of the following: halogen, cyano, nitro, amino, dialkylamino, hydroxyl, caroxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl, or methylenedioxy, wherein the alkyl moiety or aryl moiety may be substituted with halogen, cyano, nitro, alkyl, alkoxy, haloalkyl, haloalkoxy, alkoxycarbonyl, cycloalkyl, aryl, or heterocycloalkyl.

Certain intermediates of the present invention are novel. These are 3-(2-amino-4-chloro-6fluoro-3-methoxyphenyl)-1-methyl-6-trifluoromethyl-2,4(1H,3H)-pyrimidinedione, 3-(2-amino-4-chloro-6-fluoro-3-methoxyphenyl)-1-amino-6-trifluoromethyl-2,4(1H,3H)-pyrimidinedione and represented by the following formulae (III-V):

III

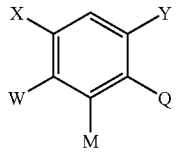

wherein X, Y, W and Q are the same as defined above; and M is nitro.

IV

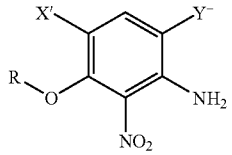

V

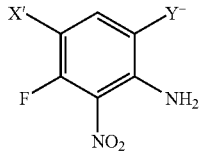

wherein X' and Y' are halogens; and R is the same as defined above.

The compounds described by the formula I can be prepared by the procedures as described herein. In general, the compounds described in this invention can be prepared by one of the two routes depending on whether the heterocyclic ring (e.g. uracil ring) is formed prior to or after the nitration at the 2 position of the phenyl ring in the final product.

As depicted in Scheme 1, the starting materials for these preparations are the compounds represented by the formula VIc. These compounds can be prepared starting from the nitro compound VIa via the amine VIb by the procedures described in literature, for example U.S. Pat. No. 4,859,229 (1989). Nitration of VIc is typically carried out by its slow addition to a mixture of sulfuric acid and nitric acid in a ratio of 9:1. Typically 34 ml of the nitration mixture is used for 2–3 mmol of VI and the addition is carried out between 0 to −30° C. followed by stirring at ambient temperature for 0.5–2 hr. Product (VII) is separated by addition of the solution to ice water and filtration of the precipitate. The product can also be extracted from aqueous layer into organic solvents such as ether or ethyl acetate and purified by crystallization or column chromatography. Alkylation of VII to VIII can be accomplished by treatment of VII with alkyl halide, haloalkyl halide, especially the respective chloride, bromide, or sulfate in the presence of a base such as potassium carbonate or sodium hydride in an inert solvent such as acetone, dimethylformamide, dimethylsulfoxide, tetrahydrofuran, methyl ethyl ketone, or acetonitrile at a temperature range of 0 to 130° C. VIII can be reduced to the amine (IX) under typical reduction conditions such as treatment with iron in acetic acid or ethanolic hydrochloric acid; or by hydrogenation using palladium on carbon or platinum oxide as catalyst. The product IX is purified by typical purification procedures of recrystallization or column chromatography.

The amine (IX) can be derivatized to yield a variety of products generally represented by the formula X. For example amides can be prepared by treatment of IX with alkyl or aryl acid halides, typically chlorides, or anhydrides in the presence of base in an inert solvent. Typically organic bases such as triethylamine, diisopropylethylamine, or pyridine can be used in inert solvents such as tetrahydrofuran, acetonitrile, or dioxane at a temperature range of ambient to reflux temperature for 2–24 hr. Pyridine can be used alone as solvent and base. Acylation catalysts such as dimethylaminopyridine (DMAP) can be added to facilitate the reaction. Typical work-up procedure includes removal of solvent followed by partitioning of the product between aqueous and organic solvents such as ether, ethyl acetate or methylene chloride. Depending upon the reactivity of the acid halide, the product typically consists of a monoamide, diamide, or a mixture of the two. These can be purified/resolved typically by column chromatography. Mono or dialkyl (amino) derivatives of IX can be prepared by its treatment with alkyl or haloalkyl halides in the presence of base such as potassium or sodium carbonate, or sodium hydride in an inert solvent such as tetrahydrofuran or dimethylformamide at a temperature of ambient to 120° C. for 2–24 hr. Mono or dicarbamoyl derivatives of IX can be prepared by its treatment with alkylhaloformates such as methyl or ethylchloroformate in the presence of base such as potassium or sodium carbonate in an inert solvent such as tetrahydrofuran or dimethylformamide at a temperature of ambient to 120° C. for 2–24 hr. Mono or di urea derivatives of IX can be prepared by its treatment with an alkyl or aryl isocyanate, for example methyl or ethyl isocayante, in the presence of a base such as triethylamine in an inert solvent such as toluene or tetrahydrofuran. Alternatively, IX is first converted into its isocyanate derivative by treatment with phosgene or triphosgene in toluene or tetrahydrofuran at reflux temperature for 2–6 hr. This isocyanate can, in turn, be treated with an alkyl or aryl amine such as methyl or ethyl amine in the presence of a base such as triethylamine in an inert solvent such as toluene or tetrahydrfuran at a temperature range of ambient to 130° C. for 2–12 hr to finish the corresponding urea. IX can be treated with an alkyl dihalide such as 1,4-diiodobutane in an inert solvent such as toluene or acetonitrile at reflux temperature in the presence of a base such as potassium or sodium carbonate to furnish the corresponding cyclized product such as a pyrrolidine derivative. IX can be treated with an aromatic or aliphatic aldehyde or ketone or its diethyl or dimethyl acetal derivative in an inert solvent such as toluene or methylene chloride to furnish the corresponding imino derivative. Alternatively, a monoacetyl derivative of IX can be treated with a dehydrochlorinating agent such as phosphorus pentachloride to furnish the corresponding iminochloride.

SCHEME 1

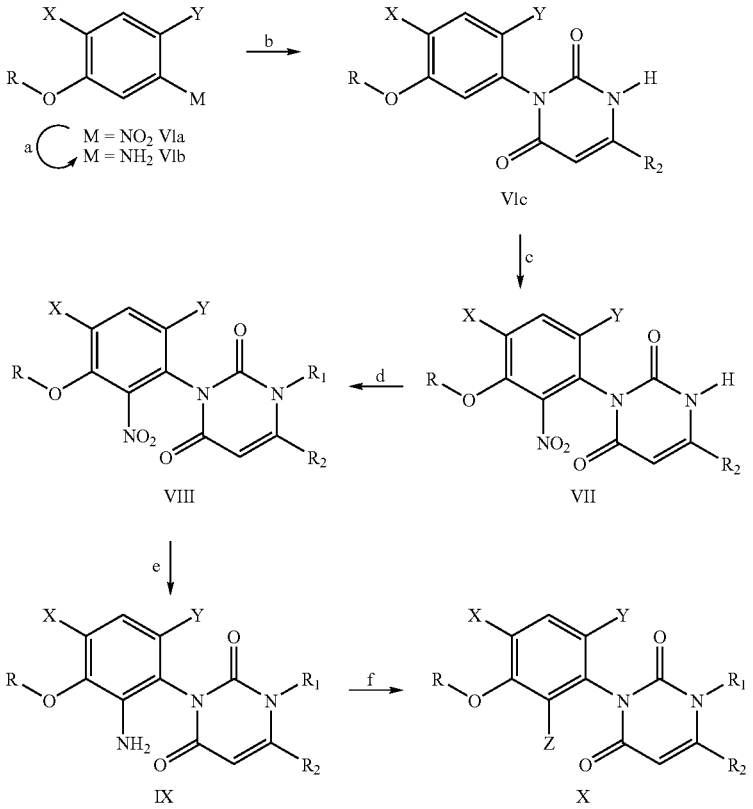

(a) catalytic reduction; (b) 1) triphosgene, 2) NaH, ethyl 3-amino-4, 4, 4-trifluorocrotonate; (c)$H_2SO_4$-$HNO_3$; (d) dimethyl sulfate, base ($R_1$ = $CH_3$); (e) Fe-AcOH; (f) $(CF_3CO)_2O$, (e.g. Z = $NHCOCF_3$)

The starting uracil derivative represented by formula XI in Scheme 2 can be prepared according to the procedure as described before. The compound XI is nitrated with concentrated nitric acid at 0° C. to ambient temperature for 15–30 minutes. Product (XII) is obtained by addition of the product mixture to ice-water followed by filtration.

SCHEME 2

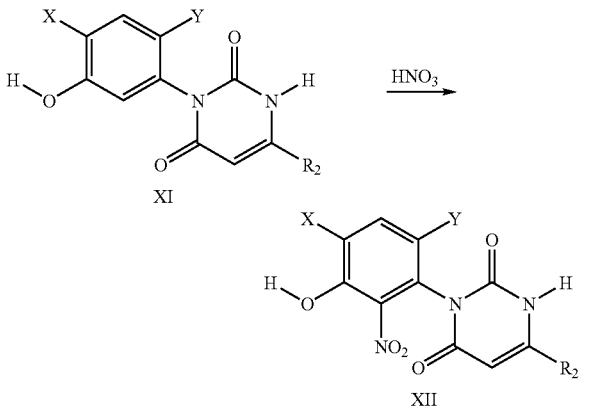

The starting uracil derivative represented by formula XIII in Scheme 3 can be prepared according to the procedure as previously described. Compound XIII can be nitrated with nitric acid at 0° C. for 15–30 minutes. Product (XIV) is obtained by addition of ice followed by filtration.

SCHEME 3

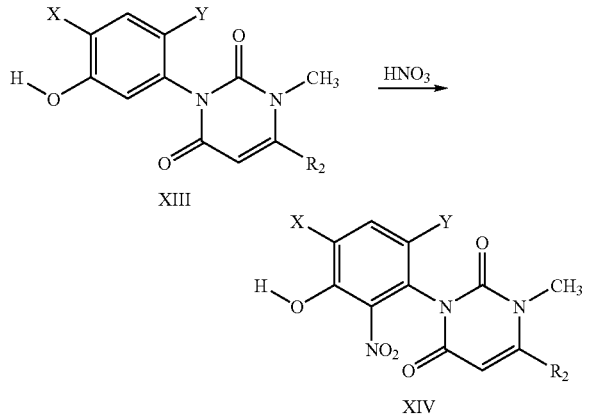

The desired starting tetrazole derivatives represented by formula XV in Scheme 4 can be prepared according to the literature procedure of WO 85/01939. These compounds can be nitrated with nitric acid at ambient temperature or at 0° C. for 15–30 minutes. Product (XVI) is isolated by addition of ice followed by extraction into an organic solvent such as ether or ethyl acetate and purified. XVII can be prepared by the reduction of XVI typically by catalytic hydrogenation in presence of catalysts such as palladium on carbon or by treatment with iron in acetic acid or in ethanolic hydrochloric acid. XXII can be prepared by reacting XVII with a halide in presence of a base at 50 to 120° C. for 1–5 hours. Further modification of XVIII to XIX is carried out according to the general procedures described for the preparation of X from IX (Scheme I).

SCHEME 4

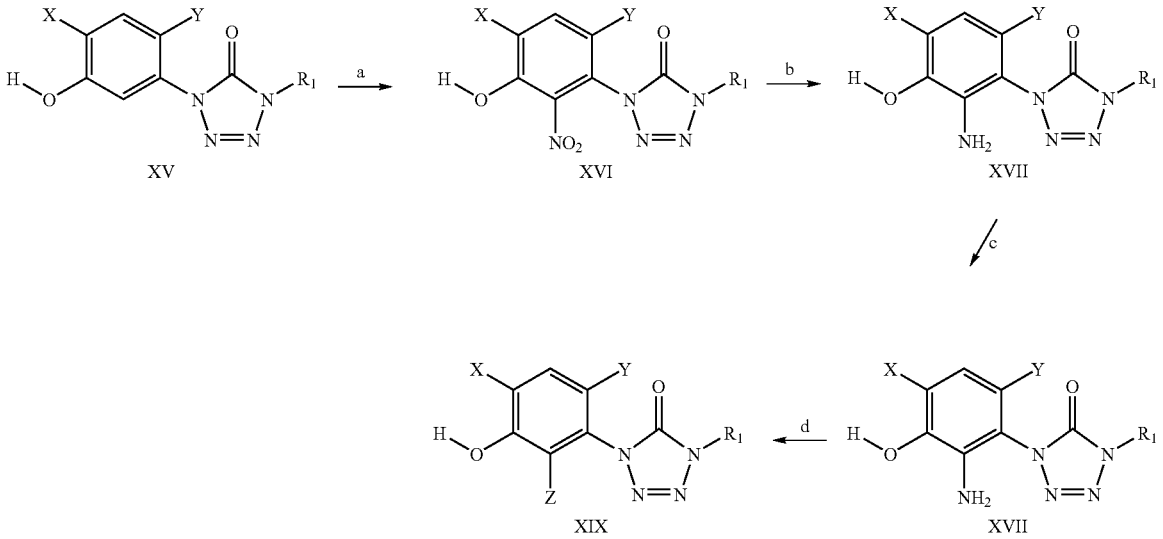

The starting triazolinone derivative represented by formula XX in Scheme 5 can be prepared according to the literature procedure of U.S. Pat. No. 4,980,480 (1990). The compound XX is nitrated with concentrated nitric acid at −15 to 0° C. for 0.5–2 hr. Product (XXI) is obtained by addition of the product mixture to ice-water followed by filtration.

SCHEME 5

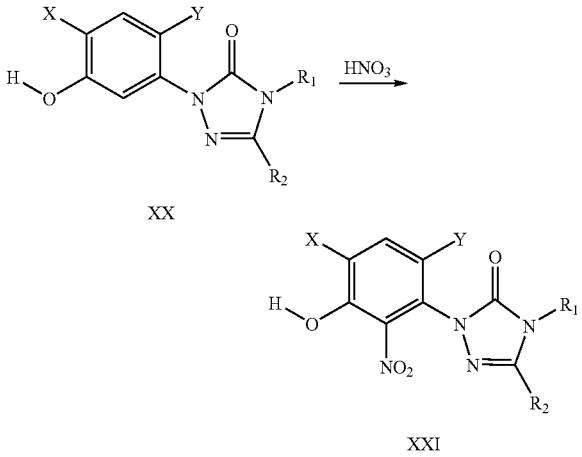

The desired starting pyrazole derivatives represented by formula XXII in Scheme 6 can be prepared according to the literature procedure of U.S. Pat. No. 5,281,571 (1994). These compounds can be nitrated in sulfuric acid-nitric acid mixture (9:1) with a ratio of 34 ml of the nitrating solution to 34 mmol of XXII. The addition is carried out between −15 to −30° C. followed by stirring at ambient temperature for 1–2 hr. Product X is isolated by addition of water followed by extraction into an organic solvent such as ether or ethyl acetate and purified. XXIV can be prepared by the reduction of XXII typically by catalytic hydrogenation in presence of catalysts such as palladium on carbon or by treatment with iron in acetic acid or in ethanolic hydrochloric acid. Further modification of XXIV to XXV is carried out according to the general procedures described for the preparation of X from IX (Scheme I).

SCHEME 6

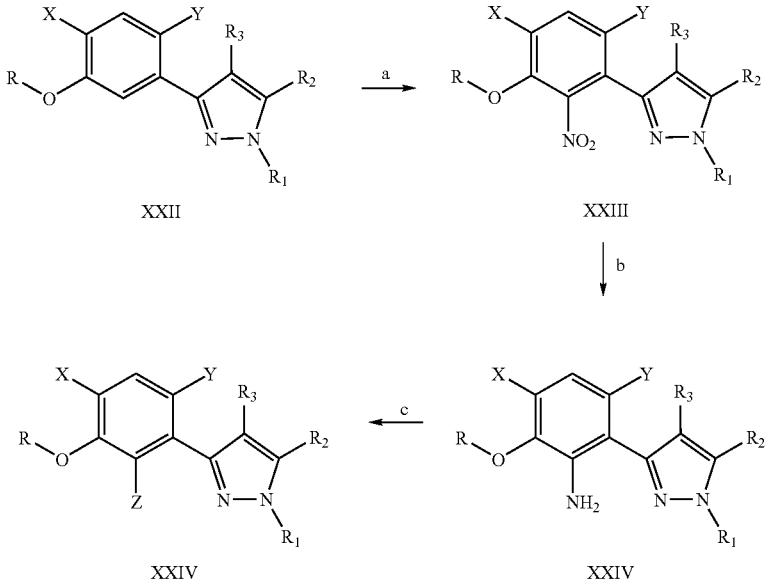

(a) $H_2SO$-$HNO_3$; (b) catalytic reduction; (e) $(CF_3CO)_2O$, (e.g. Z = $NHCOCF_3$)

The desired starting tetrahydrophthalimide derivative represented by formula XXVI in Scheme 7 can be prepared according to the literature procedure of U.S. Pat. No. 4,484,941 (1984). The compound can be nitrated with nitric acid at 0° C. to ambient temperature for half hour. The product (XXVII) is isolated by addition of ice followed by extraction into an organic solvent such as ether, ethyl acetate, or methylene chloride and purified. XXVIII can be prepared by the reduction of XXVII typically by catalytic hydrogenation in presence of catalysts such as palladium on carbon or by treatment with iron in acetic acid or in ethanolic hydrochloric acid. XXIX can be prepared by reacting XXVIII with (substituted)alkyl halide in the presence of a base such as potassium carbonate. Further modification of XXIX to XXX is carried out according to the general procedures described for the preparation of X from IX (Scheme I).

SCHEME 7

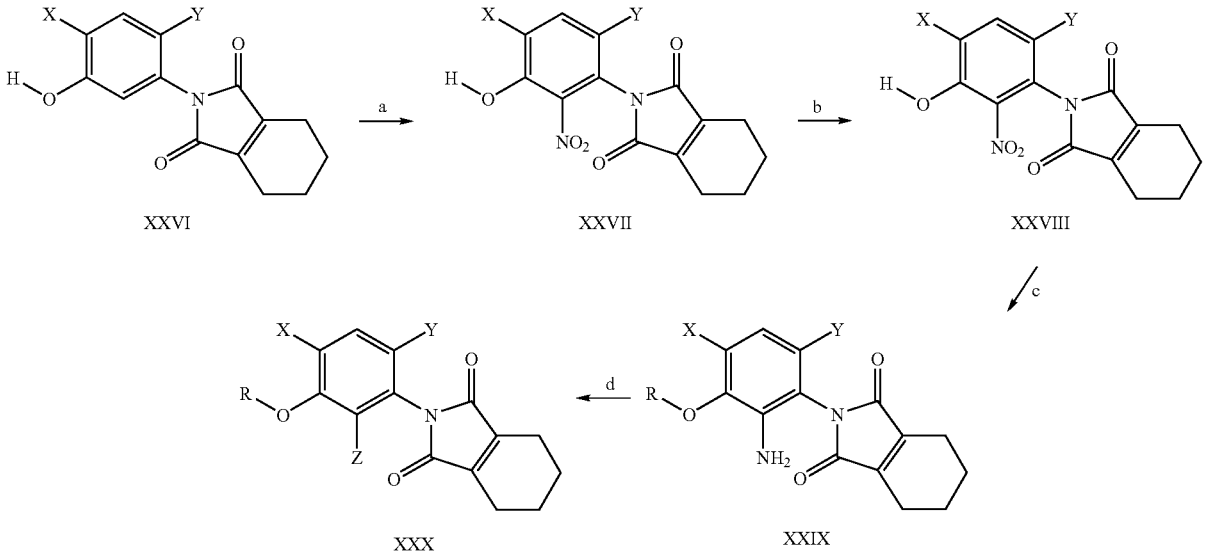

(a) $HNO_3$; (b) Fe-ACOH; (c) R-X, $K_2CO_3$; (d) $(CF_3CO)_2O$, (e.g. Z = $NHCOCF_3$)

Scheme 8 describes the preparation of intermediates represented by the formulae XXXIII and IV. The starting materials (amino phenols and alkyl derivatives represented by the formula VIb) are prepared according to the procedure as described in literature such as U.S. Pat. No. 4,670,046 (1987) which upon treatment with phthalic anhydride in acetic acid can afford phthalimide derivative (XXI). Nitration of XXXI can be carried out by its addition to a mixture of sulfuric acid and nitric acid (9:1) at −15 to −30° C. followed by addition of water and extraction of the product (XXII) in organic solvents such as ethyl acetate or ether. XXXII can be reduced to the corresponding amine (XXXIII) by conventional methods such as treatment with iron in acetic acid or ethanolic hydrochloric acid or by catalytic hydrogenation in the presence of palladium on carbon. Amino group of XXXIII can be derivatized as described before in Scheme 1 to furnish XXXIV which in turn can be deprotected to finish XXXV. Removal of the protecting phthalimido group can be accomplished by several methods such as treatment with hydrazine in a polar solvent such as dimethylsulfoxide or by treatment with on organic amine such as methyl amine in ethanol. XXV can then be derivatized to the desired compound (X) according to the known procedures as described before in Scheme 1. Alternatively, XXXII can first be subjected to deprotection to afford the amine IV which can be modified to introduce the heterocyclic ring such as the uracil ring (U in XXXVI) according to the known procedures. Nitro group in XXXVI can then be reduced to afford the amine which can then be derivatized as described previously to afford X.

SCHEME 8

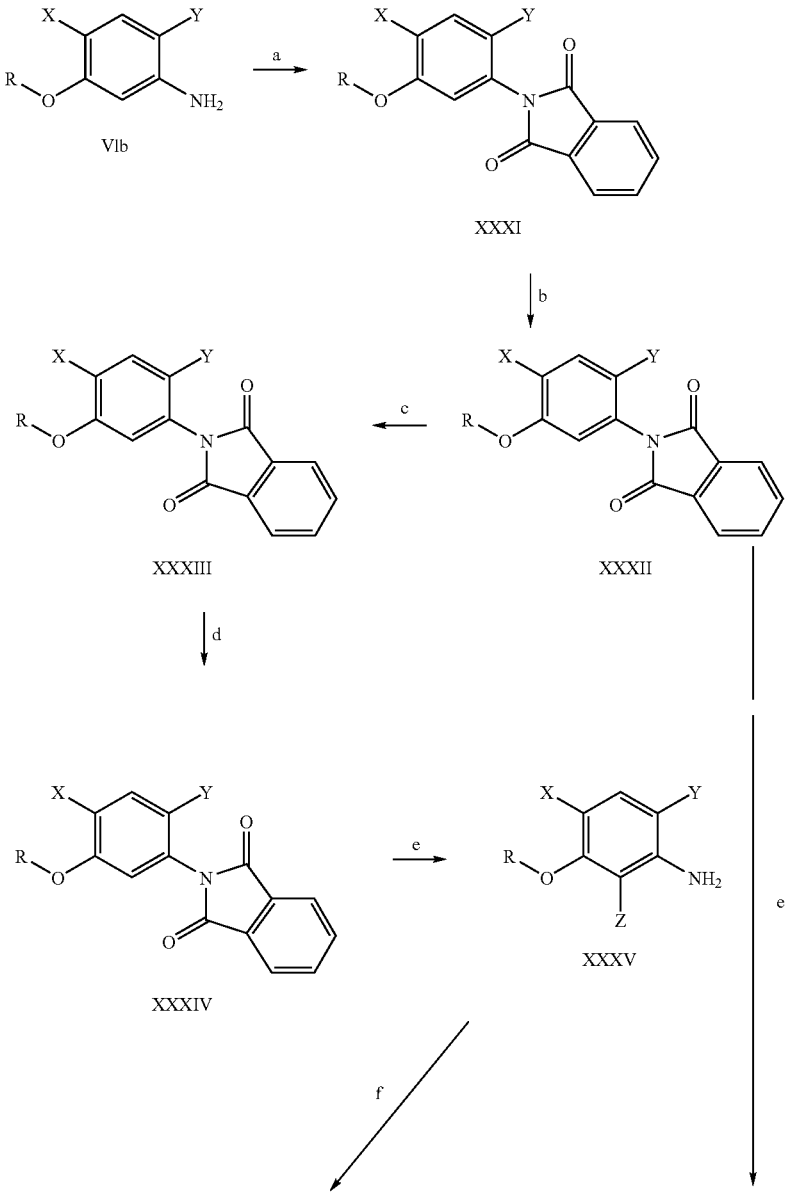

-continued

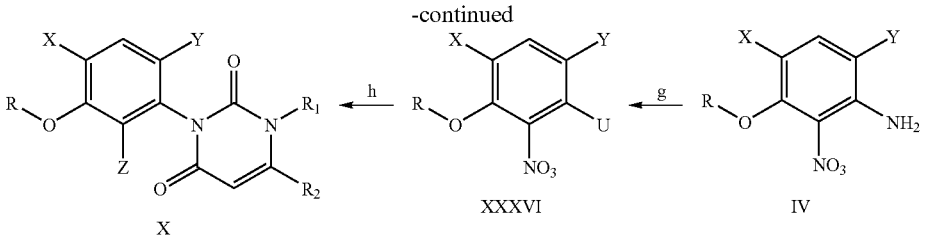

(a) AcOH, phthalic anhydride; (b) $H_2SO_4$-$HNO_3$; (c) Fe-AcOH; (d) dimethyl sulfate, base, [e.g. $z = N(CH_3)_2$]; (e) DMSO-hydrazine; (f) 1) triphosgene, 2) NaH, ethyl 3-amino-4, 4, 4-trifluorocrotonate, 3) $CH_3I$($R_1 = CH_3$, $R_2 = CF_3$); (g) 1) triphosgene, 2) NaH, ethyl 3-amino-4,4,4-

Scheme 9 delineates a process for the preparation of the intermediates represented by the formula V. Starting materials represented by the formula XXXIX are prepared by the nitration of XXXVII which gives XXXVIII which can be reduced to XXXIX according to the literature procedure of Japanese Pat. No. 01186849 (1989). The amino group in XXXIX is protected by forming amide or carbamate XL and the latter is nitrated to give XLI. Deprotection of XLI leads to the ortho-nitro aniline V. V can be converted into the desired compounds represented by XLV according to the procedures as shown in the scheme.

Scheme 10 describes the preparation of intermediate represented by the formulae XLVIII. The starting material (XLVI) can be prepared according to the method described in patents, such as U.S. Pat. No. 5,154,755 (1992). XLVI reacts with ethyl chloroformate at basic condition to give the carbamate XLVII. The latter is nitrated with a mixture of nitric acid and sulfuric acid to give the intermediate XLVII which can be N-alkylated with an alkylhalide in the presence of base to furnish XLIX.

SCHEME 9

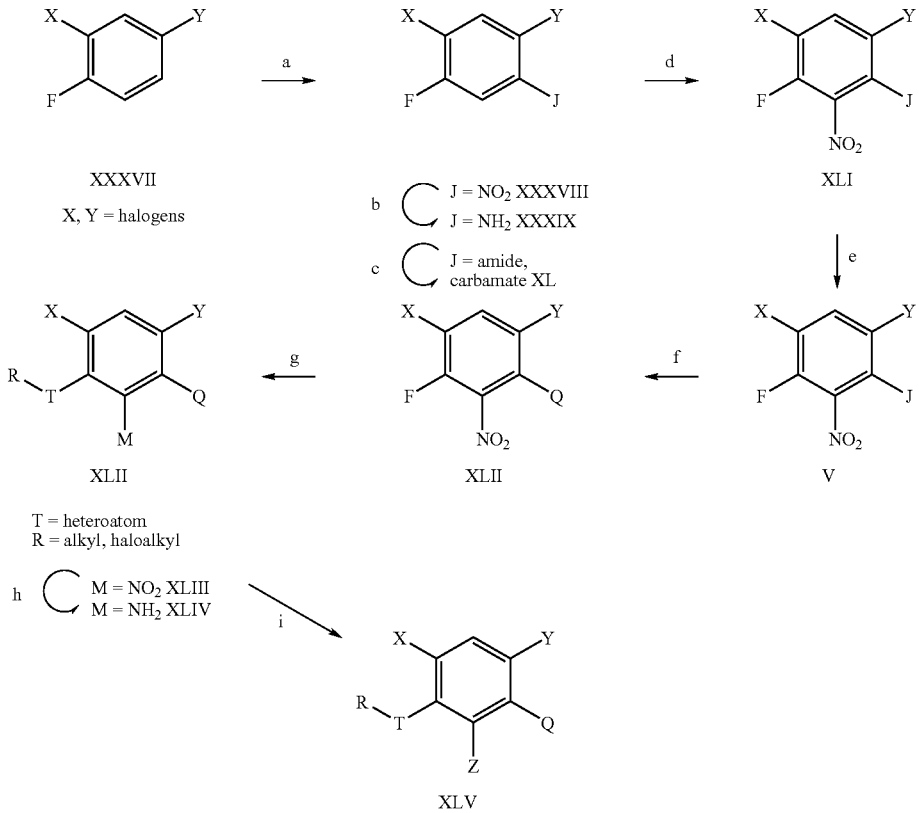

(a) $H_2SO_4$—$HNO_3$; (b) Fe—AcOH; (c) pyridine-ClCOOEt (e.g. J = NHCOOEt); (d) $H_2SO_4$—$HNO_3$; (e) HBR—AcOH; (f) 1) triphosgene, 2) NaH, ethyl 3-amino-4,4,4-trifluorocrotonate, 3) $CH_3I$ (Q = uracil ring as in $X_1$ $R_1 = CH_3$, $R_2 = CF_3$); (g) ROH, base (e.g. T = O, R = $CH_3$); (h) Fe—AcOH; (i)

SCHEME 10

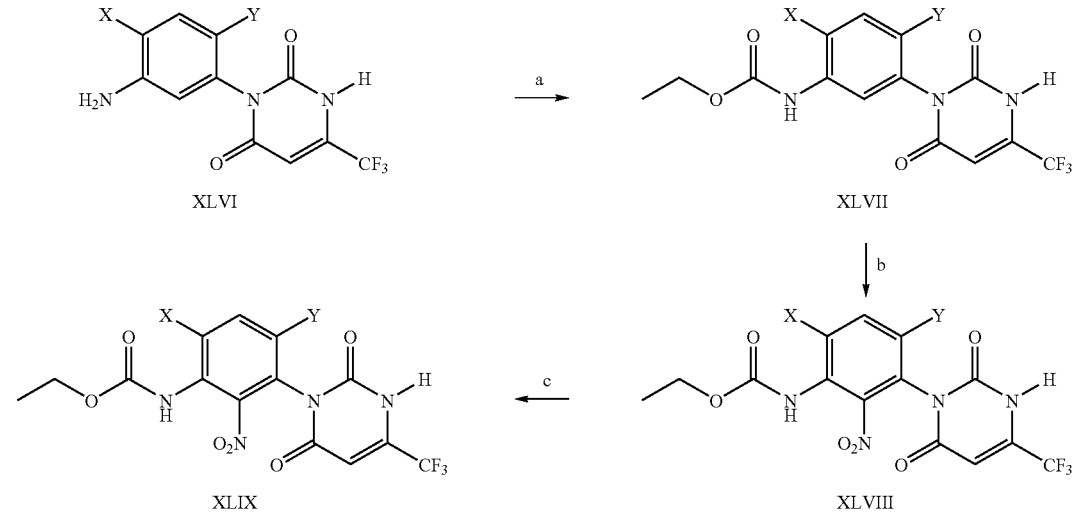

(a) ClCOOEt—$K_3CO_3$; (b) $H_2SO_4$—$HNO_3$; (c) $CH_3I$—$K_2CO_3$

Scheme 11 describes an alternative procedure for the preparation of compounds represented by the formula LVII with varying R groups. Reduction of L to LI is carried out using conventional procedures such as catalytic reduction or iron-acetic acid mixture. The aniline LI is reacted with phenyl chloroformate to afford a carbamte represented by the formula LII which is nitrated with an inorganic salt such as ammonium or potassium nitrate in an acid anhydride such as acetic anhydride according to published procedure such as described in WO 97/42188. Resultant nitro derivative LIII is cyclized to furnish the uracil derivative LIV upon reaction with an appropriately substituted amino crotonate in the presence of an inorganic or organic base exemplified by 1,8-diazabicylo[5.4.0]undec-7-ene (DBU). LIV is N-derivatized to afford LV followed by reduction to aniline LVI according to conventional procedures as described before. LVII is then derivatized to afford the final compounds represented by the formula LVII according to the procedures as described before.

SCHEME 11

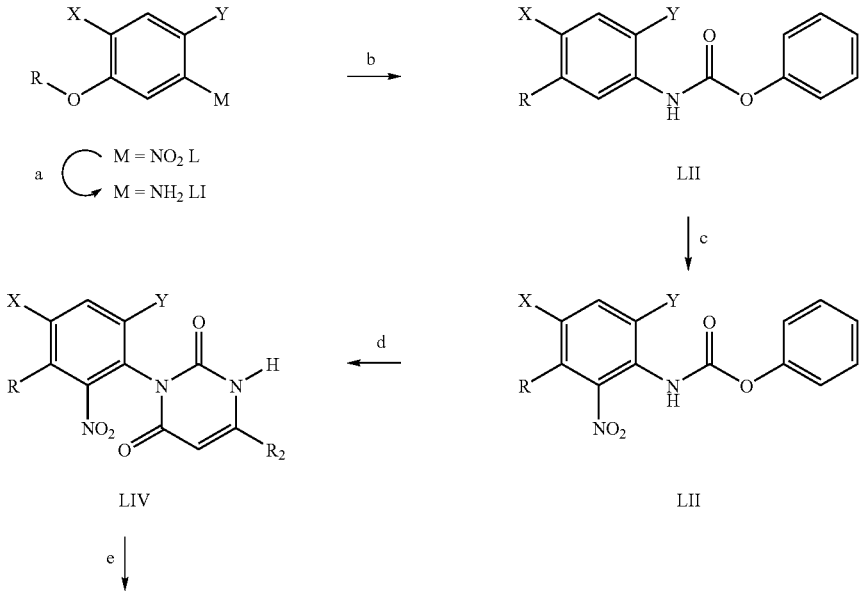

-continued

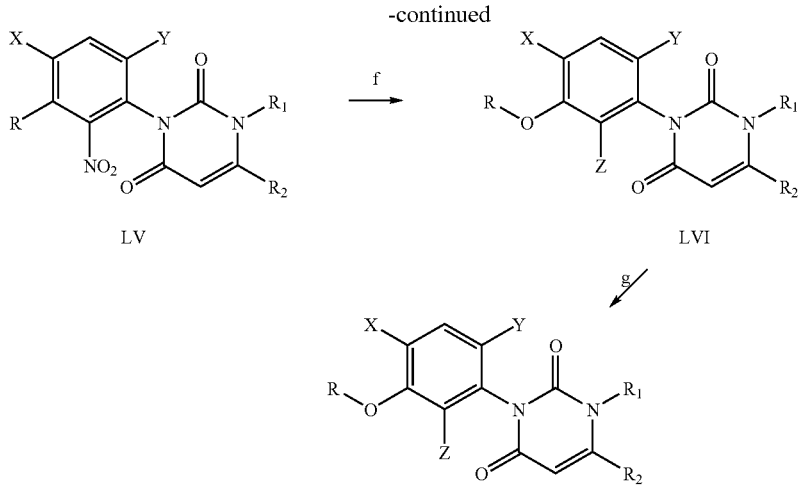

LV LVI LVI (a) catalytic reduction; $ClCO_2C_6H_5$; (c) $Ac_2O$—$NH_4NO_3$; (d) ethyl 3 amino-4,4,4-trifluorocrotonate, DBU, DMF; (e) $CH_3I$; (f) Fe—AcOH (g) $(CF_3CO)_2O$, (e.g. Z = $NHCOCF_3$)

Scheme 12 describes a process for the preparation of compounds represented by the formula LXII which are trisubstituted phenyl derivatives. Ortho-nitroaniline derivatives represented by the formula LVIII are the starting materials which are converted to a ortho-nitro uracil derivatives (LX) according to previously described procedures, e.g. via the NH uracil derivative (LIX). Nitro groups is then converted to an amino group (LXI) via conventional reduction procedures such as cataytic or iron-acetic acid reduction followed by derivatization to furnish LXII.

SCHEME 12

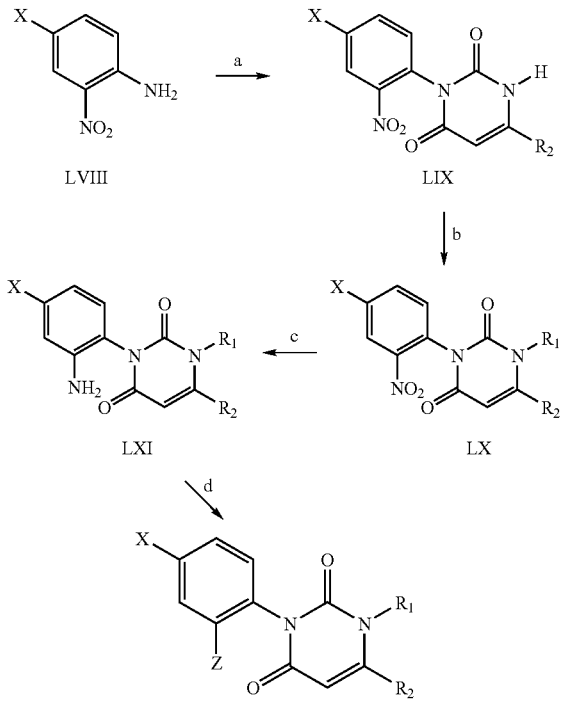

LVIII LIX LXI LX LXII

-continued (a) NaH, ethyl 3-amino-4,4,4-trifluorocrotonate;

(b) $CH_3I$; (c) Fe—AcOH; (d) $(CF_3CO)_2O$, (e.g. Z = $NHCOCF_3$

Scheme 13 describes a procedure for the preparation of trisubstituted phenyl derivatives represented by the formula LXVI. Direct nitration of LXIII, where X and Q (a heterocylce) are as previously defined, using nitration reagents such as nitric acid or a mixture of sulfuric acid-nitric acid leads to ortho-nitro compounds represented by the formula LXIV which are reduced to the corresponding aniline derivatives (LXV) by reduction procedures such as catatlytic reduction or iron-acetic acid. Aniline (LXV) is then derivatized to furnish LXVI.

SCHEME 13

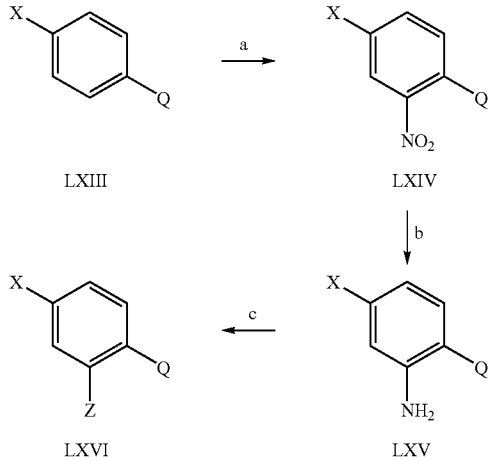

LXIII LXIV LXVI LXV (a) AcOH—$NH_4NO_3$; (b) Fe—AcOH; (c) $(CF_3CO)_2O$, (e.g. Z = $NHCOCF_3$)

Scheme 14 delineates a procedure for the preparation of tetrasubstituted phenyl derivatives represented by the formula LXXIV. The process is akin to one described in scheme 11 for the preparation of pentasubstituted phenyl derivatives (LVII). The nitro intermediates (LXVII) are reduced to the anilines (LXVIII) via conventional procedures followed by derivatization to the phenyl carbamate (LXIX) by reaction with a phenylhaloformate. Nitration to LXX (inorganic nitrate acid anhydirde) is followed by the uracil ring formation (appropriately substituted crotonate-DBU) (LXXI) and N-derivatization to furnish LXXII. Reduciton to the aniline (LXXIII) is carried out by procedures such as catalytic reduction or iron-acetic acid followed by derivatization to furnish LXXIV.

SCHEME 14

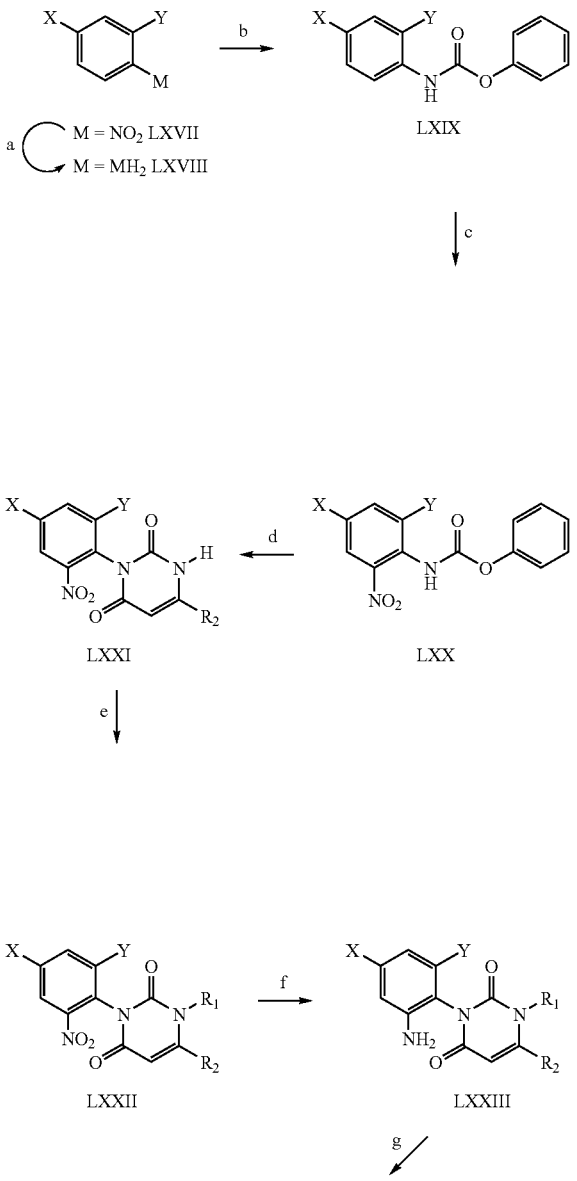

-continued

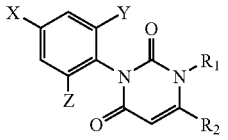

LXXIV (a) catalytic reduction; (b) $ClCO_2C_6H_5$; (c) $Ac_2O$—$NH_4NO_3$; (d) ethyl 3-amino-4,4,4-trifluorocrotonate, DBU, DMF; (e) $CH_3I$; (f) Fe—AcOH (g) $(CF_3CO)_2O$, (e.g. Z = $NHCOCF_3$)

Scheme 15 describes various procedures for the derivatization of the amino group in LXXV via diazonium salts represented by LXXVI. The diazonium salts are prepared by treatment of the aniline with an inorganic nitrite solution such as sodium or potassium nitrite in an acid such as sulfuric or hydrochloric acid or by treatment of the aniline with an organic nitrite such as t-butyl nitrite in an organic solvent such as acetonitrile. Reaction is carried out between 10–15° C. which results in a stable solution of the diazonium salt which is reduced to the corresponding hydrazine derivative represented by the formula LXXVII by reducing agents exemplified by stannic chloride. Hydrazine derivatives are then derivatized to a variety of compounds represented by the formula (LXXXVI) via conventional reactions such as acylation, alkylation, Schiff base formation, etc. The diazonium group in LXXVI is replaced by a hydroxyl to furnish the corresponding phenol (LXXVIII) by its treatment with an aqueous solution of cuprous oxide in presence of cupric nitrate or cupric sulfate at ambient temperature. LXXVIII is then derivatized to furnish LXXXVI via conventional reactions such as acylation, alkylation, etc. Treatment of the diazonium salts (LXXXVI) with disulfides (RSSR) leads to the formation of corresponding thioethers represented by the formula LXXIX which can be further modified according to conventional procedures leading to sulfur analogs represented by the formula LXXVI. LXXVI can be treated with inorganic cyanides leading to the formation of cyano derivatives (LXXXI) which can be oxidized via conventional routes to furnish carboxylic acids (LXXXV) which can then be derivatized leading to LXXXVI. The diazonium group can also be replaced with an azido group furnishing LXXX. LXXVI can be treated with inorganic iodides to afford the iodo compounds (LXXXII) which can be converted to the corresponding aldehydes (LXXXIII) (which are also directly obtainable from LXXVI via conventional procedures). LXXXIII can be reduced to furnish corresponding benzyl alcohols (LXXXIV) which can be derivatized to LXXXVI.

SCHEME 15
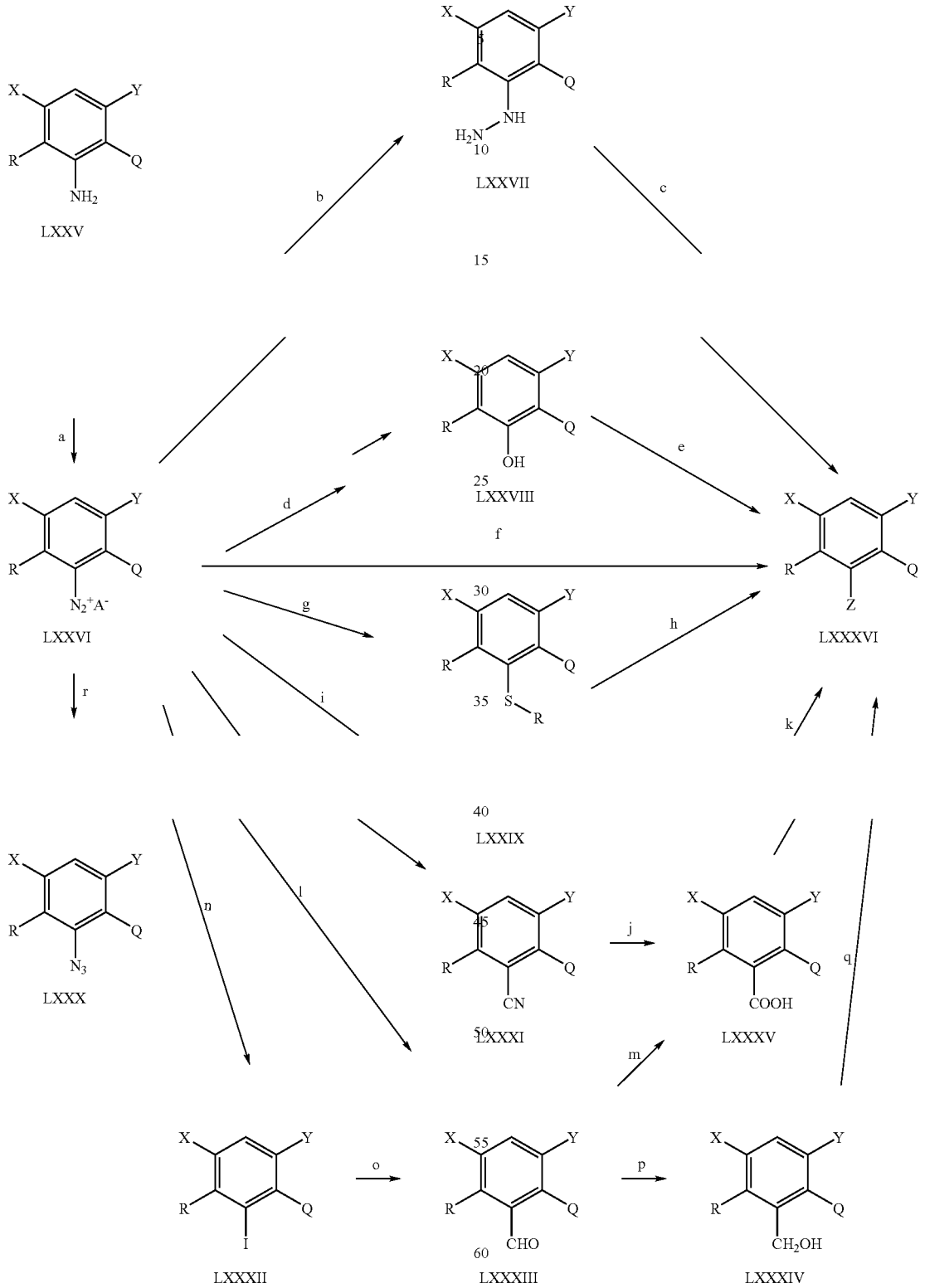
(a) $H_2SO_4$—$NaNO_2$, A = anion; (b) $SnCl_2$; (c) $(CF_3CO)_2O$, (e.g. Z = $NHCOCF_3$); (d) $Cu_2O$; (e) $C_6H_5CH_2Cl$ (e.g. Z = $OCH_2C_6H_5$);
(f) ethyl acrylate-$CuCl_2$ (e.g. Z = $CH_2CHClCOOC_2H_5$); (g) RSSR; (h) MCPBA (e.g. Z = $SO_2R$); (i) NaCN; (j) $H_2SO_4$; (k) $RNH_2$ (e.g. Z = CONHR);
(l) Oxime, $CuSO_4$—$Na_2SO_3$; (m) $KMnO_4$; (n) KI; (o) CO, Pd(II)acetate, truphenylphosphine; (p) $NaBH_4$; (q) e.g. RNCO (Z = $CH_2OCONHR$); (r) $NaN_3$ Scheme 16 describes an alternatived procedure for the formation of amides (XC). Reaction of the ortho-amino phenol LXXXVII with an aliphatic or aromatic acyl halide in an organic solvent such as 1,4-dioxane or tetrahydrofuran in the absence or presence of an inorganic or organic base such as potassium carbonate, sodium carbonate, or triethylamine, regioselectively leads to the formation of corresponding amide represented by the formula LXXIX. LXXXIX can also be produced by the hydrolysis of a corresponding alkyl ether such as methyl ether (LXXXVIII) by treatment with strong Lewis acids such as boron tribromide or boron tribromide-dimethyl sulfide complex. Phenol group in LXXIX is then derivatized by treatment with a halide in the presence of base such as sodium carbonate or potassium carbonate in an organic solvent such as as acetone, methyt-ethyl ketone, dimethylsulfoxide, or tetrahydrofuran at ambient to reflux temperatures.

SCHEME 16

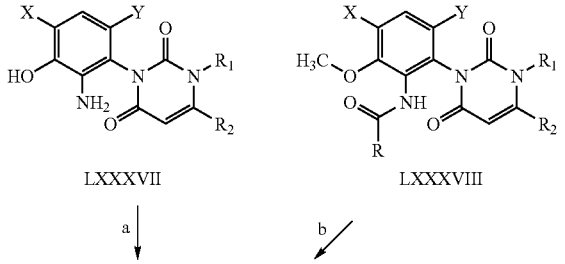

-continued

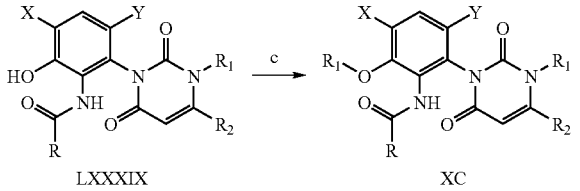

(a) Acyl halide; (b) $BBr_3.Me_2S$; (c) $R_1X$, base, (e.g. R = 2-naphthyl, $R_1$ = $CHF_2$)

Scheme 17 describes a procedure for the preparation of pyridazinone derivatives represented by the formula XCVII and XCVIII. Desired starting pyridazinone derivatives represented by formula XCI and XCIV can be prepared according to the literature procedure of WO 97/07104. These compounds can be nitrated with nitric acid or a mixture of nitric acid and sulfuric acid at ambient temperature or at 0° C. for 15–30 minutes. The products XCII and XCV are isolated by addition of ice followed by filtration. XCII and XCVI can be prepared by the reduction with iron in acetic acid or in ethanolic hydrochloric acid. Methylation of XCIII can be carried out by reacting XCIII with methyl iodide in presence of a base at 50 to 120° C. for 1–5 hours. Further modification of XCVI to XCVIII is carried out by treatment of the aniline with an organic nitrite (such as t-butyl nitrite) in an organic solvent (such as acetonitrile) and alkyl acrylate in the presence of copper(II) chloride. Modification of XCVI to XCVII is carried out by treatment of the aniline with an alkyl or aryl acid halide at 50 to 120° C. for 1–5 hours.

SCHEME 17

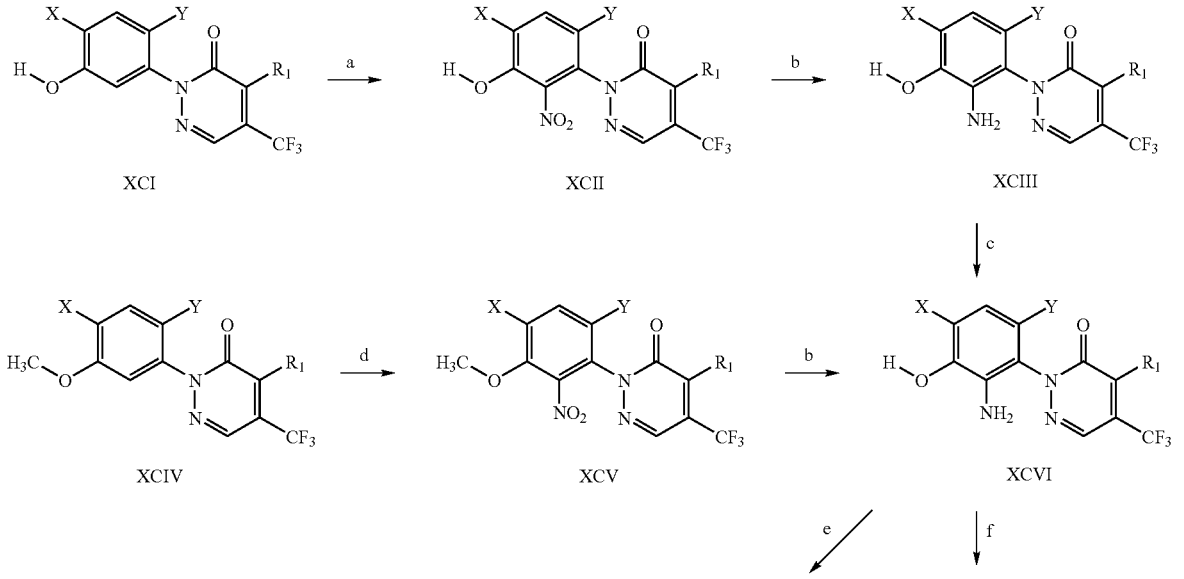

-continued

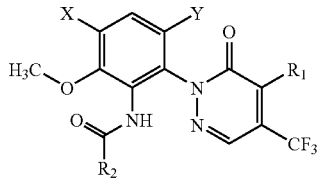

XCVII

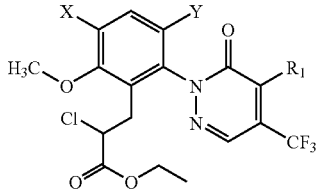

XCVIII (a) $HNO_3$; (b) Fe — AcOH; (c) $CH_3$, base, (d) $H_2SO_4$ — $HNO_3$; (e) $R_2X$, base, (f) t-BuONO-ethyl acrylate-$CuCl_2$

EXAMPLE 1

Preparation of 3-(4-chloro-6-fluoro-3-methoxy-2-nitrophenyl)-6-trifluoromethyl-2,4(1H, 3H)-pyrimidinedione (Compound no. 1-1)

3-(4-Chloro-6-fluoro-3-methoxyphenyl)-6-trifluoromethyl-2,4(1H, 3H)-pyrimidinedione (10.0 g, 29.5 mmol) was slowly added to a stirred mixture of con. sulfuric acid (36 ml) and con. nitric acid (4 ml) with stirring at −15° C. The solution was then slowly warmed to room temperature and allowed to stir for 2 hr. Addition of the solution to ice-water resulted in a light yellow precipitate which was separated by filtration to afford the title compound (9.1 g).

EXAMPLE 2

Preparation of 3-(4-chloro-6-fluoro-3-methoxy-2-nitrophenyl)-1-methyl-6-trifluoromethyl-2,4(1H, 3H)-pyrimidinedione (Compound no. 1-5)

3-(4Chloro-6-fluoro-3-methoxy-2-nitrophenyl)-6trifluoromethyl-2,4(1H, 3H)-pyrimidinedione (9 g, 23.5 mmol) was dissolved in dimethylformamide (90 ml) and to this were added potassium carbonate (3.9 g, 28.2 mmol) and dimethylsulfate (10.2 g, 47 mmol) with stirring. The solution was stirred at ambient temperature for 12 hr and water was added. Product was extracted in ethyl acetate and the organic layer was washed with water and dried over anhydrous sodium sulfate. Removal of the solvent afforded a crude product which was purified by column chromatography on silica gel. Elution of the column with methylene chloride afforded the title compound (7.8 g).

EXAMPLE 3

Preparation of 3-(2-amino-4-chloro-6-fluoro-3-methoxyphenyl)-1-methyl-6-trifluoromethyl-2,4(1H, 3H)-pyrimidinedione (Compound no. 1-4)

3-(4-Chloro-6-fluoro-3-methoxy-2-nitrophenyl)-1-methyl-6-trifluoromethyl-2,4(1H, 3H)-pyrimidinedione (7.5 g, 18.9 mmol) was dissolved in acetic acid (75 ml) and 4.2 g (75.6 mmol) of iron powder was added. The solution was stirred at ambient temperature under nitrogen atmosphere for 6 hr and water was added. Extraction was carried out with ethyl acetate. Organic layer was washed with water, brine, and dried with anhydrous sodium sulfate followed by evaporation to afford the title compound (6.8 g).

EXAMPLE 4

Preparation of 3-[4-chloro-2-(2,4difluorobenzoyl) amino-6-fluoro-3-methoxyphenyl]-1-methyl-6-trifluoromethyl-2,4(1H, 3H)-pyrimidinedione (Compound no. 2-42)

3-(2-Amino-4-chloro-6fluoro-3-methoxyphenyl)-1-methyl-6-trifluoromethyl-2,4(1H, 3H)pyrimidinedione (2.0 g, 5.4 mmol) and triethylamine (0.66 g, 6.5 mmol) were dissolved in anhydrous tetrahydrofiuran (30 ml) and stirred under ice cooling. To this solution was slowly added 2,4-difluorobenzoyl chloride (0.96 g, 5.4 mmol) and solution refluxed for 2 hr. Another batch of 2,4-difluorobenzoyl chloride (0.19 g, 1.1 mmol) was added and solution refluxed for 2 hr. Solvent was removed in vacuo and the product purified by column chromatography on silica gel using hexane-ethyl acetate (3:1) as the eluent to afford the title compound (2.2 g).

EXAMPLE 5

Preparation of 3-(4-chloro-2-diacetylamino-6-fluoro-3-methoxyphenyl)-1-methyl-6-trifluoromethyl-2,4(1H, 3H)-pyrimidinedione (Compound no. 2-2)

A mixture of 3-(2-amino-4-chloro-6-fluoro-3-methoxyphenyl)-1-methyl-6 trifluoromethyl-2,4(1H, 3H)-pyrimidinedione (0.5 g, 1.4 mmol), triethylamine (0.53 g, 5.6 mmol), acetic anhydride (0.57 g, 5.6 mmol), and anhydrous toluene (10 ml) was refluxed for 12 hr. Solvent was removed in vacuo and the product purified by chromatography on silica gel. Column was eluted with hexane-ethyl acetate (7:3) to furnish the title compound (0.34 g).

EXAMPLE 6

Preparation of 3-(4-chloro-2-dimehtylainino-6-fluoro-3-methoxyphenyl)-1-methyl-6-trifluoromethyl-2,4(1H, 3H)-pyrimidinedione (Compound no. 1-11)

To a solution of 3-(2-amino-4-chloro-6-fluoro-3-methoxyphenyl)-1-methyl-6-trifluoromethyl-2,4(1H, 3H)pyrimidinedione (0.6 g, 1.6 mmol) in toluene (10 ml) was added potassium carbonate (0.27 g, 1.92 mmol) followed by dimethylsulfate (0.69 g, 3.2 mmol). The solution was refluxed for 2 hr and solvent was removed in vacuo. Residue was chromatographed on silica gel and product eluted with methylene chloride to afford the title compound (0.12 g).

EXAMPLE 7

Preparation of 3-(4chloro-6-fluoro-3-methoxy-2-methoxycarbonylaminophenyl)-1-methyl-6-trifluoromethyl-2,4(1H, 3H)-pyrimidinedione (Compound no. 4-1)

A solution of 3-(2-amino-4-chloro-6-fluoro-3-methoxyphenyl)-1-methyl-6-trifluoromethyl-2,4(1H, 3H)-pyrimidinedione (1.25 g) and triethylamine (1 ml) in ethyl acetate (20 ml) was added to a solution of triphosgene (1.0 g) in ethyl acetate (15 ml) stirred under nitrogen The mixture was heated at reflux for 2 hr, cooled, filtered and the filtrate evaporated under reduced pressure to give a buff colored solid (1.4 g). $^1$H NMR ($CDCl_3$, 300 MHz) 3.58 (3H, s), 4.00 (3H, s), 6.38 (1H, s), 7.12 (1H, d, J=8.8 Hz) ppm.

The above isocyanate (0.5 g) dissolved in N,N-dimethylformamide (10 ml) was treated with dry methanol (2 ml) and stirred at room temperature for two days. Water and ethyl acetate were added and the solution separated. The organic phase was dried over sodium sulfate, evaporated, and chromatographed on silica gel eluting with ethyl acetate-hexane (1:3) to give the title compound as a white solid (0.17 g).

EXAMPLE 8

Preparation of 3-[2-bis(methylaminocarbonyl) amino-4-chloro-6-fluoro-3-methoxyphenyl]-1-methyl-6-trifluoromethyl-2,4(1H, 3H)-pyrimidinedione (Compound no.3-1)

To a solution of 3-(2-amino-4-chloro-6-fluoro-3-methoxyphenyl)-1-methyl-6-trifluoromethyl-2,4(1H, 3H)-pyrimidinedione (0.5 g, 1.4 mmol) and triethylamine (0.17 g, 1.7 mmol) in anhydrous toluene (10 ml) was added methyl isocyanate (0.1 g, 1.7 mmo.) with stirring. The solution was refluxed for 2 hr and solvent removed. Residue was chromatographed on silica gel in methylene chloride-methanol (99:1) to furnish the title compound (0.56 g).

EXMPLE 9

Preparation of 3-[4-chloro-2-methoxyphenyl]-1-methyl-6-trifluoromethyl-2,4(1H, 3H)-pyrimidinedione (Compound no. 1-31)

A mixture of 3-(2-amino-4-chloro-6-fluoro-3-methoxyphenyl)-1-methyl-6-trifluoromethyl-2,4(1H, 3H)-pyrimidinedione (0.5 g, 1.4 mmol) and dimethylformamide dimethylacetal (0.8 g, 7 mmol) was refluxed for 4 hr under a blanket of nitrogen. Excess reagent was removed in vacuo and product extracted with ether. Solvent was removed to afford a residue which was chromatographed on silica gel. Elution of the column with hexane-ethyl acetate (6:4) afforded the title compound (0.22 g).

EXAMPLE 10

Preparation of 3-(2-amino-4-chloro-6-fluoro-3-hydroxyphenyl)-1-methyl-6-trifluoromethyl-2,4(1H, 3H)-pyrimidinedione (Compound no. 1-16).

3-(2-Amino-4-chloro-6-fluoro-3-methoxyphenyl)-1-methyl-6trifluoromethyl-2,4(1H, 3H)-pyrimidinedione (1.1 g, 2.7 mmol) was dissolved in 50 ml of anhydrous 1,2-dichloroethane and 3.4 g (10.8 mmol) of borontribromide imethylsulfide complex was added to the solution. The solution was refluxed for 16 hr and methylene chloride (100 ml) was added. Washing with water followed by drying (anhydrous sodium sulfate) and removal of the solvent afforded a residue which was triturated with ether to afford the title compound (0.6 g).

EXAMPLE 11

Preparation of 3-(4-chloro-6-fluoro-3-hydroxy-2-nitrophenyl)-6-trifluoromethyl-2,4(1H, 3H)-pyrimidinedione (Compound no. 1-2)

3-(4-chloro-2-fluoro-5-hydroxyphenyl)6-trifluoromethyl-2,4(1H,3H)-pyrimidinedione (2.5 g) was added to an ice cooled con. nitric acid (50 ml). After stirring for 1 hr, the reaction mixture was poured into ice-cold water. The yellow crystals were collected by filtration to afford the title compound (0.9 g). The filtrate was extracted by ethyl acetate (200 ml) and washed with brine. The organic phase was dried over anhydrous sodium sulfate. After removal of the solvent, 0.6 g of title compound was obtained as yellow crystal.

EXAMPLE 12

Preparation of 3-(4-chloro-6-fluoro-3-hydroxy-2-nitrophenyl)-1-methyl-6-trifluoromethyl-2,4(1H, 3H)-pyrimidinedione (Compound no. 1-17)

3-(4-Chloro-2-fluoro-5-hydroxyphenyl)-1-methyl-6-trifluoromethyl-2,4(1H, 3H)-pyrimidinedione (1.06 g) was added to ice-cold con. nitric acid (10 ml). After stirring for 30 min, crushed ice was added. The yellow crystals were collected by filtration to afford the title compound (1.2 g).

EXAMPLE 13

Preparation of 1-(4-chloro-6-fluoro-3-hydroxy-2-nitrophenyl)-4-(3-fluoropropyl)-1,4-dihydro-5-oxo-5H-tetrazole (Compound no. 5-4)

1-(4-Chloro-2-fluoro-5-hydroxyphenyl)-4-(3-fluoropropyl)-tetrazolinone (2.91 g) was gradually added into an ice-cooled nitric acid (20 ml) and stirred for 30 minutes. Crushed ice was added followed by extraction with ethyl acetate. The ethyl acetate extract was washed with water, dried over sodium sulfate, concentrated, and filtered through a silica gel SPE column (2 g) to give the title compound as a yellow solid (3.4 g).

EXAMPLE 14

Preparation of 1-(2-amino-4-chloro-6-fluoro-3-hydroxyphenyl)-4-(3-fluoroproyl)-1,4-dihydro-5-oxo-5H-tetrazole (Compound no. 5-5)

Iron powder (2.3 g) was added to a solution of 1-(4-chloro-6-fluoro-3-hydroxy-2-nitrophenyl)-4-(3-fluoropropyl)-1,4dihydro-5-oxo-5H-tetrazole (3.4 g) in acetic acid (50 ml) and stirred at room temperature over night. The reaction mixture was filtered through a celite bed. The filtrate was concentrated under reduced pressure and purified by a silica gel column, eluted with hexane-ethyl acetate (2:1) to give yellow crystals (2.75 g).

EXAMPLE 15

Preparation of 1-(2-amino-4-chloro-6-fluoro-3-propargyloxyphenyl)-4-(3-fluoroproyl)-1,4-dihydro-5-oxo-5H-tetrazole (Compound no. 5-17)

The mixture of 1-(2-amino-4-chloro-6-fluoro-3-hyroxyphenyl)(3-fluoropropyl)-tetrazolinone (0.28 g), propargyl bromide (0.13 g), and potassium carbonate (0.14 g) in acetonitrile (5 ml) was heated under reflux for 0.5 hour. The solvent and excess reagent were removed under reduced pressure. The residue was purified by a silica gel column, eluted with ethyl acetate to give the desired product (0.33 g).

EXAMPLE 16

Preparation of 1-(2-amino-4-chloro-6-fluoro-3-isopropyloxyphenyl)-4-(3fluoropropyl)-1,4-dihydro-5-oxo-5H-tetrazole (Compound no. 5-18)

The mixture of 1-(2-amino-4-chloro-6-fluoro-3-hydroxyphenyl)-4-(3-fluoropropyl)-1,4-dihydro-5-oxo-5H-tetrazole (0.30 g), isopropyl iodide (1.2 ml), and potassium carbonate (0.14 g) in acetonitrile (5 ml) was heated under reflux for 2 hours. The reaction mixture was evaporated and purified by a silica gel column, eluted with hexane-ethyl acetate (2:1) to give the desired product (0.29 g).

EXAMPLE 17

Preparation of 1-(4-chloro-6-fluoro-3-hydroxy-2-nitrophenyl)-4-difluoromethyl-3-methyl-1,2,4-triazolinone (Compound no. 6-1)

1-(4-Chloro-2-fluoro-5-hydroxyphenyl)-4-difluoromethyl-3-methyl-1,2,4-triazolinone (0.21 g) was added to con. nitric acid (1.5 ml) at ambient temperature. The solution was vigorously stirred at ambient temperature for 15 min. Reaction mixture was poured into ice-cold water and yellow precipitate was collected by filtration to afford the title compound (0.17 g) as a 1:1 mixture with oxidative compound.

EXAMPLE 18

Preparation of 1-(2-amino-4-chloro-6-fluoro-3-hydroxyphenyl)-4-difluoromethyl-3-methyl-1,2,4-triazolinone (Compound no. 6-2)

To a stirred solution of 1-(4-chloro6-fluoro-3-hydroxy-2-nitrophenyl)-4-difluoromethyl-3-methyl-1,2,4-triazolinone (0.15 g) in a mixed solvent of con. hydrochloric acid (5 ml) and methanol (5 ml) was added 0.3 g of iron powder at ambient temperature. The resulting mixture was refluxed for 1 hr and the solution was concentrated under reduced pressure. The residue was extracted with ethyl acetate (200 ml) and the organic phase was washed with brine and dried over anhydrous sodium sulfate. Solvent was removed under reduced pressure to give title compound as a brown oil.

EXAMPLE 19

Preparation of 4-chloro-3-(4-chloro-6-fluoro-3-methoxy-2-nitrophenyl)-1-methyl-5-trifluoromethyl-1H-pyrazole (Compound no. 7-1)

4-Chloro-3-(4-chloro-2-fluoro-5-methoxyphenyl)-1-methyl-5-trifluoromethyl-1H-pyrazole (1.2 g, 3.5 mmol) was slurried with 4 ml of conc. sulfuric acid and was slowly added to a stirred 4 ml of conc. sulfuric acid-con. nitric acid (9:1) at −15° C. Solution was allowed to stir at ambient temperature for 2 hr and then added to ice water. Extraction with ethyl acetate and removal of the solvent afforded a crude product which was chromatographed on silica gel. Elution of the column with hexane-methylene chloride (4:6) furnished the title compound (0.72 g).

EXAMPLE 20

Preparation of 4-chloro-3-(2-amino-4-chloro-6-fluoro3-metoxyphenyl)-1-methyl-5-trifluoromethyl-1H-pyrazole (Compound no. 7-2)

4-Chloro-3-(4-chloro-6-fluoro-3-methoxy-2-nitrophenyl)-1-methyl-5-trifluoromethyl-1H-pyrazole (0.48 g, 1.24 mmol) was dissolved in toluene (8 ml) and 0.05 g of 10% palladium on carbon was added. The solution was vigorously stirred under hydrogen atmosphere for 4 hr at ambient temperature and the catalyst was removed by filtration. Removal of the solvent afforded a residue which was chromatographed on silica gel. Elution of the column with hexanemethylene chloride (3:7) furnished the title compound (0.38 g).

EXAMPLE 21

Preparation of 6-chloro-4-fluoro-2-nitro-3-(tetrahydrophthalimido)phenol (Compound no. 8-1)

2-Chloro-4-fluoro-5-(tetrahydrophthalimido)phenol (5.0 g) was added into nitric acid (50 ml) at 0° C., warmed up to room temperature in 30 minutes. Crushed ice was added and the solution extracted with methylene chloride. The organic phase was washed with water, dried over anhydrous sodium sulfate, and purified by a silica gel column, eluted with metliylene chloride-ethyl acetate (19:1) to give 3.67 g of the desired product.

EXAMPLE 22

Preparation of 2-amino-6-chloro-4-fluoro-3-tetrahydrophthalimido)phenol (Compound no. 8-2)

Iron powder (2.48 g) was added into a solution of 6-nitro-4fluoro-2-nitro-3-(tetrahydrophthalimido)phenol (3.67 g) in acetic acid (60 ml) and stirred at room temperature for two hours. The reaction mixture was diluted with ethyl acetate, washed with water, dried over anhydrous sodium sulfate, evaporated to give 3.6 g of the title compound.

EXAMPLE 23

Preparation of N-(2-amino-4-chloro-6-fluoro-3-propargyloxyphenyl)tetrahydrophthalimide (Compound no. 8-3).

A mixture of 2-amino-6-chloro-4-fluoro-3-(tetrahydrophthalimido)phenol (0.31 g), propargyl bromide (0.2 ml), potassium carbonate (0.14 g), and acetonitrile (5 ml) was heated under reflux for 0.5 hr. The solvent and excess reagent were removed under reduced pressure. The residue was purified by a silica gel column, eluted with ethyl acetate to give the title product (0.2 g).

EXAMPLE 24

Preparation of N-(2-amino-4-chloro-6-fluoro-3-isopropyloxyphenyl)tetrahydrophthalimide (Compound no. 8-4)

A mixture of 2-amino-6-chloro-4-fluoro-3-(tetrahydrophthalimido)phenol (0.31 g), isopropyl iodide (1.2 ml), potassium carbonate (0.14 g), and acetonitrile (5 ml) was heated under reflux for 2 hr. The solvent and excess reagent were removed under reduced pressure. The residue was purified by a silica gel column, eluted with ethyl acetate to give the title product (0.21 g).

EXAMPLE 25

Preparation of N-(2-amino-4-chloro-3-cyclopentyloxy-6-fluorophenyl) tetrahydrophthalimide (Compound no. 8-5)

A mixture of 2-amino-6-chloro-4-fluoro-3tetrahydrophthalimido)phenol (0.31 g), cyclopentyl bromide (1.3 ml), potassium carbonate (0.14 g), and acetonitrile (5 ml) was heated under reflux for 2 hr. The solvent and excess reagent were removed under reduced pressure. The residue was purified by a silica gel column, eluted with ethyl acetate to give the title product (0.17 g).

EXAMPLE 26

Preparation of 2-chloro-4-fluoro-5-(phthalimido) methoxybenzene

4-Chloro-2-fluoro-5-methoxyaniline (10.0 g, 57 mmol) and phthalic anhydride (8.5 g, 57 mmol mmol) were dissolved in glacial acetic acid (200 ml) and the solution refluxed for 2 hr. Water was added and the resultant precipitate was separated by filtration. The residue was washed with water and dried to afford the title compound (16.7 g); $^1$H NMR ($CDCl_3$, 300 MHz) 3.89 (3H, s), 6.9 (1H, d, J=6.3 Hz), 7.33 (1H, d, J=9.0 Hz), 7.82 (2H, m), 7.97 (2H, m) ppm.

EXAMPLE 27

Preparation of 6-chloro-4-fluoro-2-nitro-3-(phthalimido)methoxybenzene

2-Chloro-4-fluoro-5-(phthalimido)methoxybenzene (5.0 g, 16.4 mmol) was slowly added to a stirred mixture of con. sulfuric acid-con. nitric acid (10:1, 20 ml) at −20° C. Solution was then warmed to ambient temperature and allowed to stir for 1 hr. Addition to ice-water resulted in a light yellow precipitate which was separated by filtration. Column chromatography on silica gel in hexane-methylene chloride (3:7) furnished the title compound (3.2 g); $^1$H NMR ($CDCl_3$, 300 MHz) 4.06 (3H, s), 7.54 (1H, d, J=8.5 Hz), 7.84 (2H, m), 7.97 (2H, m) ppm.

EXAMPLE 28

Preparation of 3-chloro-5-fluoro-2-methoxy-6-(phthalimido)aniline

6-Chloro-4-fluoro-2-nitro-3-(phthalimido) methoxybenzene (0.5 g, 1.4 mmol) was dissolved in glacial acetic acid (5 ml) and reduced iron (0.32 g, 5.6 mmol) was added. The solution was stirred at ambient temperature under a stream of nitrogen for 12 hr. Water was added and the product extracted with ethyl acetate followed by washings with water, brine, and drying (anhydrous sodium sulfate). Removal of the solvent afforded the title compound (0.4 g); $^1$H NMR ($CDCl_3$, 300 MHz) 3.87 (3H,s), 4.21 (2H, br s), 6.65 (1H, d, J=9.4 Hz), 7.81 (2H, m), 7.95 (2H, m) ppm.

EXAMPLE 29

Preparation of 4-chloro-6-fluoro-3-methoxy-2-nitroaline

3-Chloro-5-fluoro-2-methoxy-6-(phthalimido)aniline (0.6 g, 1.7 mmol) was dissolved in dimethylsulfoxide (3 ml) and anhydrous hydrazine (0.22 g, 6.8 mmol) was added. The solution was stirred at ambient temperature for 12 hr under a stream of nitrogen. Water was added and the product extracted with ether. The organic layer was washed with water, dried (anhydrous sodium sulfate), and evaporated to furnish the title compound (0.22 g). $^1$H NMR ($CDCl_3$, 300 MHz) 3.98 (3H, s), 5.09 (2H, br s), 7.2 (1H, d, J=10.5 Hz) ppm.

EXAMPLE 30

Preparation of 4-chloro-6-fluoro-3-methoxy-2-nitrophenyl isocyanate

4-Chloro-4-fluoro-3-methoxy-2-nitroaniline (0.5 g, 2.27 mmol) was dissolved in anhydrous toluene (30 ml) and triethylamine (0.46 g, 4.54 mmol) was added. This solution was slowly added to a stirred solution of triphosgene (0.67 g, 2.27 mmol) in toluene (30 ml) and the solution refluxed for 2 hr. The solution was cooled and filtered. Clear filtrate was evaporated in vacuao to afford the title compound. $^1$H NMR ($CDCl_3$, 300 MHz) 3.96 (3H, s), 7.38 (1H, d, J=8.8 Hz) ppm.

EXAMPLE 31

Preparation of 3-[4-chloro-6-fluoro-3-methoxy-2-nitrophenyl]-1-methyl-6-trifluoromethyl-2,4)1H, 3H)-pyrimidinedione (Compound no. 1-5) from 4-chloro-6-fluoro-3-methoxy-2-nitrophenyl isocyanate Sodium hydride (0.06 g, 2.27 mmol) was suspended in 10 ml anhydrous dimethylformamide and to this was slowly added a solution of ethyl-3-amino-4,4,4-trifluorocrotonate (0.42 g, 2.27 mmol) in anhydrous toluene (10 ml). The solution was stirred for 15 min. until the evolution of hydrogen gas ceased. The solution was cooled to −30° C. and a solution of 4-chloro-6-fluoro-3-methoxy-2-nitrophenyl isocyanate (2.27 mmol) in anhydrous toluene (10 ml) was slowly added with stirring. The solution was then allowed to warm to room temperature and methyl iodide (1.31 g, 9.1 mmol) was added. After stirring for 4 hr at ambient temperature, water was added and product extracted with ethyl acetate. Column chromatography on silica gel in hexane:methylene chloride (4:6) afforded the title compound (0.13 g).

EXAMPLE 32

Preparation of 2-chloro-4-fluoro-5-(phthalimido) phenol

5-Amino-2-chloro-4-fluorophenol (3.0 g, 18.6 mmol) and phthalic anhydride (3.3 g, 22.3 mmol) were dissolved in glacial acetic acid (60 ml) and the solution refluxed for 2 hr. Water was added and the resultant precipitate was separated by filtration. The residue was washed with water and dried to afford the title compound (5.04 g); $^1$H NMR ($CDCl_3$+$CD_3OD$, 300 MHz) 3.68 (1H, s), 6.93 (1H, d, J=6.6 Hz), 7.27 (1H, d, J=9.1 Hz), 7.84 (2H, dd, J=3.0, 5.5 Hz), dd, J=3.0, 5.5 Hz) ppm.

EXAMPLE 33

Preparation of 6-chloro-4-fluoro-2-nitro-3 (phthalimido)phenol

2-Chloro-4-fluoro-5-(phthalimido)phenol (5.0 g, 17.1 mmol) was slowly added with stirring to con. nitric acid (50 ml) at −10° C. Solution was then warned to ambient temperature. and allowed to stir for 0.5 hr. Addition to ice-water resulted in a light yellow precipitate which was separated by filtration to afford the title compound (5.5 g); $^1$H NMR ($CDCl_3$+$CD_3OD$, 300 MHz) 4.36 (H, br s), 7.61 (1H, d, J=8.6 Hz), 7.88 (2H, dd, J=3.0, 5.5 Hz), 7.99 (2H, dd, J=3.0, 5.5 Hz) ppm.

EXAMPLE 34

Preparation of 4-chloro-2,5-difluoronitrobenzene (XXXVII)

1-Chloro-2,5-difluorobenzene (31.7 g, 0.21 mol) was dissolved in sulfuric acid (110 ml) at −40° C., then a solution of sulfuric acid (20 ml) and nitric acid (30 ml) was added dropwise. The mixture was stirred for 1 hr while temperature slowly raised to 20° C. The product was forced to crystallize by mixing the reaction mixture with ice-water (500 ml), the yellow crystals were filtered, washed with cold water and dried in fume hood overnight. (38.0 g). $^1$H NMR ($CDCl_3$, 300 MHz) 7.46 (1H, dd, J=9.8, 9.9 Hz), 7.96 (1H, dd, J=7.9, 7.9 Hz) ppm.

EXAMPLE 35

Preparation of 4-chloro-2,5-difluoroaniline (XXXIX)

1-Chloro-2,5-difluoro-4-nitrobenzene (XXXVIII) (17.5 g) was dissolved in acetic acid (150 ml) in a 1L 3-neck round bottom flask equipped with cooling condenser. To it iron powder (35.0 g) was added slowly while the solution was stirred by an overhead stirrer. The reaction was exothermic which occurred in less than 30 min and generated much heat that was absorbed by a cooling bath. After that, ethyl acetate (300 ml) was added and the mixture filtered. The solution was washed with water and dried over sodium sulfate. The product was purified by column chromatography (silica gel, hexane:ethyl acetate, 4:1) (14.3 g). $^1$H NMR ($CDCl_3$, 300 MHz) 3.89 (2H, br), 6.56 (1H, m), 7.02 (1H, m) ppm.

EXAMPLE 36

Preparation of ethyl 4-chloro-2,5-difluorophenylcarbamate (XL)

4-Chloro-2,5-difluoroaniline (XXXIX) (2.1 g, 12.8 mmol) was mixed with pyridine (20 ml) at 0° C., to it was dropwise added ethyl chloroformate (1.5 g, 13.8 mmol). After stirring for 2.5 hr while temperature slowly raised to room temperature, pyridine was evaporated and the residue crystallized in ice-water (100 ml). The crystals were filtered, washed with water and dried in fume hood overnight (2.7 g). $^1$H NMR ($CDCl_3$, 300 MHz) 1.33 (3H, t, J=7.1 Hz), 4.23 (2H, q, J=7.1 Hz), 6.89 (1H, br), 7.12 (1H, dd, J=6.5, 6.5 Hz), 8.05 (1H, dd, J=7.8, 9.6 Hz) ppm.

EXAMPLE 37

Preparation of ethyl 4-chloro-3,6-difluoro-2-nitrophenylcarbamate (XLI)

Ethyl 4-chloro-2,5-difluorophenylcarbnaate (XL) (2.4 g, 10.2 mmol) was added to a mixture of sulfuric acid (12.5 ml) and nitric acid (0.8 ml) at −30° C. After stirring for 1.5 hr (−30° C. to r.t.), it was poured into ice water (50 ml) and yellow crystals formed immediately which were filtered, washed with water and dried in fume hood overnight (2.8 g). $^1$H NMR ($CDCl_3$, 300 MHz) 1.30 (3H, t, J=7.1 Hz), 4.22 (2H, q, J=7.1 Hz), 6.97 (1H, br), 7.45 (1H, dd, J=6.3, 6.3 Hz) ppm.

EXAMPLE 38

Preparation of 4-chloro-3,6difluoro-2-nitroaniline (V)

Ethyl 4-chloro-3,6-difluoro-2-nitrophenylcarbamate (XLI) (0.9 g, 3.2 mmol) was mixed with acetic acid (30 ml) and hydrobromic acid (48%, 25 ml), the mixture was stirred at 150° C. for 4 hr and then the volume reduced to half by evaporation Ethyl acetate (50 ml) was added and the solution was washed with water (15 ml×3) and dried over sodium sulfate. The product was purified by column chromatography (silica gel, hexane) (0.56 g). $^1$H NMR ($CDCl_3$, 300 MHz) 5.73 (2H, br), 7.24 (1H, dd, J=6.1, 6.1 Hz) ppm.

EXAMPLE 39

Preparation of 3-(4-chloro-5-ethoxycaibonylamino-2-fluorophenyl)-6-trifluoromethyl-2,4(1H, 3H)-pyrimidinedione (XLVII)

Ethyl chloroformate (2.58 g) was dropwise added into a solution of 3-(5-amino-4-chloro-2-fluorophenyl)-6-trifluoromethyl-2,4(1H, 3H)-pyrimidinedione (XLVI) in pyridine (25 ml) at 0° C., and stirred at room temperature for one hr. The reaction mixture was diluted with ethyl acetate, washed with 1N hydrochloric acid followed by water, and dried over sodium sulfate. After concentration, the crystals (5.46 g) were collected by filtration. $^1$H NMR ($CDCl_3$, 300 MHz) 1.31 (3H, t, J=7.1 Hz), 4.22 (2H, q, J=7.1 Hz), 6.20 (1H, s), 7.14 (1H, br), 7.29 (1H, d, J=8.8 Hz), 7.36 (1H, d, J=6.0 Hz), 8.26 (1H, d, J=6.4 Hz) ppm.

EXAMPLE 40

Preparation of 3-(4-chloro-3-ethoxycarbonylamino-6-fluoro-2-nitrophenyl)-6-trifluoromethyl-2,4(1H, 3H)-pyrimidinedione (Compound no. 1-33)

3-(4Chloro-5-ethoxycarbonylamino-2-fluorophenyl)-6-trifluoromethyl-2,4(1H, 3H)-pyrimidinedione (XLVII) (1.0 g) was stirred with sulfuric acid (2 ml) at 0° C., then a mixture of nitric acid (1 ml) and sulfuric acid (1 ml) was dropwise added. After stirring at room temperature for 3 hr, it was poured into ice water (50 ml) and yellow crystals formed immediately which was filtered, washed with water and dried in fume hood overnight (0.5 g).

EXAMPLE 41

Preparation of 3-(4-chloro-3-ethoxycarbonylamino-6-fluoro-2-nitrophenyl)-1-methyl-6-trifluoromethyl-2,4(1H, 3H)-pyrimidinedione (Compound no. 1-34)

3-(4-chloro-3-ethoxycarbonylamino6-fluoro-2-nitrophenyl)-6-trifluoromethyl-2,4(1H, 3H)-pyrimidinedione (0.96 g) was stirred with dimethyl sulfate (0.72 ml) and potassium carbonate (0.33 g) in N,N-dimethylformamide (10 ml) at room temperature overnight. The reaction mixture was diluted with ethyl acetate, washed with water, dried over sodium sulfate, evaporated to give the title compound (1.1 g, oil).

EXAMPLE 42

Preparation of 3-[4-chloro-6-fluoro3-methyl-2-(2-naphthoyl)aminophenyl]-1-methyl-6-trifluoromethyl-2,4(1H, 3H)-pyrimidinedione (Compound no. 2-122)

Preparation of 4-chloro-2-fluoro-5-methyl-N-phenoxycarbonylaniline

4-Chloro-2-fluoro-5-methylaniline (5 g, 31.4 mmol) was dissolved in tetrahydrofuran (100 ml) and potassium carbonate (6.0 g, 37.7 mmol) and phenyl chloroformate (5.9 g, 37.7 mmol) were added. Solution was refluxed for 3 hr and the solvent was removed under reduced pressure. Product was purified by column chromatography on silica gel (eluent, methylene chloride:hexane, 6:4; 7.15 g).

Preparation of 4-chloro-2-fluoro-5-methyl-6-nitro-N-phenoxycarbonylaniline

4-Chloro-2-fluoro-5-methyl-N-phenoxycarbonylaniline (7.1 g, 25.4 mmol) was dissolved in chloroform (68 ml) and trifluoroaceticanhydride (13.5 ml) and ammonium nitrate (2.4 g, 30.5 mmol) were slowly added with stirring at ambient temperature. The stirring was continued for 18 hr when a second batch of ammonium nitrate (0.4 g, 5 mmol) was added and stirring continued for 8 hr. Water was added and solution was neutralized by slow addition of sodium bicarbonate solution followed by extration with chloroform. Oganic layer was dried and evaporated under reduced pressure to afford an oily product (8.5 g) which was used for the next step without purification.

Preparation of 3-(4-chloro-6-fluoro-3-methyl-2-nitrophenyl)-6-trifluoromethyl-2,4(1H, 3H)-pyrimidinedione Ethyl 3-amino-4,4,4-trifluorocrotonate (61.3 g, 33.1 mmol) was dissolved in dimethylformamide (47 ml) and stirred at −10 ° C. To this solution was slowly added 1,8-diazabicyclo [5.4.0]undec-7-ene (6.3 g, 41.4 mmol) and solution stirred for 0.5 hr. To this solution was slowly added a solution of 4-chloro-2-fluoro-5-methyl-6-nitro-N-phenoxycarbonylaniline (8.5 g) in dimethylformamide (25 ml) followed by stirring at ambient temperature for 14 hr. Solution was then heated to 80 ° C. and stirred at this temperature for 4 hr. Water was added and pH adjusted to 4 by addition of dilute hydrochloric acid. Product was extracted with ethyl acetate followed by evaporation of the solvent to afford the crude product (10.1 g) which was subjected to N-methylation as follows.

Preparation of 3-(4-chloro-6-fluoro-3-methyl-2-nitrophenyl)-1-methyl-6-trifluoromethyl-2,4(1H, 3H)-pyrimidinedione 3-(4-Chloro-6-fluoro-3-methyl-2-nitrophenyl)-6-trifluoromethyl-2,4(1H, 3H)-pyrimidinedione (10.1 g) was dissolved in dimethylformamide (100 ml) and potassium carbonate (5.7 g, 41.3 mmol) and dimethylsulfate (11.9 g, 55.1 mmol) were added. Solution was stirred at ambient temperature for 14 hr, water was added and product extracted with ethyl acetate. The title compound was separated by column chromatography on silica gel (eluent, hexane-ethyl aceatate, 9:1; 8.5 g).

Preparation of 3-(2-amino-4-chloro-6-fluoro-3-methylphenyl)-1-methyl-6-trifluoromethyl-2,4(1H, 3H)-pyrimidinedione 3-(4-Chloro-6-fluoro-3-methyl-2-nitrophenyl)-methyl-6-trifluoromethyl-2,4(1H, 3H)-pyrimidinedione (2.0 g, 5.2 mmol) was dissolved in acetic acid (20 ml) and iron powder (1.2 g, 21.5 mmol) was added. Solution was stirred at ambient temperature for 14 hr. Water was added and product extracted with ethyl acetate followed by evaporation under reduced pressure. Title compound was separated by column chromatography on silica gel (eluent, hexane-ethyl acetate, 7:3; 1.5 g).

Preparation of 3-[4-chloro-6-fluoro-3-methyl-2-(2-naphthoyl)aminophenyl]-1-methyl-6-trifluoromethyl-2,4(1H, 3H)-pyrimidinedione 3-(2-Amino-4-chloro-6-fluoro-3-methylphenyl)-1-methyl-6-trifluoromethyl-2,4(1H, 3H)-pyrimidinedione (0.5 g, 1.4 mmol) was dissolved in 1,4-dioxane (20 ml) and triethyl amine (0.29 g, 2.9 mmol) and 2-naphthoyl chloride (0.41 g, 2.2 mmol) were added. Solution was heated under reflux for 4 hr and solvent removed under reduced pressure. Product was subjected to column chromatography on silica gel and the title compound was eluted with hexane-ethyl acetate (8:2; 0.3 g).

EXAMPLE 43

Preparation of N-[4-chloro-6-fluoro-3-methoxy-2-(2-naphthoyl)aminophenyl]phthalimide (Compound no. 13-3)

3-Chloro-5-fluoro-2-methoxy-6-(phthalimido)aniline (0.32 g, 1 mmol), 2-naphthoyl chloride (0.23 g, 1.2 mmol), and triethyl amine (0.12 g, 1.2 mmol) were dissolved in tetrahydrofuran (20 ml) and solution refluxed for 3 hr. Solvent was then removed under reduced pressure and the residue subjected to column chromatography on silica gel. Title compound was eluted with hexane-ethyl acetate (7:3; 0.12 g).

EXAMPLE 44

Preparation of 3-(2-amino-4-chloro-3-difluoromethoxy-6-fluorophenyl)-1-methyl-6-trifluoromethyl-2,4(1H, 3H)-pyrimidinedione (Compound no. 1-38)

3-(2-Amino-4-chloro-6-fluoro-3-hydroxyphenyl)-1-methyl-6-trifluoromethyl-2,4(1H, 3H)-pyrimidinedione (1.41 g, 4.0 mmol) and potassium carbonate (0.69 g, 5.0 mmol) were suspended in dimethylformamide (50 ml) and stirred at 90° C. Chlorodifluoromethane was bubbled through the solution for 4 hr and water was added. Product was extracted with ethyl acetate and subjected to column chromatography (silica gel; eluent, methylene chloridemethanol, 99.5:0.5) to furnish the title compound (0.78 g).

EXAMPLE 45

Preparation of 3-[4-chloro-6-fluoro-3-methyl-2-(phenoxycarbonylamino)phenyl]-1-methyl-6-trifluoromethyl-2,4(1H, 3H)-pyrimidinedione (Compound no. 4-52)

3-(4-Chloro-6-fluoro-2-isocyanate-3-methylphenyl)-1-methyl-6-trifluoromethyl-2,4(1H, 3H)-pyrimidinedione 3-(2-Amine-4-chloro-6-fluoro-3-methylphenyl)-1-methyl-6-trifluoromethyl-2,4(1H, 3H)-pyrimidinedione (1.0 g, 2.9 mmol) and triethylamine (0.58 g, 5.7 mmol) were dissolved in ethylacetate (15 ml) and the solution was slowly added to a solution of triphosgene (0.85 g, 2.9 mmol) in ethyl acetate (15 ml). Solution was heated under reflux for 2 hr and filtered. Solvent was evaporated to afford the title compound as a residue which was used for the next step.

3-(4-Chloro-6-fluoro-3-methyl-2-phenoxycarbonylaminophenyl)-1-methyl-6-trifluoromethyl-2,4(1H, 3H)-pyrimidinedione 3-(4-Chloro-6-fluoro-2-isocyanato-3-methylphenyl)-1-methyl-6-trifluoromethyl-2,4(1H, 3H)-pyrimidinedione (1.4 mmol) and triethylamine (0.14 g, 1.4 mmol) were dissolved in toluene (15 ml) and the solution was treated with phenol (0.13 g, 1.4 mmol). Solution was stirred for 0.3 hr at ambient temperature and water was added. Product was extracted with ethyl acetate. Removal of the solvent followed by column chromatography on silica gel (eluent, methylene chloride) afforded the title compound (0.3 g).

EXAMPLE 46

Preparation of 3-[4-chloro-6-fluoro-3-hydroxy-2-(2-naphthoylamino)phenyl]-1-methyl-6-trifluoromethyl-2,4(1H, 3H)-pyrimidinedione (Compound no. 2-114)

3-(2-Amino-4-chloro-6-fluoro-3-hydroxyphenyl)-1-methyl-6-trifluoromethyl-2,4(1H, 3H)-pyrimidinedione (0.50 g, 1.4 mmol) and 2-naphthoyl chloride (0.27 g, 1.4 mmol) were dissolved in 1,4-dioxane (10 ml) and the solution heated under reflux for 4 hr. Solvent was evaporated under reduced pressure and the product purified by column chromatography on silica gel (eluent, hexan-ethyl acetate, 8:2) to furnish the title compound (0.60 g).

EXAMPLE 47

Preparation of 3-[4-chloro-3-difluoromethoxy-6-fluoro-2-(2-naphthoylamino)phenyl]-1-methyl-6-trifluoromethyl-2,4(1H, 3H)-pyrimidinedione (Compound no. 2-115)

3-[4-Chloro-6-fluoro-3-hydroxy-2-(2-naphthoylamino)phenyl]-1-methyl-6-trifluoromethyl-2,4(1H, 3H)-pyrimidinedione (0.51 g, 1.0 mmol) dissolved in dimethylformamide (5 ml) was slowly added to a stirred suspension of sodium hydride (0.03 g, 1.3 mmol) in dimethylformamide (5 ml) at −10° C. Chlorodifluoromethane was bubbled through the solution for 0.5 hr with stirring at −10° C. followed by addition of water. Product was extracted with ethyl acetate and solvent evaporated under reduced pressure.

Residue was subjected of column chromatography on silica gel (eluent, hexane-ether, 25:75) to furnish the title compound (0.03 g).

EXAMPLE 48

Preparation of 3-[4-chloro-2-(2-naphthoylamino)phenyl]-1-methyl-6-trifluoromethyl-2,4(1H, 3H)-pyrimidinedione (Compound no. 2-131)

To a solution of triphosgene in anhydrous ethyl acetate (150 ml) was added dropwise a solution of 4-chloro-2-nitroaniline (10 g) and triethylamine (12 g) in anhydrous ethyl acetate (50 ml) at 0° C. under nitrogen atmosphere. After addition, the resulting mixture was heated at reflux temperature for 1 hr, then allowed to cool to ambient temperature. The precipitate was removed by filtration through Celite and the filtrate was concentrated to give title compound as an brown solid.

To a suspension of sodium hydride (60% dispersion in oil, 2.5 g) in anhydrous N,N-dimethylformamide (100 ml) was added dropwise a solution of ethyl-3-amino-4,4,4-trifluorocrotonate in toluene (50 ml) at 0° C. under nitrogen atmosphere. After addition, the mixture was stirred for 20 min at same temperature, then cooled to −30° C. A solution of (4-chloro-2-nitrophenyl)isocyanate in toluene (50 ml) was added dropwise. After stirring for 20 min, the cold bath was removed and the resulting mixture was stirred overnight at ambient temperature. The reaction mixture was partitioned between ethyl acetate and 1N-hydrochloric acid. The organic phase was washed with brine (×2) and dried over anhydrous sodium sulfate. The solvent was removed in vacuo and the residue was purified by column chromatography on silica gel eluted with ethyl acetate and hexane (1:1) to afford 3-(4-chloro-2-nitrophenyl)-6-trifluoromethyl-2,4(1H, 3H)-pyrimidinedione (10.2 g) as a yellow solid.

Preparation of 3-(4-chloro-2-nitrophenyl)-1-methyl-6-trifluoromethyl-2,4(1H, 3H)-pyrimidinedione A mixture of 3-(4-chloro-2-nitrophenyl)-6-trifluoromethyl-2,4(1H, 3H)-pyrimidinedione (3 g), dimethyl sulfate (1.7 g) and potassium carbonate (1.85 g) in N,N-dimethylformamide (100 ml) was stirred at 55° C. overnight. The resulting mixture was allowed to cool to ambient temperature and filtered through Celite to remove unsoluble precipitate. The filtrate was diluted with a mixed solvent of ethyl acetate and hexane (1:1, 200 ml), washed with brine (×2) and dried over anhydrous sodium sulfate. After removal of the solvent, the residue was solidified. The yellow solid was recrystallized from ethyl acetate and hexane to give desired compound (2.3 g).

Preparation of 3-(2-amino-4-chlorophenyl)-1-methyl-6-trifluoromethyl-2,4(1H, 3H)-pyrimidinedione To a stirred suspension of 3-(4-chloro-2-nitrophenyl)-1-methyl-6-trifluoromethyl-2,4(1H, 3H)-pyrimidinedione (1 g) in methanol (20 ml) and conc. hydrochloric acid (10 ml) was added iron (powdered, 0.48 g) unded vigorous stirring. After addition, the mixture was heated at reflux temperature for 1 hr. The oil bath was removed and the solution was allowed to cool to ambient temperature. Ethyl acetate (200 ml) was added, washed with brine (×2) and dried over anhydrous sodium sulfate. After removal of the solvent, the residue was purified by column chromatography on silica gel using ethyl acetate-hexane (1:3) as the eluent to give the title compound.

Preparation of 3-[4-chloro-2-(2-naphthoylamino)phenyl]-1-methyl-6-trifluoromethyl-2,4(1H, 3H)-pyrimidinedione (Compound no. 2-131)

A solution of 3-(2-amino-4-chlorophenyl)-1-methyl-6-trifluoromethyl-2,4(1H, 3H)-pyrimidinedione (0.4 g), 2-naphthoyl chloride (0.29 g) and triethyl amine (0.19 g) in anhydrous tetrahydro furan (30 ml) was heated at reflux temperature overnight under nitrogen atmosphere.

The reaction mixture was diluted with ethyl acetate (200 ml), washed with brine (×2) and dried over anhydrous sodium sulfate. The solvent was removed unded reduced pressure and the residue was purified by column chromatography on silica gel using ethyl acetate and hexane (1:3) as the eluent give a pale yellow solid. The solid was recrystallized from ethyl acetate-hexane to give the title compound as a white crystal (0.42 g).

EXAMPLE 49

Preparation of 3-[4-chloro-6-fluoro-2-(2-naphthoylamino)phenyl]-1-methyl-6-trifluoromethyl-2,4(1H, 3H)-pyrimidinedione (Compound no. 2-145)

A mixture of (2-amino-4-chloro-6-fluorophenyl)-1-methyl-6-trifluoromethyl-2,4(1H, 3H)-pyrimidinedione (0.25 g), triethylamine (0.15 g) and 2-naphthoyl chloride (0.21 g) in anhydrous tetrahydrofuran (30 ml) was heated at refluxtemperature overnight under nitrogen atmosphere. The mixture was poured into water and extracted with ethyl acetate. The organic layer was washed with brine and dried over anhydrous sodium acetate. The solvent was removed in vacuo and the residue was purified by column chromatography on silica gel using ethyl acetate-hexane (1:4) as the eluent to give the title compound as an white solid (0.26 g).

EXAMPLE 50

Preparation of N-[4-chloro-2-(2-naphthoylamino) phenyl]phthalimide (Compound no. 13-5)

A reaction solution of N-(2-amino-4-chlorophenyl) phthalimide (0.5 g), triethylamine (0.28 g) and 2-naphthoyl chloride (0.35 g) in anhydrous tetrahydrofuran (50 ml) was heated at reflux temperature for 6 hr under nitrogen atmosphere. The resulting mixture was poured into water and extracted with ethyl acetate. The organic layer was washed with brine (×2) and dried over anhydrous sodium sulfate. The solvent was removed and the residue was purified by column chromatography on silica gel using ethyl acetate-hexane (1:5) to give the title compound (0.35 g) as a yellow solid.

EXAMPLE 51

Preparation of 3-(2-benzylthioacetylamino-4-chloro-6-fluoro-3-methoxyphenyl)-1-methyl-6-trifluoromethyl-2,4(1H, 3H)-pyrimidinedione (Compound no. 2-165)

A solution of benzylmercaptan (51.0 mg) in tetrahydrofuran (1.0 ml) was slowly added to a suspension of sodium hydride (16.4 mg) in tetrahydrofuran stirred under nitrogen at 0° C. The solution warmed to room temperature over 20 minutes and tetrabutylammonium bromide (11 mg) was added. The suspension was cooled to −78° C. and a solution of 3-(2-chloroacetylamino-4-chloro-6-fluoro-3-methoxyphenyl)-1-methyl-6-trifluoromethyl-2,4(1H, 3H)-pyrimidine (150 mg) added. After stirring for a further 30 minutes the mixture was allowed to warm to room temperature overnight. Water and ethyl acetate were added and the solution separated and the organic phase was washed with water, brine and dried over sodium sulfate. The solution was concentrated and chromatographed on silica gel eluting with methylene chloride: ethyl acetate, 10:1, to give a white solid (137 mg).

EXAMPLE 52

Preparation of 3-(2-aminocarbonylamino-4-chloro-6-fluoro-3-methoxyphenyl)-1-methyl-6-trifluoromethyl-2,4(1H, 3H)-pyrimidinedione (Compound no. 3-26)

A solution of the isocyanate (1 mM) in dioxane (20 ml), stirred at 0° C., was treated with a solution of 0.5 M ammonia in dioxane (3 mM) and 1,8-diazabicyclo[5.4.0] undec-7-ene (DBU) (3 drops). The solution was allowed to warm to room temperature and stirred overnight. Chromatography on silica gel eluting with ethyl acetate gave the product as a yellow solid (271 mg).

EXAMPLE 53

Preparation of 3-(4-chloro-6-fluoro-3-methoxy-2-thiomethylphenyl)1-methyl-6-trifluoromethyl-2,4-(1H, 3H)-pyrimidinedione (Compound no. 17-1)

A solution of t-butylnitrile (73 mg) in methylene chloride (1 ml) was added to a stirred, ice cold solution of 3-(2-amino-4-chloro-6-fluoro-3-methoxyphenyl)-1-methyl-6-trifluoromethyl-2,4(1H, 3H)-pyrimidinedione (200 mg) and methyl disulfide (102 mg) in dry methylene chloride (4 ml). It was stirred at 0° C. for 1.5 h and allowed to warm to room temperature overnight. 1 N Hydrochloric acid was added and the mixture extracted with ethyl acetate, washed with water, brine and dried over sodium sulfate. The solution was concentrated under reduced pressure and the residue chromatographed on silica gel eluting with ethyl acetate: hexane, 5:1 gave the product as a yellow powder (189 mg).

EXAMPLE 54

Preparation of 2-(4-chloro-6-fluoro-3-hydroxy-2-nitrophenyl)-5-trifluoromethylpyridazin-3-one (Compound no. 11-2)

Nitric acid (70%, 12 ml) was added to the ice-cooled 2-(4-chloro-2-fluoro-5-hydroxyphenyl)-5-trifluoromethylpyridazin-3-one (1.25 g) and stirred at room temperature for 30 minutes. Crushed ice was added. The precipitate was collected by filtration and washed with water to give 1.20 g of the desired product, m.p. 146–8° C.

EXAMPLE 55

Preparation of 2-(2-amino-4-chloro-6-fluoro-3-hydroxyphenyl)-5-trifluoromethylpyridazin-3-one (Compound no. 11-3)

To a stirred solution of 2-(4-chloro-6-fluoro-3-hydroxy-2-nitrophenyl)-5-trifluoromethylpyridazin-3-one (0.601 g) in acetic acid (6 ml) was added 0.38 g of iron powder at ambient temperature and stirred for 4 hours. The reaction mixture was partitioned between ethyl acetate and water. The organic phase was dried over anhydrous sodium sulfate. After removing the solvent under reduced pressure, the residue was purified by silica gel column chromatography, eluted with hexane-ethyl acetate (2:1) to give 0.515 g of the title compound.

EXAMPLE 56

Preparation of 2-(2-amino-4-chloro-6-fluoro-3-methoxyphenyl)-5-trifluoromethylpyridazin-3-one (Compound no. 11-4) (BY715) and 2-(4-chloro-6-fluoro-3-methoxy-2-methylaminophenyl)-5-trifluoromethylpyridazin-3-one (Compound no. 11-5)

2-(2-Amino-4-chloro-6-fluoro-3-methoxyphenyl-5-trifluoromethylpyridazin-3-one (0.515 g), methyl iodide (0.248 g), and potassium carbonate (0.219 g) were mixed in acetonitrile (10 ml) and heated at reflux for 2 hours. The reaction mixture was partitioned between ethyl acetate and water. The organic phase was dried over anhydrous sodium sulfate. After removing the solvent under reduced pressure, the residue was purified by silica gel column chromatography, eluted with hexane-ethyl acetate (4:1) to give 0.40 g of 2-(2-amino-4-chloro-6-fluoro-3-methoxyphenyl)-5-trifluoromethylpyridazin-3-one (Compound no. 11-4), m.p. 156–7° C. and 2-(4-chloro-6-fluoro-3-methoxy-2-methylaminophenyl)-5-trifluoromethylphrdazin-3-one (Compound no. 11-5)(7 mg).

EXAMPLE 57

Preparation of 2-(4-chloro-6-fluoro-3-methoxy-2-naphthoylamidophenyl)-5-trifluoromethylpyridazin-3-one (Compound no. 11-6)

2-(2-Amino-4-chloro-6-fluoro-3-methoxyphenyl)-5-trifluoromethylpyridazin-3-one (0.153 g) and 2-naphthoyl chloride (0.097 g) were mixed in dioxane (10 ml) and heated at reflux for 5 hours. The reaction mixture was partitioned between ethyl acetate and water. The organic phase was dried over anhydrous sodium sulfate. After removing the solvent under reduced pressure, the residue was purified by silica gel column chromatography, eluted with hexane-ethyl acetate (4:1) to give 0.198 g of the title compound, m.p. 190–2° c.

EXAMPLE 58

Preparation of 2-(2,4-dichloro-6-fluoro-3-methoxyphenyl)-5-trifluoromethylpyridazin-3-one (Compound no. 11-7) and 2-[4-chloro-2-(2-chloro-2-ethoxycarbonylethyl)-6-fluoro-3-methoxyphenyl]-5-trifluoromethylpyridazin-3-one (Compound no. 11-8)

Copper(II) chloride (0.119 g), t-butyl nitrite (0.115 g), and ethyl acrylate (3 ml) were placed in a flask, and cooled with a dry ice-acetone bath at −65° C. To this mixture 2-(2-amino-4-chloro-6-fluoro-3-methoxyphenyl)-5-trifluoromethylpyridazin-3-one (0.25 g) in acetonitrile (4 ml) was added and stirred. The reaction mixture was gradually warmed up to room temperature over night. The reaction mixture was partitioned between ethyl acetate and water. The organic phase was dried over anhydrous sodium sulfate. After removing the solvent under reduced pressure, the residue was purified by silica gel column chromatography, eluted with hexane-ethyl acetate (9:1) to give 0.077 g of 2-(2,4-dichloro-6-fluoro-3-methoxyphenyl)-5-trifluoromethylpyridazin-3-one and 0.033 g of 2-[4-chloro-2-(2-chloro-2-ethoxycarbonylethyl)-6-fluoro-3-methoxyphenyl]-5-trifluoromethylpyridazin-3-one.

EXAMPLE 59

Preparation of 2-(2,4-chloro-6-fluoro-3-hydroxy-2-naphthoylamidophenyl)-1-methyl-6-trifluoromethyl-2,4(1H, 3H)-pyrimidinedione (Compound no. 2-194)

Boron tribromide-emthyl sulfide complex (5.15 g) was added to a solution of 2-(4-chloro-6-fluoro-3-methoxy-2-naphthoylamidophenyl)-1-methyl-6-trifluoromethyl-2,4(1H, 3H)-pyrimidinedione in 1,2-dichloroethane (150 ml) and heated at reflux for 1 hr. The reaction mixture was partitioned between methylene chloride and water. The organic phase was dried over anhydrous sodium sulfate. After removing the solvent under reduced pressure, the residue was purified by silica gel column chromatography, eluted with hexane-ethyl acetate (4:1 and 2:1) to give the title compound (4.127 g), m.p. 150–2° C.

EXAMPLE 60

Preparation of 2-(4-chloro-3-ethoxy-6-fluoro-2-naphthoylamidophenyl)-1-methyl-6-trifluoromethyl-2,4(1H, 3H)-pyrimidinedione (Compound no. 2-196)

2-(4-Chloro-6-fluoro-3-hydroxy-2-naphthoylamidophenyl)-1-methyl-6-trifluoromethyl-2,4(1H, 3H)-pyrimidinedione (0.203 g), ethyl iodide (75 mg) and potassium carbonate (55 mg) were stirred in methylethyl ketone (9 ml) and dimethyl sulfoxide (1 ml) at room temperature over night. The reaction mixture was filtered and evaporated under reduced pressure. The residue was purified by silica gel column chromatography, eluted with hexane-ethyl acetate (4:1) to give the title compound (0.16 g).

EXAMPLE 61

Preparation of 3-[4-chloro-2-diazanyl-6-fluoro-3-methoxyphenyl]-1-methyl-6-trifluoromethyl-2,4(1H, 3H)-pyrimidinedione (Compound no. 15-1)

3-(2-Amino-4-chloro-6-fluoro-3-methoxyphenyl)-1-methyl-6-trifluoromethyl-2,4(1H, 3H)-pyrimidinedione (0.9 g, 2.4 mmol) was dissolved in conc. hydrochloric acid (5 ml) and the mixture cooled to −15° C., a solution of $NaNO_2$ (0.2 g in 2 ml of $H_2O$) was added slowly. After stirred for 20 min, a solution of $SnCl_2.2H_2O$ (1.5 g in 4 ml of conc. hydrochloric acid) was added and the reaction continued at −15° C. for 30 min, then at room temperature for 30 min. The aqueous mixture was extracted with ethyl acetate (5 ml×3) and the organic phase washed with brine and dried over $Na_2SO_4$. Column chromatography was used to purify the product (silica gel, hexane/ethyl acetate=6/4). Yield: 0.5 g, 1.3 mmol.

EXAMPLE 62

Preparation of 3-[4-chloro-2-(2-cycopropanecarbonyldiazanyl)-6-fluoro-3-methoxyphenyl]-1-methyl-6-trifluoromethyl-2,4(1H, 3H)-pyrimidinedione (Compound no. 15-2)

3-[4-chloro-2-diazanyl-6-fluoro-3-methoxyphenyl]-1-methyl-6-trifluoromethyl-2,4(1H, 3H)-pyrimidinedione (0.15 g, 0.4 mmol) was dissolved in dioxane (10 ml) and added with cyclopropanecarbonyl chloride (0.04 g, 0.4 mmol) and tiethylamine (0.04 g, 0.4 mmol). After stirred for 1 hr, the mixture was poured into water (15 ml) and extracted with ethyl acetate (10 ml×3). Organic phase was washed with brine and dried over Na2SO4. Final purification involved column chromatography (silica gel, ether). Yield: 0.15 g, 0.34 mmol.

EXAMPLE 63

Preparation of 3-{4-chloro-2-[2,2-cyclopropylmethylene)diazanyl]-6-fluoro-3-methoxyphenyl}-1-methyl-6-trifluoromethyl-2,4(1H, 3H)-pyrimidinedione (Compound no. 15-11)

3-[4-chloro-2-diazanyl-6-fluoro-3-methoxyphenyl]-1-methyl-6-trifluoromethyl-2,4(1H, 3H)-pyrimidinedione (0.12 g, 0.31 mmol) was added to a methanol (10 ml) solution of cyclopropanecarboxaldehyde (0.024 g, 0.34 mmol) and the mixture was stirred for 3 hr. After evaporation of solvent, the residue was purified by column chromatography (silica gel, hexane/ether=3/2). Yield: 0.13 g, 0.31 mmol.

EXAMPLE 64

Preparation of 3-(4-chloro-6-fluoro-2-hydroxy-3-methoxyphenyl)-1-methyl-6-trifluoromethyl-2,4(1H, 3H)-pyrimidinedione (Compound no. 16-6)

An acetonitrile (10 ml) solution of copper (II) sulfate (0.52 g, 3.26 mmol), copper (I) oxide (0.47 g, 3.26 mmol) and copper (II) nitrate hemipentahydrate (0.76 g, 3.26 mmol) was stirred at −30° C., and added with tert-butyl nitrite (0.41 g, 3.97 mmol) and then an acetonitrile (3 ml) solution of 3-(2-amino-4-chloro-6-fluoro-3-methoxyphenyl)-1-methyl-6-trifluoromethyl-2,4(1H, 3H)-pyrimidinedione (0.94 g, 2.56 mmol). After stirred for 16 hr (−30° C. to room temperature), the mixture was poured into cold 5% hydrochloric acid (30 ml) and then extracted with ethyl acetate (20 ml×3). The organic phase was washed with brine and dried over $Na_2SO_4$. Preparative TLC was used for purification (silica gel plates, 2000 microns, ether). Yield: 0.16 g, 0.44 mmol.

EXAMPLE 65

Preparation of 3-[4-chloro-6fluoro-3-methoxy-2-(2-naphthoyloxy)phenyl]-1-methyl-6-trifluoromethyl-2,4(1H, 3H)-pyrimidinedione (Compound no. 16-7)

3-(4-chloro-6-fluoro-2-hydroxy-3-methoxyphenyl)-1-methyl-6-trifluoromethyl-2,4(1H, 3H)-pyrimidinedione (0.10 g, 0.27 mmol) was dissolved in dioxane (10 ml) and the solution added with 2-naphthoyl chloride (0.062 g, 0.33 mmol), triethylamine (0.033 g, 0.33 mmol). After stirred for 2 hr, solvent was evaporated and the residue purified by column chromatography (silica gel, hexane/ether=4/1). Yield: 0.12 g, 0.23 mmol.

EXAMPLE 66

Preparation of 3-{4-chloro-2-[2-chloro-2-(ethoxycarbonyl)ethyl]-6-fluoro-3-methoxyphenyl}-1-methyl-6-trifluoromethyl-2,4(1H, 3H)-pyrimidinedione (Compounds no. 14-4 and 14-5)

A solution of 3-(2-amino-4-chloro-6-fluoro-3-methoxyphenyl)-1-methyl-6-trifluoromethyl-2,4(1H, 3H)pyrimidinedione (0.94 g, 2.56 mmol) in acetonitrile (3 ml) was slowly added to an acetonitrile (9 ml) solution of ethyl acrylate (6 ml), tert-butyl nitrite (0.41 g, 3.97 mmol), and copper (II) chloride (0.42 g, 3.12 mmol) at −20° C. After stirred for 16 hr (−20° C. to room temperature), the mixture was poured into cold 5% hydrochloric acid (30 ml) and extracted with ethyl acetate (20 ml ×3), the organic phase was washed with cold 5% $NaHCO_3$ and brine, dried over $Na_2SO_4$. Column chromatography was used for purification (silica gel, hexane/ether=9/1) which also isolated two isomers. Yield: isomer-1 (eluted earlier), 0.23 g, 0.47 mmol; isomer-2 (eluted later), 0.14 g, 0.29 mmol.

Using the procedures as described in Schemes 1-17 and Examples 1–66, the compounds of this invention can be readily prepared. Tables I–XVII list structures for few representative compounds of this invention.

TABLE I

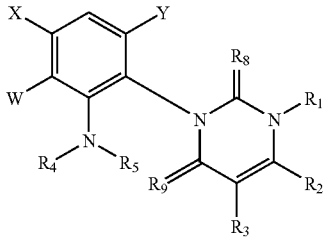

| No. | X | Y | W | $R_1$ | $R_2$ | $R_3$ | $R_4$ | $R_5$ | $R_8$ | $R_9$ |
|---|---|---|---|---|---|---|---|---|---|---|
| 1-1 | Cl | F | $OCH_3$ | H | $CF_3$ | H | O | O | O | O |
| 1-2 | Cl | F | OH | H | $CF_3$ | H | O | O | O | O |
| 1-3 | Cl | F | $OCH_3$ | H | $CF_3$ | H | H | H | O | O |
| 1-4 | Cl | F | $OCH_3$ | $CH_3$ | $CF_3$ | H | H | H | O | O |
| 1-5 | Cl | F | $OCH_3$ | $CH_3$ | $CF_3$ | H | O | O | O | O |
| 1-6 | Br | F | OH | $CH_3$ | $CF_3$ | H | O | O | O | O |
| 1-7 | Br | F | $OCH_3$ | $CH_3$ | $CF_3$ | H | H | H | O | O |
| 1-8 | Br | F | OH | $CH_3$ | $CF_3$ | H | H | H | O | O |
| 1-9 | Cl | F | $OCH_3$ | $CH_3$ | $CF_3$ | $NO_2$ | O | O | O | O |
| 1-10 | Cl | F | $OCH_3$ | $CH_3$ | $CF_3$ | $NH_2$ | H | H | O | O |
| 1-11 | Cl | F | $OCH_3$ | $CH_3$ | $CF_3$ | H | $CH_3$ | $CH_3$ | O | O |
| 1-12 | Cl | F | $OCH_3$ | $NH_2$ | $CF_3$ | H | O | O | O | O |
| 1-13 | Cl | F | $OCH_3$ | $NH_2$ | $CF_3$ | H | H | H | O | O |
| 1-14 | Cl | F | $OCH_3$ | $C_2H_5$ | $CF_3$ | H | O | O | O | O |
| 1-15 | Cl | F | $OCH_3$ | $C_2H_5$ | $CF_3$ | H | H | H | O | O |
| 1-16 | Cl | F | OH | $CH_3$ | $CF_3$ | H | H | H | O | O |
| 1-17 | Cl | F | OH | $CH_3$ | $CF_3$ | H | O | O | O | O |
| 1-18 | Cl | F | $OCH_2CN$ | $CH_3$ | $CF_3$ | H | H | H | O | O |
| 1-19 | Cl | F | propargyloxy | $CH_3$ | $CF_3$ | H | H | H | O | O |
| 1-20 | Cl | F | $OCH_2CH{=}CHCOOCH_3$ | $CH_3$ | $CF_3$ | H | H | H | O | O |
| 1-21 | Cl | F | cyclopentyloxy | $CH_3$ | $CF_3$ | H | H | H | O | O |
| 1-22 | Cl | F | benzyloxy | $CH_3$ | $CF_3$ | H | H | H | O | O |
| 1-23 | Cl | F | 3 nitro-2-pyridyloxy | $CH_3$ | $CF_3$ | H | H | H | O | O |
| 1-24 | Cl | F | $OCH_3$ | $CH_3$ | $CHF_2$ | H | H | H | O | O |
| 1-25 | Cl | F | $OCH_3$ | $CH_3$ | $CF_3$ | Cl | H | H | O | O |
| 1-26 | Cl | F | $OCH_3$ | $CH_3$ | $CF_3$ | H | H | H | S | O |
| 1-27 | Cl | F | $OCH_3$ | $CH_3$ | $CF_3$ | H | H | H | O | S |
| 1-28 | CN | F | $OCH_3$ | $CH_3$ | $CF_3$ | H | H | H | O | O |
| 1-29 | Cl | H | $OCH_3$ | $CH_3$ | $CF_3$ | H | H | H | O | O |
| 1-30 | Cl | F | $OCH_3$ | $CH_3$ | $CF_3$ | H | $=C(CCl_3)Cl$ | | O | O |
| 1-31 | Cl | F | $OCH_3$ | $CH_3$ | $CF_3$ | H | $=C(H)N(CH_3)_2$ | | O | O |
| 1-32 | Cl | F | $OCH_3$ | $CH_3$ | $CF_3$ | H | $—(CH_2)_4—$ | | O | O |
| 1-33 | Cl | F | $NHCOOCH_2CH_3$ | H | $CF_3$ | H | O | O | O | O |
| 1-34 | Cl | F | $NHCOOCH_2CH_3$ | $CH_3$ | $CF_3$ | H | O | O | O | O |
| 1-35 | Cl | F | $CH_3$ | H | $CF_3$ | H | O | O | O | O |
| 1-36 | Cl | F | $CH_3$ | $CH_3$ | $CF_3$ | H | O | O | O | O |
| 1-37 | Cl | F | $CH_3$ | $CH_3$ | $CF_3$ | H | H | H | O | O |
| 1-38 | Cl | F | $OCHF_2$ | $CH_3$ | $CF_3$ | H | H | H | O | O |
| 1-39 | Cl | F | $OCH_2$-2-naphthyl | $CH_3$ | $CF_3$ | H | H | H | O | O |
| 1-40 | Cl | F | $OCH_3$ | $CH_3$ | $CF_3$ | H | —N—N— | | O | O |
| 1-41 | H | H | H | $CH_3$ | $CF_3$ | H | H | H | O | O |
| 1-42 | H | H | H | $CH_3$ | $CF_3$ | H | O | O | O | O |
| 1-43 | CN | H | H | $CH_3$ | $CF_3$ | H | O | O | O | O |
| 1-44 | CN | H | H | $CH_3$ | $CF_3$ | H | H | H | O | O |
| 1-45 | Cl | Cl | OH | $CH_3$ | $CF_3$ | H | O | O | O | O |
| 1-46 | $OCH_3$ | F | H | $CH_3$ | $CF_3$ | H | O | O | O | O |
| 1-47 | Cl | Cl | $OCH_3$ | $CH_3$ | $CF_3$ | H | H | H | O | O |
| 1-48 | $OCH(CH_3)COOCH_2CH_3$ | H | H | $CH_3$ | $CF_3$ | H | H | H | O | O |
| 1-49 | $OCH(CH_3)COOCH_2CH_3$ | H | H | $CH_3$ | $CF_3$ | H | O | O | O | O |
| 1-50 | $OCHF_2$ | F | H | $CH_3$ | $CF_3$ | H | O | O | O | O |
| 1-51 | $OCHF_2$ | F | H | $CH_3$ | $CF_3$ | H | H | H | O | O |
| 1-52 | $CF_3$ | H | H | $CH_3$ | $CF_3$ | H | O | O | O | O |
| 1-53 | $OCHF_2$ | F | H | $CH_3$ | $CF_3$ | H | $CH(Me)CO_2Et$ | H | O | O |
| 1-54 | Cl | F | H | $CH_3$ | $CF_3$ | H | $CH(Me)CO_2Et$ | H | O | O |
| 1-55 | Cl | F | $OCH_3$ | $CH_3$ | $CF_3$ | H | $CH(Me)CO_2Et$ | H | O | O |
| 1-56 | Cl | F | OH | $NH_2$ | $CF_3$ | H | H | H | O | O |
| 1-57 | Cl | F | $OCH_2CN$ | $NH_2$ | $CF_3$ | H | H | H | O | O |
| 1-58 | Cl | F | $OCH_2COOCH_3$ | $NH_2$ | $CF_3$ | H | H | H | O | O |
| 1-59 | Cl | F | $OCH_2COOCH_2CH_3$ | $CH_3$ | $CF_3$ | H | H | H | O | O |
| 1-60 | Cl | F | $OCH(CH_3)COOCH_2CH_3$ | $CH_3$ | $CF_3$ | H | H | H | O | O |
| 1-61 | Cl | F | $OCH_2CH_3$ | $CH_3$ | $CF_3$ | H | H | H | O | O |
| 1-62 | Cl | F | $OCH_2CH_3$ | $CH_3$ | $CF_3$ | H | $CH_2CH_3$ | H | O | O |
| 1-63 | Cl | F | $OCH(CH_3)_2$ | $CH_3$ | $CF_3$ | H | H | H | O | O |
| 1-64 | Cl | F | $OCH(CH_3)_2$ | $CH_3$ | $CF_3$ | H | $CH(CH_3)_2$ | H | O | O |

TABLE I-continued

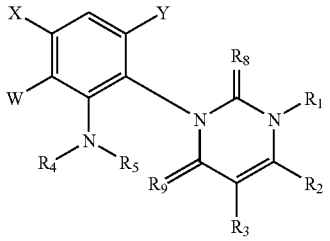

| No. | X | Y | W | $R_1$ | $R_2$ | $R_3$ | $R_4$ | $R_5$ | $R_8$ | $R_9$ |
|---|---|---|---|---|---|---|---|---|---|---|
| 1-65 | Cl | H | H | H | $CF_3$ | $NO_2$ | O | O | O | O |
| 1-66 | Cl | H | OH | $CH_3$ | $CF_3$ | H | O | O | O | O |
| 1-67 | Cl | $NO_2$ | OH | $CH_3$ | $CF_3$ | H | O | O | O | O |
| 1-68 | $OCF_3$ | H | H | $CH_3$ | $CF_3$ | H | O | O | O | O |
| 1-69 | Cl | $NO_2$ | $OCH_3$ | H | $CF_3$ | H | O | O | O | O |
| 1-70 | Cl | F | F | H | $CF_3$ | H | O | O | O | O |
| 1-71 | Cl | H | OH | $CH_3$ | $CF_3$ | H | H | H | O | O |
| 1-72 | Cl | H | $OCH_3$ | $CH_3$ | $CF_3$ | H | H | H | O | O |
| 1-73 | $OCF_3$ | H | H | $CH_3$ | $CF_3$ | H | H | H | O | O |

TABLE II

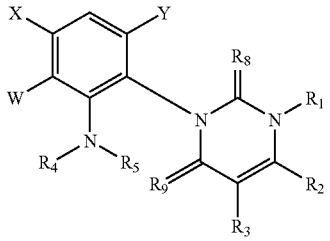

| No. | X | Y | W | $R_1$ | $R_2$ | $R_3$ | $R_4$ | $R_5$ | $R_8$ | $R_9$ |
|---|---|---|---|---|---|---|---|---|---|---|
| 2-1 | Cl | F | $OCH_3$ | $CH_3$ | $CF_3$ | H | $COCH_3$ | H | O | O |
| 2-2 | Cl | F | $OCH_3$ | $CH_3$ | $CF_3$ | H | $COCH_3$ | $COCH_3$ | O | O |
| 2-3 | Cl | F | $OCH_3$ | $CH_3$ | $CF_3$ | H | CO-t-$C_4H_9$ | H | O | O |
| 2-4 | Cl | F | $OCH_3$ | $CH_3$ | $CF_3$ | H | acryloyl | acryloyl | O | O |
| 2-5 | Cl | F | $OCH_3$ | $CH_3$ | $CF_3$ | H | methacryloyl | H | O | O |
| 2-6 | Cl | F | $OCH_3$ | $CH_3$ | $CF_3$ | H | methacryloyl | methacryloyl | O | O |
| 2-7 | Cl | F | $OCH_3$ | $CH_3$ | $CF_3$ | H | 3,3-dimethylacryloyl | H | O | O |
| 2-8 | Cl | F | $OCH_3$ | $CH_3$ | $CF_3$ | H | 3,3-dimethylacryloyl | 3,3-dimethylacryloyl | O | O |
| 2-9 | Cl | F | $OCH_3$ | H | $CF_3$ | H | $COCF_3$ | H | O | O |
| 2-10 | Cl | F | $OCH_3$ | $CH_3$ | $CF_3$ | H | $COCF_3$ | H | O | O |
| 2-11 | Cl | F | $OCH_2CN$ | $CH_3$ | $CF_3$ | H | $COCF_3$ | H | O | O |
| 2-12 | Cl | F | $OCH_3$ | $CH_3$ | $CF_3$ | $NHCOCF_3$ | $COCF_3$ | H | O | O |
| 2-13 | Cl | F | $OCH_3$ | $CH_3$ | $CF_3$ | H | $COCH_2Cl$ | H | O | O |
| 2-14 | Cl | F | $OCH_3$ | $CH_3$ | $CF_3$ | H | $COCH_2CN$ | H | O | O |
| 2-15 | Cl | F | $OCH_3$ | $CH_3$ | $CF_3$ | H | $COCOOCH_3$ | H | O | O |
| 2-16 | Cl | F | $OCOCH_2$-$COOCH_2CH_3$ | $CH_3$ | $CF_3$ | H | $COCH_2COOCH_2CH_3$ | H | O | O |
| 2-17 | Cl | F | $OCH_3$ | $CH_3$ | $CF_3$ | H | c-$C_3H_5$-carbonyl | H | O | O |
| 2-18 | Cl | F | $OCH_3$ | $CH_3$ | $CF_3$ | H | c-$C_3H_5$-carbonyl | c-$C_3H_5$-carbonyl | O | O |
| 2-19 | Cl | F | $OCH_3$ | $CH_3$ | $CF_3$ | H | cyclohexanoyl | H | O | O |
| 2-20 | Cl | F | $OCH_3$ | $CH_3$ | $CF_3$ | H | cyclohexanoyl | cyclohexanoyl | O | O |
| 2-21 | Cl | F | $OCH_3$ | $CH_3$ | $CF_3$ | H | $SO_2CH_3$ | $SO_2CH_3$ | O | O |
| | Cl | F | $OCH_3$ | $CH_3$ | $CF_3$ | H | $SO_2CH_3$ | H | O | O |
| 2-22 | Cl | F | $OCH_3$ | $CH_3$ | $CF_3$ | H | benzoyl | H | O | O |
| 2-23 | Cl | F | $OCH_3$ | $CH_3$ | $CF_3$ | H | 3-$CH_3$-benzoyl | H | O | O |
| 2-24 | Cl | F | $OCH_3$ | $CH_3$ | $CF_3$ | H | 4-$CH_3$-benzoyl | H | O | O |
| 2-25 | Cl | F | $OCH_3$ | $CH_3$ | $CF_3$ | H | 4-$CH_3$-benzoyl | 4-$CH_3$-benzoyl | O | O |
| 2-26 | Cl | F | $OCH_3$ | $CH_3$ | $CF_3$ | H | 4-$CH_3$-benzenesulfonyl | H | O | O |
| 2-27 | Cl | F | $OCH_3$ | $CH_3$ | $CF_3$ | H | 4-$C_2H_5$-benzoyl | H | O | O |
| 2-28 | Cl | F | $OCH_2CN$ | $CH_3$ | $CF_3$ | H | 4-$C_2H_5$-benzoyl | H | O | O |
| 2-29 | Cl | F | $OCH_3$ | $CH_3$ | $CF_3$ | H | 4-n-$C_3H_7$-benzoyl | 4-n-$C_3H_7$-benzoyl | O | O |
| 2-30 | Cl | F | $OCH_3$ | $CH_3$ | $CF_3$ | H | 4-t-$C_4H_9$-benzoyl | H | O | O |
| 2-31 | Cl | F | $OCH_3$ | $CH_3$ | $CF_3$ | H | 4-vinylbenzoyl | H | O | O |
| 2-32 | Cl | F | $OCH_3$ | $CH_3$ | $CF_3$ | H | 3,4-$(CH_3)_2$-benzoyl | H | O | O |
| 2-33 | Cl | F | $OCH_3$ | $CH_3$ | $CF_3$ | H | 4-$CF_3$-benzoyl | H | O | O |
| 2-34 | Cl | F | $OCH_3$ | $CH_3$ | $CF_3$ | H | 4-$CF_3$-benzoyl | 4-$CF_3$-benzoyl | O | O |

TABLE II-continued

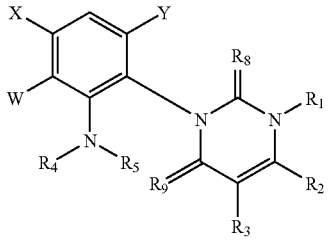

| No. | X | Y | W | $R_1$ | $R_2$ | $R_3$ | $R_4$ | $R_5$ | $R_8$ | $R_9$ |
|---|---|---|---|---|---|---|---|---|---|---|
| 2-35 | Cl | F | $OCH_3$ | $CH_3$ | $CF_3$ | H | 3,5-$(CF_3)_2$-benzoyl | 3,5-$(CF_3)_2$-benzoyl | O | O |
| 2-36 | Cl | F | $OCH_3$ | $CH_3$ | $CF_3$ | H | 4-$CH_2Cl$-benzoyl | H | O | O |
| 2-37 | Cl | F | $OCH_3$ | $CH_3$ | $CF_3$ | H | 4-$C_6H_5$-benzoyl | H | O | O |
| 2-38 | Cl | F | $OCH_3$ | $CH_3$ | $CF_3$ | H | 4-$C_6H_5$-benzoyl | 4-$C_6H_5$-benzoyl | O | O |
| 2-39 | Cl | F | $OCH_3$ | $CH_3$ | $CF_3$ | H | 2-F-benzoyl | H | O | O |
| 2-40 | Cl | F | $OCH_3$ | $CH_3$ | $CF_3$ | H | 4-F-benzoyl | H | O | O |
| 2-41 | Cl | F | $OCH_3$ | $CH_3$ | $CF_3$ | H | 2,3-$F_2$-benzoyl | H | O | O |
| 2-42 | Cl | F | $OCH_3$ | $CH_3$ | $CF_3$ | H | 2,4-$F_2$-benzoyl | H | O | O |
| 2-43 | Cl | F | $OCH_3$ | $CH_3$ | $CF_3$ | H | 2,4-$F_2$-benzoyl | 2,4-$F_2$-benzoyl | O | O |
| 2-44 | Cl | F | $OCH_3$ | $NH_2$ | $CF_3$ | H | 2,4-$F_2$-benzoyl | H | O | O |
| 2-45 | Cl | F | $OCH_2CN$ | $CH_3$ | $CF_3$ | H | 2,4-$F_2$-benzoyl | 2,4-$F_2$-benzoyl | O | O |
| 2-46 | Cl | F | $OCH_3$ | $CH_3$ | $CF_3$ | H | 2,4-$F_2$-thiobenzoyl | H | O | S |
| 2-47 | Cl | F | $OCH_3$ | $CH_3$ | $CF_3$ | H | 2,6-$F_2$-benzoyl | H | O | O |
| 2-48 | Cl | F | $OCH_3$ | $CH_3$ | $CF_3$ | H | 3,4-$F_2$-benzoyl | H | O | O |
| 2-49 | Cl | F | $OCH_3$ | $CH_3$ | $CF_3$ | H | 3,4-$F_2$-benzoyl | 3,4-$F_2$-benzoyl | O | O |
| 2-50 | Cl | F | $OCH_3$ | $CH_3$ | $CF_3$ | H | 3,5-$F_2$-benzoyl | H | O | O |
| 2-51 | Cl | F | $OCH_3$ | $CH_3$ | $CF_3$ | H | 3,5-$F_2$-benzoyl | 3,5-$F_2$-benzoyl | O | O |
| 2-52 | Cl | F | $OCH_3$ | $CH_3$ | $CF_3$ | H | 2,3,4,5,6-$F_5$-benzoyl | H | O | O |
| 2-53 | Cl | F | $OCH_3$ | $CH_3$ | $CF_3$ | H | 2-Cl-benzoyl | H | O | O |
| 2-54 | Cl | F | $OCH_3$ | $CH_3$ | $CF_3$ | H | 3-Cl-benzoyl | H | O | O |
| 2-55 | Cl | F | $OCH_3$ | $CH_3$ | $CF_3$ | H | 3-Cl-benzoyl | 3-Cl-benzoyl | O | O |
| 2-56 | Cl | F | $OCH_3$ | $CH_3$ | $CF_3$ | H | 4-Cl-benzoyl | H | O | O |
| 2-57 | Cl | F | $OCH_3$ | $CH_3$ | $CF_3$ | H | 4-Cl-benzoyl | 4-Cl-benzoyl | O | O |
| 2-58 | Cl | F | $OCH_3$ | $CH_3$ | $CF_3$ | H | 2,4-$Cl_2$-benzoyl | H | O | O |
| 2-59 | Cl | F | $OCH_3$ | $CH_3$ | $CF_3$ | H | 3,4-$Cl_2$-benzoyl | H | O | O |
| 2-60 | Cl | F | $OCH_3$ | $CH_3$ | $CF_3$ | H | 3-Br-benzoyl | 3-Br-benzoyl | O | O |
| 2-61 | Cl | F | $OCH_3$ | $CH_3$ | $CF_3$ | H | 4-Br-benzoyl | H | O | O |
| 2-62 | Cl | F | $OCH_3$ | $CH_3$ | $CF_3$ | H | 4-Br-benzoyl | 4-Br-benzoyl | O | O |
| 2-63 | Cl | F | $OCH_3$ | $CH_3$ | $CF_3$ | H | 4-$OCH_3$-benzoyl | H | O | O |
| 2-64 | Cl | F | $OCH_3$ | $CH_3$ | $CF_3$ | H | 4-$(OC_2H_5)$-benzoyl | H | O | O |
| 2-65 | Cl | F | $OCH_3$ | $CH_3$ | $CF_3$ | H | 4-$(OC_2H_5)$-benzoyl | 4-$(OC_2H_5)$-benzoyl | O | O |
| 2-66 | Cl | F | $OCH_3$ | $CH_3$ | $CF_3$ | H | 4-I-benzoyl | H | O | O |
| 2-67 | Cl | F | $OCH_3$ | $CH_3$ | $CF_3$ | H | 4-CN-benzoyl | H | O | O |
| 2-68 | Cl | F | $OCH_3$ | $CH_3$ | $CF_3$ | H | 4-$N(CH_3)_2$-benzoyl | H | O | O |
| 2-69 | Cl | F | $OCH_3$ | $CH_3$ | $CF_3$ | H | 4-$NO_2$-benzoyl | 4-$NO_2$-benzoyl | O | O |
| 2-70 | Cl | F | $OCH_3$ | $CH_3$ | $CF_3$ | H | 3,5-$(NO_2)_2$-benzoyl | H | O | O |
| 2-71 | Cl | F | $OCH_3$ | $CH_3$ | $CF_3$ | H | 4-$OCF_3$-benzoyl | 4-$OCF_3$-benzoyl | O | O |
| 2-72 | Cl | F | $OCH_3$ | $CH_3$ | $CF_3$ | H | 4-$OCF_3$-benzoyl | H | O | O |
| 2-73 | Cl | F | $OCH_3$ | $CH_3$ | $CF_3$ | H | piperonyloyl | H | O | O |
| 2-74 | Cl | F | $OCH_3$ | $CH_3$ | $CF_3$ | H | 1-naphthoyl | H | O | O |
| 2-75 | Cl | F | $OCH_3$ | $CH_3$ | $CF_3$ | H | 2-naphthoyl | H | O | O |
| 2-76 | Cl | F | $OCH_3$ | H | $CF_3$ | H | 2-naphthoyl | H | O | O |
| 2-77 | Cl | F | $OCH_3$ | $NH_2$ | $CF_3$ | H | 2-naphthoyl | H | O | O |
| 2-78 | Cl | F | $OCH_3$ | $CH_3$ | $CF_3$ | H | cinnamoyl | H | O | O |
| 2-79 | Cl | F | $OCH_3$ | $CH_3$ | $CF_3$ | H | 2,4-$F_2$-cinnamoyl | H | O | O |
| 2-80 | Cl | F | $OCH_3$ | $CH_3$ | $CF_3$ | H | 2-methylcinnamoyl | H | O | O |
| 2-81 | Cl | F | $OCH_3$ | $CH_3$ | $CF_3$ | H | α-methylcinnamoyl | H | O | O |
| 2-82 | Cl | F | $OCH_3$ | $CH_3$ | $CF_3$ | H | 2-chlorocinnamoyl | H | O | O |
| 2-83 | Cl | F | $OCH_3$ | $CH_3$ | $CF_3$ | H | 2-chlorocinnamoyl | 2-chlorocinnamoyl | O | O |
| 2-84 | Cl | F | $OCH_3$ | $CH_3$ | $CF_3$ | H | 4-chlorocinnamoyl | H | O | O |
| 2-85 | Cl | F | $OCH_3$ | $CH_3$ | $CF_3$ | H | 4-methoxycinnamoyl | H | O | O |
| 2-86 | Cl | F | $OCH_3$ | $CH_3$ | $CF_3$ | H | 3-phenylpropionyl | H | O | O |
| 2-87 | Cl | F | $OCH_2CN$ | $CH_3$ | $CF_3$ | H | 3-phenylpropionyl | H | O | O |
| 2-88 | Cl | F | $OCH_3$ | $CH_3$ | $CF_3$ | H | 4-phenylbutyryl | H | O | O |
| 2-89 | Cl | F | $OCH_3$ | $CH_3$ | $CF_3$ | H | $COCH_2OCH_2C_6H_5$ | H | O | O |
| 2-90 | Cl | F | $OCH_3$ | $CH_3$ | $CF_3$ | H | 2-furoyl | H | O | O |
| 2-91 | Cl | F | $OCH_3$ | $CH_3$ | $CF_3$ | H | 3-$CH_3$-2-furoyl | H | O | O |
| 2-92 | Cl | F | $OCH_3$ | $CH_3$ | $CF_3$ | H | furylacryloyl | H | O | O |
| 2-93 | Cl | F | $OCH_3$ | $CH_3$ | $CF_3$ | H | $COCH_2$-(2-thiophene) | H | O | O |
| 2-94 | Cl | F | OH | $CH_3$ | $CF_3$ | H | 3-$CH_3$-2-thiophenoyl | H | O | O |
| 2-95 | Cl | F | $OCH_3$ | $CH_3$ | $CF_3$ | H | 5-$CH_3$-2-thiophenoyl | H | O | O |
| 2-96 | Cl | F | $OCH_3$ | $CH_3$ | $CF_3$ | H | 5-$CH_3$-2-thiophenoyl | 5-$CH_3$-2-thiophenoyl | O | O |
| 2-97 | Cl | F | $OCH_3$ | $CH_3$ | $CF_3$ | H | thiophene-2-carbonyl | thiophene-2-carbonyl | O | O |
| 2-98 | Cl | F | $OCH_3$ | $CH_3$ | $CF_3$ | H | 3-pyridoyl | H | O | O |

TABLE II-continued

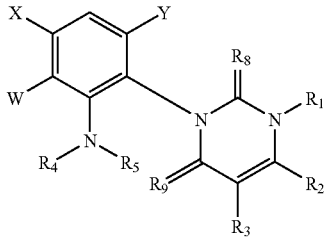

| No. | X | Y | W | $R_1$ | $R_2$ | $R_3$ | $R_4$ | $R_5$ | $R_8$ | $R_9$ |
|---|---|---|---|---|---|---|---|---|---|---|
| 2-99 | Cl | F | $OCH_3$ | $CH_3$ | $CF_3$ | H | 4-pyridoyl | H | O | O |
| 2-100 | Cl | F | $OCH_3$ | $CH_3$ | $CF_3$ | H | 2-Cl-5-pyridoyl | 2-Cl-5-pyridoyl | O | O |
| 2-101 | Cl | F | OH | $CH_3$ | $CF_3$ | H | 3-$NO_2$-2-pyridoyl | H | O | O |
| 2-102 | Cl | F | OH | $CH_3$ | $CF_3$ | H | 2-pyrimidoyl | H | O | O |
| 2-103 | Cl | F | $OCH_3$ | $CH_3$ | $CF_3$ | H | benzothiophene-2-carbonyl | H | O | O |
| 2-104 | Cl | F | $OCH_3$ | $CH_3$ | $CF_3$ | H | 2-quinoyl | H | O | O |
| 2-105 | Cl | F | $OCH_3$ | $CH_3$ | $CF_3$ | H | 2-quinoxaloyl | H | O | O |
| 2-106 | Br | F | $OCH_3$ | $CH_3$ | $CF_3$ | H | 2,4-$F_2$-benzoyl | H | O | O |
| 2-107 | Cl | F | $OCH_3$ | $CH_3$ | $CHF_2$ | H | 2,4-$F_2$-benzoyl | H | O | O |
| 2-108 | Cl | F | $OCH_3$ | $CH_3$ | $CF_3$ | Cl | 2,4-$F_2$-benzoyl | H | O | O |
| 2-109 | Cl | F | $OCH_3$ | $CH_3$ | $CF_3$ | H | 2,4-$F_2$-benzoyl | H | S | O |
| 2-110 | Cl | F | $OCH_3$ | $CH_3$ | $CF_3$ | H | 2,4-$F_2$-benzoyl | H | O | S |
| 2-111 | CN | F | $OCH_3$ | $CH_3$ | $CF_3$ | H | 2,4-$F_2$-benzoyl | H | O | O |
| 2-112 | Cl | H | $OCH_3$ | $CH_3$ | $CF_3$ | H | 2,4-$F_2$-benzoyl | H | O | O |
| 2-113 | Cl | F | $OCH_3$ | $CH_3$ | $CF_3$ | H | 3-(2-thienyl)acryloyl | H | O | O |
| 2-114 | Cl | F | OH | $CH_3$ | $CF_3$ | H | 2-naphthoyl | H | O | O |
| 2-115 | Cl | F | $OCHF_2$ | $CH_3$ | $CF_3$ | H | 2-naphthoyl | H | O | O |
| 2-116 | Cl | F | $OCH_3$ | $CH_3$ | $CF_3$ | H | $COCH_2OCOCH_3$ | $COCH_2OCOCH_3$ | O | O |
| 2-117 | Cl | F | $OCH_3$ | $CH_3$ | $CF_3$ | H | $COCH_2OCOCH_3$ | H | O | O |
| 2-118 | Cl | F | $OCH_3$ | $CH_3$ | $CF_3$ | H | $COCOOCH_2CH_3$ | H | O | O |
| 2-119 | Cl | F | $OCH_3$ | $CH_3$ | $CF_3$ | H | $COCH_2OC_6H_5$ | H | O | O |
| 2-120 | Cl | F | $OCH_3$ | $CH_3$ | $CF_3$ | H | $COCH_2OC_6H_5$ | $COCH_2OC_6H_5$ | O | O |
| 2-121 | Cl | F | $OCH_3$ | $CH_3$ | $CF_3$ | H | $COCOC_6H_5$ | H | O | O |
| 2-122 | Cl | F | $CH_3$ | $CH_3$ | $CF_3$ | H | 2-naphthoyl | H | O | O |
| 2-123 | Cl | F | $CH_3$ | $CH_3$ | $CF_3$ | H | cinnamoyl | H | O | O |
| 2-124 | Cl | F | $OCH_3$ | $CH_3$ | $CF_3$ | H | CO-2,6-dimethylphenyl | H | O | O |
| 2-125 | Cl | F | $OCH_3$ | $CH_3$ | $CF_3$ | H | 2-F-cinnamoyl | H | O | O |
| 2-126 | Cl | F | $OCH_3$ | $CH_3$ | $CF_3$ | H | 2-nitro-cinnamoyl | H | O | O |
| 2-127 | Cl | F | $OCH_3$ | $CH_3$ | $CF_3$ | H | 2-methoxy-cinnamoyl | H | O | O |
| 2-128 | Cl | F | $OCH_3$ | $CH_3$ | $CF_3$ | H | 2,6-dichloro-cinnamoyl | H | O | O |
| 2-129 | Cl | F | $OCH_3$ | $CH_3$ | $CF_3$ | H | $COCH_2CH_2$-2-methylphenyl | H | O | O |
| 2-130 | Cl | F | $OCH_3$ | $CH_3$ | $CF_3$ | H | $COCH_2CH_2$-2,5-dimethylphenyl | H | O | O |
| 2-131 | Cl | H | H | $CH_3$ | $CF_3$ | H | 2-naphthoyl | H | O | O |
| 2-132 | Cl | F | $OCH_3$ | $CH_3$ | $CF_3$ | H | $COCH_2CH_2$-2,5-dimethylphenyl | H | O | O |
| 2-133 | Cl | F | $OCH_3$ | $CH_3$ | $CF_3$ | H | $COCH_2O$-4-F-phenyl | H | O | O |
| 2-134 | Cl | F | $OCH_3$ | $CH_3$ | $CF_3$ | H | 3-chlorocinnamoyl | H | O | O |
| 2-135 | Cl | F | $OCH_3$ | $CH_3$ | $CF_3$ | H | $COCH_2O$-4-Cl-phenyl | H | O | O |
| 2-136 | Cl | F | $OCH_3$ | $CH_3$ | $CF_3$ | H | α-cyano-cinnamoyl | H | O | O |
| 2-137 | Cl | H | H | $CH_3$ | $CF_3$ | H | cinnamoyl | H | O | O |
| 2-138 | CN | H | H | $CH_3$ | $CF_3$ | H | O | O | O | O |
| 2-139 | H | H | H | $CH_3$ | $CF_3$ | H | 2-naphthoyl | 2-naphthoyl | O | O |
| 2-140 | CN | H | H | $CH_3$ | $CF_3$ | H | 2-naphthoyl | H | O | O |
| 2-141 | CN | H | H | $CH_3$ | $CF_3$ | H | cinnamoyl | H | O | O |
| 2-142 | H | H | H | $CH_3$ | $CF_3$ | H | 2-naphthoyl | H | O | O |
| 2-143 | $OCH_3$ | H | H | $CH_3$ | $CF_3$ | H | 2-naphthoyl | H | O | O |
| 2-144 | Cl | Cl | $OCH_3$ | $CH_3$ | $CF_3$ | H | 2-naphthoyl | H | O | O |
| 2-145 | Cl | F | H | $CH_3$ | $CF_3$ | H | 2-naphthoyl | H | O | O |
| 2-146 | $OCH(CH_3)COOCH_2CH_3$ | H | H | $CH_3$ | $CF_3$ | H | 2-naphthoyl | H | O | O |
| 2-147 | Cl | F | H | $CH_3$ | $CF_3$ | H | cyclopropyl | H | O | O |
| 2-148 | $OCHF_2$ | F | H | $CH_3$ | $CF_3$ | H | 2-naphthoyl | H | O | O |
| 2-149 | $CF_3$ | H | H | $CH_3$ | $CF_3$ | H | 2-naphthoyl | H | O | O |
| 2-150 | Cl | F | OH | $CH_3$ | $CF_3$ | H | phenylacetyl | H | O | O |
| 2-151 | Cl | F | $OCH_3$ | $CH_3$ | $CF_3$ | H | phenylacetyl | H | O | O |
| 2-152 | Cl | F | $OCH_3$ | $CH_3$ | $CF_3$ | H | 3-methoxy-2-naphthoyl | H | O | O |
| 2-153 | Cl | F | $OCH_3$ | $CH_3$ | $CF_3$ | H | 1-methoxy-2-naphthoyl | H | O | O |
| 2-154 | Cl | F | $OCH_3$ | $CH_3$ | $CF_3$ | H | 2,4-dichlorophenoxyacetyl | H | O | O |
| 2-155 | Cl | F | $OCH_3$ | $CH_3$ | $CF_3$ | H | 3-methyl-2-naphthoyl | H | O | O |
| 2-156 | Cl | F | $OCH_3$ | $CH_3$ | $CF_3$ | H | 6-methyl-2-naphthoyl | H | O | O |
| 2-157 | Cl | F | $OCH_3$ | $CH_3$ | $CF_3$ | H | 3-chloro-2-naphthoyl | H | O | O |
| 2-158 | Cl | F | $OCH_3$ | $CH_3$ | $CF_3$ | H | 5-bromo-2-naphthoyl | H | O | O |

TABLE II-continued

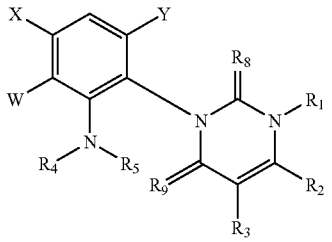

| No. | X | Y | W | $R_1$ | $R_2$ | $R_3$ | $R_4$ | $R_5$ | $R_8$ | $R_9$ |
|---|---|---|---|---|---|---|---|---|---|---|
| 2-159 | Cl | F | $OCH_3$ | $CH_3$ | $CF_3$ | H | 4-bromo-2-naphthoyl | H | O | O |
| 2-160 | Cl | F | $OCH_3$ | $CH_3$ | $CF_3$ | H | 4-bromo-2-naphthoyl | 4-bromo-2-naphthoyl | O | O |
| 2-161 | Cl | F | $OCH_3$ | $CH_3$ | $CF_3$ | H | 8-fluoro-2-naphthoyl | H | O | O |
| 2-162 | Cl | F | $OCH_3$ | $CH_3$ | $CF_3$ | H | 5-chloro-2-naphthoyl | H | O | O |
| 2-163 | Cl | F | $OCH_3$ | $CH_3$ | $CF_3$ | H | 5-cyano-2-naphthoyl | H | O | O |
| 2-164 | Cl | F | $OCH_3$ | $CH_3$ | $CF_3$ | H | chloroacetyl | H | O | O |
| 2-165 | Cl | F | $OCH_3$ | $CH_3$ | $CF_3$ | H | benzylthioacetyl | H | O | O |
| 2-166 | Cl | F | $OCH_3$ | $CH_3$ | $CF_3$ | H | bromoacetyl | H | O | O |
| 2-167 | Cl | F | $OCH_3$ | $CH_3$ | $CF_3$ | H | phenylthioacetyl | H | O | O |
| 2-168 | Cl | F | $OCH_3$ | $CH_3$ | $CF_3$ | H | methylthioacetyl | H | O | O |
| 2-169 | Cl | F | $OCH_3$ | $CH_3$ | $CF_3$ | H | 2-naphthylthio-acetyl | H | O | O |
| 2-170 | Cl | F | $OCH_3$ | $CH_3$ | $CF_3$ | H | ethoxycarbonyl-methylthioacetyl | H | O | O |
| 2-171 | Cl | F | $OCH_3$ | $CH_3$ | $CF_3$ | H | ethoxycarbonyl-ethyl-2-thioacetyl | H | O | O |
| 2-172 | Cl | F | $OCH_3$ | $CH_3$ | $CF_3$ | H | ethylthioacetyl | H | O | O |
| 2-173 | Cl | F | $OCH_3$ | $CH_3$ | $CF_3$ | H | i-propylthioacetyl | H | O | O |
| 2-174 | Cl | F | $OCH_3$ | $CH_3$ | $CF_3$ | H | propylthioacetyl | H | O | O |
| 2-175 | Br | F | $OCH_3$ | $CH_3$ | $CF_3$ | H | 2-cinnamoyl | H | O | O |
| 2-176 | Br | F | $OCH_3$ | $CH_3$ | $CF_3$ | H | 2-cinnamoyl | 2-cinnamoyl | O | O |
| 2-177 | Br | F | $OCH_3$ | $CH_3$ | $CF_3$ | H | 2-cinnamoyl | H | O | O |
| 2-178 | Br | F | $OCH_3$ | $CH_3$ | $CF_3$ | H | 2-cinnamoyl | 2-cinnamoyl | O | O |
| 2-179 | CN | F | $OCH_3$ | $CH_3$ | $CF_3$ | H | 2-cinnamoyl | H | O | O |
| 2-180 | CN | F | $OCH_3$ | $CH_3$ | $CF_3$ | H | 2-naphthoyl | H | O | O |
| 2-181 | CN | F | $OCH_3$ | $CH_3$ | $CF_3$ | H | 2-naphthoyl | H | O | O |
| 2-182 | Br | F | $OCH_3$ | $CH_3$ | $CF_3$ | H | 4-vinylbenzoyl | H | O | O |
| 2-183 | Br | F | $OCH_3$ | $CH_3$ | $CF_3$ | H | 4-vinylbenzoyl | 4-vinylbenzoyl | O | O |
| 2-184 | Cl | F | $OCH_3$ | $NH_2$ | $CF_3$ | H | 2-naphthoyl | H | O | O |
| 2-185 | Cl | F | $OCH_3$ | $NH_2$ | $CF_3$ | H | 2-cinnamoyl | H | O | O |
| 2-186 | Cl | F | $OCH_3$ | $NH_2$ | $CF_3$ | H | 2-cinnamoyl | 2-cinnamoyl | O | O |
| 2-187 | Cl | F | $OCH_3$ | $NH_2$ | $CF_3$ | H | benzyloxyacetyl | H | O | O |
| 2-188 | Cl | F | $OCH_2CN$ | $NH_2$ | $CF_3$ | H | 2-naphthoyl | H | O | O |
| 2-189 | Cl | F | $OCH_2$-$COOCH_2CH_3$ | $CH_3$ | $CF_3$ | H | 2-naphthoyl | H | O | O |
| 2-190 | Cl | F | $OCH_2$-$COOCH_2CH_3$ | $CH_3$ | $CF_3$ | H | 2-cinnamoyl | H | O | O |
| 2-191 | Cl | F | $OCH(CH_3)$-$COOCH_2CH_3$ | $CH_3$ | $CF_3$ | H | 2-naphthoyl | H | O | O |
| 2-192 | Cl | F | OH | $NH_2$ | $CF_3$ | H | 2-naphthoyl | H | O | O |
| 2-193 | 4-$CF_3$-pyridyloxy | H | H | $CH_3$ | $CF_3$ | H | 2-naphthoyl | H | O | O |
| 2-194 | Cl | F | OH | $CH_3$ | $CF_3$ | H | 2-naphthoyl | H | O | O |
| 2-195 | Cl | F | $OCH_2C{\equiv}CH$ | $CH_3$ | $CF_3$ | H | 2-naphthoyl | H | O | O |
| 2-196 | Cl | F | $OCH_2CH_3$ | $CH_3$ | $CF_3$ | H | 2-naphthoyl | H | O | O |
| 2-197 | Cl | F | $OCH(CH_3)_2$ | $CH_3$ | $CF_3$ | H | 2-naphthoyl | H | O | O |
| 2-198 | Cl | F | $OCH_3$ | $CH_3$ | $CF_3$ | H | Hexanoyl | H | O | O |
| 2-199 | Cl | F | 3-$NO_2$-pyridyloxy | $CH_3$ | $CF_3$ | H | 2-naphthoyl | H | O | O |
| 2-200 | Cl | F | $OCH_2CN$ | $CH_3$ | $CF_3$ | H | 2-naphthoyl | H | O | O |
| 2-201 | $CH_3$ | H | H | $CH_3$ | $CF_3$ | H | 2-naphthoyl | H | O | O |
| 2-202 | Cl | H | $OCH_3$ | $CH_3$ | $CF_3$ | H | 2-naphthoyl | H | O | O |
| 2-203 | $OCF_3$ | H | H | $CH_3$ | $CF_3$ | H | 2-naphthoyl | H | O | O |
| 2-204 | Cl | H | H | $CH_3$ | $CF_3$ | H | c-$C_3H_5$-carbonyl | H | O | O |
| 2-205 | $H_2NC(S)$ | H | H | $CH_3$ | $CF_3$ | H | 2-naphthoyl | H | O | O |
| 2-206 | Cl | F | $OCH_3$ | $CH_3$ | $CF_3$ | H | c-$C_3H_5$-carbonyl | H | O | O |
| 2-207 | $COOCH_3$ | H | H | $CH_3$ | $CF_3$ | H | 2-naphthoyl | H | O | O |

TABLE III

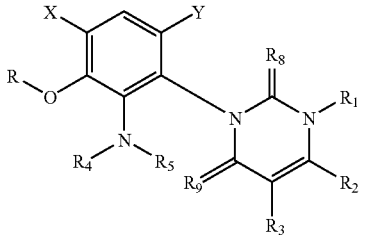

| No. | X | Y | R | $R_1$ | $R_2$ | $R_3$ | $R_4$ | $R_5$ | $R_8$ | $R_9$ |
|---|---|---|---|---|---|---|---|---|---|---|
| 3-1 | Cl | F | $CH_3$ | $CH_3$ | $CF_3$ | H | $CONHCH_3$ | $CONHCH_3$ | O | O |
| 3-2 | Cl | F | $CH_3$ | $CH_3$ | $CF_3$ | H | $CONHCH_2CH_2CH_3$ | H | O | O |
| 3-3 | Cl | F | $CH_3$ | $CH_3$ | $CF_3$ | H | $CON[CH(CH_3)_2]_2$ | H | O | O |
| 3-4 | Cl | F | $CH_3$ | $CH_3$ | $CF_3$ | H | $CONHC_6H_5$ | H | O | O |
| 3-5 | Cl | F | $CH_3$ | $CH_3$ | $CF_3$ | H | $CON(CH_3)C_6H_5$ | H | O | O |
| 3-6 | Cl | F | $CH_3$ | $CH_3$ | $CF_3$ | H | $CONHCH_2C_6H_5$ | H | O | O |
| 3-7 | Cl | F | $CH_3$ | $CH_3$ | $CF_3$ | H | $CONHCH(CH_3)—C_6H_5$ | H | O | O |
| 3-8 | Cl | F | $CH_3$ | $CH_3$ | $CF_3$ | H | $CON(CH_3)CH_2C_6H_5$ | H | O | O |
| 3-9 | Cl | F | $CH_3$ | $CH_3$ | $CF_3$ | H | $CONHCH_2$-(4-$CH_3$)phenyl | H | O | O |
| 3-10 | Cl | F | $CH_3$ | $CH_3$ | $CF_3$ | H | $CONHCH_2$-2,4-$F_2$-phenyl | H | O | O |
| 3-11 | Cl | F | $CH_3$ | $CH_3$ | $CF_3$ | H | $CONHCH_2CH_2C_6H_5$ | H | O | O |
| 3-12 | Cl | F | $CH_3$ | $CH_3$ | $CF_3$ | H | $CONHCH_2CH_2CH_2C_6H_5$ | H | O | O |
| 3-13 | Cl | F | $CH_3$ | $CH_3$ | $CF_3$ | H | CONH-2-naphthoyl | H | O | O |
| 3-14 | Cl | F | $CH_2CN$ | $CH_3$ | $CF_3$ | H | $CONHCH_2C_6H_5$ | H | O | O |
| 3-15 | Cl | F | $CH_3$ | H | $CF_3$ | H | $CONHCH_2C_6H_5$ | H | O | O |
| 3-16 | Cl | F | $CH_3$ | $NH_2$ | $CF_3$ | H | $CONHCH_2C_6H_5$ | H | O | O |
| 3-17 | Cl | F | $CH_3$ | $CH_3$ | $CHF_2$ | H | $CONHCH_2C_6H_5$ | H | O | O |
| 3-18 | Cl | F | $CH_3$ | $CH_3$ | $CF_3$ | Cl | $CONHCH_2C_6H_5$ | H | O | O |
| 3-19 | Cl | F | $CH_3$ | $CH_3$ | $CF_3$ | H | $CONHCH_2C_6H_5$ | H | S | O |
| 3-20 | Cl | F | $CH_3$ | $CH_3$ | $CF_3$ | H | $CONHCH_2C_6H_5$ | H | O | S |
| 3-21 | CN | F | $CH_3$ | $CH_3$ | $CF_3$ | H | $CONHCH_2C_6H_5$ | H | O | O |
| 3-22 | Cl | H | $CH_3$ | $CH_3$ | $CF_3$ | H | $CONHCH_2C_6H_5$ | H | O | O |
| 3-23 | Cl | F | $CH_3$ | $CH_3$ | $CF_3$ | H | $CON(C_6H_5)CH_2C_6H_5$ | H | O | O |
| 3-24 | Cl | F | $CH_3$ | $CH_3$ | $CF_3$ | H | $CONHCH(C_6H_5)C_6H_5$ | H | O | O |
| 3-26 | Cl | F | $CH_3$ | $CH_3$ | $CF_3$ | H | $CONH_2$ | H | O | O |

TABLE IV

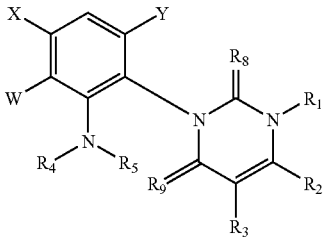

| No. | X | Y | W | $R_1$ | $R_2$ | $R_3$ | $R_4$ | $R_5$ | $R_8$ | $R_9$ |
|---|---|---|---|---|---|---|---|---|---|---|
| 4-1 | Cl | F | $OCH_3$ | $CH_3$ | $CF_3$ | H | $COOCH_3$ | H | O | O |
| 4-2 | Cl | F | $OCH_3$ | $CH_3$ | $CF_3$ | H | $COOCH_3$ | $COOCH_3$ | O | O |
| 4-3 | Cl | F | $OCH_3$ | $CH_3$ | $CF_3$ | H | COO-phenyl | H | O | O |
| 4-4 | Cl | F | $OCH_3$ | $CH_3$ | $CF_3$ | H | COO-[2,4-$(CH_3)_2$]-phenyl | H | O | O |
| 4-5 | Cl | F | $OCH_3$ | $CH_3$ | $CF_3$ | H | $COOCH_2$-phenyl | H | O | O |
| 4-6 | Cl | F | $OCH_3$ | $CH_3$ | $CF_3$ | H | $COOCH_2$-(2-F)-phenyl | H | O | O |
| 4-7 | Cl | F | $OCH_3$ | $CH_3$ | $CF_3$ | H | $COOCH_2$-(4-F)-phenyl | H | O | O |
| 4-8 | Cl | F | $OCH_3$ | $CH_3$ | $CF_3$ | H | $COOCH_2$-(2-$CF_3$)-phenyl | H | O | O |
| 4-9 | Cl | F | $OCH_3$ | $CH_3$ | $CF_3$ | H | $COOCH_2$-(4-$CF_3$)-phenyl | H | O | O |
| 4-10 | Cl | F | $OCH_3$ | $CH_3$ | $CF_3$ | H | COO-2-naphthyl | H | O | O |
| 4-11 | Cl | F | $OCH_3$ | $CH_3$ | $CF_3$ | H | COO-cyclohexyl | H | O | O |
| 4-12 | Cl | F | $OCH_3$ | $CH_3$ | $CF_3$ | H | $COOCH_2$-cyclohexyl | H | O | O |
| 4-13 | Cl | F | $OCH_3$ | $CH_3$ | $CF_3$ | H | C(O)—S-phenyl | H | O | O |
| 4-14 | Cl | F | $OCH_2CN$ | $CH_3$ | $CF_3$ | H | COO-phenyl | H | O | O |

TABLE IV-continued

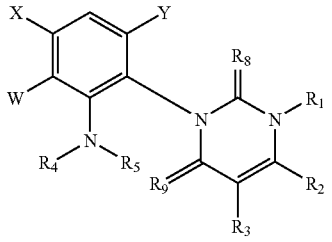

| No. | X | Y | W | $R_1$ | $R_2$ | $R_3$ | $R_4$ | $R_5$ | $R_8$ | $R_9$ |
|---|---|---|---|---|---|---|---|---|---|---|
| 4-15 | Cl | F | $OCH_3$ | H | $CF_3$ | H | COO-phenyl | H | O | O |
| 4-16 | Cl | F | $OCH_3$ | $NH_2$ | $CF_3$ | H | COO-phenyl | H | O | O |
| 4-17 | Cl | F | $OCH_3$ | $CH_3$ | $CHF_2$ | H | COO-phenyl | H | O | O |
| 4-18 | Cl | F | $OCH_3$ | $CH_3$ | $CF_3$ | Cl | COO-phenyl | H | O | O |
| 4-19 | Cl | F | $OCH_3$ | $CH_3$ | $CF_3$ | H | COO-phenyl | H | S | O |
| 4-20 | Cl | F | $OCH_3$ | $CH_3$ | $CF_3$ | H | COO-phenyl | H | O | S |
| 4-21 | CN | F | $OCH_3$ | $CH_3$ | $CF_3$ | H | COO-phenyl | H | O | O |
| 4-22 | Cl | H | $OCH_3$ | $CH_3$ | $CF_3$ | H | COO-phenyl | H | O | O |
| 4-23 | Cl | F | $OCH_2CN$ | $CH_3$ | $CF_3$ | H | $COOCH_2$-phenyl | H | O | O |
| 4-24 | Cl | F | $OCH_3$ | $CH_3$ | $CF_3$ | H | $COOCH_2$-(2,6-di-Cl)-phenyl | H | O | O |
| 4-25 | Cl | F | $OCH_3$ | $CH_3$ | $CF_3$ | H | COO-[2,4,6-$(CH_3)_3$]-phenyl | H | O | O |
| 4-26 | Cl | F | $OCH_3$ | $CH_3$ | $CF_3$ | H | $COOCH_2$-[3,4-$(CH_3)_2$]-phenyl | H | O | O |
| 4-27 | Cl | F | $OCH_3$ | $CH_3$ | $CF_3$ | H | COO-(2-t-butyl)-phenyl | H | O | O |
| 4-28 | Cl | F | $OCH_3$ | $CH_3$ | $CF_3$ | H | $COOCH_2$-2-naphthyl | H | O | O |
| 4-29 | Cl | F | $OCH_3$ | $CH_3$ | $CF_3$ | H | $COOCH_2$-(2,6-di-F)-phenyl | H | O | O |
| 4-30 | Cl | F | $OCH_3$ | $CH_3$ | $CF_3$ | H | $COOCH_2$-(3,4-di-F)-phenyl | H | O | O |
| 4-31 | Cl | F | $OCH_3$ | $CH_3$ | $CF_3$ | H | $COOCH_2$-(4-ethyl)-phenyl | H | O | O |
| 4-32 | Cl | F | $OCH_3$ | $CH_3$ | $CF_3$ | H | $COOCH_2$-(3,4-di-Cl)-phenyl | H | O | O |
| 4-33 | Cl | F | $OCH_3$ | $CH_3$ | $CF_3$ | H | $COOCH_2$-(2-$CF_3$)-phenyl | H | O | O |
| 4-34 | Cl | F | $OCH_3$ | $CH_3$ | $CF_3$ | H | $COOCH_2$-(2-$NO_2$)-phenyl | H | O | O |
| 4-35 | Cl | F | $OCH_3$ | $CH_3$ | $CF_3$ | H | $COOCH_2$-(2-$OCH_3$)-phenyl | H | O | O |
| 4-36 | Cl | F | $OCH_3$ | $CH_3$ | $CF_3$ | H | $COOCH_2$-2-pyridyl | H | O | O |
| 4-37 | Cl | F | $OCH_3$ | $CH_3$ | $CF_3$ | H | $COOCH_2$-[3,5-$(CH_3)_2$]-phenyl | H | O | O |
| 4-38 | Cl | F | $OCH_3$ | $CH_3$ | $CF_3$ | H | $COOCH_2$-[2,5-$(CH_3)_2$]-phenyl | H | O | O |
| 4-39 | Cl | F | $OCH_3$ | $CH_3$ | $CF_3$ | H | $COOCH_2$-(2,5-di-F)-phenyl | H | O | O |
| 4-40 | Cl | F | $OCH_3$ | $CH_3$ | $CF_3$ | H | $COOCH_2$-(4-$OCH_3$)-phenyl | H | O | O |
| 4-41 | Cl | F | $OCH_3$ | $CH_3$ | $CF_3$ | H | $COOCH_2$-(3,4-$OCH_2O$)-phenyl | H | O | O |
| 4-42 | Cl | F | $OCH_3$ | $CH_3$ | $CF_3$ | H | $COOCH_2$-(4-i-$C_3H_7$)-phenyl | H | O | O |
| 4-43 | Cl | F | $OCH_3$ | $CH_3$ | $CF_3$ | H | $COOCH_2$-(4-$CF_3$)-phenyl | H | O | O |
| 4-44 | Cl | F | $OCH_3$ | $CH_3$ | $CF_3$ | H | $COOCH_2$-(3-F)-phenyl | H | O | O |
| 4-45 | Cl | F | $OCH_3$ | $CH_3$ | $CF_3$ | H | $COOCH_2$-(4-$OCF_3$)-phenyl | H | O | O |
| 4-46 | Cl | F | $OCH_3$ | $CH_3$ | $CF_3$ | H | COOCH-(c-$C_3H_5$)-phenyl | H | O | O |
| 4-47 | Cl | F | $OCH_3$ | $CH_3$ | $CF_3$ | H | $COOCH(CH_3)$-phenyl | H | O | O |
| 4-48 | Cl | F | $OCH_3$ | $CH_3$ | $CF_3$ | H | $COOCH_2$-(2,3,4,5,6-penta-F)-phenyl | H | O | O |
| 4-49 | Cl | H | H | $CH_3$ | $CF_3$ | H | $COOCH_2$-(2-F)-phenyl | H | O | O |
| 4-50 | Cl | H | H | $CH_3$ | $CF_3$ | H | COO-phenyl | H | O | O |
| 4-51 | Cl | F | $CH_3$ | $CH_3$ | $CF_3$ | H | $COOCH_2$-(2-F)-phenyl | H | O | O |
| 4-52 | Cl | F | $CH_3$ | $CH_3$ | $CF_3$ | H | COO-phenyl | H | O | O |
| 4-53 | Cl | F | $CH_3$ | $CH_3$ | $CF_3$ | H | COO-3,4-dimethylphenyl | H | O | O |
| 4-54 | Cl | F | $CH_3$ | $CH_3$ | $CF_3$ | H | $COOCH_2$-2-Cl-phenyl | H | O | O |
| 4-55 | Cl | F | $CH_3$ | $CH_3$ | $CF_3$ | H | COO-2,6-dimethylphenyl | H | O | O |
| 4-56 | Cl | F | $CH_3$ | $CH_3$ | $CF_3$ | H | $COOCH_2$-2-methylphenyl | H | O | O |
| 4-57 | Cl | F | $CH_3$ | $CH_3$ | $CF_3$ | H | $COOCH_2CH_2$-phenyl | H | O | O |
| 4-58 | Cl | F | $CH_3$ | $CH_3$ | $CF_3$ | H | $COOCH_2$-2-methoxyphenyl | H | O | O |
| 4-59 | Cl | F | $CH_3$ | $CH_3$ | $CF_3$ | H | COO-2,6-dimethoxyphenyl | H | O | O |
| 4-60 | Cl | F | $CH_3$ | $CH_3$ | $CF_3$ | H | $COOCH_2$-4-methylphenyl | H | O | O |
| 4-61 | Cl | F | $CH_3$ | $CH_3$ | $CF_3$ | H | $COOCH_2$-4-Cl-phenyl | H | O | O |
| 4-62 | Cl | F | $CH_3$ | $CH_3$ | $CF_3$ | H | $COOCH_2$-2,4-dichlorophenyl | H | O | O |
| 4-63 | Cl | F | $CH_3$ | $CH_3$ | $CF_3$ | H | $COOCH_2$-3,4-dimethoxyphenyl | H | O | O |
| 4-64 | Cl | F | $CH_3$ | $CH_3$ | $CF_3$ | H | $COOCH_2$-4-nitrophenyl | H | O | O |
| 4-65 | Cl | F | $CH_3$ | $CH_3$ | $CF_3$ | H | $COOCH_2$-3-methoxyphenyl | H | O | O |
| 4-66 | Cl | F | $CH_3$ | $CH_3$ | $CF_3$ | H | $COSCH_2$-phenyl | H | O | O |
| 4-67 | Cl | F | $CH_3$ | $CH_3$ | $CF_3$ | H | $COOCH_2$-3-nitrophenyl | H | O | O |
| 4-68 | Cl | F | $CH_3$ | $CH_3$ | $CF_3$ | H | $COOCH_2$-3-methylphenyl | H | O | O |
| 4-69 | Cl | F | $CH_3$ | $CH_3$ | $CF_3$ | H | $COOCH_2$-2,4,6-trimethylphenyl | H | O | O |
| 4-70 | Cl | F | $CH_3$ | $CH_3$ | $CF_3$ | H | $COOCH_2$-2-furanyl | H | O | O |

TABLE V

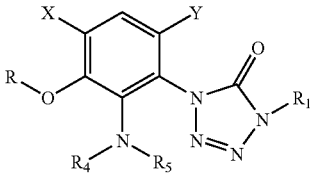

| No. | X | Y | R | $R_1$ | $R_4$ | $R_5$ |
|---|---|---|---|---|---|---|
| 5-1 | Cl | F | $CH_3$ | H | O | O |
| 5-2 | Cl | F | H | H | O | O |
| 5-3 | Cl | F | $CH_3$ | $(CH_2)_3F$ | H | H |
| 5-4 | Cl | F | H | $(CH_2)_3F$ | O | O |
| 5-5 | Cl | F | H | $(CH_2)_3F$ | H | H |
| 5-6 | Cl | Cl | $CH_3$ | H | O | O |
| 5-7 | Cl | Cl | $CH_3$ | $(CH_2)_3F$ | O | O |
| 5-8 | Cl | Cl | H | $(CH_2)_3F$ | O | O |
| 5-9 | Cl | Cl | H | $(CH_2)_3F$ | H | H |
| 5-10 | Cl | F | $CH_3$ | $(CH_2)_3F$ | $COCH_3$ | H |
| 5-11 | Cl | F | $CH_3$ | $(CH_2)_3F$ | benzoyl | H |
| 5-12 | Cl | F | $CH_3$ | $(CH_2)_3F$ | $CH_3$ | $CH_3$ |
| 5-13 | Cl | F | $CH_3$ | $(CH_2)_3F$ | $COOCH_3$ | H |
| 5-14 | Cl | F | $CH_3$ | $(CH_2)_3F$ | $CONHCH_3$ | H |
| 5-15 | Cl | Cl | $CH_2C{\equiv}CH$ | $(CH_2)_3F$ | H | H |
| 5-16 | Cl | Cl | $CH(CH_3)_2$ | $(CH_2)_3F$ | H | H |
| 5-17 | Cl | F | $CH_2C{\equiv}CH$ | $(CH_2)_3F$ | H | H |
| 5-18 | Cl | F | $CH(CH_3)_2$ | $(CH_2)_3F$ | H | H |
| 5-19 | CN | F | $CH_3$ | $(CH_2)_3F$ | benzoyl | H |
| 5-20 | Cl | H | $CH_3$ | $(CH_2)_3F$ | benzoyl | H |
| 5-21 | Cl | F | $CH_3$ | $(CH_2)_3F$ | 2,4-$F_2$-benzoyl | H |
| 5-22 | Cl | F | $CH_3$ | $(CH_2)_3F$ | 4-$C_2H_5$-benzoyl | |
| 5-23 | Cl | F | $CH_3$ | $(CH_2)_3F$ | 3-phenyl-propionyl | H |
| 5-24 | Cl | F | $CH_2CN$ | $(CH_2)_3F$ | 2,4-$F_2$-benzoyl | H |
| 5-25 | Cl | F | $CH_2CN$ | $(CH_2)_3F$ | 2-naphthoyl | H |
| 5-26 | Cl | F | $CH_3$ | $(CH_2)_3F$ | 2-naphthoyl | H |
| 5-27 | Cl | F | $CH_3$ | $(CH_2)_3F$ | 2-naphthoyl | 2-naphthoyl |
| 5-28 | Cl | F | $CH_3$ | $(CH_2)_3F$ | benzyloxyacetyl | H |

TABLE VI

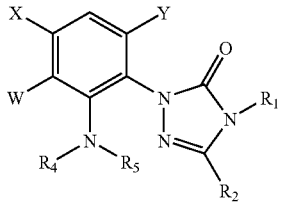

| No. | X | Y | W | $R_1$ | $R_2$ | $R_4$ | $R_5$ |
|---|---|---|---|---|---|---|---|
| 6-1 | Cl | F | OH | $CHF_2$ | $CH_3$ | O | O |
| 6-2 | Cl | F | OH | $CHF_2$ | $CH_3$ | H | H |
| 6-3 | Cl | F | $OCH_3$ | $CHF_2$ | $CH_3$ | H | H |
| 6-4 | Cl | F | $OCH_3$ | $CHF_2$ | $CH_3$ | $COCH_3$ | H |
| 6-5 | Cl | F | $OCH_3$ | $CHF_2$ | $CH_3$ | benzoyl | H |
| 6-6 | Cl | Cl | $OCH_3$ | $CHF_2$ | $CH_3$ | $CH_3$ | $CH_3$ |
| 6-7 | Cl | Cl | $OCH_3$ | $CHF_2$ | $CH_3$ | $COOCH_3$ | H |
| 6-8 | Cl | F | $OCH_3$ | $CH_3$ | $CH_3$ | benzoyl | H |
| 6-9 | Cl | F | $OCH_3$ | $CHF_2$ | $CH_2CH_3$ | benzoyl | H |
| 6-10 | Cl | Cl | $OCH_3$ | $CHF_2$ | $CH_3$ | $CONHCH_3$ | H |
| 6-11 | CN | F | $OCH_3$ | $CHF_2$ | $CH_3$ | benzoyl | H |
| 6-12 | Cl | H | $OCH_3$ | $CHF_2$ | $CH_3$ | benzoyl | H |
| 6-13 | Cl | Cl | H | $CHF_2$ | $CH_3$ | 2,4-difluoro-benzoyl | H |
| 6-14 | Cl | F | $OCH_3$ | $CHF_2$ | $CH_3$ | 2,4-difluoro-benzoyl | H |
| 6-15 | Cl | F | $OCH_3$ | $CHF_2$ | $CH_3$ | 2-naphthoyl | H |
| 6-16 | Cl | Cl | H | $CHF_2$ | $CH_3$ | 2-naphthoyl | H |
| 6-17 | Cl | Cl | $OCH_3$ | $CHF_2$ | $CH_3$ | 2-naphthoyl | H |
| 6-18 | Cl | Cl | $HNC(O)C_2H_5$ | $CHF_2$ | $CH_3$ | O | O |

TABLE VI-continued

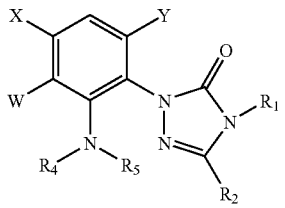

| No. | X | Y | W | $R_1$ | $R_2$ | $R_4$ | $R_5$ |
|---|---|---|---|---|---|---|---|
| 6-19 | Cl | Cl | $HNC(O)C_2H_5$ | $CHF_2$ | $CH_3$ | H | H |
| 6-20 | Cl | Cl | $NH_2$ | $CHF_2$ | $CH_3$ | H | H |
| 6-21 | Cl | F | H | $CHF_2$ | $CH_3$ | O | O |
| 6-22 | Cl | F | H | $CHF_2$ | $CH_3$ | H | H |
| 6-23 | Cl | F | H | $CHF_2$ | $CH_3$ | 2,4-$F_2$-benzoyl | H |
| 6-24 | Cl | F | H | $CHF_2$ | $CH_3$ | 2-naphthoyl | H |

TABLE VII

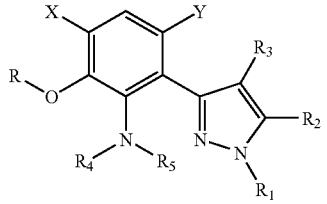

| No. | X | Y | R | $R_1$ | $R_2$ | $R_3$ | $R_4$ | $R_5$ |
|---|---|---|---|---|---|---|---|---|
| 7-1 | Cl | F | $CH_3$ | $CH_3$ | $CF_3$ | Cl | O | O |
| 7-2 | Cl | F | $CH_3$ | $CH_3$ | $CF_3$ | Cl | H | H |
| 7-3 | Cl | F | H | $CH_3$ | $CF_3$ | Cl | H | H |
| 7-4 | Cl | F | $CH_3$ | $CH_3$ | $CF_3$ | Cl | $COCH_3$ | H |
| 7-5 | Cl | F | $CH_3$ | $CH_3$ | $CF_3$ | Cl | benzoyl | H |
| 7-6 | Cl | Cl | $CH_3$ | $CH_3$ | $CF_3$ | Cl | $CH_3$ | $CH_3$ |
| 7-7 | Cl | Cl | $CH_3$ | $CH_3$ | $CF_3$ | Cl | $COOCH_3$ | H |
| 7-8 | Cl | Cl | $CH_3$ | $CH_3$ | $CF_3$ | Cl | $CONHCH_3$ | H |
| 7-9 | CN | F | $CH_3$ | $CH_3$ | $CF_3$ | Cl | benzoyl | H |
| 7-10 | Cl | H | $CH_3$ | $CH_3$ | $CF_3$ | Cl | benzoyl | H |
| 7-11 | Cl | F | $CH_3$ | $CH_2CH_3$ | $CF_3$ | Cl | benzoyl | H |
| 7-12 | Cl | F | $CH_3$ | $CH_3$ | $OCHF_2$ | Cl | benzoyl | H |
| 7-13 | Cl | F | $CH_3$ | $CH_3$ | $CF_3$ | Br | benzoyl | H |
| 7-14 | Cl | F | $CH_3$ | $CH_3$ | $CF_3$ | Cl | 2-naphthoyl | H |
| 7-15 | Cl | F | $CH_3$ | $CH_3$ | $CF_3$ | Cl | cinnamoyl | H |

TABLE VIII

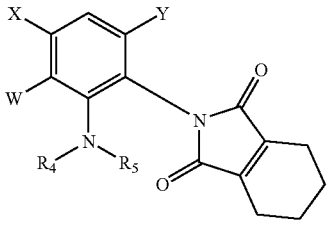

| No. | X | Y | W | $R_4$ | $R_5$ |
|---|---|---|---|---|---|
| 8-1 | Cl | F | OH | O | O |
| 8-2 | Cl | F | OH | H | H |
| 8-3 | Cl | F | $OCH_2C{\equiv}CH$ | H | H |
| 8-4 | Cl | F | $OCH(CH_3)_2$ | H | H |
| 8-5 | Cl | F | O-c-pentyl | H | H |
| 8-6 | Cl | F | $OCH_3$ | O | O |
| 8-7 | Cl | F | $OCH_3$ | H | H |

TABLE VIII-continued

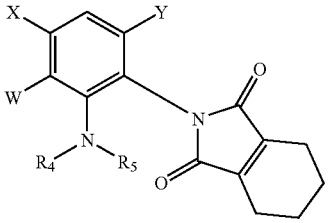

| No. | X | Y | W | $R_4$ | $R_5$ |
|---|---|---|---|---|---|
| 8-8 | Cl | F | $OCH_3$ | 2,4-$F_2$-benzoyl | H |
| 8-9 | Cl | F | $OCH_3$ | 2-naphthoyl | H |
| 8-10 | Cl | F | $OCH_3$ | 4-$C_2H_5$-benzoyl | H |
| 8-11 | Cl | F | $OCH_3$ | 3-phenyl-propionyl | H |
| 8-12 | CN | F | $OCH_3$ | 2,4-$F_2$-benzoyl | H |
| 8-13 | Cl | F | $OCH_2C{\equiv}CH$ | 2,4-$F_2$-benzoyl | H |
| 8-14 | Cl | F | $OCH_2C{\equiv}CH$ | 2-naphthoyl | H |
| 8-15 | Cl | F | $OCH_2C{\equiv}CH$ | 4-$C_2H_5$-benzoyl | H |
| 8-16 | Cl | F | $OCH_2C{\equiv}CH$ | 3-phenyl-propionyl | H |
| 8-17 | CN | F | $OCH_2C{\equiv}CH$ | 2,4-$F_2$-benzoyl | H |
| 8-18 | Cl | F | $OCH(CH_3)_2$ | 2,4-$F_2$-benzoyl | H |
| 8-19 | Cl | F | $OCH(CH_3)_2$ | 2-naphthoyl | H |
| 8-20 | Cl | F | $OCH(CH_3)_2$ | 4-$C_2H_5$-benzoyl | H |
| 8-21 | Cl | F | $OCH(CH_3)_2$ | 3-phenyl-propionyl | H |
| 8-22 | CN | F | $OCH(CH_3)_2$ | 2,4-$F_2$-benzoyl | H |
| 8-23 | Cl | F | $OCH_3$ | $COCH_3$ | H |
| 8-24 | Cl | F | $OCH_3$ | benzoyl | H |
| 8-25 | Cl | F | $OCH_3$ | $CH_3$ | $CH_3$ |
| 8-26 | Cl | F | $OCH_3$ | $COOCH_3$ | H |
| 8-27 | Cl | F | $OCH_3$ | $CONHCH_3$ | H |
| 8-28 | CN | F | $OCH_3$ | benzoyl | H |
| 8-29 | Cl | H | $OCH_3$ | benzoyl | H |
| 8-30 | Cl | F | $OCH_3$ | 4-vinyl-benzoyl | H |
| 8-31 | Cl | F | $OCH_3$ | cinnamoyl | H |
| 8-32 | Cl | $NO_2$ | H | O | O |
| 8-33 | Cl | H | H | O | O |
| 8-34 | $NO_2$ | H | H | O | O |
| 8-35 | Cl | H | H | H | H |
| 8-36 | Cl | H | H | 2-naphthoyl | H |

TABLE IX

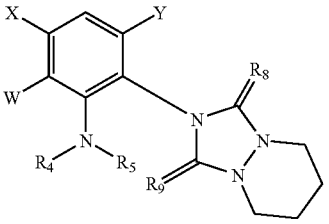

| No | X | Y | W | $R_4$ | $R_5$ | $R_8$ | $R_9$ |
|---|---|---|---|---|---|---|---|
| 9-1 | Cl | F | OH | O | O | O | O |
| 9-2 | Cl | F | OH | H | H | O | O |
| 9-3 | Cl | F | $OCH_3$ | O | O | O | O |
| 9-4 | Cl | F | $OCH_3$ | H | O | O | O |
| 9-5 | Cl | F | $OCH_3$ | $COCH_3$ | H | O | O |
| 9-6 | Cl | F | $OCH_3$ | benzoyl | H | O | O |
| 9-7 | Cl | F | $OCH_3$ | $CH_3$ | $CH_3$ | O | O |
| 9-8 | Cl | F | $OCH_3$ | $COOCH_3$ | H | O | O |
| 9-9 | Cl | F | $OCH_3$ | $CONHCH_3$ | H | O | O |
| 9-10 | CN | F | $OCH_3$ | benzoyl | H | O | O |
| 9-11 | Cl | H | $OCH_3$ | benzoyl | H | O | O |
| 9-12 | Cl | H | H | O | O | O | S |
| 9-13 | Cl | H | H | H | H | O | S |
| 9-14 | Cl | H | H | 2-naphthoyl | H | O | S |
| 9-15 | Cl | F | $OCH_3$ | 2-naphthoyl | H | O | O |
| 9-16 | Cl | F | $OCH_3$ | 2,4-$F_2$-benzoyl | H | O | O |
| 9-17 | Cl | H | H | O | O | O | O |

TABLE IX-continued

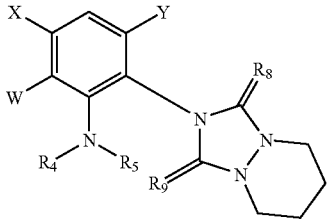

| No | X | Y | W | $R_4$ | $R_5$ | $R_8$ | $R_9$ |
|---|---|---|---|---|---|---|---|
| 9-18 | Cl | H | H | H | H | O | O |
| 9-19 | Cl | H | H | 2-naphthoyl | H | O | O |

TABLE X

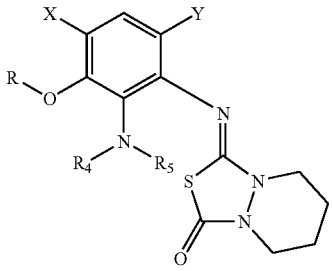

| No. | X | Y | R | $R_5$ | $R_4$ |
|---|---|---|---|---|---|
| 10-1 | Cl | F | H | O | O |
| 10-2 | Cl | F | H | H | H |
| 10-3 | Cl | F | $CH_3$ | O | O |
| 10-4 | Cl | F | $CH_3$ | H | H |
| 10-5 | Cl | F | $CH_3$ | $COCH_3$ | H |
| 10-6 | Cl | F | $CH_3$ | benzoyl | H |
| 10-7 | Cl | F | $CH_3$ | $CH_3$ | $CH_3$ |
| 10-8 | Cl | F | $CH_3$ | $COOCH_3$ | H |
| 10-9 | Cl | F | $CH_3$ | $CONHCH_3$ | H |
| 10-10 | CN | F | $CH_3$ | benzoyl | H |
| 10-11 | Cl | H | $CH_3$ | benzoyl | H |

TABLE XI

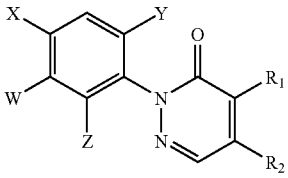

| No. | X | Y | W | $R_1$ | $R_2$ | Z |
|---|---|---|---|---|---|---|
| 11-1 | Cl | F | $OCH_3$ | H | $CF_3$ | $NO_2$ |
| 11-2 | Cl | F | OH | H | $CF_3$ | $NO_2$ |
| 11-3 | Cl | F | OH | H | $CF_3$ | $NH_2$ |
| 11-4 | Cl | F | $OCH_3$ | H | $CF_3$ | $NH_2$ |
| 11-5 | Cl | F | $OCH_3$ | H | $CF_3$ | $NHCH_3$ |
| 11-6 | Cl | F | $OCH_3$ | H | $CF_3$ | NH-2-naphthoyl |
| 11-7 | Cl | F | $OCH_3$ | H | $CF_3$ | Cl |
| 11-8 | Cl | F | $OCH_3$ | H | $CF_3$ | $CH_2CHClCOOCH_2CH_3$ |
| 11-9 | Cl | F | OH | $CH_3$ | $CF_3$ | $NO_2$ |
| 11-10 | Cl | F | OH | $CH_3$ | $CF_3$ | $NH_2$ |
| 11-11 | Cl | F | $OCH_3$ | $CH_3$ | $CF_3$ | $NH_2$ |
| 11-12 | Cl | F | $OCH_3$ | $CH_3$ | $CF_3$ | $NHCH_3$ |
| 11-13 | Cl | F | $OCH_3$ | $CH_3$ | $CF_3$ | NH-2-naphthoyl |
| 11-14 | Cl | F | $OCH_3$ | $CH_3$ | $CF_3$ | $NO_2$ |
| 11-15 | Cl | F | $OCH_3$ | $CH_3$ | $CF_3$ | $NHCOCH_3$ |

TABLE XI-continued

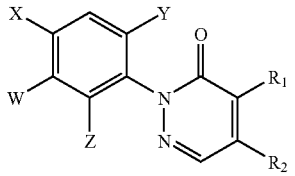

| No. | X | Y | W | $R_1$ | $R_2$ | Z |
|---|---|---|---|---|---|---|
| 11-16 | Cl | F | $OCH_3$ | $CH_3$ | $CF_3$ | NH-benzoyl |
| 11-17 | Cl | F | $OCH_3$ | $CH_3$ | $CF_3$ | $N—(CH_3)_2$ |
| 11-18 | Cl | F | $OCH_3$ | $CH_3$ | $CF_3$ | NHCOO-phenyl |
| 11-19 | Cl | F | $OCH_3$ | $CH_3$ | $CF_3$ | $NHCONHCH_3$ |
| 11-20 | CN | F | $OCH_3$ | $CH_3$ | $CF_3$ | 2-naphthoyl-NH |
| 11-21 | Cl | F | $OCH_3$ | $CH_3$ | $CH_3$ | 2-naphthoyl-NH |
| 11-22 | Cl | H | $OCH_3$ | $CH_3$ | $CF_3$ | 2-naphthoyl-NH |
| 11-23 | Cl | F | $OCH_3$ | $CH_3$ | $CF_3$ | Cl |
| 11-24 | Cl | F | $OCH_3$ | $CH_3$ | $CF_3$ | $CH_2CHClCOOCH_2CH_3$ |

TABLE XII

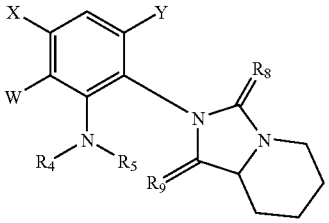

| No. | X | Y | W | $R_4$ | $R_5$ | $R_8$ | $R_9$ |
|---|---|---|---|---|---|---|---|
| 12-1 | Cl | F | OH | O | O | S | O |
| 12-2 | Cl | F | OH | H | H | S | O |
| 12-3 | Cl | F | OH | H | H | S | O |
| 12-4 | Cl | F | $OCH_3$ | H | H | S | O |
| 12-5 | Cl | F | $OCH_3$ | 2-naphthoyl | H | S | O |
| 12-6 | Cl | H | H | O | O | O | O |
| 12-7 | Cl | H | H | H | H | O | O |
| 12-8 | Cl | H | H | 2-naphthoyl | H | O | O |
| 12-9 | Cl | F | $OCH_3$ | $COCH_3$ | H | S | O |
| 12-10 | Cl | F | $OCH_3$ | benzoyl | H | S | O |
| 12-11 | Cl | F | $OCH_3$ | $CH_3$ | $CH_3$ | S | O |
| 12-12 | Cl | F | $OCH_3$ | COO-phenyl | H | S | O |
| 12-13 | Cl | F | $OCH_3$ | $CONHCH_3$ | H | S | O |

TABLE XII-continued

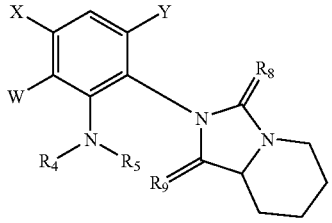

| No. | X | Y | W | $R_4$ | $R_5$ | $R_8$ | $R_9$ |
|---|---|---|---|---|---|---|---|
| 12-14 | CN | F | $OCH_3$ | 2-naphthoyl | H | S | O |
| 12-15 | Cl | H | $OCH_3$ | 2-naphthoyl | H | S | O |

TABLE XIII

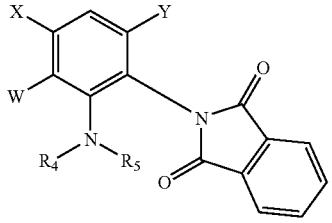

| No | X | Y | W | $R_4$ | $R_5$ |
|---|---|---|---|---|---|
| 13-1 | Cl | F | OH | O | O |
| 13-2 | Cl | F | OH | H | H |
| 13-3 | Cl | F | $OCH_3$ | 2-naphthoyl | H |
| 13-4 | Cl | F | $OCH_3$ | 2,4-difluorobenzoyl | H |
| 13-5 | Cl | H | H | 2-naphthoyl | H |
| 13-6 | Cl | F | $OCH_3$ | $COCH_3$ | H |
| 13-7 | Cl | F | $OCH_3$ | benzoyl | H |
| 13-8 | Cl | F | $OCH_3$ | $CH_3$ | $CH_3$ |
| 13-9 | Cl | F | $OCH_3$ | COO-phenyl | H |
| 13-10 | Cl | F | $OCH_3$ | $CONHCH_3$ | H |
| 13-11 | CN | F | $OCH_3$ | 2-naphthoyl | H |
| 13-12 | Cl | H | $OCH_3$ | 2-naphthoyl | H |

TABLE XIV

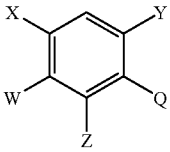

| No. | X | Y | W | Q | $R_1$ | $R_2$ | $R_3$ | Z | $R_8$ | $R_9$ |
|---|---|---|---|---|---|---|---|---|---|---|
| 14-1 | Cl | F | $OCH_3$ | Q1 | $CH_3$ | $CF_3$ | H | $CH_2CH_2CO_2CH_2CH_3$ | O | O |
| 14-2 | Cl | F | $OCH_3$ | Q1 | $CH_3$ | $CF_3$ | H | $CH{=}CHCO_2CH_2CH_3$ | O | O |
| 14-3 | Cl | F | $OCH_3$ | Q1 | $CH_3$ | $CF_3$ | H | $CH_2CHClCO_2CH_3$ | O | O |
| 14-4 | Cl | F | $OCH_3$ | Q1 | $CH_3$ | $CF_3$ | H | $CH_2CHClCO_2C_2H_5$ (isomer-1) | O | O |
| 14-5 | Cl | F | $OCH_3$ | Q1 | $CH_3$ | $CF_3$ | H | $CH_2CHClCO_2C_2H_5$ (isomer-2) | O | O |
| 14-6 | Cl | F | $OCH_3$ | Q1 | $CH_3$ | $CF_3$ | H | $CH_2CHClCO_2$-n-$C_3H_7$ (isomer-1) | O | O |
| 14-7 | Cl | F | $OCH_3$ | Q1 | $CH_3$ | $CF_3$ | H | $CH_2CHClCO_2$-n-$C_3H_7$ (isomer-2) | O | O |
| 14-8 | Cl | F | $OCH_3$ | Q1 | $CH_3$ | $CF_3$ | H | $CH_2CHClCO_2$-n-$C_4H_9$ (isomer-1) | O | O |
| 14-9 | Cl | F | $OCH_3$ | Q1 | $CH_3$ | $CF_3$ | H | $CH_2CHClCO_2$-n-$C_4H_9$ (isomer-2) | O | O |

TABLE XIV-continued

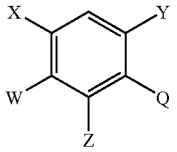

| No. | X | Y | W | Q | $R_1$ | $R_2$ | $R_3$ | Z | $R_8$ | $R_9$ |
|---|---|---|---|---|---|---|---|---|---|---|
| 14-10 | Cl | F | $OCH_3$ | Q1 | $CH_3$ | $CF_3$ | H | $CH_2CHClCO_2$-n-$C_5H_{11}$ (isomer-1) | O | O |
| 14-11 | Cl | F | $OCH_3$ | Q1 | $CH_3$ | $CF_3$ | H | $CH_2CHClCO_2$-n-$C_5H_{11}$ (isomer-2) | O | O |
| 14-12 | Cl | F | $OCH_3$ | Q1 | $CH_3$ | $CF_3$ | H | $CH_2CHClCO_2$-n-$C_6H_{13}$ (isomer-1) | O | O |
| 14-13 | Cl | F | $OCH_3$ | Q1 | $CH_3$ | $CF_3$ | H | $CH_2CHClCO_2$-n-$C_6H_{13}$ (isomer-2) | O | O |
| 14-14 | Cl | F | $OCH_3$ | Q1 | $CH_3$ | $CF_3$ | H | $CH_2CHClCO_2$-i-$C_4H_9$ (isomer-1) | O | O |
| 14-15 | Cl | F | $OCH_3$ | Q1 | $CH_3$ | $CF_3$ | H | $CH_2CHClCO_2$-i-$C_4H_9$ (isomer-2) | O | O |
| 14-16 | Cl | F | $OCH_3$ | Q1 | $CH_3$ | $CF_3$ | H | $CH_2CHClCO_2$-i-$C_5H_{11}$ (isomer-1) | O | O |
| 14-17 | Cl | F | $OCH_3$ | Q1 | $CH_3$ | $CF_3$ | H | $CH_2CHClCO_2$-i-$C_5H_{11}$ (isomer-2) | O | O |
| 14-18 | Cl | F | $OCH_3$ | Q1 | $CH_3$ | $CF_3$ | H | $CH_2CHClCO_2$-t-$C_4H_9$ | O | O |
| 14-19 | Cl | F | $OCH_3$ | Q1 | $CH_3$ | $CF_3$ | H | $CH_2CHClCO_2$—$CH_2C{\equiv}CH$ (isomer-1) | O | O |
| 14-20 | Cl | F | $OCH_3$ | Q1 | $CH_3$ | $CF_3$ | H | $CH_2CHClCO_2$—$CH_2C{\equiv}CH$ (isomer-2) | O | O |
| 14-21 | Cl | F | $OCH_3$ | Q1 | $CH_3$ | $CF_3$ | H | $CH_2CHClCO_2CH_2CF_3$ | O | O |
| 14-22 | Cl | F | $OCH_3$ | Q1 | $CH_3$ | $CF_3$ | H | $CH_2CHClCO_2$—$CH_2CF_2CHF_2$ | O | O |
| 14-23 | Cl | F | $OCH_3$ | Q1 | $CH_3$ | $CF_3$ | H | $CH_2CHClCO_2CH_2CF_2CF_2CF_3$ (isomer-1) | O | O |
| 14-24 | Cl | F | $OCH_3$ | Q1 | $CH_3$ | $CF_3$ | H | $CH_2CHClCO_2CH_2CF_2CF_2CF_3$ (isomer-2) | O | O |
| 14-25 | Cl | F | $OCH_3$ | Q1 | $CH_3$ | $CF_3$ | H | $CH_2CHClCO_2CH_2CH_2OCH_3$ | O | O |
| 14-26 | Cl | F | $OCH_3$ | Q1 | $CH_3$ | $CF_3$ | H | $CH_2CHClCO_2CH_2CH_2OC_2H_5$ | O | O |
| 14-27 | Cl | F | $OCH_3$ | Q1 | $CH_3$ | $CF_3$ | H | $CH_2CHClCO_2CH_2CH_2OPh$ (isomer-1) | O | O |
| 14-28 | Cl | F | $OCH_3$ | Q1 | $CH_3$ | $CF_3$ | H | $CH_2CHClCO_2CH_2CH_3OPh$ (isomer-2) | O | O |
| 14-29 | Cl | F | $OCH_3$ | Q1 | $CH_3$ | $CF_3$ | H | $CH_2CHClCO_2$—$CH_2CH_2CN$ | O | O |
| 14-30 | Cl | F | $OCH_3$ | Q1 | $CH_3$ | $CF_3$ | H | $CH_2CHClCO_2CH_2CH_2BrCH_2Br$ (isomer-1) | O | O |
| 14-31 | Cl | F | $OCH_3$ | Q1 | $CH_3$ | $CF_3$ | H | $CH_2CHClCO_2CH_2CH_2BrCH_2Br$ (isomer-2) | O | O |
| 14-32 | Cl | F | $OCH_3$ | Q1 | $CH_3$ | $CF_3$ | H | $CH_2CHBrCO_2C_2H_5$ (isomer 1) | O | O |
| 14-33 | Cl | F | $OCH_3$ | Q1 | $CH_3$ | $CF_3$ | H | $CH_2CHBrCO_2C_2H_5$ (isomer 2) | O | O |
| 14-34 | Cl | F | $OCH_3$ | Q1 | $CH_3$ | $CF_3$ | H | $CH_2C(CH_3)ClCO_2C_2H_5$ | O | O |
| 14-35 | Cl | F | $OCH_3$ | Q1 | $CH_3$ | $CF_3$ | H | $CH_2C(CH_3)ClCO_2$-n-$C_3H_7$ | O | O |
| 14-36 | Cl | F | $OCH_3$ | Q1 | $CH_3$ | $CF_3$ | H | $CH_2C(CH_3)ClCO_2$-n-$C_4H_9$ | O | O |
| 14-37 | Cl | F | $OCH_3$ | Q1 | $CH_3$ | $CF_3$ | H | $CH_2C(CH_3)ClCO_2$-n-$C_5H_{11}$ | O | O |
| 14-38 | Cl | F | $OCH_3$ | Q1 | $CH_3$ | $CF_3$ | H | $CH_2C(CH_3)ClCO_2$-n-$C_6H_{13}$ | O | O |
| 14-39 | Cl | F | $OCH_3$ | Q1 | $CH_3$ | $CF_3$ | H | $CH_2C(CH_3)ClCO_2$-i-$C_3H_7$ | O | O |
| 14-40 | Cl | F | $OCH_3$ | Q1 | $CH_3$ | $CF_3$ | H | $CH_2C(CH_3)ClCO_2$-i-$C_4H_9$ | O | O |
| 14-41 | Cl | F | OCH3 | Q1 | $CH_3$ | $CF_3$ | H | $CH_2C(CH_3)ClCO_2$—$CH_2Ph$ | O | O |
| 14-42 | Cl | F | $OCH_3$ | Q1 | $CH_3$ | $CF_3$ | H | $CH_2C(CH_3)ClCO_2$—$CH{=}CH_2$ | O | O |
| 14-43 | Cl | F | $OCH_3$ | Q1 | $CH_3$ | $CF_3$ | H | $CH_2C(CH_3)ClCO_2$—$CH_2CH{=}CH_2$ | O | O |
| 14-44 | Cl | F | $OCH_3$ | Q1 | $CH_3$ | $CF_3$ | H | $CH_2C(CH_3)ClCO_2$—$CH_2C{\equiv}CH$ | O | O |
| 14-45 | Cl | F | $OCH_3$ | Q1 | $CH_3$ | $CF_3$ | H | $CH_2C(CH_3)ClCO_2$—$CH_2CF_2CHF_2$ | O | O |
| 14-46 | Cl | F | $OCH_3$ | Q1 | $CH_3$ | $CF_3$ | H | $CH_2C(CH_3)ClCO_2$—$CH(CF_3)_2$ | O | O |
| 14-47 | Cl | F | $OCH_3$ | Q1 | $CH_3$ | $CF_3$ | H | $CH_2C(CH_3)ClCO_2$—$CH_2CH_2OCH_3$ | O | O |
| 14-48 | Cl | F | $OCH_3$ | Q1 | $CH_3$ | $CF_3$ | H | $CH_2C(CH_3)ClCO_2$—$CH_2CH_2SCH_3$ | O | O |
| 14-49 | Cl | F | $OCH_3$ | Q1 | $CH_3$ | $CF_3$ | H | $CH_2C(CH_3)ClCO_2$-tetrahydrofurfuryl | O | O |
| 14-50 | Cl | F | $OCH_3$ | Q1 | $CH_3$ | $CF_3$ | H | $CH_2C(CH_2CO_2CH_3)ClCO_2C_2H_5$ | O | O |
| 14-51 | Cl | F | $OCH_3$ | Q1 | $CH_3$ | $CF_3$ | H | $CH_2C(CN)ClCO_2C_2H_5$ | O | O |
| 14-52 | Cl | F | H | Q5 | $CHF_2$ | $CH_3$ | — | $CH_2CHClCO_2C_2H_5$ | — | — |
| 14-53 | Cl | F | $OCH_3$ | Q6 | — | — | — | $CH_2CHClCO_2C_2H_5$ | O | O |
| 14-54 | Cl | F | $CH_3$ | Q1 | $CH_3$ | $CF_3$ | H | $CH_2CClCOOCH_2CH_3$ | O | O |
| 14-55 | Cl | F | $CH_3$ | Q1 | $CH_3$ | $CF_3$ | H | $CH_2CClCOOCH_2CH_3$ | O | O |
| 14-56 | Cl | F | $OCH_3$ | Q3 | $CH_3$ | $CF_3$ | Cl | $CH_2CClCOOCH_2CH_3$ | — | — |
| 14-57 | Cl | H | H | Q1 | $CH_3$ | $CF_3$ | H | CO-phenyl | O | O |
| 14-58 | Cl | H | H | Q1 | $CH_3$ | $CF_3$ | H | (cis)CHCH-2-naphthyl | O | O |
| 14-59 | Cl | H | H | Q1 | $CH_3$ | $CF_3$ | H | (trans)CHCH-2-naphthyl | O | O |
| 14-60 | Cl | F | H | Q1 | $CH_3$ | $CF_3$ | H | $CH_2(Cl)CHCOOCH_2CH_3$ | O | O |
| 14-61 | Cl | F | $OCH_3$ | Q5 | $CH_3$ | $CF_3$ | H | $CH_2(Cl)CHCOOCH_2CH_3$ | O | O |
| 14-62 | Cl | F | $OCH_2CH_3$ | Q1 | $CH_3$ | $CF_3$ | H | Cl | O | O |
| 14-63 | Cl | F | $OCH_2CH_3$ | Q1 | $CH_3$ | $CF_3$ | H | $CH_2CHClCOOCH_2CH_3$ | O | O |
| 14-64 | Cl | F | $OCH_2CH_3$ | Q1 | $CH_3$ | $CF_3$ | H | $CH_2CHClCOOCH_2CH_3$ | O | O |
| 14-65 | Cl | F | $OCH_2CH_3$ | Q1 | $CH_3$ | $CF_3$ | H | $CH_2CHClCOOCH_2CH_2CH_3$ | O | O |

TABLE XIV-continued

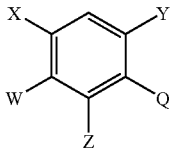

| No. | X | Y | W | Q | $R_1$ | $R_2$ | $R_3$ | Z | $R_8$ | $R_9$ |
|---|---|---|---|---|---|---|---|---|---|---|
| 14-66 | Cl | F | $OCH_2CH_3$ | Q1 | $CH_3$ | $CF_3$ | H | $CH_2CHClCOOCH_2CH_2CH_3$ | O | O |
| 14-67 | Cl | F | $OCH(CH_3)_2$ | Q1 | $CH_3$ | $CF_3$ | H | Cl | O | O |
| 14-68 | Cl | F | $OCH(CH_3)_2$ | Q1 | $CH_3$ | $CF_3$ | H | $CH_2CHClCOOCH_2CH_3$ | O | O |
| 14-69 | Cl | F | $OCH(CH_3)_2$ | Q1 | $CH_3$ | $CF_3$ | H | $CH_2CHClCOOCH_2CH_3$ | O | O |
| 14-70 | $CH_3$ | H | H | Q1 | $CH_3$ | $CF_3$ | H | $CH_2CHClCOOCH_2CH_3$ | O | O |
| 14-71 | $COOCH_3$ | H | H | Q1 | $CH_3$ | $CF_3$ | H | $CH_2CHClCOOCH_2CH_2CH_3$ | O | O |
| 14-72 | Cl | F | $OCH_3$ | Q8 | $CH_3$ | $CF_3$ | H | $CH_2CHClCOOCH_2CH_2CH_3$ | O | O |
| 14-73 | Cl | F | $OCH_3$ | Q1 | $CH_3$ | $CF_3$ | H | $CH_2CHClCOOH$ | O | O |
| 14-74 | Cl | F | $OCH_3$ | Q9 | H | $CF_3$ | Cl | $NO_2$ | — | — |
| 14-75 | Cl | F | $OCH_3$ | Q9 | H | $CF_3$ | Cl | $NH_2$ | — | — |
| 14-76 | Cl | F | $OCH_3$ | Q9 | H | $CF_3$ | Cl | NH-2-naphthoyl | — | — |
| 14-77 | Cl | F | $OCH_3$ | Q9 | H | $CF_3$ | Cl | $CH_2CHClCOOCH_2CH_3$ | — | — |

TABLE XV

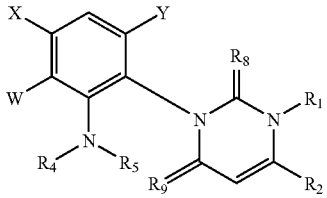

| No. | X | Y | W | $R_1$ | $R_2$ | $R_4$ | $R_5$ | $R_8$ | $R_9$ |
|---|---|---|---|---|---|---|---|---|---|
| 15-1 | Cl | F | $OCH_3$ | $CH_3$ | $CF_3$ | $NH_2$ | H | O | O |
| 15-2 | Cl | F | $OCH_3$ | $CH_3$ | $CF_3$ | c-$C_3H_5$-carbonyl-NH— | H | O | O |
| 15-3 | Cl | F | $OCH_3$ | $CH_3$ | $CF_3$ | benzoyl-NH— | H | O | O |
| 15-4 | Cl | F | $OCH_3$ | $CH_3$ | $CF_3$ | 2,4-$F_2$-benzoyl-NH— | H | O | O |
| 15-5 | Cl | F | $OCH_3$ | $CH_3$ | $CF_3$ | 2-naphthoyl-NH— | H | O | O |
| 15-6 | Cl | F | $OCH_3$ | $CH_3$ | $CF_3$ | ethoxycarbonyl-NH— | H | O | O |
| 15-7 | Cl | F | $OCH_3$ | $CH_3$ | $CF_3$ | phenoxycarbonyl-NH— | H | O | O |
| 15-8 | Cl | F | $OCH_3$ | $CH_3$ | $CF_3$ | 2,4-$F_2$—PhNHC(O)—NH— | H | O | O |
| 15-9 | Cl | F | $OCH_3$ | $CH_3$ | $CF_3$ | $H_5C_2OC(O)N(CH_3)C(O)$—NH— | H | O | O |
| 15-10 | Cl | F | $OCH_3$ | $CH_3$ | $CF_3$ | $H_2C$=CHCH=N— | H | O | O |
| 15-11 | Cl | F | $OCH_3$ | $CH_3$ | $CF_3$ | c-$C_3H_5$—CH=N— | H | O | O |
| 15-12 | Cl | F | $OCH_3$ | $CH_3$ | $CF_3$ | $H_3CC(CH_3)$=N— | H | O | O |
| 15-13 | Cl | F | $OCH_3$ | $CH_3$ | $CF_3$ | $H_3COCH_2C(CH_3)$=N— | H | O | O |
| 15-14 | Cl | F | $OCH_3$ | $CH_3$ | $CF_3$ | $H_3CSCH_2CH_2CH$=N— | H | O | O |
| 15-15 | Cl | F | $OCH_3$ | $CH_3$ | $CF_3$ | $PhCH_2CH$=N— | H | O | O |
| 15-16 | Cl | F | $OCH_3$ | $CH_3$ | $CF_3$ | $H_5C_2OC(O)CH_2C(CH_3)$=N— | H | O | O |
| 15-17 | Cl | F | $OCH_3$ | $CH_3$ | $CF_3$ | $PhCH(CH_3)CH$=N— | H | O | O |
| 15-18 | Cl | F | $OCH_3$ | $CH_3$ | $CF_3$ | 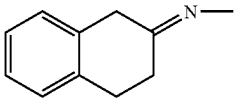 | H | O | O |
| 15-19 | Cl | F | $OCH_3$ | $CH_3$ | $CF_3$ | 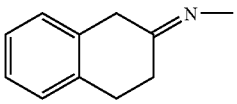 | H | O | O |
| 15-20 | Cl | F | $OCH_3$ | $CH_3$ | $CF_3$ | 2,4-$F_2$—PhCH=N— | H | O | O |
| 15-21 | Cl | F | $OCH_3$ | $CH_3$ | $CF_3$ | $F_3CC(CF_3)$=N— | H | O | O |
| 15-22 | Cl | F | $OCH_3$ | $CH_3$ | $CF_3$ | 2-naphthyl-CH=N— | H | O | O |

TABLE XVI

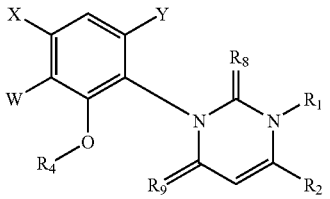

| No. | X | Y | W | $R_1$ | $R_2$ | $R_4$ | $R_8$ | $R_9$ |
|---|---|---|---|---|---|---|---|---|
| 16-1 | Cl | Cl | H | $CH_3$ | $CF_3$ | H | O | O |
| 16-2 | Cl | Cl | H | $CH_3$ | $CF_3$ | $CH_3$ | O | O |
| 16-3 | Cl | Cl | H | $CH_3$ | $CF_3$ | 2,4-$F_2$-benzyl | O | O |
| 16-4 | Cl | Cl | H | $CH_3$ | $CF_3$ | 2,4-$F_2$-benzoyl | O | O |
| 16-5 | Cl | Cl | H | $CH_3$ | $CF_3$ | 2-naphthoyl | O | O |
| 16-6 | Cl | F | $OCH_3$ | $CH_3$ | $CF_3$ | H | O | O |
| 16-7 | Cl | F | $OCH_3$ | $CH_3$ | $CF_3$ | 2-naphthoyl | O | O |
| 16-8 | Cl | F | $OCH_3$ | $CH_3$ | $CF_3$ | $CH_2$-2-naphthyl | O | O |
| 16-9 | Cl | F | $OCH_3$ | $CH_3$ | $CF_3$ | 2-naphthoyl | O | S |
| 16-10 | Cl | F | OCH3 | $CH_3$ | $CF_3$ | 2-naphthoyl | S | O |
| 16-11 | CN | F | $OCH_3$ | $CH_3$ | $CF_3$ | 2-naphthoyl | O | O |
| 16-12 | Cl | H | $OCH_3$ | $CH_3$ | $CF_3$ | 2-naphthoyl | O | O |
| 16-13 | Cl | F | $OCH_3$ | $CH_3$ | $CF_3$ | CONH-phenyl | O | O |
| 16-14 | Cl | F | $OCH_3$ | $CH_3$ | $CF_3$ | $CONHCH_3$ | O | O |

TABLE XVII

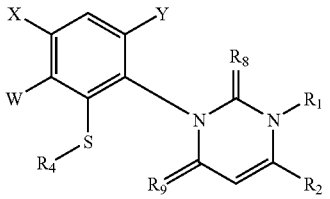

| No. | X | Y | W | $R_1$ | $R_2$ | $R_4$ | $R_8$ | $R_9$ |
|---|---|---|---|---|---|---|---|---|
| 17-1 | Cl | F | $OCH_3$ | $CH_3$ | $CF_3$ | methyl | O | O |
| 17-2 | Cl | F | $OCH_3$ | $CH_3$ | $CF_3$ | isopropyl | O | O |
| 17-3 | Cl | F | $OCH_3$ | $CH_3$ | $CF_3$ | benzyl | O | O |
| 17-4 | Cl | F | $OCH_3$ | $CH_3$ | $CF_3$ | 2-naphthyl | O | O |
| 17-5 | Cl | F | $OCH_3$ | $CH_3$ | $CF_3$ | 2-hydroxyethyl | O | O |
| 17-6 | Cl | F | $OCH_3$ | $CH_3$ | $CF_3$ | benzyl | O | S |
| 17-7 | Cl | F | $OCH_3$ | $CH_3$ | $CF_3$ | benzyl | S | O |
| 17-8 | CN | F | $OCH_3$ | $CH_3$ | $CF_3$ | benzyl | O | O |
| 17-9 | Cl | H | $OCH_3$ | $CH_3$ | $CF_3$ | benzyl | O | O |
| 17-10 | Cl | F | $OCH_2CH_3$ | $CH_3$ | $CF_3$ | benzyl | O | O |

TABLE XVIII $^1$H NMR data

| No. | NMR($CDCl_3$, 300MHz) ppm |
|---|---|
| 1-1 | ($CDCl_3$+$CD_3OD$)4.04(3H, s), 6.19(1H, s), 7.57(1H, d, J=8.6Hz) |
| 1-2 | (DMSO-$d_6$), 3.30(2H, br s), 6.54(1H, s), 8.12(1H, d, J=9.2Hz) |
| 1-3 | ($CDCl_3$+$CD_3OD$)3.85(3H, s), 6.2(1H, s), 6.58(1H, d, J=9.4Hz) |
| 1-4 | 3.57(3H, br q, J=1.2Hz), 3.86(3H, s), 4.04(2H, br s), 6.37(1H, s), 6.66(1H, d, J=9.4Hz) |
| 1-5 | 3.55(3H, br q, J=1.1Hz), 4.04(3H, s), 6.33(1H, s), 7.51(1H, d, J=8.6Hz) |
| 1-6 | 3.57(3H, q, J=1.1Hz), 6.38(1H, s), 7.85(1H, d, J=8.0Hz), 10.57(1H, br) |
| 1-7 | 3.52(3H, q, J=0.7Hz), 3.82(3H, s), 4.13(2H, br), 6.32(1H, s), 6.79(1H, d, J=9.1Hz) |
| 1-8 | 3.48(3H, s), 4.90(3H, br), 6.30(1H, s), 6.69(1H, d, J=9.0Hz) |
| 1-9 | (Acetone-$d_6$)3.68(3H, br q, J=1.4Hz), 4.05(3H, s), 8.03(1H, d, J=9.1Hz) |

TABLE XVIII-continued $^1$H NMR data

| No. | NMR($CDCl_3$, 300MHz) ppm |
|---|---|
| 1-10 | 3.52(3H, br s), 3.86(3H, s), 4.05(2H, br s), 4.63(2H, br s), 6.66(1H, d, J=9.7Hz) |
| 1-11 | 2.74(6H, s), 3.57(3H, br s), 3.84(3H, s), 6.35(1H, s), 7.01(1H, d, J=8.8Hz) |
| 1-12 | 4.05(3H, s), 4.61(2H, s), 6.24(1H, s), 7.52(1H, d, J=8.6Hz) |
| 1-13 | 3.78(3H, s), 5.24(2H, s), 5.41(2H, br s), 6.21(1H, s), 6.56(1H, d, J=9.5Hz) |
| 1-14 | 1.43(3H, m), 4.06(3H, s), 4.31(2H, m), 6.32(1H, s), 7.56(1H, m) |
| 1-15 | 1.15(3H, m), 3.85(3H, s), 3.35(2H, m), 6.48(1H, s), 6.55(1H, m) |
| 1-16 | ($CDCl_3$+$CD_3OD$)3.55(3H, br q, J=1.1Hz), 6.36(1H, s), 6.61(1H, d, J=92) |
| 1-17 | 3.57(3H, d, J=1.2Hz), 6.38(1H, s), 7.67(1H, d, J=8.3Hz), 10.47(1H, br s) |
| 1-18 | 3.51(3H, br q, J=0.9Hz), 4.94(2H, s), 5.66(2H, br s), 6.39(1H, s), 6.65(1H, d, J=9.3Hz) |
| 1-19 | 2.58(1H, m), 3.55(3H, br q, J=1.3Hz), 4.17(2H, br s), 4.7(2H, d, J=2.4Hz), 6.35(1H, s), 6.65(1H, d, J=9.3Hz) |
| 1-20 | 3.57(3H, d, J=0.8Hz), 3.78(3H, s), 4.02(2H, br s), 4.65(2H, dd, J=1.4, 1.9Hz), 6.28(1H, dt, J=15.7, 1.9Hz), 6.65(1H, d, J=9.3Hz), 7.01(1H, dt, J=15.7, 4.4Hz) |
| 1-21 | 1.63–1.94(8H, m), 3.55(3H, s), 3.97(2H, s), 4.8(1H, m), 6.34(1H, s), 6.65(1H, d, J=9.6Hz) |
| 1-22 | 3.54(3H, br q, J=1.1Hz), 3.94(2H, br s), 5.0(2H, s), 6.34(1H, s), 6.69(1H, d, J=9.4Hz), 7.3–7.5(5H, m) |
| 1-23 | 3.58(3H, br q, J=1.2Hz), 4.15(2H, br s), 6.38(1H, s), 6.78(1H, d, J=9.2Hz), 7.22(1H, m), 8.36(2H, m) |
| 1-30 | 3.52(3H, br q, J=1.1Hz), 3.75(3H, s), 6.31(1H, s), 7.22(1H, d, J=8.8Hz) |
| 1-31 | 2.87(3H, s), 2.96(3H, s), 3.53(3H, s), 3.64(3H, s), 6.30(1H, s), 6.86(1H, d, J=8.9Hz), 7.68(1H, s) |
| 1-32 | 1.83(4H, m), 3.21(4H, m), 3.55(3H, br s), 3.72(3H, s), 6.34(1H, s), 6.86(1H, d, J=8.9Hz) |
| 1-33 | 1.27(3H, t, J=7.1Hz), 4.20(2H, q, J=7.1Hz), 6.21(1H, s), 7.62(1H, d, J=8.8Hz) |
| 1-34 | 1.26(3H, t, J=7.1Hz), 4.16(2H, q, J=7.1Hz), 3.53(3H, s), 6.35(1H, s), 7.70(1H, d, J=8.5Hz) |
| 1-36 | 2.40(3H, d, J=1.1Hz), 3.54(3H, d, J=1.3Hz), 6.33(1H, s), 7.51 (1H, d, J=8.5Hz) |
| 1-37 | 2.23(3H, d, J=0.9Hz), 3.57(3H, d, J=1.1Hz), 6.38(1H, s), 6.74(1H, d, J=9.4Hz) |
| 1-38 | 3.57(3H, d, J=1.1Hz), 4.17(2H, br s), 6.37(1H, s), 6.50(1H, t, J=74.0Hz), 6.72(1H, d, J=9.1Hz) |
| 1-40 | 3.56(3H, d, J=1.1Hz), 3.96(3H, s), 6.36(1H, s), 7.07(1H, d, J=8.7Hz) |
| 1-41 | 3.54(3H, d, J=1.1Hz), 6.38(1H, s), 6.89(2H, m), 7.00(1H, dd, J=7.9, 1.5Hz), 7.26(1H, td, J=7.7, 1.5Hz), 7.85(2H, br s) |
| 1-42 | 3.55(3H, d, J=1.2Hz), 6.38(1H, s), 7.38(1H, dd, J=7.9, 1.4Hz), 7.66(1H, td, J=7.9, 1.4Hz), 7.79(1H, td, J=7.9, 1.4Hz), 8.27(1H, dd, J=7.9, 1.4Hz) |
| 1-43 | 3.56(3H, d, J=1.1Hz, 6.39(1H, s), 7.58(1H, d, J=8.2Hz), 8.05(1H, dd, J=8.2, 1.8Hz), 8.54(1H, d, J=1.8Hz) |
| 1-44 | 3.57(3H, d, J=1.1Hz), 6.39(1H, s), 7.13(3H, m) |
| 1-45 | 3.58(3H, d, J=1.2Hz), 6.38(1H, s), 7.87(1H, s), 10.61(1H, br s) |
| 1-46 | 3.55(3H, d, J=1.2Hz), 3.93(3H, s), 6.37(1H, s), 7.27(2H, m), 7.77(1H, dd, J=2.1, 1.0Hz) |
| 1-47 | 3.50(3H, d, J=0.9Hz), 3.81(3H, s), 3.96(2H, s), 6.31(1H, s), 6.88(1H, s) |
| 1-48 | 1.27(3H, t, J=7.1Hz, 1.58(3H, d, J=6.8Hz), 3.55(3H, d, J=1.1Hz), 3.64(2H, br s), 4.22(2H, m), 4.70(1H, q, J=6.8Hz), 6.36(1H, s), 6.38(2H, m), 6.88(1H, d, J=9.2Hz) |
| 1-49 | 1.29(3H, t, J=7.1Hz), 1.68(3H, d, J=6.8Hz), 3.54(3H, d, J=1.0Hz), 4.26(2H, m), 4.82(1H, q, J=6.8Hz), 6.36(1H, s), 7.25(2H, m), 7.74(1H, m) |
| 1-50 | 3.57(3H, q, J=1.2Hz), 6.38(1H, s), 6.65(1H, t, J=71.1Hz), 7.37(1H, dd, J=9.3, 2.7Hz), 7.85(1H, dd, J=2.7, 2.5Hz) |
| 1-51 | 3.49(3H, d, J=1.0Hz), 6.30(3H, m), 6.42(1H, t, J=73.2Hz), 7.8(2H, br s) |
| 1-52 | 3.57(3H, d, J=1.2Hz), 6.40(1H, s), 7.57(1H, d, J=8.2Hz), 8.04(1H, dd, J=8.2, 1.6Hz), 8.53(1H, m) |
| 1-53 | 1.27(1.5H, t, J=7.1Hz), 2.28(1.5H, t, J=7.1Hz), 1.44(1.5Hz, d, J=6.9Hz), 1.45(15H, d, J=6.9Hz), 3.58(3H, s), 4.08(1H, m) 4.20(2H, q, J=7.1Hz), 4.39(0.5H, d, J=7.2Hz), 4.43(0.5H, d J=7.2Hz), 6.26(1H, m), 6.39(2H, m), 6.50(1H, t, J=73.3Hz) |
| 1-54 | 1.27(1.5H, t, J=7.1Hz), 1.28(1.5H, t, J=7.1Hz), 1.44(1.5H, d, J=6.9Hz), 1.46(1.5H, d, J=6.9Hz), 3.57(3H, m), 4.11(1H, m), 4.22(2H, m), 4.35(0.5H, d, J=7.4Hz), 4.43(0.5H, d, J=7.1Hz), |

TABLE XVIII-continued

| No. | $^1$H NMR data NMR($CDCl_3$, 300MHz) ppm |
|---|---|
| | 6.36(0.5H, s), 6.38(0.5H, s), 6.49(1H, m), 6.62(1H, dd, J=9.1, 2.0Hz) |
| 1-55 | 1.22(1.5H, t, J=7.1Hz), 1.23(1.5H, t, J=7.1Hz), 1.36(1.5H, d, J=6.9Hz), 1.38(1.5H, d, J=6.9Hz), 3.55(3H, m), 3.82(1.5H, s), 3.86(1.5H, s), 4.0–4.4(4H, m), 6.36(1H, s), 6.76(0.5H, d, J=9.1Hz), 6.79(0.5H, d, J=9.1Hz) |
| 1-56 | 4.73(2H, br s), 5.50(3H, br), 6.16(1H, s), 6.53(1H, d, J=9.3Hz) |
| 1-57 | 4.42(2H, br s), 4.70(2H, br s), 4.72(2H, s), 6.16(1H, s), 6.60(1H, d, J=9.1Hz) |
| 1-58 | 3.77(3H, s), 4.64(2H, br s), 4.87(2H, s), 5.28(2H, br s), 6.27(1H, s), 6.52(1H, d, J=9.2Hz), |
| 1-59 | 1.29(3H, t, J=7.1Hz), 3.55(3H, q, J=1.0Hz), 4.23(2H, q, J=7.1Hz), 4.64(2H, s), 4.82(2H, br s), 6.35(1H, s), 6.60(1H, d, J=9.2Hz) |
| 1-60 | 1.27(3H, t, J=7.1Hz), 1.659(1.5H, d, J=7.0Hz), 1.666(1.5H, d, J=7.0Hz), 3.55(3H, s), 4.20(2H, q, J=7.1Hz), 4.73(1H, m), 6.346(0.5H, s), 6.355(0.5H, s), 6.61(1H, d, J=9.3Hz) |
| 1-61 | 1.41(3H, t, J=7.0Hz), 3.52(3H, q, J=1.0Hz), 4.04(2H, q, J=7.0Hz), 4.10(2H, br s), 6.32(1H, s), 6.62(1H, d, J=9.5Hz) |
| 1-62 | 1.16(3H, t, J=7.1Hz), 1.42(3H, t, J=7.1Hz), 2.99(2H, q, J=7.1Hz), 3.57(3H, q, J=1.1Hz), 4.03(2H, q, J=7.1Hz), 4.14(1H, br s), 6.35(1H, s), 6.63(1H, d, J=9.4Hz) |
| 1-63 | 1.35(6H, d, J=6.2Hz), 3.55(3H, q, J=1.2Hz), 3.95(2H, br s), 4.50(1H, q, J=6.2Hz), 6.34(1H, s), 6.66(1H, d, J=9.4Hz) |
| 1-64 | 1.06(3H, t, J=6.3Hz), 1.37(6H, d, J=6.2Hz), 3.57(3H, q, J=1.2Hz), 3.83(2H, br s), 4.52(1H, q, J=6.2Hz), 6.35(1H, s), 6.70(1H, d, J=9.3Hz) |
| 1-65 | 7.62(1H, d, J=8.5Hz), 8.37(1H, d, J=2.6Hz, 8.4Hz), 8.83(1H, d, J=2.6Hz) |
| 1-66 | 3.56(3H, s), 6.37(1H, s), 6.86(1H, d, J=8.4Hz), 7.77(1H, d, J=8.4Hz), 10.75(1H, broad) |
| 1-67 | 3.56(3H, s), 6.37(1H, s), 8.55(1H, s) |
| 1-68 | 3.56(3H, s), 6.39(1H, s), 7.45(1H, d, J=8.7Hz), 7.64(1H, 2d, J=1.7Hz, 6.7Hz), 8.13(1H, d, J=1.7Hz) |
| 1-69 | 4.15(3H, s), 6.14(1H, s), 8.51(1H, s), 12.8(1H, broad) |
| 1-70 | 6.26(1H, s), 7.62(1H, 2d, J=6.1Hz, 8.3Hz, 8.3(1H, broad) |
| 1-71 | 3.56(3H, s), 4.8(3H, broad), 6.38(1H, s), 6.59(1H, d, J=8.7Hz), 6.85(1H, d, J=8.7Hz) |
| 1-72 | 3.56(3H, s), 3.89(3H, s), 6.37(1H, s), 6.75(1H, d, J=8.7Hz), 6.87(1H, d, J=8.7Hz) |
| 1-73 | 3.55(3H, s), 3.75(2H, s), 6.36(1H, s), 6.73(2H, m), 7.01(1H, 2d, J=2.4Hz, 6.9Hz) |
| 2-1 | 2.04(3H, s), 3.57(3H, br q, J=1.1Hz), 3.86(3H, s), 6.30(1H, s), 7.22(1H, d, J=9.6Hz) |
| 2-2 | 2.29(3H, s), 2.33(3H, s), 3.53(3H, br s), 3.78(3H, s), 6.3(1H, s), 7.42(1H, d, J=8.8Hz) |
| 2-3 | 1.14(9H, s), 3.56(3H, s), 3.82(3H, s), 6.29(1H, s), 7.19(1H, d, J=9.0Hz), 7.61(1H, br s) |
| 2-4 | 3.49(3H, br q, J=1.0Hz), 3.75(3H, s), 5.70–5.79(2H, m), 6.26(1H, s), 6.40–6.55(4H, m), 7.42(1H, d, J=8.7Hz) |
| 2-5 | 1.95(3H, s), 3.55(3H, br s), 3.84(3H, s), 5.45(1H, s), 5.70(1H, s), 6.27(1H, s), 7.20(1H, d, J=9.0Hz), 7.62(1H, br s) |
| 2-6 | 1.90(3H, s), 1.91(3H, s), 3.49(3H, br s), 3.79(3H, s), 5.46(2H, s), 5.64(1H, s), 5.66(1H, s), 6.27(1H, s), 7.30(1H, d, J=8.8Hz) |
| 2-7 | 1.86(3H, s), 2.05(3H, s), 3.56(3H, br s), 3.82(3H, s), 5.66(1H, br s), 6.27(1H, s), 7.17(1H, d, J=9.0Hz), 7.23(1H, br s) |
| 2-8 | 1.85(6H, m), 2.12(6H, m), 3.47(3H, br q, J=1.0Hz), 3.77(3H, s), 5.91(1H, m), 5.98(1H, m), 6.25(1H, s), 7.34(1H, d, J=8.7Hz) |
| 2-9 | ($CDCl_3$+$CD_3OD$)3.86(3H, s), 6.16(1H, s), 7.37(1H, d, J=8.9Hz) |
| 2-10 | 3.54(3H, br s), 3.86(3H, s), 6.31(1H, s), 7.32(1H, d, J=9.0Hz) |
| 2-11 | ($CDCl_3$+$CD_3OD$)3.55(3H, br s), 4.87(2H, s), 6.35(1H, s), 7.44(1H, d. J=8.7Hz) |
| 2-12 | ($CDCl_3$+$CD_3OD$)3.59(3H, br s), 3.87(3H, s), 7.37(1H, d, J=8.8Hz) |
| 2-13 | 3.56(3H, br q, J=1.1Hz), 3.89(3H, s), 4.08(2H, s), 6.3(1H, s), 7.25(1H, d, J=9Hz) |
| 2-14 | 3.52(3H, br q, J=1.1Hz), 3.74(2H, m), 3.85(3H, s), 6.39(1H, s), 7.53(1H, d, J=9.3Hz), 9.03(1H, m) |
| 2-15 | 3.56(3H, s), 3.91(3H, s), 3.95(3H, s), 6.29(1H, s), 7.24(1H, d, J=9.0Hz), 9.00(1H, s) |
| 2-16 | 1.27(3H, t, J=7.1Hz), 1.28(3H, t, J=7.1Hz), 3.42(2H, s), 3.57(3H, br s), 4.04(2H, s), 4.10–4.30(4H, m), 6.40(1H, s), 7.33(1H, d, J=9.8Hz), 8.07(1H, s) |
| 2-17 | 0.95(2H, m), 1.10(2H, m), 1.50(1H, m), 3.55(3H, s), 6.37(1H, s), 7.22(1H, d, J=9.0Hz), 7.92(1H, br s), 8.41(1H, br, s) |

TABLE XVIII-continued

| No. | $^1$H NMR data NMR($CDCl_3$, 300MHz) ppm |
|---|---|
| 2-18 | 0.70–1.20(8H, m), 1.96(1H, m), 2.15(1H, m), 3.54(3H, br s), 3.75(3H, s), 6.35(1H, s), 7.38(1H, d, J=8.6Hz) |
| 2-19 | 1.40(5H, m), 1.70(5H, m), 2.25(1H, m), 3.32(3H, s), 3.82(3H, s), 6.34(1H, s), 7.17(1H, d, J=9.0Hz), 7.68(3H, s) |
| 2-20 | 1.20(10H, m), 1.70(10H, m), 2.50(2H, m), 3.50(3H, s), 3.68(3H, s), 6.31(1H, s), 7.36(1H, m) |
| 2-21 | 3.37(3H, s), 3.44(3H, s), 3.55(3H, br s), 4.18(3H, s), 6.33(1H, s), 7.43(1H, d, J=8.8Hz) 3.2(3H, s), 3.55(3H, s), 3.96(3H, s), 6.35(1H, s), 6.48(1H, br s), 7.29(1H, d, J=8.8Hz) |
| 2-22 | 3.52(3H, br s), 3.64(3H, s), 6.29(1H, s), 6.85(1H, d, J=9.1Hz), 7.4(5H, m), 7.68(1H, s) |
| 2-23 | 2.39(3H, s), 3.52(3H, s), 3.82(3H, s), 6.23(1H, s), 7.20(1H, d, J=9.0Hz), 7.32(2H, m), 7.53(2H, m), 8.02(1H, s) |
| 2-24 | 2.42(3H, s), 3.53(3H, s), 3.82(3H, s), 6.22(1H, s), 7.20(1H, d, J=9.0Hz), 7.26(2H, d, J=7.8Hz), 7.67(2H, d, J=7.8Hz), 7.91(1H, s) |
| 2-25 | 2.32(3Hx2, s), 3.28(3H, s), 3.82(3H, s), 6.02(1H, s), 7.10(4H, d, J=7.9Hz), 7.26(1H, d, J=9.0Hz), 7.73(4H, m) |
| 2-26 | 2.40(3H, s), 3.44(3H, s), 3.54(3H, d, J=1.1Hz), 6.29(1H, s), 6.55(1H, br s), 7.18(1H, d, J=8.9Hz), 7.25(2H, d, J=8.3Hz), 7.68(2H, d, J=8.3Hz) |
| 2-27 | 1.26(3H, t, J=7.7Hz), 2.71(2H, q, J=7.7Hz), 3.54(3H, s), 3.83(3H, s), 6.23(1H, s), 7.21(1H, d, J=9.0Hz), 7.29(2H, d, J=8.2Hz), 7.70(2H, d, J=8.2Hz), 7.86(1H, br s) |
| 2-28 | 1.26(3H, t, J=7.6Hz), 2.71(2H, q, J=7.6Hz), 3.51(3H, br s), 4.78 (2H, s), 6.25(1H, s), 7.28(3H, m), 7.73(2H, m), 7.84(1H, br s) |
| 2-29 | 0.95(6H, t, J=7.2Hz), 1.66(4H, m), 2.64(4H, m), 3.53(3H, br s), 3.83(3H, s), 6.23(1H, s), 7.21(1H, d, J=9.3Hz), 7.27(4H, m), 7.70(2H, m), 8.00(2H, m) |
| 2-30 | 1.35(9H, s), 3.55(3H, s), 3.83(3H, s), 6.23(1H, s), 7.20(1H, m), 7.49(2H, d, J=8.6Hz), 7.73(2H, d, J=8.6Hz), 7.88(1H, br s) |
| 2-31 | 3.54(3H, s), 3.83(3H, s), 5.40(1H, d, J=10.9Hz), 5.87(1H, d, J=17.6Hz), 6.78(1H, dd, J=17.6, 10.9Hz), 7.22(1H, d, J=9.0Hz), 7.49(2H, d, J=8.2Hz), 7.75(1H, d, J=82Hz), 8.01(1H, br s) |
| 2-32 | 2.31(3H, s), 2.32(3H, s), 3.54(3H, d, J=1.0Hz), 3.82(3H, s), 6.23 (1H, s), 7.19(1H, d, J=9.1Hz), 7.22(1H, d, J=7.8Hz), 7.50(1H, dd, J=7.8, 1.7Hz), 7.56(1H, br s), 7.86(1H, br s) |
| 2-33 | 3.62(3H, s), 3.84(3H, s), 6.25(1H, s), 7.25(1H, d, J=8.9Hz), 7.75 (2H, d, J=8.3Hz), 7.89(2H, d, J=8.3Hz), 7.92(2H, br s) |
| 2-34 | 3.54(3H, br s), 3.84(3H, s), 6.26(1H, s), 7.30(1H, d, J=9.3Hz), 7.72(4H, m), 7.94(2H, m), 8.17(2H, m) |
| 2-36 | 3.56(3H, d, J=1.1Hz), 3.85(3H, s), 4.64(2H, s), 6.25(1H, s), 7.24(1H, d, J=9.0Hz), 7.52(2H, d, J=8.3Hz), 7.79(2H, d, J=8.3Hz), 7.91(1H, br s) |
| 2-37 | 3.53(3H, s), 3.83(3H, s), 6.25(1H, s), 7.20(1H, d, J=9.0Hz), 7.45(3H, m), 7.63(4H, m), 7.84(2H, d, J=8.2Hz), 8.13(1H, s) |
| 2-38 | 3.32(3H, s), 3.86(3H, s), 6.08(1H, s), 7.52(15H, m), 7.95(4H, m) |
| 2-39 | 3.56(3H, br s), 3.89(3H, s), 6.27(1H, s), 7.15–7.3(2H, m), 7.24(1H, d, J=9.1Hz), 7.54(1H, m), 7.92(1H, m), 8.43(1H, br d, J=13.8Hz) |
| 2-40 | 3.53(3H, br s), 3.83(3H, s), 6.23(1H, s), 7.12(2H, m), 7.22(1H, d, J=9.1Hz), 7.79(2H, m), 7.97(1H, br s) |
| 2-41 | 3.57(3H, br q, J=1.1Hz), 3.9(3H, s), 6.29(1H, s), 7.2(1H, m), 7.26(1H, d, J=9.1Hz), 7.36(1H, m), 7.63(1H, m), 8.29(1H, d, J=11.1Hz) |
| 2-42 | 3.56(3H, br s), 3.89(3H, s), 6.27(1H, s), 6.97(2H, m), 7.25(1H, d, J=9Hz), 7.97(1H, m), 8.37(1H, br d, J=13.3Hz) |
| 2-43 | 3.44(3H, br s), 3.96(3H, s), 6.24(1H, s), 6.64(2H, m), 6.86(2H, m), 7.35(1H, d, J=8.8Hz), 7.78(2H, m) |
| 2-44 | 3.88(3H, s), 6.26(1H, s), 6.98(2H, m), 7.23(1H, d, J=9Hz), 7.96(1H, m), 8.46(1H, m) |
| 2-45 | 3.43(3H, br q, J=1.3Hz), 5.1(2H, s), 6.36(1H, s), 6.9–7.15(4H, m), 7.77(1H, d, J=9.1Hz), 7.7–7.9(2H, m) |
| 2-46 | 3.52(3H, s), 3.91(3H, s), 6.75–7.05(2H, m), 6.95(1H, s), 7.39(1H, d, J=8.9Hz), 8.03(1H, m), 8.56(1H, m) |
| 2-47 | 3.55(3H, br s), 3.91(3H, s), 6.32(1H, s), 6.93(2H, m), 7.25(1H, d, J=8.9Hz), 7.39(1H, m), 8.03(1H, br s) |
| 2-48 | 3.55(3H, br q, J=1.0Hz), 3.83(3H, s), 6.26(1H, s), 7.24(1H, d, J=9.1Hz), 7.25(1H, m), 7.54(1H, m), 7.65(1H, m), 8.05(1H, br s) |
| 2-49 | 3.39(3H, br s), 3.77(3H, s), 6.1(1H, s), 7.10–7.40(2H, m), 7.34(1H, d, J=8.8Hz), 7.60–8.00(4H, m) |
| 2-50 | 3.54(3H, br s), 3.81(3H, s), 6.26(1H, s), 7.01(1H, m), 7.25(1H, d, J=9.3Hz), 7.31(2H, m), 8.28(1H, s) |

TABLE XVIII-continued $^1$H NMR data

| No. | NMR($CDCl_3$, 300MHz) ppm |
|---|---|
| 2-51 | 3.43(3H, br s), 3.79(3H, s), 6.15(1H, s), 6.95–7.75(7H, m) |
| 2-53 | 3.56(3H, d, J=1.2Hz), 3.91(3H, s), 6.32(1H, s), 7.26(1H, d, J=9.0Hz), 7.35(1H, ddd, J=8.6, 6.1, 2.5Hz), 7.42(2H, m), 7.52(1H, dd, J=7.4, 1.2Hz), 7.83(1H, br s) |
| 2-54 | 3.53(3H, s), 3.82(3H, s), 6.26(1H, s), 7.22(1H, d, J=9.0Hz), 7.39 (1H, dd, J=7.8, 7.9Hz), 7.53(1H, m), 7.62(1H, m), 7.77(1H, m), 8.06(1H, br s) |
| 2-55 | 3.36(3H, s), 3.81(3H, s), 6.11(1H, s), 7.30(3H, m), 7.43(2H, m), 7.76(4H, m) |
| 2-56 | 3.53(3H, s), 3.83(3H, s), 6.23(1H, s), 7.23(1H, d, J=9.0Hz), 7.44(2H, d, J=8.7Hz), 7.72(2H, d, J=8.7Hz), 7.92(1H, s) |
| 2-57 | 3.32(3H, s), 3.78(3H, s), 6.06(1H, s), 7.34(5H, m), 7.80(4H, m) |
| 2-58 | 3.56(3H, d, J=1.0Hz), 3.89(3H, s), 6.32(1H, s), 7.27(1H, d, J=9.0Hz), 7.31(1H, dd, J=8.1, 1.9Hz), 7.47(2H, m), 7.92(1H, br s) |
| 2-59 | 3.55(3H, d, J=1.1Hz), 3.84(3H, s), 6.25(1H, s), 7.25(1H, d, J=9.1Hz), 7.54(1H, d, J=8.3Hz), 7.60(1H, dd, J=8.3, 2.0Hz) 7.88(1H, br s), 7.89(1H, d, J=2.0Hz) |
| 2-60 | 3.54(3H, br s), 3.83(3H, s), 6.26(1H, s), 7.24(1H, d, J=9.0Hz), 7.34(2H, m), 7.65–7.75(2H, m), 7.92–8.25(4H, m) |
| 2-61 | 3.53(3H, s), 3.82(3H, s), 6.23(1H, s), 7.22(1H, d, J=9.0Hz), 7.61(4H, m), 7.95(1H, s) |
| 2-62 | 3.33(3H, s), 3.80(3H, s), 6.06(1H, s), 7.31(1H, d, J=9.0Hz), 7.51(4H, m), 7.73(4H, m) |
| 2-63 | 3.54(3H, d, J=1.1Hz), 3.83(3H, s), 3.87(3H, s), 6.22(1H, s), 6.95(2H, d, J=8.8Hz), 7.21(1H, d, J=9.1Hz), 7.75(2H, d, J=8.8Hz), 7.78(1H, br s) |
| 2-64 | 1.44(3H, t, J=7.0Hz), 3.52(3H, s), 3.82(3H, s), 4.06(2H, q, J=7.0Hz), 6.22(1H, s), 6.90(2H, d, J=9.0Hz), 7.20(1H, d, J=9.0Hz), 7.73(2H, d, J=9.0Hz), 7.91(1H, s) |
| 2-66 | 3.55(3H, d, J=1.0Hz), 3.84(3H, s), 6.25(1H, s), 7.25(1H, d, J=9.1Hz), 7.51(2H, d, J=8.6Hz), 7.85(2H, d, J=8.6Hz), 7.88(1H, br s) |
| 2-67 | 3.85(3H, s), 6.22(1H, s), 7.25(1H, d, J=9.9Hz), 7.76(2H, d, J=8.4Hz), 7.85(2H, d, J=8.4Hz), 7.96(1H, br s) |
| 2-69 | 3.40(3H, br s), 3.79(3H, s), 6.12(1H, s), 7.36(1H, d, J=8.7Hz), 8.06(4H, m), 8.25(4H, m) |
| 2-70 | 3.50(3H, br s), 3.87(3H, s), 6.32(1H, s), 7.51(1H, d, J=8.8Hz), 9.07(2H, m), 9.12(1H, m), 9.91(1H, br s) |
| 2-71 | 3.33(3H, s), 3.77(3H, s), 7.20(4H, m), 7.31(1H, d, J=8.8Hz), 7.92(4H, m) |
| 2-72 | 3.54(3H, s), 3.83(3H, s), 6.24(1H, s), 7.25(3H, m), 7.82(2H, m), 8.02(1H, s) |
| 2-73 | 3.54(3H, br s), 3.83(3H, s), 6.05(2H, s), 6.23(1H, s), 6.85(1H, d, J=7.8Hz), 7.21(1H, d, J=8.8Hz), 7.25–7.34(2H, m), 7.80(1H, br s) |
| 2-74 | 3.52(3H, s), 3.84(3H, s), 6.25(1H, s), 7.24(1H, d, J=9.0Hz), 7.50(4H, m), 7.90(3H, m), 8.20(1H, br s) |
| 2-75 | 3.64(3H, s), 3.85(3H, s), 6.24(1H, s), 7.24(1H, d, J=9.0Hz), 7.80(7H, m), 8.32(1H, s) |
| 2-76 | 3.87(3H, s), 6.1(1H, s), 7.31(1H, d, J=9.0Hz), 7.60(2H, m), 7.80–8.05(5H, m), 8.38(1H, s) |
| 2-77 | 3.83(3H, s), 4.69(2H, s), 6.21(1H, s), 7.35(1H, d, J=8.9Hz), 7.50–7.60(3H, m), 7.80–7.85(4H, m), 8.07(1H, s) |
| 2-78 | 3.56(3H, s), 3.86(3H, s), 6.28(1H, s), 6.49(1H, d, J=15.6H), 7.21(1H, d, J=9.0Hz), 7.39(4H, m), 7.50(2H, m), 7.63(1H, d, J=15.6Hz) |
| 2-79 | 3.57(3H, s), 3.86(3H, s), 6.28(1H, s), 6.54(1H, d, J=15.7Hz), 6.84–6.94(3H, m), 7.22(1H, d, J=9.0Hz), 7.36(1H, br s), 7.48(1H, q, J=7.7Hz), 7.67(1H, d, J=15.7Hz) |
| 2-80 | 2.41(3H, s), 3.57(3H, s), 3.86(3H, s), 6.29(1H, s), 6.40(1H, d, J=15.4Hz), 7.19–7.32(4H, m), 7.33(1H, br s), 7.53(1H, d, J=7.2Hz), 7.93(1H, d, J=15.4Hz) |
| 2-81 | 2.12(3H, d, J=1.3Hz), 3.57(3H, d, J=0.9Hz), 3.88(3H, s), 6.29(1H, s), 7.20(1H, d, J=9.1Hz), 7.36(5H, m), 7.66(1H, br s) |
| 2-82 | 3.57(3H, br s), 3.85(3H, s), 6.29(1H, s), 6.48(1H, d, J=15.6Hz), 7.16(1H, d, J=9.0Hz), 7.28(2H, m), 7.40(1H, dd, J=7.9, 1.6Hz), 7.53(1H, dd, J=7.4, 1.6Hz), 7.67(1H, br s), 7.98(1H, d, J=15.6Hz) |
| 2-83 | 3.46(3H, br s), 3.83(3H, s), 6.24(1H, s), 6.80(1H, d, J=15.5Hz), 6.91(1H, d, J=15.5Hz), 7.30(2H, m), 7.39(2H, m), 7.45(1H, d, J=8.8Hz), 7.56(1H, dd, J=7.6, 1.8Hz), 7.59(1H, dd, J=7.6, 1.8Hz), 8.18(1H, d, J=15.5Hz), 8.20(1H, d, J=15.5Hz) |

TABLE XVIII-continued $^1$H NMR data

| No. | NMR($CDCl_3$, 300MHz) ppm |
|---|---|
| 2-84 | 3.56(3H, br s), 3.84(3H, s), 6.29(1H, s), 6.45(1H, d, J=15.6Hz), 7.18(1H, d, J=9.0Hz), 7.54(2H, d, J=8.6Hz), 7.40(2H, d, J=8.6Hz), 7.55(1H, d, J=15.6Hz), 7.59(1H, br s) |
| 2-85 | 3.56(3H, br s), 3.84(3H, s), 3.85(3H, s), 6.28(1H, s), 6.35(1H, d, J=15.5Hz), 6.89(2H, d, J=8.7Hz), 7.19(1H, d, J=9.0Hz), 7.35(1H, br s), 7.45(2H, d, J=8.7Hz), 7.58(1H, d, J=15.5Hz) |
| 2-86 | 2.60(2H, q, J=7.7Hz), 2.91(2H, t, J=7.7Hz), 3.56(3H, s), 3.69(3H, s), 6.26(1H, s), 7.1–7.3(6H, m) |
| 2-87 | 2.66(2H, m), 2.92(2H, m), 3.55(3H, s), 4.52(2H, s), 6.28(1H, s), 7.1–7.4(6H, m) |
| 2-88 | 1.90(2H, tt, J=7.5, 7.4Hz), 2.29(2H, d, J=7.4Hz), 2.61(2H, t, J=7.5Hz), 3.52(3H, d, J=0.7Hz), 3.84(3H, s), 6.28(1H, s), 7.13–7.32(7H, m) |
| 2-89 | 3.54(3H, s), 3.82(3H, s), 4.02(2H, s), 4.55(2H, s), 6.15(1H, s), 7.16(1H, d, J=9.0Hz), 7.4(5H, m), 8.55(1H, s) |
| 2-90 | 3.56(3H, d, J=1.1Hz), 3.87(3H, s), 6.26(1H, s), 6.55(1H, dd, J=3.6, 1.8Hz), 7.17(1H, dd, J=3.6, 0.5Hz), 7.22(1H, d, J=9.1Hz), 7.54(1H, dd, J=1.8, 0.5Hz), 8.18(1H, br s) |
| 2-91 | 2.25(3H, s), 3.46(3H, s), 3.81(3H, s), 6.25(1H, s), 6.39(1H, s), 7.18(1H, d, J=9.0Hz), 7.39(1H, s), 8.30(1H, s) |
| 2-92 | 3.56(3H, d, J=0.8Hz), 3.85(3H, s), 6.28(1H, s), 6.39(1H, d, J=15.2Hz), 6.48(1H, dd, J=3.4, 1.8Hz), 6.60(1H, d, J=3.4Hz), 7.19(1H, d, J=9.0Hz), 7.34(1H, br s), 7.40(1H, d, J=15.2Hz), 7.48(1H, d, J=1.8Hz) |
| 2-93 | 3.45(3H, s), 3.66(3H, s), 3.80(2H, s), 6.16(1H, s), 7.00(4H, m), 7.55(1H, br s) |
| 2-94 | 2.46(3H, s), 3.56(3H, s), 3.88(3H, s), 6.26(1H, s), 6.94(1H, m), 7.20(1H, d, J=9.0Hz), 7.36(1H, m), 7.65(1H, s) |
| 2-95 | 2.45(3H, s), 3.47(3H, s), 3.78(3H, s), 6.17(1H, s), 6.70(1H, m), 7.13(1H, d, J=9.0Hz), 7.32(1H, m), 7.63(1H, s) |
| 2-96 | 2.41(6H, s), 3.26(3H, s), 3.78(3H, s), 5.97(1H, s), 6.59(2H, m), 7.24(1H, d, J=9.0Hz), 7.39(2H, m) |
| 2-97 | 3.31(3H, s), 3.84(3H, s), 6.03(1H, s), 7.05(2H, m), 7.40(2H, m), 7.70(3H, m) |
| 2-98 | 3.54(3H, s), 3.84(3H, s), 6.25(1H, s), 7.25(1H, d, J=9.7Hz), 7.41(1H, dd, J=7.7, 4.8Hz), 8.01(1H, d, J=7.7Hz), 8.32(1H, br s), 8.78(1H, br s), 9.01(1H, br s) |
| 2-100 | 3.42(3H, q, J=1.0Hz), 3.79(3H, s), 6.12(1H, s), 7.35(1H, d, J=8.6Hz), 7.56(1H, d, J=8.0Hz), 7.39(1H, d, J=8.0Hz), 8.15(1H, dd, J=8.0, 2.2Hz), 8.16(1H, dd, J=8.0, 2.2Hz), 8.77(1H, d, J=2.2Hz), 8.91(1H, d, J=2.2Hz) |
| 2-101 | 3.59(3H, br q, J=1.2Hz), 6.36(1H, s), 6.99(1H, dd, J=4.9, 8.3Hz), 7.27(1H, d, J=8.7Hz), 8.44(1H, dd, J=1.7, 4.8Hz), 8.6(1H, dd, J=1.7, 8.3Hz), 9.79(1H, br s) |
| 2-102 | ($CDCl_3$+$CD_3OD$)3.54(3H, br s), 6.33(2H, s), 6.82(1H, t, J=5.0Hz), 7.2(1H, d, J=8.8Hz), 8.38(2H, d, J=5.0Hz) |
| 2-103 | 3.55(3H, q, J=1.0Hz), 3.89(3H, s), 6.26(1H, s), 7.22(1H, d, J=9.1Hz), 7.45(3H, m), 7.83(3H, m), 7.99(1H, br s) |
| 2-104 | 3.58(3H, s), 3.92(3H, s), 6.26(1H, s), 7.20(1H, d, J=9.0Hz), 7.65(1H, m), 7.85(2H, m), 8.17(2H, m), 8.33(1H, m), 10.05(1H, s) |
| 2-105 | 3.60(3H, br s), 3.92(3H, s), 6.27(1H, s), 7.27(1H, d, J=9.0Hz), 7.93(2H, m), 8.20(2H, m), 9.60(1H, s), 10.12(1H, s) |
| 2-106 | 3.56(3H, q, J=0.7Hz), 3.86(3H, s), 6.27(1H, s), 6.95(2H, m), 7.41(1H, d, J=8.7Hz), 7.95(1H, m) |
| 2-113 | 3.56(3H, q, J=1.0Hz), 3.86(3H, s), 6.26(1H, d, J=15.2Hz), 6.28(1H, s), 7.05(1H, dd, J=5.0, 3.6Hz), 7.20(1H, d, J=9.0Hz), 7.25(1H, d, J=3.6Hz), 7.27(1H, br s), 7.38(1H, d, J=5.0Hz), 7.75(1H, d, J=15.2Hz) |
| 2-114 | 3.56(3H, d, J=0.9Hz), 6.40(1H, s), 7.28(1H, d, J=9.21Hz), 7.50–7.65(2H, m), 7.70–7.80(1H, m), 7.80–8.0(3H, m), 8.35(1H, m), 8.63(1H, br s) |
| 2-115 | 3.54(3H, d, J=0.9Hz), 6.24(1H, s), 6.51(1H, t, J=73.1Hz), 7.32(1H, d, J=8.8Hz), 7.50–7.65(2H, m), 7.70–7.82(1H, m), 7.85–7.95(3H, m), 8.07(1H, br s), 8.29(1H, br s) |
| 2-116 | 2.09(3H, s), 2.14(3H, s), 3.50(3H, d, J=1.0Hz), 3.79(3H, s), 4.8–5.0(4H, m), 6.29(1H, s), 7.47(1H, d, J=8.9Hz) |
| 2-117 | 2.18(3H, s), 3.56(3H, d, J=1.1Hz), 3.86(3H, s), 4.58(2H, s), 6.30(1H, s), 7.24(1H, d, J=9.0Hz) |
| 2-118 | 1.40(3H, t, J=7.1Hz), 3.56(3H, d, J=1.0Hz), 3.91(3H, s), 4.39(2H, q, J=7.1Hz), 6.29(1H, s), 7.25(1H, d, J=9.1Hz), 9.01(1H, br s) |
| 2-119 | 3.54(3H, s), 3.72(3H, s), 4.56(2H, s), 6.24(1H, s), 6.85–7.40(6H, m), 8.50(1H, br s) |
| 2-120 | 3.45(3H, s), 3.85(3H, s), 4.8–5.15(4H, m), 6.27(1H, s), 6.8–7.0(6H, m), 7.20–730(4H, m), 7.48(1H, d, J=8.7Hz) |

TABLE XVIII-continued

| No. | $^1$H NMR data NMR($CDCl_3$, 300MHz) ppm |
|---|---|
| 2-121 | 3.59(3H, s), 3.93(3H, s), 6.35(1H, s), 7.26(1H, d, J=9.0Hz), 7.40–7.70(3H, m), 8.20(2H, m), 8.97(1H, br s) |
| 2-122 | 2.33(3H, s), 3.49(3H, d, J=0.9Hz), 6.24(1H, s), 7.34(1H, d, J=9.1Hz), 7.50–7.62(2H, m), 7.75–7.95(5H, m), 8.31(1H, br s) |
| 2-123 | 2.28(3H, s), 3.54(3H, s), 6.29(1H, s), 6.59(1H, d, J=15.5Hz), 7.20–7.50(6H, m), 7.63(1H, d, J=15.5Hz) |
| 2-124 | 2.29(6H, s), 3.56(3H, s), 3.93(3H, s), 6.32(1H, s), 7.05(2H, m), 7.20(2H, m), 7.47(1H, br s) |
| 2-125 | 3.57(3H, s), 3.87(3H, s), 6.29(1H, s), 6.62(1H, d, J=15.7Hz), 7.1–7.5(5H, m), 7.72(1H, d, J=15.7Hz) |
| 2-126 | 3.52(3H, s), 3.80(3H, s), 6.24(1H, s), 6.32(1H, d, J=15.6Hz), 7.11(1H, br d, J=8.8Hz), 7.4–7.6(4H, m), 7.95(2H, m) |
| 2-127 | 3.56(3H, s), 3.86(3H, s), 3.89(3H, s), 6.28(1H, s), 6.64(1H, d, J=15.7Hz), 6.95(2H, m), 7.19(1H, d, J=9.0Hz), 7.35(7H, m); 7.46(1H, dd, J=7.6, 1.4Hz), 7.88(1H, d, J=15.7Hz) |
| 2-128 | 3.59(3H, s), 3.88(3H, s), 6.31(1H, s), 6.65(1H, d, J=15.9Hz), 7.20(2H, m), 7.35(2H, d, J=8.1Hz), 7.37(1H, br s), 7.72(1H, d, J=15.9Hz) |
| 2-129 | 2.28(3H, s), 2.53(2H, t, J=7.3Hz), 2.88(2H, t, J=7.3Hz), 3.56(3H, s), 3.73(3H, s), 6.26(1H, s), 7.11(5H, m), 7.35(1H, br s) |
| 2-130 | 2.33(3H, s), 2.36(3H, s), 3.57(3H, s), 3.86(3H, s), 6.29(1H, s), 6.40(1H, d, J=15.4Hz), 7.09(2H, br s), 7.20(1H, d, J=9.0Hz), 7.33(1H, br s), 7.35(1H, s), 7.90(1H, d, J=15.4Hz) |
| 2-131 | 3.54(3H, d, J=1.0Hz), 6.37(1H, s), 7.21(1H, d, J=8.6Hz), 7.33(1H, dd, J=8.6, 2.1Hz), 7.60(2H, m), 7.77(1H, dd, J=8.6, 1.8Hz), 7.88(3H, m), 7.98(1H, br s), 8.01(1H, d, J=2.1Hz), 8.26(1H, d, J=1.3Hz) |
| 2-132 | 2.21(3H, s), 2.27(3H, s), 2.48(2H, t, J=7.8Hz), 2.81(2H, t, J=7.8Hz), 3.57(3H, s), 3.73(3H, s), 6.27(1H, s), 6.92(2H, m), 7.02(1H, d, J=7.6Hz), 7.12(1H, br d, J=8.6Hz), 7.51(1H, br s) |
| 2-133 | 3.55(3H, d, J=1.0Hz), 3.76(3H, s), 4.52(2H, s), 6.26(1H, s), 6.88(2H, dd, J=9.1, 2.4Hz), 7.02(2H, dd, J=9.1, 8.1Hz), 7.20(1H, d, J=9.0Hz), 8.48(1H, br s) |
| 2-134 | 3.57(3H, s), 3.86(3H, s), 6.28(1H, s), 6.50(1H, d, J=15.5Hz), 7.23(1H, d, J=9.0Hz), 7.35(4H, m), 7.50(1H, br s), 7.58(1H, d, J=15.5Hz) |
| 2-135 | 3.55(3H, d, J=1.0Hz), 3.76(3H, s), 4.52(2H, s), 6.26(1H, s), 6.87(2H, d, J=9.0Hz), 7.20(1H, d, J=9.0Hz), 7.29(2H, d, J=9.0Hz), 8.45(1H, br s) |
| 2-136 | 3.58(3H, d, J=1.0Hz), 3.93(3H, s), 6.33(1H, s), 7.26(1H, d, J=9.1Hz), 7.54(3H, m), 7.95(2H, d, J=8.3Hz), 8.14(1H, s), 8.28(1H, s) |
| 2-137 | 3.55(3H, s), 6.37(1H, s), 6.40(1H, d, J=15.5Hz), 7.16(1H, d, J=8.6Hz), 7.19(1H, br s), 7.29(1H, dd, J=8.5, 1.9Hz), 7.38(3H, m), 7.48(2H, m), 7.70(1H, d, J=15.5Hz), 7.99(1H, br s) |
| 2-139 | 3.19(3H, s), 5.98(1H, s), 7.17(1H, dd, J=8.0, 1.2Hz), 7.2–7.6(7H, m), 7.7–7.9(6H, m), 7.93(2H, dd, J=8.6, 1.7Hz), 8.53(2H, br s) |
| 2-140 | 3.56(3H, d, J=1.0Hz), 6.40(1H, s), 7.42(1H, d, J=8.3Hz), 7.60(3H, m), 7.78(1H, dd, J=8.6, 1.8Hz), 7.92(3H, m), 8.01(1H, br s), 8.29(1H, br s), 8.38(1H, d, J=1.6Hz) |
| 2-141 | 3.59(3H, s), 6.41(1H, s), 6.42(1H, d, J=15.5Hz), 7.16(1H, br s), 7.38(4H, m), 7.52(2H, m), 7.59(1H, dd, J=8.2, 1.7Hz), 7.75(1H, d, J=15.5Hz), 8.40(1H, br s) |
| 2-142 | 3.47(3H, s), 6.29(1H, s), 7.1–7.9(11H, m), 8.21(1H, d) |
| 2-143 | 3.55(3H, d, J=1.0Hz), 3.87(3H, s), 6.38(1H, s), 6.89(1H, dd, J=8.9, 2.9Hz), 7.18(1H, d, J=8.9Hz), 7.58(3H, m), 7.79(1H, dd, J=8.6, 1.7Hz), 7.90(4H, m), 8.29(1H, br s) |
| 2-144 | 3.54(3H, d, J=1.0Hz), 3.87(3H, s), 6.25(1H, s), 7.60(3H, m) 7.8–8.0(5H, m), 8.30(1H, br s) |
| 2-145 | 3.57(3H, d, J=1.0Hz), 6.38(1H, s), 7.12(1H, dd, J=9.3, 2.2Hz), 7.59(2H, m), 7.78(1H, dd, J=8.6, 1.8Hz), 7.8–8.0(5H, m), 8.28(1H, br s) |
| 2-146 | 1.27(1.5H, t, J=7.1Hz), 1.27(1.5H, t, J=7.1Hz), 1.62(3H, d, J=6.7Hz), 3.53(3H, s), 4.23(2H, m), 4.79(1H, m), 6.35(1H, s), 6.85(1H, m), 7.15(1H, d, J=9.0Hz), 7.5–7.6(3H, m), 7.77(1H, dd, J=8.6, 1.6Hz), 7.89(4H, m), 8.26(1H, s) |
| 2-147 | 0.84(2H, m), 1.03(2H, m), 1.50(1H, m), 3.58(3H, d, J=1.0Hz), 6.36(1H, s), 7.05(1H, d, J=7.8Hz), 7.35(1H, br s), 7.88(1H, br s) |
| 2-148 | 3.57(3H, d, J=1.0Hz, 6.39(1H, s), 6.61(1H, t, J=72.7Hz), 6.88(1H, dd, J=10.2, 2.6Hz), 7.59(2H, m), 7.76(2H, m), 7.90(3H, m), 8.05(1h, br s), 8.27(1H, s) |

TABLE XVIII-continued

| No. | $^1$H NMR data NMR($CDCl_3$, 300MHz) ppm |
|---|---|
| 2-149 | 3.56(3H, d, J=1.0Hz), 6.38(1H, s), 7.43(1H, d, J=8.4Hz), 7.6(3H, m), 7.78(1H, dd, J=8.6, 1.8Hz), 7.90(3H, m), 8.09(1H, br s), 8.28(2H, s) |
| 2-150 | 3.41(3H, d, J=1.1Hz), 3.71(1H, s), 3.80(2H, s), 6.11(1H, s), 7.1–7.4(6H, m), 8.88(1H, s) |
| 2-151 | 3.50(3H, d, J=1.0Hz), 3.58(3H, s), 3.62(2H, s), 6.15(1H, s) 7.14(1H, d, J=9.1Hz), 7.2–7.4(6H, m) |
| 2-152 | 3.58(3H, s), 3.90(3H, s), 4.14(3H, s), 6.25(1H, s), 7.21(1H, d, J=9.0Hz), 7.26(1H, s), 7.44(1H, m), 7.55(1H, m), 7.76(1H, m), 7.85(1H, m), 8.58(1H, s), 10.10(1H, s) |
| 2-153 | 3.57(3H, s), 3.91(3H, s), 4.10(3H, s), 6.22(1H, s), 7.22(1H, d, J=9.0Hz), 7.23(1H, s), 7.64(2H, m), 7.91(1H, m), 7.99(1H, d, J=8.7Hz), 8.22(1H, m), 10.20(1H, s) |
| 2-154 | 3.56(3H, s), 3.87(3H, s), 4.55(2H, s), 6.27(1H, s), 6.82(1H, d, J=8.8Hz), 7.21(2H, m), 7.44(1H, s), 8.72(1H, s) |
| 2-155 | 2.52(3H, s), 3.56(3H, s), 3.90(3H, s), 6.31(1H, s), 7.20(1H, d, J=9.0Hz), 7.55(2H, m), 7.81(4H, m), 10.15(1H, s) |
| 2-156 | 2.55(3H, s), 3.52(3H, s), 3.83(3H, s), 6.22(1H, s), 7.20(1H, d, J=9.0Hz), 7.41(1H, m), 7.66(1H, s), 7.79(3H, m), 8.15(1H, s), 8.26(1H, s) |
| 2-157 | 3.58(3H, s), 3.94(3H, s), 6.35(1H, s), 7.25(1H, d, J=9.0Hz), 7.61(2H, m), 7.78(2H, s), 7.92(2H, m), 8.04(1H, s) |
| 2-158 | 3.55(3H, s), 3.84(3H, s), 6.24(1H, s), 7.22(1H, d, J=9.0Hz), 7.42(1H, m), 7.90(3H, m), 8.14(1H, s), 8.32(2H, m) |
| 2-159 | 3.56(3H, s), 3.96(3H, s), 6.35(1H, s), 7.13(1H, d, J=9.0Hz), 7.70(6H, m), 8.15(1H, s) |
| 2-160 | 3.55(3H, s), 3.86(3H, s), 6.24(1H, s), 7.22(1H, d, J=9.0Hz), 7.74(4H, m), 7.92(4H, m), 8.10(4H, m) |
| 2-161 | 3.55(3H, s), 3.86(3H, s), 6.25(1H, s), 7.23(2H, m), 7.57(1H, m), 7.72(1H, m), 7.91(2H, m), 8.18(1H, s) |
| 2-162 | 3.55(3H, s), 3.85(3H, s), 6.24(1H, s), 7.23(1H, d, J=9.0Hz), 7.49(1H, m), 7.69(1H, m), 7.90(3H, m), 8.13(1H, m), 8.34(2H, m) |
| 2-163 | 3.56(3H, s), 3.86(3H, s), 6.25(1H, s), 7.25(1H, d, J=9.0Hz), 7.66(1H, m), 8.05(3H, m), 8.19(1H, m), 8.32(1H, d, J=8.7Hz), 8.39(1H, s) |
| 2-164 | 3.35(3H, s), 3.89(3H, s), 4.10(2H, s), 6.37(1H, s), 7.25(1H, d, J=9.0Hz), 8.33(1H, s) |
| 2-165 | 3.10(2H, s), 3.57(3H, s), 3.90(2H, s), 4.11(3H, s), 6.30(1H, s), 7.20(1H, d, J=9.0Hz), 7.27(5H, s), 8.65(1H, s) |
| 2-166 | 3.57(3H, s), 3.90(5H, s), 4.10(2H, s), 6.37(1H, s), 7.25(1H, d, J=9.0Hz), 8.15(1H, s) |
| 2-167 | 3.50(3H, s), 3.55(3H, s), 3.69(2H, s), 6.16(1H, s), 7.18(1H, d, J=9.0Hz), 7.28(5H, m), 8.33(1H, s) |
| 2-168 | 2.14(3H, s), 3.20(2H, s), 3.56(3H, s), 3.83(3H, s), 6.29(1H, s), 7.20(1H, d, J=9.0Hz), 8.67(1H, s) |
| 2-169 | 3.36(3H, s), 3.52(3H, s), 3.79(2H, m), 5.96(1H, s), 7.17(1H, d, J=9.0Hz), 7.49(3H, m), 7.75(3H, m), 8.75(1H, m) |
| 2-170 | 1.28(3H, t, J=7.1Hz), 3.32(2H, s), 3.36(2H, s), 3.55(3H, s), 3.88(3H, s), 4.18(2H, q, J=7.1Hz), 6.30(1H, s), 7.21(1H, d, J=9.0Hz), 8.33(1H, s) |
| 2-171 | 1.26(3H, t, J=7.1Hz), 2.62(2H, m), 2.85(2H, m), 3.26(2H, s), 3.56 (3H, s), 3.88(3H, s), 4.15(2H, q, J=7.1Hz), 6.35(1H, s), 7.21(1H, d, J=9.0Hz), 8.66(1H, s) |
| 2-172 | 1.27(3H, t, J=7.4Hz), 2.60(2H, m), 3.27(2H, s), 3.56(3H, s), 3.88 (3H, s), 6.28(1H, s), 7.20(1H, d, J=9.0Hz), 8.73(1H, s) |
| 2-173 | 1.26(6H, m), 2.97(1H, m), 3.29(2H, s), 3.57(3H, s), 3.87(3H, s), 6.28(1H, s), 7.20(1H, d, J=9.0Hz), 8.79(1H, s) |
| 2-174 | 0.99(3H, m), 1.60(2H, m), 2.53(2H, m), 3.25(2H, s), 3.57(3H, s), 3.90(3H, s), 6.28(1H, s), 7.20(1H, d, J=9.0Hz), 8.80(1H, s) |
| 2-175 | 3.53(3H, q, J=3.9H), 3.79(3H, s), 6.30(1H, s), 6.90(1H, d, J=15.7Hz), 7.36(3H, m), 7.53(4H, m), 9.84(1H, s) |
| 2-176 | 3.41(3H, s), 3.79(3H, s), 6.23(1H, s), 7.58(1H, d, J=8.5Hz), 6.84(1H, d, J=15.6Hz), 6.90(1H, d, J=15.6Hz), 7.35(6H, m), 7.50(4H, m), 7.79(1H, d, J=5.6Hz), 7.82(1H, d, J=15.6Hz) |
| 2-177 | 3.50(3H, s), 3.79(3H, s), 6.23(1H, s), 7.30(1H, d, J=8.7Hz), 7.56(2H, m), 7.85(4H, m), 8.31(1H, s), 8.40(1H, s) |
| 2-178 | 3.21(3H, s), 3.88(3H, s), 6.04(1H, s), 7.59(5H, m), 7.87(8H, m), 8.50(1H, s), 8.57(1H, s) |
| 2-179 | 3.57(3H, s), 4.03(3H, s), 6.29(1H, s), 6.52(1H, d, J=15.6Hz), 7.28(1H, d, J=8.4Hz), 7.38(3H, m), 7.47(2H, m), 7.62(1H, d, J=15.6Hz), 7.80(1H, s) |
| 2-180 | 3.50(3H, s), 4.00(3H, s), 6.22(1H, s), 7.27(1H, d, J=8.5Hz), 7.59(2H, m), 7.87(4H, m), 8.32(1H, s), 8.38(1H, s) |
| 2-181 | 3.52(3H, s), 3.80(3H, s), 6.23(1H, s), 7.17(1H, d, J=9.1Hz), |

TABLE XVIII-continued

| No. | $^1$H NMR data NMR($CDCl_3$, 300MHz) ppm |
|---|---|
| | 7.58(2H, m), 7.87(4H, m), 8.26(1H, d, J=55.6Hz), 8.31(1H, s) |
| 2-182 | 3.53(3H, q, J=0.8Hz), 3.80(3H, s), 5.41(1H, d, J=10.9Hz), 5.87(1H, d, J=17.6Hz), 6.23(1H, s), 6.75(1H, dd, J=17.6, 10.9Hz), 7.37(1H, d, J=8.8Hz), 7.47(2H, d, J=8.3Hz), 7.73(2H, d, J=8.3Hz), 8.00(1H, s) |
| 2-183 | 3.28(3H, s), 3.80(3H, s), 5.34(1H, d, J=11.0Hz), 5.35(1H, d, J=11.0Hz), 5.80(1H, d, J=17.6Hz), 5.81(1H, d, J=17.6Hz), 6.03(1H, s), 6.67(1H, dd, J=17.6, 11.0Hz), 7.35(2H, d, J=8.0), 7.53(4H, d, J=8.4Hz), 8.11(4H, d, J=8.4Hz) |
| 2-184 | 3.82(3H, s), 4.75(2H, s), 6.07(1H, s), 7.16(1H, d, J=9.1Hz), 7.57(2H, m), 7.76(1H, m), 7.87(3H, s), 8.25(1H, m), 8.27(1H, s) |
| 2-185 | 3.39(2H, s), 3.78(3H, s), 6.26(1H, s), 7.3–7.6(7H, m), 9.89(1H, s) |
| 2-186 | 3.80(3H, s), 4.58(2H, s), 6.14(1H, s), 6.81(1H, d, J=15.5Hz), 6.93(1H, d, J=15.5Hz), 7.3–7.6(10H, m), 7.77(1H, d, J=15.5Hz), 7.82(1H, d, J=15.5Hz) |
| 2-187 | 3.78(3H, s), 3.78(2H, s), 4.58(2H, s), 4.70(2H, s), 6.07(1H, s), 7.14(1H, d, J=9.1Hz), 7.35(5H, m), 8.58(1H, s) |
| 2-188 | 4.67(2H, s), 4.76(2H, d, J=5.3Hz), 6.10(1H, s), 7.26(1H, d, J=8.8Hz), 7.57(2H, m), 7.77(1H, m), 7.87(3H, s), 8.19(1H, m), 8.30(1H, s) |
| 2-189 | 1.28(3H, t, J=7.1Hz), 3.55(3H, s), 4.26(2H, q, J=7.1Hz), 4.82(2H, s), 6.22(1H, s), 7.21(1H, d, J=8.8Hz), 7.57(2H, m), 7.94(4H, m), 8.52(1H, s), 10.46(1H, s) |
| 2-190 | 1.30(3H, t, J=7.1Hz), 3.58(3H, s), 4.31(2H, q, J=7.1Hz), 4.78(2H, s), 6.27(1H, s), 6.67(1H, d, J=15.7Hz), 7.15(1H, d, J=8.9Hz), 7.38(3H, m), 7.95(2H, m), 7.62(1H, d J=15.7Hz) |
| 2-191 | 1.27(3H, t, J=7.1Hz), 1.29(3H, t, J=7.1Hz), 1.69(3H, d, J=7.0Hz), 1.70(3H, d, J=7.0Hz), 3.56(3H, s), 3.63(3H, s), 4.25(4H, m), 4.95(2H, m), 6.12(1H, s), 6.41(1H, s), 7.19(2H, d, J=8.9Hz), 7.56(4H, m), 7.95(8H, m), 8.54(1H, s), 8.69(1H, s), 10.41(1H, s), 10.65(1H, s) |
| 2-192 | 4.95(2H, s), 6.23(1H, s), 7.25(1H, d, J=10.0Hz), 7.59(2H, m), 7.87(4H, s), 8.27(1H, m), 9.28(1H, s) |
| 2-193 | 3.56(3H, q, J=0.5Hz), 6.40(1H, s), 7.16(1H, dd, J=8.7, 2.6Hz), 7.34(1H, d, J=8.7Hz), 7.5–7.7(3H, m), 7.7–8.0(6H, m), 8.10(1H, dd, J=8.6, 1.6Hz), 8.18(1H, br d), 8.27(1H, br s) |
| 2-194 | 3.53(3H, q, J=0.8Hz), 6.36(1H, s), 7.25(1H, d, J=9.1Hz), 7.60(2H, m), 7.76(1H, dd, J=8.7, 1.8Hz), 7.90(3H, m), 8.21(1H, s), 8.33(1H, d, J=1.5Hz) |
| 2-195 | 2.45(1H, d, J=2.4Hz), 3.55(3H, q, J=0.8Hz), 4.77(2H, dd, J=6.1, 2.4Hz), 6.23(1H, s), 7.23(1H, d, J=9.0Hz), 7.59(2H, m), 7.90(4H, m), 8.32(1H, d, J=0.7Hz), 8.36(1H, s) |
| 2-196 | 1.28(3H, t, J=7.1Hz), 3.51(3H, q, J=0.5Hz), 4.05(2H, q, J=7.1Hz), 6.25(1H, s), 7.57(2H, m), 7.88(4H, m), 8.31(1H, s), 8.38(1H, s) |
| 2-197 | 1.20(3H, t, J=6.2Hz), 1.29(3H, t, J=6.2Hz), 3.54(3H, q, J=0.6Hz), 4.43(1H, q, J=6.2Hz), 6.23(1H, s), 7.59(2H, m), 7.80(1H, m), 7.90(3H, s), 8.20(1H, s), 8.30(1H, s) |
| 2-198 | 0.89(3H, t), 1.25(4H, m), 1.53(2H, m), 2.23(2H, m), 3.56(3H, q, J=0.9Hz), 3.83(3H, s), 6.30(1H, s), 7.20(1H, d, J=9.0Hz), 7.58(1H, br s) |
| 2-199 | 3.54(3H, q, J=0.7Hz), 6.29(1H, s), 6.73(1H, dd, J=8.3, 4.5Hz), 7.43(1H, d, J=9.9Hz), 7.57(2H, m), 7.86(5H, m), 8.21(1H, dd, J=8.3, 1.7Hz), 8.37(1H, dd, J=4.5, 1.7Hz), 8.45(1H, br s) |
| 2-200 | 3.52(3H, q, J=1.0Hz), 4.82(2H, d, J=1.5Hz), 6.26(1H, s), 7.31(1H, d, J=8.8Hz), 7.59(2H, m), 7.93(5H, m), 8.35(1H, d, J=1.1Hz) |
| 2-201 | 2.43(3H, s), 3.54(3H, q, J=0.9Hz), 6.36(1H, s), 7.18(2H, m), 7.59(2H, m), 7.8(6H, m), 8.28(1H, s) |
| 2-202 | 3.51(3H, s), 3.87(3H, s), 6.24(1H, s), 7.12(1H, d, J=8.8Hz), 7.42(1H, d, J=8.8Hz), 7.59(2H, m), 7.81(1H, m), 7.91(3H, m), 8.06(1H, s), 6.31(1H, s) |
| 2-203 | 3.53(3H, s), 6.34(1H, s), 7.17(1H, m), 7.26(1H, m), 7.57(2H, m), 7.73(1H, 2d, J=1.6Hz, 8.6Hz), 7.88(4H, m), 8.18(1H, s), 8.23(1H, s) |
| 2-204 | 0.78(2H, m), 0.97(2H, m), 1.4(1H, m), 3.55(3H, s), 6.34(1H, s), 7.12(1H, m), 7.24(1H, m), 7.43(1H, m), 7.85(1H, broad) |
| 2-205 | 3.36(3H, s), 6.22(1H, s), 7.24(1H, d, J=8.4Hz), 7.41(2H, m), 7.65(4H, m), 7.86(1H, 2d, J=2.0Hz, 8.4Hz), 8.0–8.2(4H, m) 8.55(1H, s) |
| 2-206 | 0.76–0.93(4H, m), 1.50(1H, m), 3.55(3H, s), 3.85(3H, s), 6.31(1H, s), 7.19(1H, d, J=8.9Hz), 7.6(1H, broad) |
| 2-207 | 3.44(3H, s), 3.82(3H, s), 6.24(1H, s), 7.32(1H, d, J=8.3Hz), 7.48(2H, m), 7.6–7.8(5H, m), 8.10(1H, s), 8.23(1H, s), 8.78(1H, s) |

TABLE XVIII-continued

| No. | $^1$H NMR data NMR($CDCl_3$, 300MHz) ppm |
|---|---|
| 3-1 | 2.74(3H, d, J=4.7Hz), 2.76(3H, d, J=4.7Hz), 3.53(3H, br q, J=1.3Hz), 3.83(3H, s), 6.3(1H, s), 6.66(1H, m), 7.35(1H, m), 7.39(1H, d, J=8.8Hz) |
| 3-2 | 0.76(3H, t, J=7.4Hz), 1.28(2H, m), 2.96(2H, m), 3.57(3H, s), 3.84(3H, s), 5.22(1H, m), 6.33(1H, s), 6.70(1H, s), 7.14(1H, d, J=9.0Hz) |
| 3-3 | 1.22(12H, m), 3.54(3H, br s), 3.83(3H, s), 3.86(2H, m), 6.25(1H, s), 6.45(1H, s), 7.04(1H, d, J=9.1Hz) |
| 3-4 | 3.52(3H, s), 3.76(3H, s), 6.30(1H, s), 6.90–7.25(6H, m), 7.37(1H, s), 7.61(1, s) |
| 3-6 | 3.46(3H, s), 3.77(3H, m), 4.19(2H, m), 5.75(1H, m), 6.19(1H, s), 6.90–7.30(7H, m) |
| 3-7 | (rotameric mixture)1.16(3H, d, J=6.8Hz), 1.23(3H, d, J=6.8Hz), 3.47(3H, s), 3.53(3H, s), 3.77(6H, s), 4.72(2H, m), 5.72(2H, m), 6.11(1H, s), 6.33(1H, s), 6.95–7.35(14H, m) |
| 3-8 | 2.99(3H, s), 3.55(3H, s), 3.63(3H, s), 4.38(1H, d, J=16.2Hz), 4.58(1H, d, J=16.2Hz), 6.27(1H, s), 6.58(1H, s), 7.12(1H, d, J=9.1Hz), 7.19(2H, m), 7.33(3H, m) |
| 3-9 | 2.31(3H, s), 3.47(3H, s), 3.79(3H, s), 4.17(2H, m), 5.58(1H, m), 6.18(1H, s), 6.74(1H, s), 6.90–7.15(5H, m) |
| 3-10 | ($CDCl_3$+$CD_3OD$)3.52(3H, br s), 3.82(3H, s), 4.29(2H, m), 6.23(1H, s), 6.50(1H, m), 6.70–6.85(2H, m), 7.14(1H, d, J=9.0Hz), 7.22(1H, m) |
| 3-11 | 2.57(2H, m), 3.21(2H, m), 3.54(3H, s), 3.74(3H, s), 5.51(1H, m), 6.27(1H, s), 7.00–7.30(7H, m) |
| 3-12 | ($CDCl_3$+$CD_3OD$)1.72(2H, m), 2.58(2H, m), 3.11(2H, m), 3.53(3H, s), 3.85(3H, s), 5.78(1H, m), 6.28(1H, s), 7.05–7.35(7H, m) |
| 3-13 | 3.55(3H, s), 3.81(3H, s), 6.35(1H, s), 7.08(1H, m), 7.1(1H, d, J=9.0Hz), 7.25–7.45(3H, m), 7.55–7.80(5H, m) |
| 3-23 | 3.59(3H, s), 3.64(3H, s), 4.62(1H, d, J=14.8Hz), 4.98(1H, d, J=14.8Hz), 6.33(1H, s), 6.47(1H, s), 6.95–7.50(11H, m) |
| 3-24 | 3.40(3H, s), 3.78(3H, s), 5.88(1H, m), 5.98(1H, m), 6.12(1H, s), 7.00–7.30(12H, m) |
| 3-26 | 3.56(3H, s), 3.89(3H, s), 4.86(2H, s), 6.50(1H, s), 6.33(1H, s), 7.25(1H, d, J=9.0Hz) |
| 4-1 | 3.54(3H, s), 3.64(3H, s), 3.84(3H, s), 6.24(1H, s), 7.25(1H, s) |
| 4-2 | 2.87(3H, s), 2.96(3H, s), 3.53(3H, s), 3.63(3H, s), 6.3(1H, s), 6.85(1H, d, J=8.9Hz) |
| 4-3 | 3.51(3H, d, J=1.0Hz), 3.95(3H, s), 6.35(1H, s), 6.81(1H, br s), 7.03(2H, m), 7.22(1H, d, J=9.0Hz), 7.23(1H, m), 7.34(2H, m) |
| 4-4 | 2.22(6H, s), 3.50(3H, d, J=0.5Hz), 3.94(3H, s), 6.35(1H, s), 6.72(1H, dd, J=8.2, 2.5Hz), 6.77(1H, d, J=2.5Hz), 6.84(1H, br s), 7.07(1H, d, J=8.2Hz), 7.20(1H, d, J=9.0Hz) |
| 4-5 | 3.49(3H, d, J=1.0Hz), 3.83(3H, s), 5.05(1H, d, J=12.3Hz), 5.12(1H, d, J=12.3Hz), 6.20(1H, s), 6.68(br s), 7.15(1H, d, J=9.0Hz), 7.26–7.37(5H, m) |
| 4-7 | 3.50(3H, br s), 3.82(3H, s), 5.01(1H, d, J=12.2Hz), 5.07(1H, d, J=12.2Hz), 6.20(1H, s), 6.69(1H, br s), 7.02(2H, m), 7.17(1H, d, J=9.0Hz), 7.28(2H, m) |
| 4-10 | 3.48(3H, br s), 3.99(3H, s), 6.37(1H, s), 6.98(1H, br s), 7.14(1H, dd, J=8.9, 2.3Hz), 7.24(1H, d, J=9.0Hz), 7.43–7.51(3H, m), 7.37(7.84(3H, m) |
| 4-11 | 1.20–1.85(10H, m), 3.56(3H, br s), 3.86(3H, s), 4.57(1H, m), 6.32(1H, s), 6.53(1H, s), 7.17(1H, d, J=9.0Hz) |
| 4-13 | 3.54(3H, d, J=1.1Hz), 3.78(3H, s), 6.33(1H, s), 7.15(1H, br s), 7.17(1H, d, J=9.0Hz), 7.43–7.52(5H, m) |
| 4-23 | 3.50(3H, s), 4.75(2H, m), 5.13(2H, m), 6.24(1H, s), 6.54(1H, s), 7.25(1H, d, J=8.7Hz), 7.35(5H, m) |
| 4-24 | 3.57(3H, s), 3.86(3H, s), 5.37(2H, m), 6.30(1H, s), 6.70(1H, s), 7.16(1H, d, J=9.0Hz), 7.20–7.40(3H, m) |
| 4-25 | 2.06(6H, s), 2.25(3H, s), 3.52(3H, s), 3.94(3H, s), 6.32(1H, s), 6.83(2H, s), 7.09(1H, br s), 7.20(1H, d, J=9.0Hz) |
| 4-26 | 2.25(6H, s), 3.51(3H, s), 3.83(3H, s), 5.01(2H, m, 6.21(1H, s), 6.65(1H, br s), 7.00–7.20(4H, m) |
| 4-27 | 1.30(9H, s), 3.50(3H, s), 3.96(3H, s), 6.32(1H, s), 6.84(1H, m), 7.10–7.40(5H, m) |
| 4-28 | 3.43(3H, s), 3.82(3H, s), 5.25(2H, m), 6.12(1H, s), 6.73(1H, br s), 7.16(1H, d, J=9.0Hz), 7.30–7.55(3H, m), 7.70–7.85(4H, m) |
| 4-29 | 3.57(3H, s), 3.85(3H, s), 5.17(1H, d, J=11.9Hz), 5.27(2H, d, J=11.9Hz), 6.28(1H, s), 6.64(1H, br s), 6.92(2H, m), 7.17(1H, d, J=9.0Hz), 7.34(1H, m) |
| 4-30 | 3.49(3H, s), 3.84(3H, s), 4.99(1H, d, J=12.6Hz), 5.06(1H, d, J=12.6Hz), 6.23(1H, s), 6.64(1H, br s), 7.00–7.25(4H, m) |
| 4-31 | 1.23(3H, t, J=7.6Hz), 2.64(2H, q, J=7.6Hz), 3.50(3H, d, |

TABLE XVIII-continued

| No. | $^1$H NMR data NMR($CDCl_3$, 300MHz) ppm |
|---|---|
| | J=0.9Hz), 3.83(3H, s), 5.02(1H, d, J=12.1Hz), 5.08(1H, d, J=12.1Hz), 6.22(1H, s), 6.67(1H, br s), 7.10–7.30(5H, m) |
| 4-32 | 3.52(3H, s), 3.85(3H, s), 5.03(2H, m), 6.24(1H, s), 6.64(1H, br s), 7.10–7.21(2H, m), 7.38–7.44(2H, m) |
| 4-33 | 3.52(3H, d, J=0.8Hz), 3.85(3H, s), 5.22(1H, d, J=13.2Hz), 5.31(1H, d, J=13.2Hz), 6.22(1H, s), 6.71(1H, br s), 7.18(1H, d, J=9.0Hz), 7.40–7.60(3H, m), 7.68(1H, m) |
| 4-34 | 3.54(3H, s), 3.88(3H, s), 5.49(2H, s), 6.28(1H, s), 7.24(1H, d, J=9.0Hz), 7.45–7.70(3H, m), 8.09(1H, m) |
| 4-35 | 3.53(3H, s), 3.83(3H, s), 3.84(3H, s), 5.12(1H, d, J=12.5Hz), 5.18(1H, d, J=12.5Hz), 6.24(1H, s), 6.72(1H, br s), 6.80–6.95(2H, m), 7.15(1H, d, J=9.0Hz), 7.20–7.40(2H, m) |
| 4-36 | 3.51(3H, d, J=1.0Hz), 3.87(3H, s), 5.17(1H, d, J=13.5Hz), 5.24(1H, d, J=13.5Hz), 6.24(1H, s), 6.89(1H, br s), 7.18(1H, d, J=9.0Hz), 7.20–7.29(2H, m), 7.68(1H, m), 8.58(1H, m) |
| 4-37 | 2.31(6H, s), 3.52(3H, s), 3.84(3H, s), 5.01(2H, m), 6.23(1H, s), 6.65(1H, br s), 6.92(2H, br s), 6.96(1H, br s), 7.16(1H, d, J=9.0Hz) |
| 4-38 | 2.25(3H, s), 2.31(3H, s), 3.53(3H, d, J=0.9Hz), 3.84(3H, s), 5.04(1H, d, J=12.2Hz), 5.09(1H, d, J=12.2Hz), 6.25(1H, s), 6.65(1H, br s), 7.08(3H, m), 7.16(1H, d, J=9.0Hz) |
| 4-39 | 3.53(3H, br s), 3.86(3H, s), 5.14(2H, m), 6.27(1H, s), 6.70(1H, br s), 6.90–7.10(3H, m), 7.19(1H, d, J=9.0Hz) |
| 4-40 | 3.51(3H, d, J=0.9Hz), 3.81(3H, s), 3.82(3H, s), 4.98(1H, d, J=12.0Hz), 5.05(1H, d, J=12.0Hz), 6.22(1H, s), 6.63(1H, br s), 6.87(2H, m), 7.16(1H, d, J=9.0Hz), 7.25(2H, m) |
| 4-41 | 3.53(3H, d, J=0.9Hz), 3.83(3H, s), 4.95(1H, d, J=12.1Hz), 5.01(1H, d, J=12.1Hz), 5.96(2H, s), 6.25(1H, s), 6.63(1H, br s), 6.78(3H, m), 7.17(1H, d, J=9.0Hz) |
| 4-42 | 1.24(6H, d, J=6.9Hz), 2.91(1H, m), 3.50(3H, d, J=0.9Hz), 3.82(3H, s), 5.02(1H, d, J=12.1Hz), 5.08(1H, d, J=12.1Hz), 6.23(1H, s), 6.70(1H, br s), 7.15(1H, d, J=9.0Hz), 7.22(4H, m) |
| 4-43 | 3.48(3H, d, J=1.0Hz), 3.85(3H, s), 5.10(1H, d, J=13.0Hz), 5.18(1H, d, J=13.0Hz), 6.18(1H, s), 6.72(1H, br s), 7.18(1H, d, J=9.0Hz), 7.41(2H, m), 7.60(2H, m) |
| 4-44 | 3.50(3H, d, J=1.0Hz), 3.85(3H, s), 5.05(1H, d, J=12.8Hz), 5.12(1H, d, J=12.8Hz), 6.22(1H, s), 6.68(1H, br s), 6.95–7.10(3H, m), 7.18(1H, d, J=9.0Hz), 7.30(1H, m) |
| 4-45 | 3.49(3H, d, J=0.9Hz), 3.82(3H, s), 5.05(1H, d, J=12.6Hz), 5.11(1H, d, J=12.6Hz), 6.21(1H, s), 6.79(1H, br s), 7.10–7.20(3H, m), 7.31–7.36(2H, m) |
| 4-46 | 0.89(4H, br s), 3.54(3H, d, J=1.0Hz), 3.75(3H, s), 4.15(2H, m), 6.28(1H, s), 6.56(1H, br s), 7.15(1H, d, J=9.0Hz), 7.26(5H, m) |
| 4-47 | 1.50(3H, d, J=6.6Hz), 3.48(3H, s), 3.84(3H, s), 5.69(1H, q, J=6.6Hz), 5.97(1H, s), 6.73(1H, br s), 7.14(1H, d, J=9.0Hz), 7.20–7.40(5H, m) |
| 4-48 | 3.57(3H, d, J=0.9Hz), 3.86(3H, s), 5.19(1H, d, J=12.3Hz), 5.25(1H, d, J=12.3Hz), 6.31(1H, s), 6.61(1H, br s), 7.20(1H, d, J=9.0Hz) |
| 4-49 | 3.52(3H, d, J=0.9Hz), 5.22(2H, s), 6.33(1H, s), 6.53(1H, br s), 7.00–7.45(7H, m) |
| 4-50 | 3.54(3H, s), 6.36(1H, s), 6.84(1H, br s), 7.05–7.45(8H, m) |
| 4-51 | 2.20(3H, s), 3.45(3H, d, J=0.8Hz), 5.10(2H, m), 6.22(1H, s), 6.90–7.10(2H, m), 7.15–7.27(3H, m) |
| 4-52 | 2.42(3H, s), 3.52(3H, s), 6.37(1H, s), 7.00–7.40(6H, m) |
| 4-53 | 2.21(6H, s), 3.50(3H, br d J=0.5Hz), 3.94(3H, s), 6.35(1H, s), 6.73(2H, m), 6.84(1H, br s), 7.07(1H, d, J=8.1Hz), 7.20(1H, d, J=9.0Hz) |
| 4-54 | 3.53(3H, br d, J=1.1Hz), 3.85(3H, s), 5.16(1H, d, J=12.9Hz), 5.25(1H, d, J=12.9Hz), 6.24(1H, s), 6.71(1H, br s), 7.18(1H, d, J=9.0Hz), 7.2–7.4(4H, m) |
| 4-55 | 2.11(6H, s), 3.52(3H, s), 3.95(3H, s), 6.33(1H, s), 7.03(3H, br s), 7.08(1H, br s), 7.22(1H, d, J=9.0Hz) |
| 4-56 | 3.51(3H, br d, J=1.1Hz), 3.83(3H, s), 5.07(1H, d, J=12.3Hz), 5.14(1H, d, J=12.3Hz), 6.23(1H, s), 6.68(1H, br s), 7.1–7.3(4H, m) |
| 4-57 | 2.88(2H, t, J=6.5Hz), 3.55(3H, s), 3.77(3H, s), 4.25(2H, t, J=6.5Hz), 6.29(1H, s), 6.52(1H, br s), 7.1–7.4(6H, m) |
| 4-58 | 3.52(3H, br d, J=1.0Hz), 3.83(3H, s), 3.84(3H, s), 5.12(1H, d, J=12.5Hz), 5.17(1H, d, J=12.5Hz), 6.24(1H, s), 6.71(1H, br s), 6.90(2H, m), 7.15(1H, d, J=9.0Hz), 7.2–7.3(2H, m) |
| 4-59 | 3.59(3H, s), 3.74(6H, s), 6.32(1H, s), 6.56(2H, d, J=8.5Hz), 7.11(1H, t, J=8.5Hz), 7.14(1H, br s), 7.18(1H, d, J=9.0Hz) |
| 4-60 | 2.34(3H, s), 3.50(3H, br d, J=2.1Hz), 3.83(3H, s), 5.00(1H, d, J=12.1Hz), 5.07(1H, d, J=12.1Hz), 6.20(1H, s), 6.64(1H, br s), |

TABLE XVIII-continued

| No. | $^1$H NMR data NMR($CDCl_3$, 300MHz) ppm |
|---|---|
| | 7.1–7.2(5H, m) |
| 4-61 | 3.50(3H, br d, J=1.0Hz), 3.83(3H, s), 5.01(1H, d, J=12.5Hz), 5.07(1H, d, J=2.5Hz), 6.20(1H, s), 6.66(1H, br s), 7.17(1H, d, J=9.0Hz), 7.2–7.3(4H, m) |
| 4-62 | 3.53(3H, br d, J=1.0Hz), 3.85(3H, s), 5.12(1H, d, J=13.0Hz), 5.20(1H, d, J=13.0Hz), 6.25(1H, s), 6.67(1H, br s), 7.19(1H, d, J=0.9Hz), 7.2~7.3(2H, m), 7.41(1H, d, J=1.9Hz) |
| 4-63 | 3.51(3H, br d, J=1.0Hz), 3.83(3H, s), 3.89(3H, s), 4.99(1H, d, J=12.0Hz), 5.04(1H, d, J=12.0Hz), 6.20(1H, s), 6.59(1H, br s), 6.8–6.9(3H, m), 7.16(1H, d, J=9.0Hz) |
| 4-64 | 3.51(3H, br d, J=0.9Hz), 3.86(3H, s), 5.15(1H, d, J=13.5Hz), 5.21(1H, d, J=13.5Hz), 6.21(1H, s), 6.68(1H, br s), 7.21(1H, d, J=9.0Hz), 7.46(2H, d, J=8.7Hz), 8.21(2H, d, J=8.7Hz) |
| 4-65 | 3.50(3H, br d, J=1.0Hz), 3.81(3H, s), 3.85(3H, s), 5.02(1H, d, J=12.5Hz), 5.10(1H, 12.5Hz), 6.21(1H, s), 6.67(1H, br s), 6.8–6.9(3H, m), 7.17(1H, d, J=9.0Hz), 7.25(1H, t, J=7.7Hz) |
| 4-66 | 3.53(3H, br d, J=0.9Hz), 3.82(3H, s), 4.11(2H, s), 6.29(1H, s), 7.04(1H, br s), 7.20(1H, d, J=9.0Hz), 7.25(5H, m) |
| 4-67 | 3.52(3H, br d, J=1.0Hz), 3.86(3H, s), 5.17(1H, d, J=13.2Hz), 5.21(1H, d, J=13.2Hz), 6.24(1H, s), 6.65(1H, br s), 7.20(1H, d, J=9.0Hz), 7.53(1H, t, J=8.0Hz), 7.63(1H, d, J=8.0Hz), 8.18(2H, m) |
| 4-68 | 2.35(3H, s), 3.50(3H, br d, J=1.0Hz), 3.83(3H, s), 5.02(1H, d, J=12.2Hz), 5.10(1H, d, J=12.2Hz), 6.22(1H, s), 6.65(1H, br s), 7.1–7.3(5H, m) |
| 4-69 | 2.27(3H, s), 2.30(6H, s), 3.54(3H, br d, J=1.1Hz), 3.83(3H, s), 5.10(1H, d, J=11.8Hz), 5.16(1H, d, J=11.8Hz), 6.25(1H, s), 6.63(1H, br s), 6.87(2H, s), 7.13(1H, d, J=9.0Hz) |
| 4-70 | 3.55(3H, br d, J=1.1Hz), 3.83(3H, s), 4.99(1H, d, J=13.1Hz), 5.08(1H, d, J=13.1Hz), 6.27(1H, s), 6.35(2H, m), 6.63(1H, br s), 7.17(1H, d, J=9.0Hz), 7.41(1H, m) |
| 5-1 | 2.05(1H, br s), 4.05(3H, s), 7.66(1H, d, J=8.8Hz) |
| 5-2 | 4.36(2H, br s), 7.61(1H, d, J=8.7Hz) |
| 5-3 | 2.30(2H, dt, J=27.2, 5.6Hz), 3.85(3H, s), 4.22(2H, t, J=6.8Hz), 4.42(2H, br s, 4.60(2H, dt J=46.9, 5.6Hz), 6.65(1H, d, J=9.5Hz) |
| 5-4 | 2.24(2H, dt, J=26.7, 5.7Hz), 4.19(2H, t, J=6.9Hz), 4.61(2H, dt, J=47.0, 5.7Hz), 7.86(1H, d, J=9.0Hz) |
| 5-5 | 2.30(2H, dt, J=26.4, 5.7Hz), 4.17(2H, t, J=6.8Hz), 4.55(2H, dt, J=47.0, 5.7Hz), 4.88(2H, br s), 6.55(1H, d, J=9.6Hz), 8.07(1H, br) |
| 5-6 | 4.06(3H, s), 7.87(1H, s) |
| 5-7 | 2.13(2H, m), 3.06(3H, s), 3.93(2H, t, J=4.8Hz), 4.60(2H, br d, J=47.0Hz), 7.53(1H, s) |
| 5-8 | 2.30(2H, dt, J=26.4, 5.6Hz), 4.24(2H, t, J=6.7Hz), 4.58(2H, dt, J=46.8, 5.6Hz), 7.87(1H, s), 9.62(1H, s) |
| 5-9 | 2.06(1H, s), 2.30(2H, dtt, J= 27.7, 6.8, 5.4Hz), 4.24(2H, t, J=6.8Hz), 4.60(2H, dt, J=46.9, 5.4Hz), 5.90(2H, s), 6.77(1H, s) |
| 5-15 | 2.30(2H, dtt, J=26.0, 6.1, 5.5Hz), 2.62(1H, d, J=2.4Hz), 4.21(2H, t, J=6.8Hz), 4.48(2H, s), 4.60(2H, dt, J=46.9, 5.5Hz), 4.73(2H, d, J=2.4Hz), 6.92(1H, s) |
| 5-16 | 1.35(6H, d, J=6.2Hz), 2.29(2H, dtt, J=27.7, 5.9, 5.5Hz), 4.21(2H, t, J=6.8Hz), 4.29(2H, br s), 4.53(1H, q, J=6.2Hz), 4.59(2H, dt, J=6.9, 5.5Hz), 6.92(1H, s) |
| 5-17 | 2.30(2H, dt, J=26.4, 5.7Hz), 2.75(1H, t, J=2.5Hz), 4.19(2H, t, J=6.8Hz), 4.61(2H, dt, J=47.0, 5.7Hz), 4.72(2H, d, J=2.5Hz), 5.02(2H, br s), 6.61(1H, d, J=9.4Hz) |
| 5-18 | 1.35(6H, d, J=6.0Hz), 2.30(2H, dtt, J=26.9, 6.8, 5.4Hz), 4.21(2H, t, J=6.8Hz), 4.37(2H, br s), 4.52(1H, penta, J=6.0Hz), 4.59(2H, dt, J=46.5, 5.4Hz), 6.65(1H, d, J=9.6Hz) |
| 5-26 | 2.08(2H, m), 3.84(3H, s), 4.09(2H, t, J=6.7Hz), 4.31(2H, dt, J=46.9, 5.6Hz), 7.26(1H, d, J=9.1Hz), 7.55(2H, m), 7.89(4H, m), 8.40(1H, s), 8.53(1H, br s) |
| 5-27 | 1.67(2H, dt, J=26.5, 5.8Hz), 3.86(3H, s), 3.89(2H, s), 3.97(2H, dt, J=42.4, 5.6Hz), 7.27(1H, d, J=8.7Hz), 7.52(4H, m), 7.78(4H, m), 7.88(4H, m), 8.54(2H, s) |
| 5-28 | 2.22(2H, dt, J=26.2, 5.8Hz), 3.81(3H, s), 4.01(2H, s), 4.13(2H, d, J=6.8Hz), 4.52(2H, dt, J=46.9, 5.6Hz), 4.64(2H, s), 7.23(1H, d, J=9.1Hz), 7.36(5H, m), 8.67(1H, br s) |
| 6-1 | 2.48(3H, s), 7.03(1H, t, J=57.9Hz), 7.65(1H, d, J=8.6Hz), 9.88(1H, s) |
| 6-2 | 2.48(3H, s), 4.26(2H, br s), 5.70(1H, br s), 6.59(1H, d, J=9.4Hz), 7.07(1H, t, J=58.0Hz) |
| 6-13 | 2.53(3H, s), 6.89(1H, ddd, J=12.5, 8.3, 2.4Hz), 7.05(1H, m), 7.10(1H, t, J=58.0Hz), 7.33(1H, d, J=2.2Hz), 8.21(1H, ddd, J=9.1, 9.1, 6.5Hz), 8.57(1H, d, J=2.2Hz), 8.72(1H, br d, J=16.5Hz) |

TABLE XVIII-continued

| No. | $^1$H NMR data NMR($CDCl_3$, 300MHz) ppm |
|---|---|
| 6-14 | 2.37(3H, s), 3.88(3H, s), 6.94(1H, ddd, J=10.9, 8.3, 2.3Hz), 6.99(1H, m), 7.05(1H, t, J=58.0Hz), 7.26(1H, d, J=9.1Hz), 8.04(1H, ddd, J=8.8, 8.8, 6.5Hz), 8.48(1H, br d, J=13.4Hz) |
| 6-15 | 2.31(3H, s), 3.88(3H, s), 7.03(1H, t, J=58.0Hz), 7.25(1H, d, J=9.4Hz), 7.60(2H, m), 7.8–8.0(4H, m), 8.25(1H, s), 8.40(1H, s) |
| 6-16 | 2.54(3H, s), 7.12(1H, d, J=58.0Hz), 7.35(1H, d, J=2.3Hz), 7.61(2H, m), 7.83(1H, dd, J=8.5, 1.8Hz), 7.90(3H, m), 8.29(1H, s), 8.48(1H, d, J=2.3Hz), 8.64(1H, br s) |
| 6-17 | 2.29(3H, s), 3.89(3H, s), 7.03(1H, t, J=58.0Hz), 7.53(1H, s), 7.60(2H, m), 7.92(4H, m), 8.07(1H, br s), 8.37(1H, br s) |
| 6-18 | 1.29(3H, t, J=7.1Hz), 2.45(3H, s), 4.3(2H, q, J=7.1Hz), 6.7(1H, broad), 7.03(1H, t, J=58.0Hz), 7.83(1H, s) |
| 6-19 | 1.27(3H, t, J=7.0Hz), 2.48(3H, s), 4.18(2H, q, J=7.0Hz), 4.51(2H, s), 6.67(1H, s), 6.91(1H, s), 7.08(1H, t, J=58.0Hz) |
| 6-20 | 2.38(3H, s), 4.77(4H, s), 7.16(1H, t, J=57.7Hz), 7.17(1H, s) |
| 6-21 | 2.47(3H, s), 7.04(1H, t, J=7.2Hz), 7.59(1H, 2d, J=2.3Hz, 8.6Hz), 7.91(1H, t, J=2.1Hz) |
| 6-22 | 2.47(3H, s), 3.65(2H, s), 6.75(1H, 2d, J=2.2Hz, 9.4Hz), 7.07(1H, t, J=57.9Hz), 7.20(1H, t, J=1.8Hz) |
| 6-23 | 2.52(3H, s), 6.9–7.1(3H, m), 7.10(1H, t, J=57.9Hz), 7.14(1H, 2d), 8.06(1H, m), 9.76(1H, s) |
| 6-24 | 2.51(3H, s), 6.93(1H, 2d, J=2.2Hz, 8.9Hz), 7.12(1H, t, J=58.0Hz), 7.12(1H, s), 7.61(2H, m), 7.9–8.0(3H, m), 8.07(1H, 2d, J=1.7Hz), 8.68(1H, s), 9.74(1H, s) |
| 7-1 | 4.01(3H, s), 4.03(3H, br q, J=1.0Hz), 7.43(1H, d, J=8.4Hz) |
| 7-2 | 3.84(3H, s), 4.06(3H, s), 4.57(2H, s), 6.57(1H, d, J=9.3Hz) |
| 7-3 | 4.07(3H, br d, J=0.9Hz), 6.61(1H, d, J=9.2Hz) |
| 7-14 | 3.87(3H, s), 3.91(3H, s), 7.23(1H, d, J=8.9Hz), 7.60(2H, m), 7.80–7.96(4H, m), 8.13(1H, br s), 8.32(1H, br s) |
| 7-15 | 3.86(3H, s), 3.97(3H, s), 6.45(1H, d, J=15.6Hz), 7.20(1H, d, J=8.9Hz), 7.30–7.52(6H, m), 7.60(1H, d, J=15.6Hz) |
| 8-1 | 1.84(4H, m), 2.44(4H, m), 7.62(1H, d, J=8.5Hz), 9.88(1H, br) |
| 8-2 | 1.79(4H, m), 2.41(4H, m), 5.53(3H, br), 6.53(1H, d, J=9.1Hz) |
| 8-3 | 1.81(4H, m), 2.43(4H, m), 2.58(1H, t, J=2.4Hz), 4.24(2H, br s), 4.69(2H, t, J=2.4Hz), 6.60(1H, d, J=9.2Hz) |
| 8-4 | 1.35(6H, d, J=6.2Hz), 1.82(4H, m), 2.43(4H, m), 4.11(2H, br s), 4.48(1H, q, J=6.2Hz), 6.60(1H, d, J=9.4Hz) |
| 8-5 | 1.77(4H, m), 1.82(4H, m), 2.43(4H, m), 2.34(4H, m), 4.04(2H, br s), 4.79(1H, m), 6.61(1H, d, J=9.4Hz) |
| 8-6 | 1.82(4H, m), 2.42(4H, m), 4.03(3H, s), 7.48(1H, d, J=8.6Hz) |
| 8-7 | 1.80(4H, m), 2.08(2H, br s), 2.41(4H, m), 3.83(3H, s), 6.60(1H, d, J=9.4Hz) |
| 8-8 | 1.78(4H, m), 2.38(4H, m), 3.86(3H, s), 6.96(2H, m), 7.25(1H, d, J=9.0Hz), 8.01(1H, m), 8.19(1H, d, J=12.6Hz) |
| 8-9 | 1.68(4H, m), 2.32(4H, m), 3.82(3H, s), 7.22(1H, d, J=9.1Hz), 7.59(2H, m), 7.91(5H, m), 8.34(1H, s) |
| 8-13 | 1.76(4H, m), 2.34(4H, m), 2.37(1H, t, J=2.4Hz), 4.77(2H, t, J=2.4Hz), 6.95(2H, m), 7.27(1H, d, J=8.9Hz), 8.04(1H, m), 8.38(1H, br d, J=12.5Hz) |
| 8-18 | 1.28(6H, d, J=6.2Hz), 1.76(4H, m), 2.32(4H, m), 4.45(1H, q, J=6.2Hz), 6.95(2H, m), 7.24(1H, d, J=9.0Hz), 8.00(1H, m), 8.31(1H, br d, J=12.7Hz) |
| 8-30 | 1.71(4H, m), 2.33(4H, m), 3.80(3H, s), 5.39(1H, d, J=10.9Hz), 5.86(1H, d, J=17.6Hz), 6.75(1H, dd, J=17.6, 10.9Hz), 7.21(1H, d, J=9.0Hz), 7.47(2H, d, J=8.2Hz), 7.77(2H, d, J=8.2Hz), 7.85(1H, s) |
| 8-31 | 1.76(4H, m), 2.38(4H, m), 3.82(3H, s), 6.52(1H, d, J=15.6Hz), 7.19(1H, d, J=9.0Hz), 7.37(3H, m), 7.47(3H, m), 7.65(1H, d, J=15.6Hz) |
| 8-32 | 1.85(4H, m), 2.45(4H, m), 8.31(2H, s) |
| 8-33 | 1.81(4H, m), 2.43(4H, m), 7.37(1H, d, J=8.5Hz), 7.69(1H, 2d, J=2.3Hz, 8.5Hz), 8.10(1H, d, J=2.3Hz) |
| 8-34 | 1.86(4H, m), 2.46(4H, m), 7.72(1H, d, J=8.8Hz), 8.56(1H, 2d, J=2.6Hz, 8.8Hz), 8.92(1H, d, J=2.6Hz) |
| 8-35 | 1.80(4H, m), 2.40(4H, m), 3.83(2H, s), 6.79(2H, m), 6.91(1H, d, J=8.3Hz) |
| 8-36 | 1.78(4H, m), 2.40(4H, m), 7.15–7.30(2H, m), 7.6(2H, m), 7.9(4H, m), 8.14(1H, d, J=2.2Hz), 8.34(1H, s), 8.59(1H, s) |
| 9-1 | 1.91(4H, m), 3.67(4H, m), 7.65(1H, d, J=8.3Hz) |
| 9-3 | 1.87(4H, m), 3.62(4H, m), 4.03(3H, s), 7.53(1H, d, J=8.5Hz) |
| 9-4 | 1.88(4H, m), 3.65(4H, m), 3.85(3H, s), 4.28(2H, s), 6.64(1H, d, J=9.5Hz) |
| 9-12 | 2.01(4H, m), 3.73(2H, m), 3.92(1H, m), 4.15(1H, m), 7.53(1H, d, J=8.5Hz), 7.76(1H, J=8.5, 2.4Hz), 8.21(1H, d, J=2.4Hz) |
| 9-13 | 1.90(4H, m), 3.69(2H, m), 3.95(2H, m), 4.85(2H, br s), 679(2H, m), 7.00(1H, d, J=8.3Hz) |
| 9-14 | 1.94(4H, m), 3.69(2H, m), 4.03(2H, m), 7.27(2H, m), 7.59(2H, m), 7.94(4H, m), 8.19(1H, d, J=2.0Hz), 8.47(1H, s), 9.11(1H, br s) |
| 9-15 | 1.70(4H, m), 3.50(4H, m), 3.83(3H, s), 7.23(1H, d, J=9.0Hz), 7.59(2H, m), 7.92(4H, m), 8.34(1H, s), 8.43(1H, s) |
| 9-16 | 1.82(4H, m), 3.58(4H, m), 3.87(3H, s), 6.9–7.1(2H, m), 7.27(1H, d, J=9.0Hz), 8.07(1H, m), 8.49(1H, d, J=13.1Hz) |
| 9-17 | 1.89(4H, m), 3.65(4H, m), 7.53(1H, d, J=8.6Hz), 7.72(1H, 2d, J=2.3Hz, 8.5Hz), 8.13(1H, d, J=2.3Hz) |
| 9-18 | 1.85(4H, m), 3.63(4H, m), 4.03(2H, s), 6.82(2H, m), 7.09(1H, 2d, J=0.6Hz, 8.0Hz) |
| 9-19 | 1.80(4H, m), 3.60(4H, m), 7.22(1H, 2d, J=2.3Hz, 8.7Hz), 7.35(1H, d, J=8.7Hz), 7.56(2H, m), 7.89(4H, m), 8.08(1H, d, J=2.3Hz), 8.43(1H, s), 9.41(1H, s) |
| 11-1 | 4.05(3H, s), 7.30(1H, m), 7.53(1H, d, J=8.7Hz), 8.01(1H, d, J=2.1Hz) |
| 11-2 | 7.33(1H, m), 7.70(1H, d, J=8.4Hz), 8.06(1H, d, J=2.1Hz), 10.29(1H, s) |
| 11-3 | 6.53(1H, d, J=9.5Hz), 6.53(3H, br), 7.40(1H, s), 8.17(1H, s) |
| 11-4 | 3.86(3H, s), 4.33(2H, br s), 6.65(1H, d, J=9.5Hz), 7.34(1H, dq, J=2.2, 1.0Hz), 8.10(1H, d, J=2.2Hz) |
| 11-5 | 3.31(3H, s), 3.79(3H, s), 4.33(2H, br s), 7.21(1H, d, J=1.1Hz), 7.49(1H, d, J=8.8Hz), 7.95(1H, d, J=2.2Hz) |
| 11-6 | 3.86(3H, s), 7.26(1H, d, J=9.2Hz), 7.27(1H, dq, J=2.2, 1.1Hz), 7.56(2H, m), 7.88(4H, m), 7.97(1H, d, J=2.2Hz), 8.38(1H, s), 8.79(1H, s) |
| 11-7 | 3.93(3H, s), 7.30(1H, d, J=6.7Hz), 7.35(1H, dq, J=2.2, 1.1Hz), 8.08(1H, d, J=2.2Hz) |
| 11-8 | 1.20, 1.23(3H, t, J=7.1Hz), 3.20(2H, m), 3.94(3H, s), 4.16(2H, q, J=7.1Hz), 4.52(1H, m), 7.32(2H, m), 8.08(1H, m) |
| 11-9 | 2.43(3H, q, J=2.2Hz), 7.67(1H, d, J=8.5Hz), 8.01(1H, s), 10.2(1H, br) |
| 11-10 | 2.46(3H, q, J=1.8Hz), 2.63(3H, br), 6.60(1H, d, J=9.4Hz), 8.08(1H, s) |
| 11-11 | 2.45(3H, q, J=1.9Hz), 3.87(3H, s), 6.66(1H, d, J=9.6Hz), 8.06(1H, s) |
| 11-12 | 2.44(3H, q, J=1.9Hz), 2.58(3H, s), 3.84(3H, s), 6.60(1H, d, J=9.4Hz), 8.03(1H, s) |
| 11-13 | 2.38(3H, q, J=1.8Hz), 3.68(3H, s), 7.26(1H, d, J=9.3Hz), 7.59(2H, m), 7.80(1H, m), 7.91(4H, m), 8.11(1H, s), 8.30(1H, s) |
| 12-1 | 1.64(3H, m), 1.91(1H, m), 2.10(1H, m), 2.35(1H, m), 3.16(1H, m), 4.17(1H, m), 4.82(1H, m), 7.66(1H, d, J=8.2Hz), 10.4(1H, broad) |
| 12-2 | 1.61(3H, m), 1.91(1H, m), 2.10(1H, m), 2.38(1H, m), 3.13(1H, m), 4.11(1H, m), 4.14(2H, s), 4.87(1H, m), 5.49(1H, s), 6.64(1H, d, J=9.0Hz) |
| 12-3 | 1.61(3H, m), 1.90(1H, m), 2.08(1H, m), 2.35(1H, m), 3.10(1H, m), 4.07(1H, m), 4.2(2H, broad), 4.88(1H, m), 5.5(1H, broad), 6.63(1H, d, J=9.0Hz) |
| 12-4 | 1.60(3H, m), 1.89(1H, m), 2.09(1H, m), 2.34(1H, m), 3.09(1H, m), 3.85(3H, s), 4.11(1H, m), 4.3(2H, broad), 4.87(1H, m), 6.63(1H, d, J=9.3Hz) |
| 12-5 | 1.4–1.7(3H, m), 1.7–2.4(3H, m), 2.95(1H, m), 3.85(3H, s), 3.97(1H, m), 4.71(1H, m), 7.26(1H, m), 7.60(2H, m), 7.93(4H, m), 8.15(1H, s), 8.44(1H, s) |
| 12-6 | 1.54(3H, m), 1.78(1H, m), 2.07(1H, m), 2.27(1H, m), 2.95(1H, m), 4.01(1H, m), 4.22(1H, m), 7.44(1H, d, J=8.5Hz), 7.69(1H, 2d, J=2.3Hz, 8.5Hz), 8.11(1H, d, J=2.3Hz) |
| 12-7 | 1.50(3H, m), 1.78(1H, m), 2.05(1H, m), 2.28(1H, m), 2.89(1H, m), 3.90(1H, m), 3.95(2H, s), 4.15(1H, m), 6.81(2H, m), 6.99(1H, d, J=7.9Hz) |
| 12-8 | 1.41(3H, m), 1.68(1H, m), 1.93(1H, m), 2.24(1H, m), 2.83(1H, m), 3.88(1H, m), 4.11(1H, m), 7.23(2H, m), 7.54(2H, m), 7.87(4H, m), 7.97(1H, s), 8.38(1H, s), 9.11(1H, s) |
| 13-1 | 4.36(1H, br s), 7.61(1H, d, J=8.6Hz), 7.88(2H, m), 7.99(2H, m) |
| 13-2 | 5.42(1H, br s), 6.58(1H, d, J=9.4Hz), 7.95(4H, m) |
| 13-3 | 3.86(3H, s), 7.28(1H, d, J=9.0Hz), 7.50–7.95(10H, m), 8.03(1H, br s), 8.28(1H, br s) |
| 13-4 | 3.89(3H, s), 6.89.(2H, m), 7.30(1H, d, J=9.0Hz), 7.70–7.95(5H, m), 8.34(1H, m) |
| 13-5 | 7.33(2H, m), 7.56(2H, m), 7.7–8.0(8H, m), 8.19(1H, d, J=1.4Hz), 8.32(1H, s), 8.56(1H, br s) |
| 14-1 | 1.23(3H, t, J=7.1Hz), 2.51(2H, m), 2.75(2H, m), 3.55(3H, s), 3.90(3H, s), 4.10(2H, q, J=7.1Hz), 6.36(1H, s), 7.20(1H, d, J=8.9Hz) |

TABLE XVIII-continued

| No. | $^1$H NMR data NMR($CDCl_3$, 300MHz) ppm |
|---|---|
| 14-2 | 1.30(3H, t, J=7.1Hz), 3.56(3H, s), 3.82(3H, s), 4.23(2H, q, J=7.1Hz), 6.36(1H, s), 6.60(1H, d, J=16.2Hz), 7.31(1H, d, J=8.6Hz), 7.36(1H, d, J=16.2Hz) |
| 14-3 | 3.01(1H, m), 3.25(1H, m), 3.57(3H, s), 3.70, 3.73(3H, 2s), 3.93, 3.94(3H, 2s), 4.55(1H, m), 6.36, 6.37(1H, 2s), 7.26(1H, d, J=8.8Hz) |
| 14-4 | 1.23(3H, t, J=7.1Hz), 3.03(1H, m), 3.22(1H, m), 3.55(3H, s), 3.94(3H, s), 4.14(2H, m), 4.51(1H, m), 6.37(1H, s), 7.26(1H, d, J=8.8Hz) |
| 14-5 | 1.24(3H, t, J=7.1Hz), 2.95(1H, m), 3.31(1H, m), 3.56(3H, s), 3.93(3H, s), 4.16(2H, m), 4.54(1H, m), 6.35(1H, s), 7.26(1H, d, J=8.8Hz) |
| 14-6 | 0.89(3H, t, J=7.4Hz), 1.61(2H, m), 3.02(1H, m), 3.23(1H, m), 3.56(3H, s), 3.94(3H, s), 4.07(2H, m), 4.53(1H, m), 6.37(1H, s), 7.25(1H, d, J=8.8Hz) |
| 14-7 | 0.90(3H, t, J=7.4Hz), 1.62(2H, m), 2.96(1H, m), 3.31(1H, m), 3.56(1H, s), 3.94(3H, s), 4.08(2H, m), 4.56(1H, m), 6.36(1H, s), 7.25(1H, d, J=8.9Hz) |
| 14-8 | 0.90(3H, t, J=7.3Hz), 1.33(2H, m), 1.58(2H, m), 3.03(1H, m), 3.22(1H, m), 3.55(3H, s), 3.94(3H, s), 4.08(2H, m), 4.52(1H, m), 6.37(1H, s), 7.26(1H, d, J=8.8Hz) |
| 14-9 | 0.91(3H, t, J=7.3Hz), 1.33(2H, m), 1.59(2H, m), 2.98(1H, m), 3.32(1H, m), 3.56(3H, s), 3.93(3H, s), 4.11(2H, m), 4.56(1H, m) 6.35(1H, s), 7.25(1H, d, J=8.8Hz) |
| 14-10 | 0.88(3H, t, J=6.7Hz), 1.27(4H, m), 1.60(2H, m), 3.02(1H, m), 3.22(1H, m), 3.56(3H, s), 3.94(3H, s), 4.09(2H, m), 4.52(1H, m), 6.37(1H, s), 7.25(1H, d, J=8.9Hz) |
| 14-11 | 0.89(3H, t, J=6.7Hz), 1.31(4H, m), 1.61(2H, m), 2.96(1H, m), 3.30(1H, m), 3.56(3H, s), 3.93(3H, s), 4.10(2H, m), 4.56(1H, m), 6.35(1H, s), 7.26(1H, d, J=8.9Hz) |
| 14-12 | 0.87(3H, t, J=6.4Hz), 1.27(6H, m), 1.59(2H, m), 3.03(1H, m), 3.22(1H, m), 3.56(3H, s), 3.94(1H, s), 4.08(2H, m), 4.52(1H, m), 6.37(1H, s), 7.25(1H, d, J=8.8Hz) |
| 14-13 | 0.88(3H, t, J=6.9Hz), 1.28(6H, m), 1.59(2H, m), 2.96(1H, m), 3.32(1H, t), 3.56(3H, s), 3.94(3H, s), 4.10(2H, m), 4.56(1H, m), 6.35(1H, s), 7.26(1H, d, J=8.8Hz) |
| 14-14 | 0.88(6H, m), 1.90(1H, m), 3.02(1H, m), 3.23(1H, m), 3.56(3H, s), 3.87(2H, m), 3.94(3H, s), 4.54(1H, m), 6.37(1H, s), 7.25(1H, d, J=8.9Hz) |
| 14-15 | 0.89(6H, m), 1.91(1H, m), 2.96(1H, m), 3.32(1H, m), 3.56(3H, s), 3.89(2H, m), 3.94(3H, s), 4.58(1H, m), 6.35(1H, s), 7.26(1H, d, J=8.9Hz) |
| 14-16 | 0.89(6H, m), 1.50(2H, m), 1.60(1H, m), 3.02(1H, m), 3.21(1H, m), 3.56(3H, s), 3.94(3H, s), 4.13(2H, m), 4.52(1H, m), 6.37(1H, s), 7.25(1H, d, J=8.9Hz) |
| 14-17 | 0.88(6H, m), 1.49(2H, m), 1.62(1H, m), 2.96(1H, m), 3.30(1H, m), 3.56(3H, s), 3.93(3H, s), 4.14(2H, m), 4.56(1H, m), 6.35(1H, s), 7.25(1H, d, J=8.9Hz) |
| 14-18 | 1.44, 1.46(9H, 2s), 2.90(1H, m), 3.31(1H, m), 3.56(3H, s), 3.92, 3.93(3H, 2s), 4.42(1H, m), 6.34, 6.37(1H, 2s), 7.26(1H, d, J=9.0Hz). |
| 14-19 | 2.51(1H, m), 3.05(1H, m), 3.20(1H, m), 3.56(3H, s), 3.94(3H, s), 4.59(1H, m), 4.68(2H, m), 6.37(1H, s), 7.26(1H, s), J=8.9Hz) |
| 14-20 | 2.51(1H, m), 2.99(1H, m), 3.20(1H, m), 3.56(3H, s), 3.94(3H, s), 4.61(1H, m), 4.70(2H, m), 6.36(1H, s), 7.26(1H, d, J=8.9Hz) |
| 14-21 | 3.0–3.3(2H, m), 3.56(3H, s), 3.93, 3.94(3H, 2s), 4.3–4.6(2H, m), 4.69(1H, m), 6.35, 6.37(1H, 2s), 7.28(1H, d, J=8.8Hz) |
| 14-22 | 3.06(1H, m), 3.24(1H, m), 3.56(3H, s), 3.93, 3.94(3H, 2s), 4.4–4.6(2H, m), 5.86(1H, m), 6.36, 6.37(1H, 2s), 7.28(1H, d, J=8.8Hz) |
| 14-23 | 3.04–3.21(2H, m), 3.56(3H, s), 4.47, 4.65(2H, 2m), 4.69(1H, m), 6.37(1H, s), 7.28(1H, d, J=8.7Hz) |
| 14-24 | 3.02(1H, m), 3.24(1H, m), 3.56(3H, s), 3.93(3H, s), 4.61(2H, m), 4.70(1H, m), 6.35(1H, s), 7.28(1H, d, J=8.7Hz) |
| 14-25 | 2.98(1H, m), 3.30(1H, m), 3.34(3H, s), 3.53(2H, m), 3.56(3H, s), 3.94(3H, s), 4.25(2H, m), 4.62(1H, m), 6.35(1H, s), 7.26(1H, d, J=8.9Hz) |
| 14-26 | 1.18(3H, m), 3.05(1H, m), 3.27(1H, m), 3.4–3.6(4H, m), 3.56(3H, s), 3.93, 3.94(3H, 2s), 4.29(2H, m), 4.61(1H, m), 6.35, 6.37(1H, 2s), 7.26(1H, d, J=8.8Hz) |
| 14-27 | 3.04(1H, m), 3.21(1H, m), 3.54(3H, s), 3.91(3H, s), 4.10(2H, m), 4.45(2H, m), 4.61(1H, m), 6.35(1H, s), 6.92(3H, m), 7.27(3H, m) |
| 14-28 | 2.99(1H, m), 3.30(1H, m), 3.55(3H, s), 3.90(3H, s), 4.12(2H, m), 4.46(2H, m), 4.64(1H, m), 6.34(1H, s), 6.93(3H, m), 7.26(3H, m) |
| 14-29 | 2.66(2H, m), 3.07(1H, m), 3.21(1H, m), 3.56(3H, s), 3.95(3H, s), 4.30(2H, m), 4.63(1H, m), 6.35, 6.38(1H, 2s), 7.28(1H, d, J=8.9Hz) |
| 14-30 | 3.08(1H, m), 3.22(1H, m), 3.56(3H, s), 3.70(2H, m), 3.95(3H, s), 4.30(1H, m), 4.51(2H, m), 4.65(1H, m), 6.38(1H, s), 7.27(1H, d, J=8.7Hz). |
| 14-31 | 3.02(1H, m), 3.42(1H, m), 3.57(3H, s), 3.72(2H, m), 3.95(3H, s), 4.29(1H, m), 4.52(2H, m), 4.66(1H, m), 6.36(1H, s), 7.27(1H, d, J=8.8Hz) |
| 14-32 | 1.22(3H, t, J=7.1HZ), 3.13(1H, m), 3.31(1H, m), 3.55(3H, s), 3.95(3H, s), 4.13(2H, m), 4.46(1H, m), 6.38(1H, s), 7.25(1H, d, J=8.9Hz). |
| 14-33 | 1.23(3H, t, J=7.1Hz), 3.08(1H, m), 3.41(1H, m), 3.57(3H, s), 3.93(3H, s), 4.12(2H, m), 4.49(1H, m), 6.36(1H, s), 7.25(1H, d, J=8.9HZ) |
| 14-34 | 1.27(3H, m), 1.61, 1.64(3H, 2s), 3.20(1H, m), 3.54(3H, s), 3.61(1H, m), 3.84(3H, s), 4.18(2H, m), 6.32, 6.37(1H, 2s), 7.27(1H, 2d) |
| 14-35 | 0.94(3H, m), 1.62, 1.65(3H, 2s), 1.67(2H, m), 3.21(1H, m), 3.54(3H, s), 3.62(1H, m), 3.84(3H, s), 4.09(2H, m), 6.33, 6.37(1H, 2s), 7.27(1H, 2d, J=8.8Hz, 8.8Hz) |
| 14-36 | 0.94(3H, m), 1.41(2H, m), 1.61, 1.65(3H, 2s), 1.63(2H, m), 3.21(1H, m), 3.54(3H, s), 3.60(1H, m), 3.84(3H, s), 4.12(2H, m), 6.32, 6.37(1H, 2s), 7.27(1H, 2d, J=8.8Hz, 8.9Hz) |
| 14-37 | 0.90(3H, m), 1.33(4H, m), 1.61, 1.64(3H, 2s), 1.65(2H, m), 3.20(1H, m), 3.54(3H, s), 3.59(1H, m), 3.84(3H, s), 4.12(2H, m), 6.32, 6.37(1H, 2s), 7.27(1H, 2d, J=8.9Hz, 8.7Hz) |
| 14-38 | 0.89(3H, m), 1.30(6H, m), 1.61, 1.64(3H, 2s), 1.65(2H, m), 3.20(1H, m), 3.54(3H, s), 3.59(1H, m), 3.84(3H, s), 4.11(2H, m), 6.32, 6.36(1H, 2s), 7.27(1H, 2d, J=8.8Hz, 8.8Hz) |
| 14-39 | 1.26(6H, m), 1.59, 1.62(3H, 2s), 3.20(1H, m), 3.54(3H, s), 3.63 (1H, m), 3.85(3H, s), 4.98(1H, m), 6.32, 6.37(1H, 2s), 7.27(1H, 2d, J=8.8Hz, 8.8Hz) |
| 14-40 | 0.94(6H, m), 1.62, 1.65(3H, 2s), 1.96(1H, m), 3.21(1H, m), 3.54(3H, s), 3.62(1H, m), 3.84(3H, s), 3.92(2H, m), 6.32, 6.37(1H, 2s), 7.27(1H, 2d, J=8.8Hz, 8.8Hz) |
| 14-41 | 1.63, 1.66(3H, 2s), 3.22(1H, m), 3.53(3H, s), 3.63(1H, m), 3.79(3H, s), 5.16(2H, m), 6.29, 6.36(1H, 2s), 7.25(1H, 2d, J=8.8Hz, 8.8Hz), 7.35(5H, m) |
| 14-42 | 1.64, 1.67(3H, 2s), 3.23(1H, m), 3.52, 3.55(3H, 2s), 3.66(1H, m), 3.84(3H, s), 4.71(1H, m), 5.00(1H, m), 6.33, 6.37(1H, 2s), 7.18(1H, m), 7.27(1H, 2d, J=8.8Hz, 8.8Hz) |
| 14-43 | 1.63, 1.66(3H, 2s), 3.21(1H, m), 3.54(3H, s), 3.62(1H, m), 3.84(3H, s), 4.63(2H, m), 5.31(2H, m), 5.89(1H, m), 6.33, 6.37(1H, 2s), 7.27(1H, 2d, J=8.9Hz, 8.7Hz) |
| 14-44 | 1.63(3H, m), 2.52(1H, m), 3.18(1H, m), 3.56(3H, s), 3.60(1H, m), 3.84(3H, s), 4.74(2H, m), 6.34, 6.37(1H, 2s), 7.26, 7.27(1H, 2d, J=8.7Hz, 8.8Hz) |
| 14-45 | 1.65, 1.68(3H, 2s), 3.19(1H, m), 3.51(1H, m), 3.55(3H, s), 3.83(3H, s), 4.49(2H, m), 5.86(1H, m), 6.34, 6.37(1H, 2s), 7.28(1H, 2d, J=8.8Hz, 8.8Hz) |
| 14-46 | 1.67, 1.68(3H, 2s), 3.18(1H, m), 3.53, 3.55(3H, 2s), 3.66(1H, m), 3.82, 3.83(3H, 2s), 5.73(1H, m), 6.35, 6.37(1H, 2s), 7.31(1H, 2d, J=8.9Hz, 8.8Hz) |
| 14-47 | 1.63, 1.65(3H, 2s), 3.20.(1H, m), 3.36, 3.37(3H, 2s), 3.55(3H, s), 3.63(3H, m), 3.84(3H, s), 4.29(2H, m), 6.33, 6.36(1H, 2s), 7.27(1H, 2d, J=8.8Hz, 8.8Hz) |
| 14-48 | 1.62, 1.64(3H, 2s), 2.16(3H, t, J=2.4Hz), 2.73(2H, m), 3.20(1H, m), 3.55(3H, s), 3.59(1H, m), 3.84(3H, s), 4.30(2H, m), 6.33, 6.36(1H, 2s), 7.27(1H, 2d, J=8.8Hz, 8.8Hz) |
| 14-49 | 1.63, 1.65(3H, 2s), 1.8–2.1(4H, m), 3.20(1H, m), 3.54(3H, s), 3.61(1H, m), 3.81(2H, m), 3.84(3H, s), 4.13(3H, m), 6.33, 6.36(1H, s), 7.27(1H, 2d, J=8.7Hz, 8.9Hz) |
| 14-50 | 3.05(2H, m), 3.29(1H, m), 3.52, 3.57(3H, 2s), 3.59(1H, m), 3.68(3H, s), 3.76(3H, s), 3.79, 3.80(3H, 2s), 6.32, 6.35(1H, 2s), 7.29(1H, 2d, J=8.9Hz, 8.8Hz) |
| 14-51 | 1.31, 1.35(3H, 2t, J=7.2Hz, 7.1Hz), 3.50(1H, m), 3.55, 3.57(3H, 2s), 3.68(1H, m), 3.92, 3.94(3H, 2s), 4.31(2H, m), 6.35, 6.38(1H, 2s), 7.34(1H, 2d, J=8.9Hz, 8.9Hz) |
| 14-52 | 1.26(3H, t, J=7.1Hz), 2.48(3H, s), 3.07(1H, m), 3.38(1H, m), 4.21(2H, q, J=7.1Hz), 4.51(1H, m), 7.07(1H, t, J=58.0Hz), 7.23(2H, m) |
| 14-53 | 1.24(3H, t, J=7.1Hz), 1.90(4H, m), 3.15(1H, m), 3.43(1H, m), 3.65(4H, m), 3.92(3H, s), 4.18(2H, m), 4.48(1H, m), 7.26(1H, d, J=10.5Hz) |
| 14-54 | 1.16(3H, t, J=7.2Hz), 2.36(3H, s), 3.04(1H, m), 3.26(1H, |

TABLE XVIII-continued

| No. | $^1$H NMR data NMR($CDCl_3$, 300MHz) ppm |
|---|---|
| | m), 3.48(3H, s), 4.00–4.25(3H, m), 6.30(1H, s), 7.20(1H, d, J=8.8Hz) |
| 14-55 | 1.18(3H, t, J=7.2Hz), 2.37(3H, s), 3.03(1H, m), 3.31(1H, m), 3.50(3H, s), 4.00–4.25(3H, m), 6.28(1H, s), 7.20(1H, d, J=8.7Hz) |
| 14-56 | 1.21(3H, t, J=7.2Hz), 3.10–3.45(2H, m), 3.90(3H, s), 4.07(3H, br d, J=0.9Hz), 4.16(2H, q, J=7.2Hz), 4.54(1H, br t, J=7.3Hz), 7.20(1H, d, J=8.6Hz) |
| 14-57 | 3.45(3H, d, J=1.1Hz), 6.21(1H, s), 7.30(1H, d, J=8.4Hz), 7.46(2H, t, J=7.5Hz), 7.5–7.8(5H, m) |
| 14-58 | 3.31(3H, d, J=0.9Hz), 6.29(1H, s), 6.32(1H, d, J=12.2Hz), 6.80(1H, d, J=12.1Hz), 7.15(1H, d, J=8.5Hz), 7.28(2H, m), 7.35(1H, dd, J=8.5, 2.3Hz), 7.42(2H, m), 7.6–7.8(4H, m) |
| 14-59 | 3.48(3H, s), 6.34(1H, s), 6.72(1H, d, J=16.0Hz), 7.02(1H, d, J=8.4Hz), 7.18(1H, d, J=16.0Hz), 7.30(1H, dd, J=10.7, 2.3Hz), 7.39(2H, m), 7.48(1H, dd, J=8.7, 1.2Hz), 7.73(5H, m) |
| 14-60 | 1.25(1.5H, t, J=7.1Hz), 1.26(1, 5H, t, J=7.1Hz), 2.92(1H, m), 3.26(1H, m), 3.57(3H, m), 4.22(2H, m), 4.36(1H, m), 6.37(0.5H, s), 6.38(0.5H, s), 7.2–7.3(2H, m) |
| 14-61 | 1.21(3H, m), 2.49(3H, s), 3.33(2H, m), 3.90(3H, s), 4.18(2H, m), 4.52(1H, t, J=7.2Hz), 7.05(1H, t, J=58.0Hz), 7.25(1H, d, J=8.9Hz) |
| 14-62 | 1.46(3H, t, J=7.0), 3.58(3H, s), 4.12(2H, q, J=7.0Hz), 6.37(1H, s), 7.26(1H, d, J=8.7Hz) |
| 14-63 | 1.22(3H, t, J=7.2Hz), 1.47(3H, t, J=7.0), 3.00(1H, dd, 14.2, 5.2Hz), 3.23(1H, dd, J=14.2, 8.4Hz), 3.55(3H, q, J=0.8Hz), 4.12(2H, q, J=7.0), 4.12(2H, m), 4.57(1H, dd, J=8.4, 5.2Hz), 6.37(1H, s), 7.26(1H, d, J=8.7Hz) |
| 14-64 | 1.23(3H, t, J=7.1Hz), 1.46(3H, t, J=7.0Hz), 2.94(1H, dd, 14.4, 6.4Hz), 3.32(1H, dd, J=14.4, 7.0Hz), 3.55(3H, q, J=0.8Hz), 4.10(2H, q, J=7.0Hz), 4.17(2H, q, J=7.1Hz), 4.61(1H, dd, J=7.0, 6.4Hz), 6.34(1H, s), 7.25(1H, d, J=8.9Hz) |
| 14-65 | 0.89(3H, t, J=7.3Hz), 1.46(3H, t, J=7.0Hz), 1.62(2H, qt, J=7.3, 6.9Hz), 3.03(1H, dd, J=14.2, 5.4Hz), 3.21(1H, dd, J=14.2, 8.3Hz), 3.55(3H, q, J=1.0Hz), 4.04(2H, q, J=7.0Hz), 4.10(2H, m), 4.59(1H, dd, J=8.3, 5.4Hz), 6.37(1H, s), 7.25(1H, d, J=8.8Hz) |
| 14-66 | 0.90(3H, t, J=7.3Hz), 1.46(3H, t, J=7.0Hz), 1.63(2H, qt, J=7.3, 6.9Hz), 2.94(1H, dd, J=14.4, 6.8Hz), 3.32(1H, dd, J=14.4, 6.9Hz), 3.55(3H, q, J=1.0Hz), 4.07(2H, q, J=7.0Hz), 4.10(2H, m), 4.64(1H, dd, J=6.9, 6.8Hz), 6.35(1H, s), 7.25(1H, d, J=8.9Hz) |
| 14-67 | 1.38(6H, t, J=6.2), 3.57(3H, q, J=1.2Hz), 4.58(1H, q, J=6.2Hz), 6.37(1H, s), 7.27(1H, d, J=8.7Hz) |
| 14-68 | 1.22(3H, t, J=7.1Hz), 1.34, 1.39(6H, t, J=6.2Hz), 3.03(1H, dd, J=14.2, 5.3Hz), 3.26(1H, dd, J=14.2, 8.3Hz), 3.55(3H, s), 4.14(3H, q, J=7.1Hz), 4.58(1H, dd, J=8.3, 5.3Hz), 4.68(1H, q, J=6.2Hz), 6.36(1H, s), 7.25(1H, d, J=8.9Hz) |
| 14-69 | 1.22(3H, t, J=7.1Hz), 1.35, 1.37(6H, t, J=6.2Hz), 2.94(1H, dd, J=14.4, 6.5Hz), 3.35(1H, dd, J=14.4, 7.1Hz), 3.56(3H, s), 4.16(3H, q, J=7.1Hz), 4.64(1H, q, J=6.2Hz), 4.66(1H, dd, J=7.1, 6.5Hz), 6.34(1H, s), 7.25(1H, d, J=8.9Hz) |
| 14-70 | 1.25(3H, t, J=7.1Hz), 2.39(3H, s), 2.89(1H, dd, J=14.8, 7.8Hz), 3.23(1H, dd, J=14.8, 6.1Hz), 3.56(3H, q, J=1.0Hz), 4.17(2H, q, J=7.1Hz), 4.39(1H, dd, J=7.8, 6.1Hz), 6.37, 6.38(1H, s), 7.00(1H, d, J=8.0Hz), 7.22(1H, d, J=8.0Hz), 7.27(1H, s) |
| 14-71 | 0.89(3H, m), 1.63(2H, m), 3.00(1H, m), 3.54, 3.55(3H, s), 3.93(3H, s), 4.09(1H, m), 6.36, 6.38(1H, s), 7.23(1H, d, J=8.2Hz), 8.07(1H, dd, J=8.2, 1.9Hz), 8.16(1H, d, J=1.9Hz) |
| 14-72 | 0.86, 0.88(3H, t, J=6.8Hz), 1.57, 1.62(2H, m), 2.43(3H, s), 2.96(1H, dd, J=14.2, 6.9Hz), 3.39(1H, dd, J=14.7, 7.2Hz), 3.93(3H, s), 4.05(2H, m), 4.54(1H, dd, J=7.2, 6.9Hz), 7.28, 7.29(1H, d, J=8.8Hz), 8.02, 8.04(1H, s) |
| 14-73 | 3.14(2H, m), 3.54(3H, 2s), 3.94(3H, 2s), 4.63(1H, m), 6.38(1H, 2s), 7.25(1H, d, J=8.9Hz), 9.5(1H, broad) |
| 14-74 | 4.06(3H, s), 7.47(1H, d, J=8.4Hz), 8.10(1H, m), 8.80(1H, m) |
| 14-75 | 3.87(3H, s), 6.61(1H, d, J=9.4Hz), 8.12(1H, m), 8.88(1H, m) |
| 15-1 | 3.53(3H, s), 3.7(2H, broad), 6.4(1H, broad), 6.29(1H, s), 6.68(1H, d, J=9.1Hz) |
| 15-2 | 0.7–0.9(4H, m), 1.23(1H, m), 3.51(3H, s), 3.87(3H, s), 6.24(1H, s), 6.47(1H, s), 6.83(1H, d, J=9.0Hz), 8.02(1H, s) |
| 15-3 | 3.02(3H, s), 3.92(3H, s), 5.99(1H, s), 6.74(1H, s), 6.79(1H, d, J=9.0Hz), 7.38(2H, 2d), 7.53(1H, 2d), 7.72(2H, d, J=7.2Hz), 8.85(1H, s) |
| 15-4 | 3.31(3H, s), 4.05(3H, s), 6.20(1H, s), 6.86(2H, m), 6.89(1H, d, J=9.1Hz), 7.03(1H, m), 8.12(1H, m), 8.23(1H, m) |

TABLE XVIII-continued

| No. | $^1$H NMR data NMR($CDCl_3$, 300MHz) ppm |
|---|---|
| 15-5 | 2.91(3H, s), 3.91(3H, s), 5.99(1H, s), 6.76(1H, d, J=9.0Hz), 6.81(1H, s), 7.59(2H, m), 7.82(4H, m), 8.32(1H, s), 8.98(1H, s) |
| 15-6 | 1.21(3H, t, J=7.1Hz), 3.55(3H, s), 3.95(3H, s), 4.07(2H, q, J=7.1Hz), 6.28(1H, bs), 6.31(1H, s), 6.43(1H, bs), 6.87(1H, d, J=9.1Hz) |
| 15-7 | 3.46(3H, s), 3.93(3H, s), 6.29(1H, s), 6.52(1H, bs), 6.90(1H, d, J=9.0Hz), 7.10(3H, m), 7.21(1H, m), 7.34(2H, m) |
| 15-8 | 3.28(3H, s), 3.90(3H, s), 6.11(1H, s), 6.66(1H, s), 6.84(3H, m), 6.93(1H, d, J=8.9Hz), 7.87(1H, s), 8.07(1H, m) |
| 15-9 | 1.33(3H, t, J=7.1Hz), 3.16(3H, s), 3.50(3H, s), 4.05(3H, s), 4.18(2H, m), 6.29(1H, s), 6.68(1H, s), 6.85(1H, d, J=9.1Hz), 9.73(1H, s) |
| 15-10 | 3.54(3H, s), 3.85(3H, s), 5.40(2H, m), 5.96(1H, m), 6.32(1H, s), 6.72(1H, d, J=9.2Hz), 7.32(1H, d), 8.13(1H, s) |
| 15-11 | 0.51(2H, m), 0.82(2H, m), 1.27(1H, m), 3.56(3H, s), 3.83(3H, s), 6.34(1H, s), 6.67(2H, m), 7.82(1H, s) |
| 15-12 | 1.76(3H, s), 1.80(3H, s), 3.54(3H, s), 3.87(3H, s), 6.31(1H, s), 6.69(1H, d, J=9.1Hz), 7.63(1H, s) |
| 15-13 | 1.69(3H, s), 3.39(3H, s), 3.54(3H, s), 3.83(3H, s), 4.13(2H, s), 6.30(1H, s), 6.66(1H, d, J=9.3Hz), 9.79(1H, s) |
| 15-14 | 2.07(3H, s), 2.33(2H, m), 2.52(2H, m), 3.56(3H, s), 3.86(3H, s), 6.33(1H, s), 6.72(1H, d, J=9.2Hz), 7.06(1H, t, J=5.2Hz), 7.92(1H, s) |
| 15-15 | 3.30(2H, d, J=5.9Hz), 3.52(3H, s), 3.84(3H, s), 6.33(1H, s), 6.72(1H, d, J=9.1Hz), 7.07(2H, d, J=7.5Hz), 7.28(4H, m), 7.95(1H, s) |
| 15-16 | 1.25(3H, t, J=7.1Hz), 1.93(3H, s), 2.98(2H, 2d), 3.54(3H, s), 3.89(3H, s), 4.11(2H, q, J=7.1Hz), 6.30(1H, s), 6.74(1H, d, J=9.1Hz), 7.76(1H, s) |
| 15-17 | 1.24(3H, m), 3.46(1H, m), 3.50, 3.55(3H, 2s), 3.84(3H, s), 6.33, 6.37(1H, 2s), 6.71(1H, d, J=9.2Hz), 7.10(3H, m), 7.28(3H, m), 7.91(1H, s) |
| 15-18 | 2.32(2H, m), 2.81(2H, m), 3.55(3H, s), 3.57(2H, m), 3.94(3H, s), 6.32(1H, s), 6.74(1H, d, J=9.1Hz), 7.18(4H, m), 7.75(1H, s) |
| 15-19 | 2.46(2H, m), 2.91(2H, m), 3.25(2H, m), 3.57(3H, s), 3.87(3H, s), 6.36(1H, s), 6.69(1H, d, J=9.1Hz), 7.19(4H, m), 7.64(1H, s) |
| 15-20 | 3.51(3H, s), 3.90(3H, s), 6.35(1H, s), 6.77(3H, m), 7.25(1H, m), 7.83(1H, s), 8.36(1H, s) |
| 15-21 | 3.54(3H, s), 3.86(3H, s), 6.31(1H, s), 6.37(1H, s), 6.79(1H, d, J=9.3Hz) |
| 15-22 | 3.53(3H, s), 3.90(3H, s), 6.41(1H, s), 6.74(1H, d, J=9.2Hz), 7.39(1H, m), 7.48(2H, m), 7.66(2H, m), 7.80(3H, m), 8.34(1H, s) |
| 16-1 | 3.55(3H, s), 6.36(1H, s), 6.61(1H, d, J=2.1Hz), 7.04(1H, d, J=2.1Hz), 7.97(1H, s) |
| 16-2 | 3.56(3H, s), 3.81(3H, s), 6.35(1H, s), 6.94(1H, d, J=2.0Hz), 7.16(1H, d, J=2.0Hz) |
| 16-3 | 3.54(3H, s), 5.11(2H, s), 6.34(1H, s), 6.8–6.9(2H, m), 6.96(1H, d, J=2.0Hz), 7.19(1H, d, J=2.1Hz), 7.25(1H, m) |
| 16-4 | 3.53(3H, s), 6.35(1H, s), 6.86(1H, m), 7.00(1H, m), 7.49(1H, d, J=2.2Hz), 7.71(1H, d, J=2.2Hz), 8.02(1H, m) |
| 16-5 | 3.42(3H, s), 6.31(1H, s), 7.49(1H, d, J=2.2Hz), 7.61(3H, m), 7.93(4H, m), 8.58(1H, m) |
| 16-6 | 3.54(3H, s), 3.86(3H, s), 6.35(1H, s), 6.82(1H, d, J=9.2Hz), 6.9(1H, broad) |
| 16-7 | 3.44(3H, s), 3.88(3H, s), 6.26(1H, s), 7.29(1H, d, J=8.9Hz), 7.63(2H, m), 7.95(3H, m), 8.09(1H, 2d, J=1.7Hz, 8.6Hz), 8.71(1H, s) |
| 17-1 | 2.39(3H, s), 3.56(3H, s), 3.97(3H, s), 6.37(1H, s), 7.28(1H, d, J=9.0Hz) |
| 17-2 | 1.15(6H, m), 3.56(3H, s), 3.73(2H, m), 3.95(3H, s), 6.36(2H, s), 7.28(1H, d, J=9.0Hz) |
| 17-3 | 3.51(3H, s), 4.01(3H, s), 4.10(2H, m), 6.32(1H, s), 7.24(5H, m), 7.30(1H, d, J=8.6Hz) |
| 17-4 | 3.14(3H, s), 3.83(3H, s), 6.19(1H, s), 7.46(8H, m) |
| 17-5 | 3.14(2H, m), 3.57(5H, m), 3.96(3H, s), 6.40(1H, s), 7.28(1H, d, J=9.0Hz) |

The compounds of the present invention exhibit excellent herbicidal effects when used as an active ingredient of a herbicide. The herbicide can be used for a wide range of applications, for example on crop lands such as paddy fields, upland farms, orchards and mulberry fields, and non-crop lands such as forests, farm roads, playgrounds, and factory sites. The application method may be suitably selected for soil treatment application and foliar application.

The compounds of the present invention are capable of controlling noxious weeds including grass (gramineae) such as barnyardgrass (Echinochloa crus-galli), large crabgrass (Digitaria sanguinalis), green foxtail (Setaria viridis), goosegrass (Eleusine indica L.), wild oat (Avena fatua L.), Johnsongrass (Sorghum halepense), quackgrass (Agropyron repens), alexandergrass (Brachiaria plantaginea), paragrass (Panicum purpurascen), sprangletop (Leptochloa chinensis) and red sprangletop (Leptochloa panicea); sedges (or Cyperaceae) such as rice flatsedge (Cyperus iria L.), purple nutsedge (Cyperus rotundus L.), Japanese bulrush (Scirpus Juncoides), flatsedge (Cyperus serotinus), small-flower umbrellaplant (Cyperus difformis), slender spikerush (Eleocharis acicularis), and water chestnut (Eleocharis kuroguwai); alismataceae such as Japanese ribbon wapato (Sagittaria pygmaea), arrow-head (Sagittaria trifolia) and narrowleaf waterplantain (Alisma canaliculatum); pontederiaceae such as monochoria (Monochoria vaginalis) and monochoria species (Monochoria korsakowii); scrophulanaceae such as false pimpernel (Lindernia pyxidaria) and abunome (Dopatrium Junceum); lythraceae such as toothcup (Rotala indica) and red stem (Ammannia multiflora); and broadleaves such as redroot pigweed (Amaranthus retroflexus), velvetleaf (Abutilon theophrasti), morningglory (Ipomoea hederacea), lambsquarters (Chenopodium album), prickly sida (Sida spinose L.), common purslane (Portulaca oleracea L.), slender amaranth (Amaranthus viridis L.), sicklepod (Cassia obtusifolia), black nightshade (Solanum nigrum L.), pale smartweed (Polygonum lapathifolium L.), common chickweek (Stellaria media L.), conunon cocklebur (Xanthium strumarium L.), flexuous bittercress (Cardamine flexuosa WITH.), henbit (Lamium amplexicaule L.) and threeseeded copperleaf(Acalypha australis L.). Accordingly, it is useful for controlling noxious weeds non-selectively or selectively in the cultivation of a crop plant such as corn (Zea mays L.), soybean (Glycine max Merr.), cotton (Gossypium spp.), wheat (Triticum spp.), rice (Oryza sativa L.), barley (Hordeum vulgare L.), oat (Avena sativa L.), sorgo (Sorghum bicolor Moench), rape (Brassica napus L.), sunflower (Helianthus annuus L.), sugar beet (Beta vulgaris L.), sugar cane (Saccharum offcinarum L.), Japanese lawngrass (Zoysia Japonica stend), peanut (Arachis hypogaea L.) or flax (Linum usitatissimum L.).

For use as herbicides, the active ingredients of this invention are formulated into herbicidal compositions by mixing herbicidally active amounts with inert ingredients known to the art to facilitate either the suspension, dissolution or emulsification of the active ingredient for the desired use. The type of formulation prepared recognizes the facts that formulation, crop and use pattern all can influence the activity and utility of the active ingredient in a particular use. Thus for agricultural use the present herbicidal compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These herbicidal formulations may be applied to the target area (where suppression of unwanted vegetation is the objective) as dusts, granules or water or solvent diluted sprays. These formulation may contain as little as 0.1% to as much as 97% active ingredient by weight.

Dusts are admixtures of the active ingredient with finely ground materials such as clays (some examples include kaolin and montmorillonite clays), talc, granite dust or other organic or inorganic solids which act as dispersants and carriers for the active ingredient; these finely ground materials have an average particle size of less than 50 microns. A typical dust formulation will contain 1% active ingredient and 99% carrier.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredient with the granules with or without a sticking agent to facilitate adhesion of the active ingredient to the granule surface, or by dissolving the active ingredient in a solvent, spraying the dissolved active ingredient and solvent onto the granule then drying to remove the solvent. Granular formulations are useful where in-furrow or banded application is desired Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredient (5 to 50% by weight), carrier, wetting agent, dispersing agent, anti-freeze, viscosity modifiers and pH modifiers. For application, suspension concentrates are typically diluted with water and sprayed on the target area Solution concentrates are solutions of the active ingredient (1 to 70%) in solvents which have sufficient solvency to dissolve the desired amount of active ingredient. Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient, is made as a suspension concentrate (1–50% active ingredient) and the second active is made as a emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The herbicidal compounds of this invention may be formulated or applied with a insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UW protectants may be added in amounts of 0.01% to 5% to enhance the biological activity, stability, wetting, spreading on foliage or uptake of the active ingredients on the target area or to improve the suspensibility, dispersion, redispersion, emulsifiability, UW stability or other physical or physicochemical property of the active ingredient in the spray tank, spray system or target area The compositions of the present invention may be used in admixture with or in combination with other agricultural chemicals, fertilizers, adjuvants, surfactants, emulsifiers, oils, polymers or phytotoxicity-reducing agents such as herbicide safeners. In such a case, they may exhibit even better effects or activities. As other agricultural chemicals, herbicides, fungicides, antibiotics, plant hormones, plant growth regulators, insecticides, or acaricides may, for example, be mentioned. Especially with herbicidal compositions having the compounds of the present invention used in admixture with or in combination with one or more active ingredients of other herbicides, it is possible to improve the herbicidal activities, the range of application time(s) and the range of applicable weed types. Further, the compounds of the present invention and an active ingredient of another herbicide may be separately formulated so they may be mixed for use at the time of application, or both may be formulated together. The present invention covers such herbicidal compositions.

The blend ratio of the compounds of the present invention with the active ingredient of other herbicides can not generally be defined, since it varies depending on the time and method of application, weather conditions, soil type and type of formulation. However one active ingredient of other herbicide may be incorporated usually in an amount of 0.01 to 100 parts by weight, per one part by weight of the compounds of the present invention. Further, the total dose of all of the active ingredients is usually from 1 to 10000 g/ha, preferably from 5 to 500 g/ha. The present invention covers such herbicidal compositions.

As the active ingredients of other herbicides, the following (common name) may be mentioned. Herbicidal compositions having the compounds of the present invention used in combination with other herbicides, may occasionally exhibit a synergistic effect.

1. Those that are believed to exhibit herbicidal effects by disturbing auxin activities of plants, including a phenoxy acetic acid type such as 2,4-D, 2,4-DB, 2,4DP, MCPA, MCPP, MCPB or naproanilide (including the free acids, esters or salts thereof), an aromatic carboxylic type such as 2,3,6 TBA, dicamba, dichlobenil, a pyridine type such as picloram (including free acids and salts thereof), triclopyr or clopyralid and others such as naptalam, benazolin, quinclorac, quinmerac or diflufenzopyr (BAS 654H),
2. Those that are believed to exhibit herbicidal effects by inhibiting photosynthesis of plants including a urea type such as diuron, linuron, isoproturon, chlorotoluron, metobenzuron, tebuthiuron or fluometuron, a triazine type such as simazine, atrazine, cyanazine, terbuthylazine, atraton, hexazinone, metribuzin, simetyn, ametryn, prometryn, dimethametryn or triaziflam, a uracil type such as bromacil, terbacil or lenacil, an anilide type such as propanil or cypromid, a carbamate type such as desmedipham or phenmedipham, a hydroxybenzonitrile type such as bromoxynil or ioxynil, and others such as pyridate, bentazon and methazole,
3. A quaternary ammonium salt type such as paraquat, diquat or difenzoquat, which is believed to be converted to free radicals by itself to form active oxygen in the plant and thus to exhibit quick herbicidal effects.
4. Those which are believed to exhibit herbicidal effects by inhibiting chlorophyll biosynthesis in plants and abnormally accumulating a photsensitizing peroxide substance in the. plant body, including a diphenyl ether type such as nitrofen, lactofen, acifluorfen-sodium, oxyfluorfen, fomesafen, bifenox, or chlomethoxyfen, a cyclic imide type such as chlorphthaliim, flumioxazin, cinidon-ethyl, or flumiclorac-pentyl, and others such as oxadiazon, sulfentrazone, thidiazimin, azafenidin, carfentrazone, isopropazole, fluthiacet-methyl, pentoxazone, pyraflufenethyl and oxadiargyl.
5. Those which are believed to exhibit herbicidal effects characterized by whitening activities by inhibiting chromogenesis of plants such as carotenoids including a pyridazinone type such as norflurazon, chloridazon or metflurazon, a pyrazol type such as pyrazolate, pyrazoxyfen or benzofenap, and others such as fluridone, fluramone, diflufencam, methoxyphenone, clomazone, amitrole, sulcotrione, mesotrione, isoxaflutole and isoxachlortole.
6. Those which exhibit herbicidal effects specifically to gramineous plants including an aryloxyphenoxypropionic acid type (either as a mixture of isomers or as a resolved isomer) such as diclo-fop-methyl, pyrofenop-sodium, fluazifop butyl or fluazifop-p-butyl, hailoxyfop-methyl, quizalofop p-ethyl, quizalafop p-tefiryl, fenoxaprop ethyl or fenoxaprop-p-ethyl, flamprop-M-methyl or flamprop-m-isopropyl or cyhalofop-butyl and a cyclohexanedione type such as alloxydim-sodium, sethoxydim, clethodim, tepraloxydim or tralkoxydim.

7. Those which are believed to exhibit herbicidal effects by inhibiting amino acid biosynthesis of plants, including a sulfonylurea type such as chlorimuron-ethyl, nicosulfuron, metsulfuron-methyl, triasulfuron, primisulfuron, tribenuron-methyl, chlorosulfuron, bensulfuron-methyl, sulfometuron-methyl, prosulfuron, halosulfuron or halosulfuron-methyl, thifensulfuron-methyl, rimsulfuron, azimsulfuron, flazasulfuron, imazosulfuron, cyclosulfamuron, flupyrsulfuron, iodosulfuron, ethoxysulfuron, flucarbazone, sulfosulfuron, oxasufluron a triazolopyrimidinesulfonamide type such as flumetsulam, metosulam, chloransulam or chloransulam-methyl, an imidazolinone type such as imazapyr, imazethapyr, imazaquin, imazamox, imazameth, imazamethabenz methyl, a pyrimidinesalicyclic acid type such as pyrthiobac-sodium, bispyribacsodium, pyriminobac-methyl or pyribenzoxim (LGC40863), and others such as glyphosate, glyphosate-ammonium, glyphosate-isopropylamine or sulfosate.

8. Those which are believed to exhibit herbicidal effects by interfering with the normal metabolism of inorganic nitrogen assimilation such as glufosinate, glufosinate-ammonium, phosphinothricin or bialophos.

9. Those which are believed to exhibit herbicidal effects by inhibiting cell division of plant cells, including a dinitroaniline type such as trifluralin, oryzalin, nitralin, pendamethalin, ethafluralin, benefin and prodiamine, an amide type such as bensulide, napronamide, and pronamide, a carbamate type such as propham, chlorpropham, barban, and asulam, an organophosphorous type such as amiprofos-methyl or butamifos and others such as DCPA and dithiopyr.

10. Those which are believed to exhibit herbicidal effects by inhibiting protein synthesis of plant cells, including a chloroacetanilide type such as alachlor, metolachor (including combinations with safeners such as benoxacor, or resolved isomeric mixtures of metolachlor including safeners such as benoxacor) propachlor, acetochlor (including combinations with herbicide safeners such as dichlonnid or MON 4660 or resolved isomeric mixtures of acetochlor containing safeners such as dichlormid or MON 4660), propisochlor or dimethenamid or an oxyacetamide type such as flufenacet.

11. Those in which the mode of action causing the herbicidal effects are not well understood including the dithiocarbaamates such as thiobencarb, EPTC, diallate, triallate, molinate, pebulate, cycloate, butylate, vernolate or prosulfocarb and miscellaneous herbicides such as MSMA, DSMA, endothall, ethofumesate, sodium chlorate, pelargonic acid and fosamine. A few formulation examples of the present invention are given as follows.

Formulation Example 1. Emulsifiable Concentrate

| Ingredient Trade Name | Chemical Name | Supplier | Function | % wt./wt. |
|---|---|---|---|---|
| Compound 2-75 | | | Active Ingredient | 5.0 |
| Toximul H-A | Calcium sulfonate and nonionic surfactant blend | Stepan Co. | Emulsifier | 2.5 |
| Toximul D-A | Calcium sulfonate and nonionic surfactant blend | Stepan Co. | Emulsifier | 7.5 |
| Aromatic 200 | Aromatic hydrocarbon | Exxon Chemical Co. | Solvent | QS to 100% |

Formulation Example 2. Suspension Concentrate

| Ingredient Trade Name | Chemical Name | Supplier | Function | % wt./wt. |
|---|---|---|---|---|
| Compound 2-75 | | | Active Ingredient | 10.00 |
| Proylene glycol | | | Anti-freeze | 5.00 |
| Antifoam 1530 | Silicone defoamer | Dow Corning | Anti-foam | 0.50 |
| Rhodopol 23 | Xanthan gum | Rhone-Poulenc | Suspending Aid | 0.25 |
| Morwet D425 | Napthalene formaldehyde condensate | Witco Corp. | Dispersant | 3.00 |
| Igepal CA-720 | Octylphenol ethoxylate | Rhone-Poulenc | Wetting agent | 3.00 |
| Proxel GXL | 1,2 benziso-thiazolin-3-one | ICI Americas | Preservative | 0.25 |
| Water | | | Diluent | 68.00 |

Formulation Example 3. Wettable Powder

| Ingredient Trade Name | Chemical Name | Supplier | Function | % wt./wt. |
|---|---|---|---|---|
| Compound 2-75 | | | Active Ingredient | 50.00 |
| Geropon T-77 | Sodium-N-methyl methyl-N-olcoyl taurate | Rhone-Poulenc | Wetting agent | 3.00 |
| Lomar PW | Napthalene Sulfonate | Henkel Corp. | Dispersant | 5.00 |
| Kaolin clay | Kaolin clay | J. M. Huber | Filler | 42.00 |

Formulation Example 4. Water Dispersible Granule

| Ingredient Trade Name | Chemical Name | Supplier | Function | % wt./wt. |
|---|---|---|---|---|
| Compound 2-75 | | | Active Ingredient | 50.00 |
| Morwet EFW | Witco Corp. agent | Wetting | 2.00 | |
| Morwet D-425 | Napthalene formaldehyde condensate | Witco Corp. | Dispersant | 10.00 |
| ASP 400 | Kaolin Clay | Engelhard Corp. | Filler | 38.00 |

Test Example

A standard greenhouse herbicide activity screening system was used to evaluate the herbicidal efficacy and crop safety of these test compounds. Seven broadleaf weed species including redroot pigweed (Amaranthus retroflexus, AMARE, velvetleaf (Abutilon theophrasti, ABUTH), sicklepod (Cassia obtusifolia, CASOB), ivyleaf morningglory (Ipomoea hederacea, IPOHE), lambsquarters (Chenopodium album, CHEAL), common ragweed (Ambrosia artemisizfolia L., AMBEL), and cocklebur (Xanthium strumarium, XANST) were used as test species. Four grass weed species including green foxtail (Setaria viridis, SETVI), barnyardgrass (Echinochloa crus-galli, ECHCG), johnsongrass (Sorghum halepense, SORHA), and large crabgrass (Digitaria sanguinalis, DIGSA) were also used. In addition, three crop species, field corn (Zea mays L., var. Dekalb 535, CORN), soybean (Glycine max L., var. Pella 86, SOY), and is upland rice (Oryza sp., var. Tebonnet, RICE) were included.

Pre-emerge Test

All plants were grown in 10 cm square plastic pots which were filled with a sandy loam soil mix. For pre-emerge tests, seeds were planted one day prior to application of the test compounds. For post-emerge tests, seeds were planted 8–21 days prior to the test to allow emergence and good foliage development prior to application of the test substances. At the time of the post-emerge application, plants of all species were usually at the 2–3 leaf stage of development.

All test compounds Were dissolved in acetone and applied to the test units in a volume of 187 1 /ha. Test materials were applied at rates ranging from 15 g ai/ha to 1000 g ai/ha using a track sprayer equipped with a TJ8100E even flow flat fan spray nozzle. Plants were arranged on a shelf so that the top of the canopy (post-emerge) or top of the soil surface (pre-emerge) was 40–45 cm below the nozzle. Pressurized air was used to force the test solution through the nozzle as it was mechanically advanced (via electrically driven chain drive) over the top of all test plants/pots. This application simulates a typical commercial field herbicide application.

Post-emerge Test

In the post-emerge test, a commercial non-ionic surfactant was also included (0.25% v/v) to enhance wetting of the leaf surfaces of target plants. Immediately after application, test units of the pre-emerge applications were watered at the soil surface to incorporate the test materials. Subsequently, these test units were bottom-watered. Post-emerge test units were always bottom-watered.

At 14 days after application of the test materials, phytotoxicity ratings were recorded. A rating scale of 0–100 was used as previously described in Research Methods in Weed Science, 2nd edition, B. Truelove, Ed., Southern Weed Science Society, Auburn University, Auburn, Ala. 1977. Briefly, "0" corresponds to no damage and "100" corresponds to complete death of all plants in the test unit. This scale was used both to determine efficacy against weed species and damage to crop species. Herbicide activity data for various compounds of this invention, which are shown by compound No. in Tables 1–8, are shown in Tables 11 and 12. The data demonstrate significant differences between compounds for both efficacy against weeds and selectivity for crop species. For selected compounds, excellent activity against a majority of the weed species was observed with minimal damage to at least one of the crop species.

Following table XIX shows comparative data for the pre-emerge herbicidal activity of compound 1.4 of present invention and the compound 2 reported in the Japanese Pat. No. Toku Kai Hei 5-25144 (1993). The data clearly shows the high level of activity observed with compound 1.4.

TABLE XIX

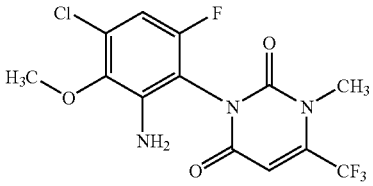

1.4

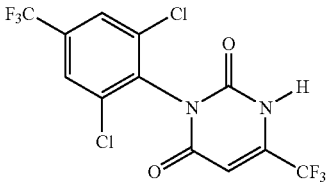

2

Comparative herbicidal activity of compounds 1.4 and 2

| Cmpd. no. | Rate (g ai/ha) | AMARE | ABUTH | CASOB | IPOHE | CHEAL | XANST | SETVI | ECHCG | SORHA | DIGSA | MAIZE | SOY | RICE |
|---|---|---|---|---|---|---|---|---|---|---|---|---|---|---|
| 1.4 | 3.9 | 30 | 95 | 0 | 0 | 30 | 0 | 0 | 0 | 0 | 0 | 0 | 0 | 0 |
| | 7.8 | 100 | 100 | 30 | 0 | 60 | 0 | 60 | 0 | 0 | 30 | 0 | 0 | 0 |
| | 15.6 | 90 | 100 | 100 | 0 | 100 | 20 | 80 | 0 | 0 | 30 | 0 | 0 | 10 |
| | 31.3 | 100 | 100 | 0 | 50 | 100 | 10 | 80 | 10 | 30 | 30 | 0 | 15 | 20 |
| | 62.5 | 100 | 100 | 80 | 90 | 100 | 50 | 100 | 30 | 40 | 95 | 0 | 40 | 50 |
| | 125 | 100 | 100 | 95 | 100 | 100 | 50 | 100 | 95 | 95 | 100 | 40 | 90 | 60 |
| | 250 | 100 | 100 | 100 | 100 | 100 | 90 | 100 | 100 | 100 | 100 | 95 | 100 | 65 |

TABLE XIX-continued
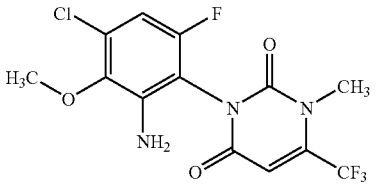
1.4
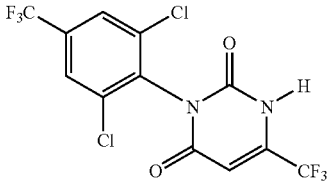
2
Comparative herbicidal activity of compounds 1.4 and 2
| Cmpd. no. | Rate (g ai/ha) | AMARE | ABUTH | CASOB | IPOHE | CHEAL | XANST | SETVI | ECHCG | SORHA | DIGSA | MAIZE | SOY | RICE |
|---|---|---|---|---|---|---|---|---|---|---|---|---|---|---|
| 2 | 3.9 | 0 | 0 | 0 | 0 | 0 | 0 | 0 | 0 | 0 | 0 | 0 | 0 | 0 |
| | 7.8 | 0 | 0 | 0 | 0 | 0 | 0 | 0 | 0 | 0 | 0 | 0 | 0 | 0 |
| | 15.6 | 0 | 0 | 0 | 0 | 0 | 0 | 0 | 0 | 0 | 0 | 0 | 0 | 0 |
| | 31.3 | 0 | 0 | 0 | 0 | 0 | 0 | 0 | 0 | 0 | 0 | 0 | 0 | 0 |
| | 62.5 | 0 | 0 | 0 | 0 | 0 | 0 | 0 | 0 | 0 | 0 | 0 | 0 | 0 |
| | 125 | 0 | 0 | 30 | 0 | 30 | 0 | 0 | 0 | 0 | 0 | 0 | 0 | 0 |
| | 250 | 0 | 50 | 50 | 0 | 50 | 60 | 0 | 0 | 0 | 0 | 0 | 0 | 15 |
TABLE XX
Pre-emerge Herbicidal Activity
| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 1-2 | 63 | 0 | 50 | 90 | 0 | 0 | — | 20 | 0 | 0 | 0 | 0 | 0 | 0 |
| | 250 | 0 | 10 | 100 | 0 | 0 | — | 0 | 0 | 0 | 30 | 0 | 0 | 10 |
| 1-4 | 63 | 100 | 100 | 90 | 100 | 100 | 100 | 100 | 100 | 85 | 100 | 90 | 70 | 60 |
| | 250 | 100 | 100 | 100 | 100 | 100 | 100 | 100 | 100 | 100 | 100 | 100 | 100 | 80 |
| 1-5 | 63 | 20 | 30 | 0 | 0 | 60 | 0 | 0 | 0 | 0 | 0 | 0 | 0 | 0 |
| | 250 | 95 | 100 | 0 | 10 | 100 | 20 | 90 | 0 | 20 | 70 | 10 | 0 | 10 |
| 1-9 | 63 | 100 | 100 | 100 | 100 | 100 | 100 | 100 | 100 | 100 | 100 | 100 | 90 | 95 |
| 1-10 | 63 | 70 | 100 | 20 | 0 | 30 | 0 | 0 | 0 | 0 | 0 | 0 | 0 | 0 |
| | 250 | 100 | 100 | 50 | 60 | 100 | 60 | 100 | 0 | 0 | 30 | 50 | 0 | 0 |
| 1-11 | 63 | 100 | 100 | 20 | 20 | 100 | 50 | 80 | 0 | 90 | 90 | 10 | 0 | 20 |
| | 250 | 100 | 100 | 60 | 90 | 100 | 100 | 100 | 95 | 98 | 100 | 70 | 60 | 70 |
| 1-13 | 63 | 100 | 100 | 80 | 100 | 100 | 100 | 100 | 90 | 95 | 100 | 95 | 60 | 95 |
| | 250 | 100 | 100 | 100 | 100 | 100 | 100 | 100 | 100 | 100 | 100 | 100 | 95 | 100 |
| 1-15 | 63 | 0 | 20 | 0 | 0 | 40 | — | 70 | 0 | 0 | 0 | 0 | 0 | 10 |
| | 250 | 20 | 90 | 0 | 0 | 50 | — | 80 | 0 | 20 | 90 | 0 | 0 | 30 |
| 1-16 | 63 | 0 | 0 | 0 | 0 | 0 | 0 | 0 | 0 | 0 | 0 | 0 | 0 | 0 |
| | 250 | 0 | 0 | 0 | 0 | 70 | 0 | 0 | 0 | 0 | 0 | 0 | 0 | 0 |
| 1-18 | 63 | 100 | 100 | 70 | 100 | 100 | — | 95 | 0 | 70 | 70 | 100 | 40 | 30 |
| | 250 | 100 | 100 | 100 | 100 | 100 | — | 99 | 80 | 100 | 90 | 95 | 90 | 70 |
| 1-19 | 63 | 95 | 100 | 90 | 60 | 100 | — | 100 | 90 | 90 | 95 | 60 | 50 | 80 |
| | 250 | 100 | 100 | 100 | 100 | 100 | — | 100 | 100 | 100 | 100 | 70 | 80 | 95 |
| 1-20 | 63 | 100 | 100 | 100 | 40 | 100 | — | 80 | 50 | 30 | 50 | 0 | 15 | 60 |
| | 250 | 100 | 100 | 100 | 100 | 100 | — | 100 | 100 | 70 | 90 | 70 | 65 | 70 |
| 1-21 | 63 | 98 | 70 | 0 | 0 | 100 | 0 | 95 | 0 | 0 | 70 | 0 | 0 | 0 |
| | 250 | 100 | 100 | 0 | 40 | 100 | 100 | 100 | 95 | 90 | 100 | 0 | 0 | 10 |
| 1-22 | 63 | 95 | 100 | 0 | 0 | 95 | — | 90 | 0 | 0 | 0 | 0 | 0 | 0 |
| | 250 | 100 | 100 | 0 | 20 | 100 | — | 100 | 60 | 60 | 60 | 20 | 10 | 50 |
| 1-30 | 63 | 0 | 50 | 0 | 0 | 85 | — | 10 | 0 | 0 | 0 | 0 | 0 | 10 |
| | 250 | 60 | 100 | 70 | 70 | 100 | — | 100 | 0 | 10 | 90 | 20 | 10 | 30 |
| 1-31 | 63 | 80 | 100 | 70 | 0 | 95 | — | 50 | 0 | 0 | 0 | 0 | 0 | 0 |
| | 250 | 100 | 100 | 95 | 80 | 100 | — | 100 | 40 | 90 | 90 | 90 | 50 | 10 |
| 1-32 | 63 | 0 | 90 | 40 | 0 | 90 | 0 | 0 | 0 | 0 | 0 | 0 | 0 | 20 |
| | 250 | 100 | 100 | 40 | 50 | 100 | 50 | 100 | 95 | 30 | 100 | 20 | 0 | 40 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 1-37 | 63 | 100 | 100 | 80 | 100 | 100 | — | 100 | 90 | 90 | 100 | 90 | 15 | 60 |
| | 250 | 100 | 100 | 100 | 100 | 100 | — | 100 | 100 | 100 | 100 | 100 | 90 | 90 |
| 1-38 | 63 | 100 | 100 | 100 | 100 | 100 | — | 100 | 95 | 90 | 100 | 80 | 70 | 90 |
| | 250 | 100 | 100 | 100 | 100 | 100 | — | 100 | 100 | 100 | 100 | 90 | 90 | 100 |
| 1-51 | 63 | 90 | 90 | 0 | 50 | 90 | 30 | 30 | 0 | 10 | 20 | 10 | 0 | 10 |
| | 250 | 100 | 100 | 30 | 80 | 100 | 80 | 90 | 50 | 60 | 90 | 60 | 70 | 70 |
| 1-53 | 63 | 100 | 100 | 0 | 50 | 100 | 50 | 50 | 0 | 50 | 40 | 50 | 95 | 50 |
| | 250 | 100 | 100 | 50 | 95 | 100 | 90 | 95 | 80 | 90 | 90 | 90 | 100 | 90 |
| 1-54 | 63 | 100 | 100 | 30 | 100 | 100 | 100 | 90 | 45 | 80 | 80 | 100 | 95 | 60 |
| | 250 | 100 | 100 | 80 | 100 | 100 | 100 | 100 | 100 | 100 | 100 | 100 | 99 | 95 |
| 1-55 | 63 | 70 | 90 | 0 | 0 | 95 | — | 0 | 10 | 20 | 50 | 0 | 10 | 0 |
| | 250 | 70 | 90 | 0 | 0 | 95 | — | 0 | 10 | 20 | 50 | 0 | 10 | 0 |
| 1-59 | 63 | 100 | 100 | 30 | 100 | 100 | — | 30 | 0 | 30 | 30 | 70 | 30 | 30 |
| | 250 | 100 | 100 | 80 | 100 | 100 | — | 90 | 70 | 85 | 90 | 90 | 90 | 70 |
| 1-60 | 63 | 100 | 100 | 70 | 90 | 100 | — | 95 | 50 | 80 | 95 | 90 | 50 | 40 |
| | 250 | 100 | 100 | 100 | 100 | 100 | — | 100 | 95 | 100 | 100 | 100 | 95 | 95 |
| 1-61 | 63 | 95 | 100 | 30 | 60 | 100 | 60 | 95 | 75 | 70 | 40 | 30 | 60 | 50 |
| | 250 | 100 | 100 | 80 | 90 | 100 | 100 | 100 | 99 | 99 | 99 | 90 | 95 | 95 |
| 1-63 | 63 | 100 | 100 | 20 | 20 | 100 | — | 95 | 40 | 50 | 80 | 0 | 10 | 80 |
| | 250 | 100 | 100 | 90 | 95 | 100 | — | 100 | 100 | 99 | 100 | 30 | 90 | 95 |
| 2-1 | 63 | 60 | 100 | 80 | 95 | 90 | 50 | 80 | 10 | 30 | 20 | 50 | 30 | 80 |
| | 250 | 100 | 100 | 100 | 100 | 100 | 100 | 95 | 70 | 70 | 100 | 100 | 80 | 90 |
| 2-2 | 63 | 100 | 100 | 60 | 90 | 100 | 40 | 90 | 30 | 60 | 90 | 50 | 10 | 10 |
| | 250 | 100 | 100 | 90 | 100 | 100 | 100 | 100 | 90 | 90 | 95 | 90 | 70 | 50 |
| 2-3 | 63 | 100 | 100 | 60 | 60 | 100 | — | 90 | 0 | 10 | 30 | 40 | 0 | 20 |
| | 250 | 100 | 100 | 100 | 100 | 100 | — | 100 | 40 | 30 | 60 | 80 | 30 | 50 |
| 2-4 | 63 | 80 | 30 | 0 | 20 | 50 | — | 0 | 0 | 0 | 0 | 0 | 0 | 0 |
| | 250 | 95 | 100 | 0 | 70 | 100 | — | 80 | 0 | 0 | 50 | 20 | 20 | 10 |
| 2-5 | 63 | 90 | 100 | 40 | 90 | 100 | — | 100 | 10 | 60 | 50 | — | 10 | 70 |
| | 250 | 100 | 100 | 100 | 100 | 100 | — | 100 | 90 | 90 | 95 | — | — | 80 |
| 2-6 | 63 | 0 | 0 | 0 | 0 | 0 | — | 0 | 0 | 0 | 0 | 0 | 0 | 0 |
| | 250 | 50 | 0 | 0 | 0 | 0 | — | 80 | 0 | 20 | 10 | 0 | 0 | 0 |
| 2-7 | 63 | 90 | 100 | 60 | 70 | 100 | — | 95 | 40 | 90 | 95 | 70 | 10 | 60 |
| | 250 | 100 | 100 | 100 | 100 | 100 | — | 100 | 100 | 95 | 100 | 95 | 70 | 90 |
| 2-8 | 63 | 40 | 0 | 0 | 0 | 60 | — | 90 | 0 | 40 | 80 | 60 | 15 | 50 |
| | 250 | 100 | 100 | 0 | 100 | 100 | — | 90 | 0 | 40 | 80 | 60 | 15 | 50 |
| 2-10 | 63 | 50 | 100 | 50 | 60 | 100 | 100 | 40 | 0 | 0 | 90 | 45 | 0 | 0 |
| | 250 | 100 | 100 | 90 | 100 | 100 | 100 | 100 | 95 | 80 | 95 | 100 | 40 | 30 |
| 2-11 | 63 | 30 | 90 | 0 | 70 | 100 | — | 0 | 0 | 0 | 0 | 0 | 0 | 10 |
| | 250 | 100 | 100 | 60 | 100 | 100 | — | 100 | 40 | 50 | 60 | 20 | 10 | 50 |
| 2-12 | 63 | 30 | 50 | 30 | 40 | 0 | 0 | 0 | 0 | 0 | 0 | 0 | 0 | 0 |
| | 250 | 100 | 70 | 40 | 70 | 30 | 0 | 0 | 0 | 0 | 0 | 0 | 0 | 0 |
| 2-14 | 63 | 50 | 90 | 0 | 0 | 50 | — | 60 | 0 | 0 | 0 | 0 | 0 | 0 |
| | 250 | 100 | 100 | 60 | 100 | 100 | — | 100 | 0 | 30 | 20 | 60 | 0 | 30 |
| 2-15 | 63 | 0 | 20 | 0 | 20 | 60 | 0 | 0 | 0 | 0 | 0 | 0 | 0 | 10 |
| | 250 | 80 | 90 | 0 | 30 | 40 | 0 | 0 | 0 | 0 | 0 | 0 | 0 | 0 |
| 2-16 | 63 | 50 | 80 | 0 | 0 | 95 | — | 0 | 0 | 0 | 0 | 0 | 0 | 0 |
| | 250 | 100 | 100 | 100 | 90 | 100 | — | 100 | 40 | 80 | 100 | 0 | 20 | 15 |
| 2-18 | 63 | 40 | 0 | 0 | 0 | 10 | — | 0 | 0 | 0 | 0 | 0 | 0 | 0 |
| | 250 | 100 | 100 | 40 | 40 | 90 | — | 80 | 0 | 0 | 0 | 30 | 0 | 20 |
| 2-19 | 63 | 80 | 90 | 0 | 10 | 95 | — | 20 | 0 | 0 | 40 | 30 | 5 | 10 |
| | 250 | 100 | 100 | 10 | 100 | 100 | — | 100 | 50 | 60 | 100 | 90 | 40 | 60 |
| 2-23 | 63 | 100 | 100 | 70 | 100 | 100 | 100 | 100 | 80 | 40 | 70 | 25 | 60 | 80 |
| | 250 | 100 | 100 | 100 | 100 | 100 | 100 | 100 | 100 | 90 | 100 | 90 | 100 | 95 |
| 2-24 | 63 | 100 | 100 | 90 | 100 | 100 | 100 | 100 | 95 | 95 | 100 | 90 | 95 | 90 |
| | 250 | 100 | 100 | 100 | 100 | 100 | 100 | 100 | 100 | 100 | 100 | 100 | 98 | 99 |
| 2-26 | 63 | 0 | 0 | 0 | 0 | 0 | 0 | 0 | 0 | 0 | 0 | 0 | 0 | 0 |
| | 250 | 80 | 0 | 0 | 0 | 90 | 0 | 0 | 0 | 0 | 0 | 0 | 0 | 0 |
| 2-27 | 63 | 100 | 100 | 60 | 80 | 100 | 100 | 100 | 50 | 30 | 95 | 30 | 20 | 70 |
| | 250 | 100 | 100 | 100 | 100 | 100 | 100 | 100 | 100 | 80 | 100 | 70 | 90 | 90 |
| 2-28 | 63 | 100 | 100 | 5 | 80 | 100 | — | 50 | 0 | 10 | 50 | 10 | 0 | 60 |
| | 250 | 100 | 100 | 100 | 100 | 100 | — | 100 | 20 | 50 | 90 | 70 | 10 | 70 |
| 2-29 | 63 | 100 | 100 | 60 | 30 | 100 | 0 | 100 | 0 | 0 | 60 | 0 | 0 | 40 |
| | 250 | 100 | 100 | 100 | 100 | 100 | 60 | 100 | 50 | 80 | 90 | 45 | 15 | 65 |
| 2-30 | 63 | 0 | 0 | 0 | 0 | 0 | 0 | 0 | 0 | 0 | 0 | 0 | 0 | 0 |
| | 250 | 0 | 20 | 0 | 0 | 70 | 0 | 20 | 0 | 0 | 0 | 0 | 0 | 0 |
| 2-31 | 63 | 100 | 100 | 100 | 100 | 100 | — | 100 | 40 | 60 | 90 | 70 | 20 | 40 |
| | 250 | 100 | 100 | 100 | 100 | 100 | — | 100 | 100 | 85 | 100 | 100 | 40 | 90 |
| 2-32 | 63 | 100 | 100 | 95 | 100 | 100 | — | 100 | 99 | 90 | 100 | 90 | 40 | 80 |
| | 250 | 100 | 100 | 100 | 100 | 100 | — | 100 | 100 | 100 | 100 | 100 | 95 | 99 |
| 2-33 | 63 | 100 | 100 | 100 | 100 | 100 | — | 100 | 30 | 60 | 100 | 10 | 70 | 70 |
| | 250 | 100 | 100 | 100 | 100 | 100 | — | 100 | 95 | 90 | 100 | 90 | 90 | 80 |
| 2-34 | 63 | 100 | 100 | 100 | 100 | 100 | 100 | 95 | 70 | 20 | 70 | 15 | 25 | 40 |
| | 250 | 100 | 100 | 100 | 100 | 100 | 100 | 100 | 99 | 85 | 100 | 90 | 90 | 90 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 2-36 | 63 | 100 | 100 | 10 | 0 | 90 | 0 | 25 | 0 | 0 | 0 | 0 | 0 | 0 |
| | 250 | 100 | 100 | 70 | 60 | 100 | 30 | 90 | 10 | 20 | 30 | 10 | 0 | 40 |
| 2-37 | 63 | 0 | 0 | 0 | 0 | 0 | 0 | 0 | 0 | 0 | 0 | 0 | 0 | 0 |
| | 250 | 30 | 30 | 0 | 0 | 50 | 0 | 0 | 0 | 0 | 0 | 0 | 0 | 0 |
| 2-39 | 63 | 100 | 100 | 100 | 95 | 100 | 100 | 100 | 90 | 60 | 99 | 70 | 70 | 90 |
| | 250 | 100 | 100 | 100 | 100 | 100 | 100 | 100 | 100 | 100 | 100 | 90 | 95 | 99 |
| 2-40 | 63 | 100 | 100 | 80 | 90 | 100 | 100 | 100 | 85 | 60 | 90 | 95 | 50 | 95 |
| | 250 | 100 | 100 | 100 | 100 | 100 | 100 | 100 | 100 | 100 | 100 | 100 | 95 | 100 |
| 2-41 | 63 | 100 | 100 | 80 | 90 | 100 | 100 | 95 | 50 | 30 | 70 | 80 | 35 | 50 |
| | 250 | 100 | 100 | 100 | 100 | 100 | 100 | 100 | 100 | 100 | 100 | 100 | 95 | 90 |
| 2-42 | 63 | 100 | 100 | 80 | 100 | 100 | 100 | 100 | 100 | 95 | 100 | 100 | 85 | 90 |
| | 250 | 100 | 100 | 100 | 100 | 100 | 100 | 100 | 100 | 100 | 100 | 100 | 98 | 99 |
| 2-44 | 63 | 100 | 100 | 60 | 90 | 100 | 100 | 90 | 30 | 50 | 60 | 80 | 10 | 20 |
| | 250 | 100 | 100 | 100 | 100 | 100 | 100 | 100 | 99 | 95 | 100 | 100 | 70 | 80 |
| 2-45 | 63 | 70 | 0 | 0 | 0 | 60 | — | 0 | 00 | 0 | 0 | 0 | 0 | 0 |
| | 250 | 100 | 70 | 0 | 0 | 90 | — | 30 | 0 | 0 | 0 | 0 | 0 | 0 |
| 2-46 | 63 | 100 | 50 | 30 | 0 | 100 | — | 90 | 0 | 30 | 30 | 30 | 0 | 20 |
| | 250 | 100 | 100 | 100 | 60 | 100 | — | 100 | 50 | 90 | 70 | 100 | 90 | 70 |
| 2-47 | 63 | 100 | 100 | 90 | 100 | 100 | 50 | 100 | 0 | 60 | 100 | 90 | 40 | 70 |
| | 250 | 100 | 100 | 100 | 100 | 100 | 100 | 100 | 99 | 90 | 100 | 100 | 99 | 95 |
| 2-48 | 63 | 100 | 100 | 100 | 100 | 100 | 100 | 100 | 85 | 95 | 95 | 100 | 90 | 90 |
| | 250 | 100 | 100 | 100 | 100 | 100 | 100 | 100 | 100 | 95 | 100 | 100 | 99 | 99 |
| 2-49 | 63 | 100 | 100 | 0 | 0 | 100 | 100 | 80 | 0 | 0 | 20 | 0 | 0 | 20 |
| | 250 | 100 | 100 | 100 | 90 | 100 | 100 | 95 | 10 | 0 | 100 | 40 | 15 | 60 |
| 2-50 | 63 | 100 | 100 | 60 | 70 | 100 | 60 | 90 | 10 | 30 | 70 | 90 | 5 | 25 |
| | 250 | 100 | 100 | 100 | 100 | 100 | 100 | 100 | 100 | 80 | 100 | 100 | 70 | 90 |
| 2-52 | 63 | 100 | 10 | 0 | 0 | 50 | 0 | 40 | 0 | 0 | 0 | 0 | 0 | 0 |
| 2-53 | 63 | 100 | 100 | 95 | 100 | 100 | 80 | 100 | 40 | 40 | 90 | 95 | 25 | 80 |
| | 250 | 100 | 100 | 100 | 100 | 100 | 100 | 100 | 99 | 100 | 100 | 100 | 90 | 90 |
| 2-54 | 63 | 100 | 100 | 100 | 85 | 100 | 100 | 100 | 90 | 90 | 100 | 90 | 90 | 70 |
| | 250 | 100 | 100 | 100 | 100 | 100 | 100 | 100 | 100 | 100 | 100 | 100 | 98 | 90 |
| 2-56 | 63 | 100 | 100 | 100 | 100 | 100 | 100 | 100 | 90 | 99 | 100 | 40 | 80 | 30 |
| | 250 | 100 | 100 | 100 | 100 | 100 | 100 | 100 | 100 | 100 | 100 | 90 | 95 | 95 |
| 2-58 | 63 | 100 | 100 | 30 | 20 | 100 | 50 | 100 | 50 | 70 | 90 | 15 | 40 | 80 |
| | 250 | 100 | 100 | 99 | 100 | 100 | 100 | 100 | 100 | 100 | 100 | 100 | 95 | 95 |
| 2-59 | 63 | 100 | 100 | 30 | 20 | 100 | 50 | 100 | 40 | 40 | 70 | 10 | 10 | 25 |
| | 250 | 100 | 100 | 100 | 100 | 100 | 90 | 100 | 9 | 90 | 100 | 100 | 70 | 75 |
| 2-61 | 63 | 100 | 100 | 40 | 90 | 100 | 80 | 10 | 85 | 80 | 90 | 30 | 10 | 75 |
| | 250 | 100 | 100 | 100 | 100 | 100 | 100 | 100 | 100 | 100 | 100 | 80 | 95 | 95 |
| 2-63 | 63 | 100 | 100 | 100 | 100 | 100 | 100 | 100 | 95 | 90 | 100 | 95 | 60 | 95 |
| | 250 | 100 | 100 | 100 | 100 | 100 | 100 | 100 | 100 | 100 | 100 | 100 | 100 | 100 |
| 2-64 | 63 | 90 | 100 | 0 | 0 | 90 | 0 | 100 | 0 | 10 | 40 | 0 | 0 | 10 |
| | 250 | 100 | 100 | 100 | 40 | 100 | 60 | 100 | 60 | 50 | 70 | 20 | 35 | 60 |
| 2-66 | 63 | 100 | 100 | 35 | 40 | 100 | 0 | 95 | 0 | 20 | 60 | 10 | 0 | 10 |
| | 250 | 100 | 100 | 90 | 80 | 100 | 60 | 100 | 60 | 95 | 99 | 20 | 15 | 60 |
| 2-67 | 63 | 100 | 100 | 100 | 100 | 100 | 100 | 100 | 50 | 80 | 100 | 100 | 90 | 90 |
| | 250 | 100 | 100 | 100 | 100 | 100 | 100 | 100 | 95 | 100 | 100 | 100 | 99 | 90 |
| 2-69 | 63 | 90 | 100 | 0 | 0 | 100 | 50 | 70 | 0 | 0 | 20 | 0 | 0 | 20 |
| | 250 | 100 | 100 | 80 | 40 | 100 | 60 | 95 | 10 | 30 | 90 | 0 | 10 | 30 |
| 2-70 | 63 | 70 | 100 | 0 | 0 | 80 | 0 | 0 | 0 | 0 | 0 | 0 | 0 | 0 |
| | 250 | 100 | 90 | 40 | 60 | 100 | 30 | 60 | 0 | 0 | 20 | 10 | 0 | 10 |
| 2-72 | 63 | 100 | 100 | 30 | 20 | 100 | 0 | 60 | 0 | 0 | 30 | 0 | 0 | 10 |
| | 250 | 100 | 100 | 90 | 20 | 100 | 50 | 100 | 50 | 50 | 100 | 50 | 5 | 40 |
| 2-73 | 63 | 100 | 100 | 100 | 90 | 100 | — | 100 | 90 | 75 | 100 | 40 | 50 | 80 |
| | 250 | 100 | 100 | 100 | 100 | 100 | — | 100 | 100 | 100 | 100 | 100 | 95 | 100 |
| 2-74 | 63 | 100 | 100 | 40 | 0 | 100 | — | 70 | 0 | 0 | 20 | 0 | 0 | 30 |
| | 250 | 100 | 100 | 70 | 50 | 100 | — | 100 | 100 | 100 | 100 | 40 | 15 | 60 |
| 2-75 | 63 | 100 | 100 | 100 | 20 | 100 | — | 100 | 20 | 20 | 70 | 0 | 0 | 30 |
| | 250 | 100 | 100 | 100 | 60 | 100 | — | 100 | 100 | 60 | 100 | 20 | 0 | 80 |
| 2-77 | 63 | 70 | 30 | 0 | 0 | 90 | — | 0 | 0 | 0 | 0 | 0 | 0 | 0 |
| | 250 | 100 | 100 | 30 | 30 | 100 | — | 60 | 0 | 0 | 30 | 20 | 0 | 20 |
| 2-78 | 63 | 100 | 100 | 100 | 20 | 100 | — | 90 | 10 | 10 | 30 | 10 | 0 | 40 |
| | 250 | 100 | 100 | 100 | 100 | 100 | — | 100 | 100 | 80 | 100 | 100 | 10 | 95 |
| 2-81 | 63 | 100 | 100 | 90 | 60 | 100 | — | 100 | 70 | 90 | 100 | 70 | 0 | 70 |
| | 250 | 100 | 100 | 100 | 100 | 100 | — | 100 | 100 | 90 | 100 | 80 | 90 | 90 |
| 2-82 | 63 | 100 | 100 | 80 | 0 | 100 | — | 80 | 0 | 0 | 30 | 0 | 0 | 10 |
| | 250 | 100 | 100 | 100 | 0 | 100 | — | 100 | 0 | 20 | 80 | 0 | 0 | 10 |
| 2-83 | 63 | 60 | 10 | 0 | 0 | 30 | — | 0 | 0 | 0 | 0 | 0 | 0 | 0 |
| | 250 | 100 | 100 | 0 | 0 | 90 | — | 40 | 0 | 20 | 30 | 0 | 0 | 0 |
| 2-84 | 63 | 80 | 0 | 0 | 0 | 40 | — | 0 | 0 | 0 | 00 | 0 | 0 | 0 |
| | 250 | 100 | 80 | 0 | 0 | 100 | — | 50 | 0 | 0 | 0 | 0 | 0 | 0 |
| 2-86 | 63 | 100 | 100 | 100 | 90 | 100 | — | 100 | 95 | 99 | 100 | 20 | 95 | 90 |
| | 250 | 100 | 100 | 95 | 100 | 100 | — | 100 | 100 | 100 | 100 | 100 | 99 | 99 |
| 2-87 | 63 | 100 | 100 | 100 | 90 | 100 | — | 90 | 60 | 50 | 80 | 15 | 5 | 40 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | 250 | 100 | 100 | 100 | 100 | 100 | — | 100 | 90 | 85 | 100 | 100 | 75 | 90 |
| 2-89 | 63 | 100 | 100 | 95 | 95 | 100 | — | 100 | 50 | 60 | 99 | 20 | 10 | 40 |
| | 250 | 100 | 100 | 100 | 100 | 100 | — | 100 | 90 | 90 | 100 | 40 | 30 | 90 |
| 2-92 | 63 | 50 | 100 | 40 | 30 | 100 | — | 30 | 0 | 0 | 0 | 0 | 0 | 0 |
| | 250 | 100 | 100 | 100 | 100 | 100 | — | 90 | 20 | 40 | 20 | 90 | 20 | 10 |
| 2-98 | 63 | 100 | 100 | 100 | 100 | 100 | 100 | 80 | 30 | 30 | 40 | 50 | 70 | 60 |
| | 250 | 100 | 100 | 100 | 100 | 100 | 100 | 100 | 100 | 95 | 95 | 90 | 90 | 90 |
| 2-100 | 63 | 100 | 100 | 30 | 100 | 100 | 90 | 100 | 70 | 85 | 90 | 100 | 45 | 75 |
| | 250 | 100 | 100 | 100 | 100 | 100 | 100 | 100 | 90 | 100 | 100 | 90 | 95 | 90 |
| 2-102 | 63 | 30 | 0 | 0 | 0 | 0 | — | 0 | 0 | 0 | 0 | 0 | 0 | 0 |
| | 250 | 0 | 0 | 0 | 0 | 0 | — | 0 | 0 | 0 | 0 | 0 | 0 | 0 |
| 2-105 | 63 | 100 | 100 | 30 | 20 | 100 | — | 100 | 20 | 40 | 90 | 0 | 10 | 50 |
| | 250 | 100 | 100 | 60 | 95 | 100 | — | 100 | 100 | 95 | 100 | 0 | 10 | 70 |
| 2-115 | 63 | 100 | 100 | 20 | 0 | 100 | — | 90 | 80 | 20 | 90 | 0 | 0 | 40 |
| | 125 | 100 | 100 | 80 | 90 | 100 | — | 99 | 95 | 30 | 100 | 0 | 0 | 40 |
| 2-117 | 63 | 90 | 100 | 80 | 100 | 100 | — | 30 | 10 | 10 | 30 | 10 | 10 | 30 |
| | 250 | 100 | 100 | 100 | 100 | 100 | — | 100 | 70 | 60 | 90 | 95 | 35 | 90 |
| 2-118 | 63 | 40 | 90 | 90 | 10 | 90 | — | 0 | 0 | 0 | 0 | 0 | 0 | 0 |
| | 250 | 100 | 100 | 40 | 80 | 100 | — | 50 | 0 | 0 | 20 | 25 | 10 | 30 |
| 2-119 | 63 | 100 | 100 | 60 | 70 | 100 | — | 100 | 70 | 75 | 70 | 30 | 20 | 70 |
| | 250 | 100 | 100 | 90 | 100 | 100 | — | 100 | 95 | 100 | 100 | 40 | 90 | 100 |
| 2-120 | 63 | 90 | 100 | 40 | 50 | 100 | — | 70 | 60 | 50 | 80 | 0 | 0 | 80 |
| | 250 | 100 | 100 | 70 | 80 | 100 | — | 100 | 90 | 95 | 100 | 60 | 90 | 95 |
| 2-121 | 63 | 100 | 100 | 0 | 0 | 80 | — | 0 | 0 | 0 | 0 | 0 | 0 | 0 |
| | 250 | 100 | 100 | 50 | 90 | 100 | — | 60 | 0 | 0 | 30 | 10 | 10 | 0 |
| 2-122 | 63 | 100 | 100 | 30 | 30 | 100 | 30 | 80 | 20 | 30 | 100 | 0 | 0 | 20 |
| | 250 | 100 | 100 | 50 | 90 | 100 | 90 | 100 | 80 | 60 | 100 | 50 | 10 | 45 |
| 2-123 | 63 | 100 | 100 | 60 | 100 | 100 | 95 | 80 | 40 | 30 | 60 | 0 | 0 | 30 |
| | 250 | 100 | 100 | 90 | 100 | 100 | 100 | 100 | 80 | 70 | 100 | 90 | 15 | 80 |
| 2-124 | 63 | 40 | 0 | 0 | 0 | 20 | — | 0 | 0 | 0 | 0 | 0 | 0 | 0 |
| | 250 | 100 | 80 | 20 | 20 | 80 | — | 10 | 0 | 0 | 0 | 10 | 0 | 10 |
| 2-125 | 63 | 100 | 100 | 30 | 0 | 100 | — | 50 | 10 | 20 | 30 | 0 | 0 | 0 |
| | 250 | 100 | 100 | 70 | 100 | 100 | — | 90 | 50 | 50 | 90 | 50 | 10 | 45 |
| 2-126 | 63 | 100 | 100 | 10 | 10 | 100 | — | 40 | 10 | — | 30 | 0 | 0 | 10 |
| | 250 | 100 | 100 | 70 | 90 | 100 | — | 100 | 40 | — | 90 | 30 | 5 | 60 |
| 2-127 | 63 | 90 | 100 | 0 | 0 | 100 | — | 20 | 0 | — | 30 | 0 | 0 | 0 |
| | 250 | 100 | 100 | 40 | 50 | 100 | — | 80 | 40 | — | 100 | 0 | 0 | 10 |
| 2-128 | 63 | 100 | 30 | 0 | 0 | 100 | — | 30 | 0 | — | 20 | 0 | 0 | 0 |
| | 250 | 100 | 90 | 0 | 40 | 100 | — | 100 | 30 | — | 70 | 10 | 5 | 0 |
| 2-129 | 63 | 90 | 100 | 60 | 50 | 100 | — | 90 | 30 | — | 60 | 40 | 50 | 40 |
| | 250 | 100 | 100 | 90 | 70 | 100 | — | 100 | 80 | — | 100 | 90 | 90 | 80 |
| 2-130 | 63 | 40 | 100 | 0 | 0 | 60 | — | 50 | 0 | — | 20 | 0 | 0 | 0 |
| | 250 | 100 | 100 | 40 | 30 | 100 | — | 100 | 30 | — | 90 | 25 | 5 | 15 |
| 2-131 | 63 | 90 | 85 | 60 | 30 | 90 | — | 40 | 10 | — | 40 | 10 | 0 | 15 |
| | 250 | 95 | 100 | 95 | 85 | 100 | — | 90 | 60 | — | 80 | 20 | 0 | 50 |
| 2-132 | 63 | 100 | 100 | 50 | 20 | 100 | — | 90 | 30 | 30 | 60 | 0 | 5 | 15 |
| | 250 | 100 | 100 | 100 | 40 | 100 | — | 100 | 40 | 50 | 100 | 10 | 15 | 45 |
| 2-133 | 63 | 100 | 100 | 55 | 80 | 100 | — | 95 | 65 | 75 | 95 | 5 | 20 | 70 |
| | 250 | 100 | 100 | 100 | 100 | 100 | — | 100 | 95 | 100 | 100 | 70 | 80 | 93 |
| 2-134 | 63 | 100 | 60 | 10 | 20 | 100 | — | 35 | 0 | 0 | 20 | 0 | 0 | 10 |
| | 250 | 100 | 80 | 30 | 30 | 100 | — | 80 | 30 | 30 | 90 | 0 | 0 | 20 |
| 2-135 | 63 | 95 | 90 | 10 | 20 | 100 | — | 80 | 10 | — | 60 | 0 | 0 | 0 |
| | 250 | 100 | 100 | 60 | 100 | 100 | — | 100 | 30 | — | 95 | 5 | 0 | 35 |
| 2-136 | 63 | 40 | 80 | 0 | 0 | 90 | — | 10 | 0 | — | 0 | 0 | 0 | 0 |
| | 250 | 90 | 100 | 40 | 100 | 100 | — | 40 | 0 | — | 10 | 10 | 0 | 10 |
| 2-137 | 63 | 100 | 80 | 50 | 30 | 100 | — | 30 | 10 | 0 | 50 | 0 | 0 | 20 |
| | 250 | 100 | 100 | 50 | 30 | 100 | — | 60 | 50 | 70 | 100 | 70 | 10 | 50 |
| 2-140 | 63 | 100 | 100 | 40 | 10 | 100 | — | 50 | 40 | 10 | 40 | 0 | 0 | 30 |
| | 250 | 100 | 100 | 100 | 100 | 100 | — | 80 | 80 | 60 | 95 | 60 | 15 | 85 |
| 2-141 | 63 | 100 | 100 | 30 | 40 | 100 | — | 30 | 30 | — | 35 | 10 | 0 | 30 |
| | 250 | 100 | 100 | 90 | 100 | 100 | — | 70 | 95 | — | 70 | 50 | 45 | 70 |
| 2-142 | 63 | 0 | 0 | 0 | 0 | 40 | — | 0 | 0 | 0 | 0 | 0 | 0 | 0 |
| | 250 | 40 | 0 | 0 | 0 | 70 | — | 0 | 0 | 0 | 0 | 0 | 0 | 0 |
| 2-143 | 63 | 100 | 100 | 0 | 0 | 100 | — | 30 | 30 | 30 | 30 | 0 | 0 | 20 |
| | 250 | 100 | 100 | 90 | 35 | 100 | — | 70 | 85 | 80 | 100 | 5 | 5 | 65 |
| 2-144 | 63 | 99 | 70 | 0 | 0 | 100 | — | 40 | 20 | 10 | 20 | 0 | 0 | 20 |
| | 250 | 100 | 100 | 20 | 30 | 100 | — | 90 | 75 | 70 | 70 | 0 | 0 | 45 |
| 2-145 | 63 | 100 | 90 | 40 | 10 | 100 | — | 60 | 35 | 30 | 90 | 10 | 0 | 10 |
| | 250 | 100 | 100 | 90 | 100 | 100 | — | 100 | 60 | 50 | 100 | 10 | 0 | 60 |
| 2-146 | 63 | 30 | 70 | 20 | 40 | 90 | — | 0 | 0 | 0 | 0 | 0 | 0 | 0 |
| | 250 | 80 | 10 | 0 | 20 | 100 | — | 0 | 0 | 0 | 0 | 0 | 0 | 0 |
| 2-147 | 63 | 100 | 100 | 40 | 80 | 100 | 80 | 100 | 90 | 90 | 90 | 90 | 100 | 99 |
| | 250 | 100 | 100 | 100 | 100 | 100 | 100 | 100 | 100 | 100 | 100 | 100 | 100 | 100 |
| 2-148 | 63 | 100 | 100 | 50 | 50 | 100 | 0 | 80 | 90 | 0 | 95 | 0 | 0 | 0 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | 250 | 100 | 100 | 95 | 99 | 100 | 100 | 95 | 100 | 30 | 100 | 0 | 0 | 60 |
| 2-149 | 63 | 100 | 99 | 0 | 30 | 100 | 0 | 50 | 50 | 30 | 90 | 20 | 0 | 0 |
| | 250 | 100 | 100 | 50 | 70 | 100 | 100 | 90 | 100 | 50 | 100 | 50 | 20 | 50 |
| 2-151 | 63 | 0 | 30 | 0 | 0 | 0 | — | 0 | 0 | 0 | 0 | 0 | 0 | 0 |
| | 250 | 0 | 100 | 70 | 40 | 80 | — | 0 | 0 | 40 | 40 | 0 | 30 | 30 |
| 2-152 | 63 | 100 | 60 | 0 | 0 | 95 | — | 30 | 10 | 0 | 50 | 0 | 0 | 0 |
| | 250 | 100 | 90 | 50 | 0 | 100 | — | 70 | 70 | 30 | 80 | 0 | 0 | 30 |
| 2-153 | 63 | 100 | 20 | 0 | 0 | 70 | — | 30 | 0 | 10 | 0 | 0 | 0 | 0 |
| | 250 | 100 | 50 | 0 | 0 | 90 | — | 90 | 0 | 0 | 40 | 0 | 0 | 20 |
| 2-154 | 63 | 100 | 100 | 60 | 80 | 100 | — | 70 | 50 | 80 | 85 | 80 | 10 | 35 |
| | 250 | 100 | 100 | 95 | 100 | 100 | — | 100 | 95 | 95 | 95 | 90 | 90 | 70 |
| 2-155 | 63 | 100 | 100 | 0 | 0 | 100 | — | 60 | 50 | 30 | 85 | 0 | 0 | 30 |
| | 125 | 100 | 100 | 30 | 40 | 100 | — | 95 | 70 | 70 | 100 | 10 | 15 | 60 |
| 2-157 | 63 | 100 | 100 | 30 | 40 | 100 | — | 30 | 30 | — | 35 | 10 | 0 | 30 |
| | 250 | 100 | 100 | 90 | 100 | 100 | — | 70 | 95 | — | 70 | 50 | 45 | 70 |
| 2-158 | 63 | 100 | 80 | 0 | 0 | 100 | — | 0 | 50 | 0 | 80 | 0 | 0 | 0 |
| | 250 | 100 | 95 | 0 | 0 | 100 | — | 95 | 80 | 20 | 95 | 10 | 0 | 10 |
| 2-161 | 63 | 100 | 100 | 0 | 20 | 100 | — | 100 | 90 | 0 | 95 | 0 | 0 | 0 |
| | 250 | 100 | 100 | 50 | 90 | 100 | — | 100 | 99 | 30 | 100 | 10 | 0 | 40 |
| 2-163 | 63 | 100 | 95 | 10 | 40 | 100 | 65 | 60 | 0 | 0 | 35 | 0 | 0 | 0 |
| | 250 | 100 | 100 | 60 | 95 | 100 | 95 | 95 | 75 | 30 | 100 | 0 | 0 | 30 |
| 2-168 | 63 | 90 | 60 | 30 | 40 | 100 | — | 10 | 0 | 0 | 0 | 0 | 0 | 20 |
| | 250 | 100 | 100 | 80 | 90 | 100 | — | 95 | 20 | 90 | 80 | 50 | — | 60 |
| 2-169 | 63 | 70 | 0 | 20 | 10 | 65 | — | 0 | 0 | 0 | 0 | 0 | 0 | 10 |
| | 250 | 80 | 90 | 30 | 20 | 100 | — | 30 | 0 | 20 | 80 | 20 | 0 | 40 |
| 2-170 | 63 | 70 | 90 | 30 | 40 | 100 | — | 60 | 0 | 20 | 30 | 30 | 10 | 10 |
| | 250 | 100 | 100 | 60 | 70 | 100 | — | 90 | 50 | 80 | 90 | 10 | 15 | 0 |
| 2-171 | 63 | 50 | 90 | 10 | 10 | 70 | — | 30 | 0 | 10 | 20 | 10 | 0 | 0 |
| | 250 | 100 | 100 | 30 | 60 | 100 | — | 90 | 10 | 30 | 80 | 10 | 0 | 10 |
| 2-172 | 63 | 70 | 90 | 20 | 60 | 30 | — | 20 | 0 | 0 | 20 | 30 | 0 | 10 |
| | 250 | 100 | 100 | 80 | 95 | 100 | — | 65 | 60 | 40 | 100 | 100 | 10 | 50 |
| 2-173 | 63 | 30 | 95 | 30 | 0 | 90 | — | 40 | 0 | 0 | 30 | 0 | 0 | 0 |
| | 250 | 100 | 100 | 70 | 40 | 100 | — | 80 | 20 | 10 | 80 | 95 | 20 | 50 |
| 2-174 | 63 | 90 | 100 | 40 | 30 | 80 | 10 | 20 | 0 | 10 | 20 | 0 | 0 | 10 |
| | 250 | 100 | 100 | 80 | 100 | 100 | 90 | 90 | 60 | 90 | 70 | 90 | 60 | 50 |
| 2-175 | 63 | 100 | 100 | 30 | 70 | 100 | — | 0 | 0 | 0 | 0 | 0 | 0 | 20 |
| | 250 | 100 | 100 | 30 | 50 | 100 | — | 60 | 40 | 30 | 60 | 50 | 0 | 40 |
| 2-176 | 63 | 50 | 0 | 0 | 0 | 90 | — | 0 | 0 | 0 | 0 | 0 | 0 | 0 |
| | 250 | 90 | 70 | 0 | 40 | 100 | — | 20 | 0 | 0 | 20 | 0 | 0 | 0 |
| 2-177 | 63 | 100 | 70 | 0 | 40 | 100 | — | 40 | 0 | 0 | 30 | 10 | 0 | 10 |
| | 250 | 100 | 100 | 40 | 90 | 100 | — | 70 | 40 | 30 | 70 | 50 | 10 | 20 |
| 2-178 | 63 | 0 | 0 | 0 | 0 | 20 | — | 0 | 0 | 0 | 0 | 0 | 0 | 0 |
| | 250 | 0 | 0 | 0 | 0 | 0 | — | 0 | 0 | 0 | 0 | 0 | 0 | 0 |
| 2-179 | 63 | 100 | 100 | 30 | 60 | 100 | — | 50 | 20 | 30 | 20 | 0 | 0 | 20 |
| | 250 | 100 | 100 | 100 | 70 | 100 | — | 90 | 85 | 95 | 95 | 5 | 10 | 60 |
| 2-180 | 63 | 100 | 100 | 40 | 60 | 100 | — | 30 | 10 | — | 20 | 60 | 0 | 40 |
| | 250 | 100 | 100 | 50 | 100 | 100 | — | 90 | 80 | — | 90 | 100 | 5 | 70 |
| 2-181 | 63 | 100 | 100 | 10 | 30 | 100 | — | 70 | 40 | — | 60 | 80 | 0 | 15 |
| | 250 | 100 | 100 | 90 | 80 | 100 | — | 95 | 80 | — | 90 | 70 | 5 | 80 |
| 2-182 | 63 | 90 | 100 | 10 | 0 | 100 | — | 30 | 10 | — | 30 | 30 | 0 | 15 |
| | 250 | 100 | 100 | 60 | 100 | 100 | — | 90 | 60 | — | 90 | 60 | 10 | 70 |
| 2-183 | 63 | 0 | 0 | 0 | 0 | 0 | — | 0 | 0 | — | 0 | 0 | 0 | 0 |
| | 250 | 30 | 10 | 0 | 0 | 40 | — | 0 | 0 | — | 0 | 0 | 0 | 0 |
| 2-184 | 63 | 100 | 100 | 50 | 50 | 100 | — | 50 | 30 | — | 60 | 35 | 0 | 30 |
| | 250 | 100 | 100 | 75 | 100 | 100 | — | 100 | 80 | — | 100 | 70 | 30 | 60 |
| 2-185 | 63 | 100 | 90 | 0 | 60 | 100 | — | 30 | 10 | 20 | 20 | 20 | 0 | 20 |
| | 250 | 100 | 100 | 60 | 60 | 100 | — | 50 | 10 | 20 | 40 | 50 | 5 | 40 |
| 2-187 | 63 | 100 | 100 | 60 | 75 | 100 | — | 50 | 20 | — | 90 | 35 | 0 | 40 |
| | 250 | 100 | 100 | 100 | 100 | 100 | — | 100 | 60 | — | 100 | 90 | 90 | 90 |
| 2-188 | 63 | 100 | 90 | 0 | 10 | 100 | — | 30 | 30 | 10 | 10 | 0 | 0 | 10 |
| | 250 | 80 | 100 | 0 | 90 | 100 | — | 50 | 60 | 30 | 60 | 20 | 0 | 10 |
| 2-189 | 40.5 | 95 | 70 | 0 | 0 | 100 | — | 0 | 0 | 0 | 0 | 0 | 0 | 0 |
| | 162 | 90 | 100 | 10 | 20 | 100 | — | 0 | 0 | 0 | 0 | 0 | 0 | 0 |
| 2-190 | 63 | 95 | 100 | 30 | 0 | 100 | — | 0 | 0 | 0 | 0 | 0 | 0 | 10 |
| | 250 | 100 | 100 | 70 | 90 | 100 | — | 30 | 0 | 0 | 30 | 20 | 0 | 20 |
| 2-191 | 63 | 100 | 80 | 10 | 10 | 100 | — | 40 | 0 | 0 | 0 | 0 | 0 | 10 |
| | 250 | 100 | 100 | 30 | 40 | 100 | — | 80 | 10 | 50 | 70 | 10 | 0 | 20 |
| 2-192 | 63 | — | — | — | — | — | — | — | — | — | — | — | — | — |
| | 250 | 90 | 85 | 0 | 30 | 80 | — | 0 | 0 | 0 | 0 | 0 | 0 | 0 |
| 2-194 | 63 | 75 | 90 | 0 | 0 | 40 | 0 | 0 | 0 | 0 | 0 | 0 | 0 | 0 |
| | 250 | 100 | 100 | 10 | 20 | 85 | 0 | 20 | 0 | 0 | 10 | 10 | 0 | 10 |
| 2-196 | 63 | 100 | 100 | 0 | 20 | 100 | 30 | 90 | 40 | 10 | 90 | 10 | 0 | 20 |
| | 250 | 100 | 100 | 60 | 70 | 100 | 90 | 100 | 85 | 20 | 100 | 0 | 0 | 50 |
| 2-197 | 63 | 100 | 90 | 0 | 30 | 100 | 100 | 50 | 0 | 0 | 80 | 0 | 0 | 30 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | 250 | 100 | 100 | 50 | 50 | 100 | 100 | 100 | 50 | 20 | 100 | 50 | 0 | 80 |
| 2-198 | 63 | 100 | 100 | 50 | 100 | 100 | 100 | 90 | 50 | 50 | 100 | 50 | 50 | 30 |
| | 250 | 100 | 100 | 100 | 100 | 100 | 100 | 100 | 100 | 99 | 100 | 100 | 90 | 80 |
| 2-199 | 63 | 100 | 100 | 100 | 100 | 100 | — | 100 | 99 | 100 | 100 | 100 | 95 | 99 |
| | 250 | 100 | 100 | 100 | 100 | 100 | — | 100 | 100 | 100 | 100 | 100 | 100 | 100 |
| 2-200 | 63 | 100 | 100 | 80 | 100 | 100 | 100 | 100 | 99 | 100 | 100 | 100 | 75 | 80 |
| | 250 | 100 | 100 | 100 | 100 | 100 | 100 | 100 | 100 | 100 | 100 | 100 | 100 | 100 |
| 2-201 | 63 | 95 | 98 | 0 | 55 | 98 | 30 | 0 | 15 | 0 | 45 | 0 | 0 | 0 |
| | 250 | 95 | 100 | 0 | 80 | 100 | 80 | 75 | 75 | 30 | 95 | 35 | 0 | 30 |
| 2-202 | 63 | 100 | 100 | 30 | 100 | 100 | — | 40 | 90 | — | 30 | 0 | 0 | 40 |
| | 250 | 100 | 100 | 80 | 100 | 100 | — | 100 | 100 | — | 100 | 60 | 50 | 90 |
| 2-203 | 63 | 70 | 75 | 30 | 10 | 100 | — | 20 | 0 | 0 | 60 | 0 | 0 | 10 |
| | 250 | 100 | 100 | 90 | 70 | 100 | — | 70 | 80 | 40 | 90 | 30 | 0 | 20 |
| 2-204 | 63 | 100 | 99 | 60 | 50 | 70 | 50 | 95 | 20 | 40 | 35 | 20 | 50 | 0 |
| | 250 | 100 | 100 | 75 | 100 | 100 | 85 | 99 | 70 | 80 | 100 | 95 | 70 | 30 |
| 2-205 | 63 | 100 | 100 | 0 | 0 | 100 | 80 | 70 | 80 | 40 | 70 | 0 | 0 | 20 |
| | 250 | 100 | 100 | 40 | 95 | 100 | 90 | 100 | 99 | 85 | 99 | 15 | 50 | 70 |
| 2-206 | 63 | 0 | 70 | 20 | 50 | 50 | — | 0 | 0 | 0 | 0 | 10 | 50 | 60 |
| | 250 | 80 | 100 | 60 | 90 | 100 | — | 70 | 90 | 40 | 80 | 100 | 100 | 80 |
| 3-1 | 63 | 0 | 0 | 0 | 0 | 20 | 0 | 0 | 0 | 0 | 0 | 0 | 0 | 0 |
| | 250 | 30 | 20 | 0 | 0 | 80 | 0 | 0 | 0 | 0 | 0 | 0 | 0 | 0 |
| 3-4 | 63 | 0 | 0 | 0 | 0 | 0 | — | 20 | 0 | 0 | 0 | 0 | 0 | 0 |
| | 250 | 100 | 100 | 60 | 50 | 100 | — | 60 | 0 | 10 | 10 | 10 | 0 | 15 |
| 3-6 | 63 | 90 | 100 | 100 | 100 | 100 | — | 100 | 40 | 30 | 30 | 10 | 0 | 30 |
| | 250 | 100 | 100 | 100 | 95 | 100 | — | 100 | 80 | 80 | 100 | 100 | 90 | 80 |
| 3-23 | 63 | 0 | 0 | 0 | 0 | 0 | — | 0 | 0 | 0 | 0 | 0 | 0 | 0 |
| | 250 | 0 | 40 | 0 | 0 | 70 | — | 0 | 0 | 0 | 0 | 0 | 0 | 0 |
| 3-26 | 63 | 80 | 75 | 40 | 50 | 80 | 10 | 0 | 0 | 0 | 0 | 0 | 0 | 0 |
| | 250 | 100 | 100 | 90 | 100 | 90 | 90 | 85 | 30 | 50 | 80 | 20 | 30 | 40 |
| 4-1 | 63 | 100 | 100 | 95 | 100 | 100 | — | 100 | 10 | 60 | 60 | 70 | 10 | 50 |
| | 250 | 100 | 100 | 100 | 100 | 100 | — | 100 | 100 | 100 | 100 | 100 | 80 | 95 |
| 4-2 | 63 | 100 | 100 | 0 | 0 | 100 | 30 | 70 | 0 | 0 | 40 | 20 | 0 | 10 |
| | 250 | 100 | 100 | 80 | 100 | 100 | 100 | 100 | 80 | 70 | 90 | 70 | 5 | 20 |
| 4-7 | 63 | 100 | 100 | 70 | 80 | 100 | — | 100 | 70 | 80 | 100 | 10 | 60 | 70 |
| | 250 | 100 | 100 | 100 | 100 | 100 | — | 100 | 90 | 95 | 100 | 40 | 95 | 100 |
| 4-23 | 63 | 100 | 100 | 80 | 100 | 100 | — | 80 | 80 | 70 | 80 | 70 | 35 | 60 |
| | 250 | 100 | 100 | 100 | 80 | 100 | — | 100 | 95 | 90 | 100 | 40 | 90 | 90 |
| 4-24 | 63 | 100 | 50 | 0 | 20 | 100 | — | 90 | 10 | 10 | 30 | 0 | 0 | 10 |
| | 250 | 100 | 100 | 80 | 30 | 100 | — | 100 | 50 | 40 | 70 | 0 | 5 | 50 |
| 4-25 | 63 | 30 | 0 | 0 | 0 | 60 | — | 0 | 0 | 0 | 0 | 0 | 0 | 0 |
| | 250 | 100 | 60 | 20 | 0 | 100 | — | 50 | 0 | 0 | 10 | 10 | 0 | 0 |
| 4-26 | 63 | 70 | 80 | 0 | 0 | 100 | — | 75 | 0 | 0 | 10 | 0 | 0 | 0 |
| | 250 | 100 | 100 | 0 | 10 | 100 | — | 95 | 30 | 20 | 90 | 0 | 0 | 45 |
| 4-27 | 63 | 70 | 80 | 0 | 20 | 80 | — | 30 | 0 | 0 | 0 | 10 | 0 | 10 |
| | 250 | 100 | 100 | 30 | 50 | 100 | — | 50 | 0 | 0 | 0 | 40 | 0 | 50 |
| 4-28 | 63 | 40 | 20 | 0 | 0 | 70 | — | 20 | 0 | 0 | 0 | 0 | 0 | 0 |
| | 250 | 70 | 60 | 0 | 0 | 100 | — | 60 | 0 | 0 | 0 | 0 | 0 | 15 |
| 4-29 | 63 | 100 | 100 | 40 | 70 | 100 | — | 100 | 70 | 70 | 100 | 25 | 80 | 50 |
| | 250 | 100 | 100 | 80 | 90 | 100 | — | 100 | 90 | 90 | 100 | 50 | 95 | 85 |
| 4-30 | 63 | 100 | 100 | 90 | 60 | 100 | — | 100 | 60 | 30 | 90 | 20 | 30 | 90 |
| | 250 | 100 | 100 | 95 | 100 | 100 | — | 100 | 90 | 80 | 100 | 45 | 70 | 90 |
| 4-31 | 63 | 100 | 30 | 0 | 0 | 90 | — | 90 | 10 | 10 | 50 | 0 | 0 | 10 |
| | 250 | 100 | 100 | 10 | 40 | 100 | — | 100 | 30 | 20 | 100 | 10 | 10 | 30 |
| 4-32 | 63 | 50 | 0 | 0 | 0 | 80 | — | 30 | 0 | 0 | 20 | 0 | 0 | 0 |
| | 250 | 100 | 70 | 30 | 40 | 100 | — | 95 | 50 | 30 | 80 | 5 | 10 | 30 |
| 4-33 | 63 | 100 | 50 | 0 | 0 | 100 | — | 100 | 20 | 30 | 45 | 10 | 10 | 20 |
| | 250 | 100 | 100 | 50 | 70 | 100 | — | 100 | 80 | 80 | 90 | 30 | 50 | 40 |
| 4-34 | 63 | 100 | 100 | 40 | 30 | 100 | — | 80 | 50 | 40 | 90 | 25 | 10 | 50 |
| | 250 | 100 | 100 | 95 | 80 | 100 | — | 100 | 90 | 80 | 95 | 80 | 90 | 95 |
| 4-36 | 63 | 90 | 100 | 80 | 100 | 100 | — | 60 | 30 | — | 30 | 70 | 90 | 60 |
| | 250 | 100 | 100 | 100 | 100 | 100 | — | 100 | 90 | — | 100 | 95 | 100 | 95 |
| 4-37 | 63 | 100 | 100 | 30 | 30 | 100 | — | 90 | 10 | — | 60 | 0 | 0 | 10 |
| | 250 | 100 | 90 | 40 | 50 | 100 | — | 100 | 60 | — | 90 | 15 | 0 | 30 |
| 4-38 | 63 | 100 | 80 | 30 | 60 | 100 | — | 100 | 30 | — | 95 | 10 | 10 | 35 |
| | 250 | 100 | 100 | 60 | 50 | 100 | — | 100 | 60 | — | 100 | 10 | 20 | 60 |
| 4-39 | 63 | 100 | 100 | 30 | 80 | 100 | — | 100 | 60 | — | 100 | 30 | 70 | 80 |
| | 250 | 100 | 100 | 90 | 100 | 100 | — | 100 | 80 | — | 100 | 30 | 90 | 80 |
| 4-40 | 63 | 100 | 100 | 60 | 30 | 100 | — | 100 | 60 | — | 100 | 10 | 0 | 30 |
| | 250 | 100 | 100 | 90 | 90 | 100 | — | 100 | 85 | — | 100 | 80 | 75 | 70 |
| 4-41 | 63 | 100 | 100 | 100 | 100 | 100 | — | 100 | 80 | — | 100 | 40 | 15 | 40 |
| | 250 | 100 | 100 | 100 | 100 | 100 | — | 100 | 90 | — | 100 | 80 | 65 | 80 |
| 4-42 | 63 | 30 | 60 | 0 | 0 | 40 | — | 30 | 0 | — | 10 | 10 | 0 | 0 |
| | 250 | 90 | 100 | 100 | 40 | 100 | — | 100 | 40 | — | 60 | 0 | 0 | 0 |
| 4-43 | 63 | 10 | 20 | 0 | 0 | 30 | — | 0 | 0 | — | 0 | 0 | 0 | 0 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | 250 | 60 | 50 | 40 | 10 | 80 | — | 70 | 10 | — | 60 | 10 | 0 | 10 |
| 4-44 | 63 | 100 | 100 | 100 | 100 | 100 | — | 100 | 80 | — | 100 | 60 | 70 | 70 |
| | 250 | 100 | 100 | 100 | 100 | 100 | — | 100 | 95 | — | 100 | 50 | 95 | 65 |
| 4-45 | 63 | 30 | 50 | 0 | 10 | 50 | — | 0 | 0 | — | 0 | 0 | 0 | 0 |
| | 250 | 100 | 90 | 40 | 40 | 95 | — | 50 | 40 | — | 70 | 15 | 20 | 10 |
| 4-46 | 63 | 80 | 50 | 30 | 10 | 100 | — | 40 | 20 | 20 | 70 | 0 | 0 | 10 |
| | 250 | 100 | 100 | 40 | 85 | 100 | — | 100 | 60 | 60 | 95 | 15 | 5 | 50 |
| 4-47 | 63 | 70 | 100 | 0 | 30 | 100 | — | 80 | 60 | — | 70 | 0 | 30 | 20 |
| | 250 | 100 | 100 | 70 | 100 | 100 | — | 100 | 98 | — | 100 | 15 | 90 | 70 |
| 4-48 | 63 | 100 | 100 | 40 | 80 | 100 | — | 100 | 50 | 60 | 100 | 40 | 30 | 20 |
| | 250 | 100 | 100 | 100 | 100 | 100 | — | 100 | 70 | 90 | 100 | 35 | 50 | 70 |
| 4-49 | 63 | 100 | 95 | 30 | 40 | 100 | 80 | 70 | 10 | 50 | 70 | 10 | 0 | 30 |
| | 250 | 100 | 100 | 60 | 100 | 100 | 60 | 100 | 75 | 90 | 100 | 10 | 15 | 25 |
| 4-50 | 63 | 20 | 20 | 0 | 0 | 40 | 0 | 0 | 0 | 0 | 0 | 0 | 0 | 0 |
| | 250 | 100 | 100 | 0 | 30 | 100 | 0 | 10 | 0 | 0 | 30 | 20 | 0 | 10 |
| 4-53 | 63 | 100 | 100 | 20 | 30 | 100 | — | 80 | 10 | 30 | 40 | 20 | 0 | 10 |
| | 250 | 100 | 100 | 60 | 80 | 100 | — | 100 | 85 | 85 | 100 | 90 | 25 | 50 |
| 4-54 | 63 | 100 | 100 | 30 | 30 | 90 | — | 90 | 50 | 30 | 60 | 0 | 0 | 10 |
| | 250 | 100 | 90 | 80 | 70 | 100 | — | 100 | 85 | 80 | 100 | 10 | 5 | 60 |
| 4-55 | 63 | 30 | 80 | 0 | 20 | 90 | — | 40 | 0 | 0 | 0 | 0 | 0 | 0 |
| | 250 | 90 | 100 | 30 | 70 | 100 | — | 90 | 30 | 60 | 70 | 70 | 30 | 60 |
| 4-56 | 63 | 100 | 100 | 10 | 40 | 100 | — | 90 | 50 | 50 | 50 | 0 | 35 | 50 |
| | 250 | 100 | 100 | 100 | 100 | 100 | — | 95 | 80 | 90 | 95 | 50 | 80 | 90 |
| 4-57 | 63 | 95 | 100 | 10 | 50 | 100 | — | 80 | 20 | 10 | 60 | 20 | 0 | 20 |
| | 250 | 100 | 100 | 100 | | 100 | — | 100 | 75 | 70 | 95 | 50 | 45 | 70 |
| 4-58 | 63 | 100 | 100 | 70 | 30 | 100 | — | 80 | 30 | 20 | 30 | 10 | 0 | 30 |
| | 250 | 100 | 100 | 100 | 100 | 100 | — | 100 | 70 | 60 | 100 | 50 | 25 | 70 |
| 4-59 | 63 | 100 | 100 | 20 | 95 | 100 | — | 30 | 10 | 40 | 40 | 50 | 5 | 0 |
| | 250 | 100 | 100 | 90 | 100 | 100 | — | 90 | 90 | 95 | 100 | 90 | 80 | 70 |
| 4-60 | 63 | 100 | 100 | 90 | 50 | 100 | — | 90 | 40 | 30 | 100 | 10 | 0 | 60 |
| | 250 | 100 | 100 | 100 | 100 | 100 | — | 100 | 70 | 50 | 100 | 60 | 30 | 70 |
| 4-61 | 63 | 100 | 60 | 40 | 30 | 100 | — | 80 | 30 | 20 | 50 | 0 | 0 | 0 |
| | 250 | 100 | 70 | 30 | 60 | 100 | — | 75 | 50 | 50 | 90 | 0 | 0 | 50 |
| 4-62 | 63 | 100 | 100 | 50 | 60 | 100 | — | 80 | 10 | 10 | 50 | 10 | 0 | 10 |
| | 250 | 100 | 100 | 100 | 30 | 100 | — | 100 | 60 | 50 | 90 | 10 | 10 | 70 |
| 4-63 | 63 | 100 | 100 | 40 | 40 | 100 | — | 70 | 30 | 30 | 70 | 10 | 0 | 40 |
| | 250 | 100 | 100 | 100 | 100 | 100 | — | 100 | 70 | 50 | 95 | 75 | 35 | 90 |
| 4-64 | 63 | 100 | 100 | 20 | 40 | 100 | — | 100 | 30 | 40 | 100 | 30 | 0 | 30 |
| | 250 | 100 | 100 | 90 | 70 | 100 | — | 100 | 70 | 80 | 100 | 80 | 45 | 80 |
| 4-65 | 63 | 100 | 100 | 80 | 90 | 100 | — | 100 | 80 | — | 100 | 10 | 55 | 65 |
| | 250 | 100 | 100 | 90 | 100 | 100 | — | 100 | 90 | — | 100 | 70 | 75 | 90 |
| 4-66 | 63 | 100 | 100 | 30 | 60 | 100 | — | 70 | 30 | — | 80 | 30 | 0 | 20 |
| | 250 | 100 | 100 | 70 | 90 | 100 | — | 100 | 90 | — | 100 | 95 | 50 | 65 |
| 4-67 | 63 | 100 | 100 | 40 | 80 | 100 | — | 90 | 40 | — | 100 | 10 | 5 | 60 |
| | 250 | 100 | 100 | 60 | 90 | 100 | — | 100 | 80 | — | 100 | 10 | 15 | 40 |
| 4-68 | 63 | 100 | 100 | 40 | 40 | 100 | — | 100 | 60 | — | 100 | 35 | 45 | 50 |
| | 250 | 100 | 100 | 100 | 100 | 100 | — | 100 | 98 | — | 100 | 80 | 80 | 90 |
| 4-69 | 63 | 30 | 80 | 0 | 0 | 70 | — | 95 | 30 | — | 100 | 0 | 0 | 10 |
| | 250 | 80 | 90 | 50 | 40 | 90 | — | 100 | 70 | — | 100 | 10 | 0 | 30 |
| 4-70 | 63 | 100 | 100 | 50 | 100 | 100 | — | 60 | 40 | — | 60 | 80 | 90 | 40 |
| | 250 | 100 | 100 | 80 | 100 | 100 | — | 100 | 95 | — | 100 | 95 | 95 | 70 |
| 5-3 | 63 | 60 | 100 | 0 | 0 | 100 | — | 70 | 0 | 0 | 30 | 0 | 0 | 20 |
| | 250 | 100 | 100 | 30 | 10 | 100 | — | 100 | 20 | 95 | 100 | 10 | 0 | 20 |
| 5-15 | 63 | 0 | 0 | 0 | 0 | 0 | — | 0 | 0 | 0 | 0 | 0 | 0 | 0 |
| | 250 | 0 | 0 | 0 | 0 | 0 | — | 0 | 0 | 0 | 0 | 0 | 0 | 0 |
| 5-16 | 63 | 0 | 0 | 0 | 0 | 0 | — | 0 | 0 | 0 | 0 | 0 | 0 | 0 |
| | 250 | 0 | 0 | 0 | 0 | 20 | — | 0 | 0 | 0 | 0 | 0 | 0 | 0 |
| 5-17 | 63 | 30 | 40 | 0 | 0 | 70 | — | 95 | 0 | 40 | 30 | 0 | 0 | 20 |
| | 250 | 100 | 100 | 30 | 0 | 100 | — | 100 | 40 | 70 | 50 | 0 | 0 | 20 |
| 5-18 | 63 | 30 | 40 | 0 | 0 | 70 | — | 95 | 0 | 40 | 30 | 0 | 0 | 20 |
| | 250 | 0 | 70 | 10 | 0 | 95 | — | 90 | 0 | 30 | 20 | 0 | 0 | 10 |
| 5-26 | 63 | 100 | 70 | 10 | 0 | 100 | — | 60 | 20 | 0 | 30 | 0 | 0 | 15 |
| | 250 | 100 | 100 | 80 | 40 | 100 | — | 90 | 30 | 30 | 80 | 10 | 0 | 40 |
| 5-28 | 63 | 100 | 100 | 100 | 60 | 100 | — | 50 | 30 | 20 | 30 | 15 | 10 | 30 |
| | 250 | 100 | 100 | 100 | 100 | 100 | — | 85 | 60 | 30 | 90 | 20 | 20 | 60 |
| 6-13 | 63 | 60 | 10 | 0 | 0 | 40 | — | 80 | 10 | — | 80 | 0 | 0 | 0 |
| | 250 | 100 | 40 | 0 | 0 | 100 | — | 100 | 40 | — | 90 | 0 | 0 | 10 |
| 6-14 | 63 | 90 | 100 | 40 | 60 | 100 | — | 100 | 100 | — | 100 | 70 | 90 | 90 |
| | 250 | 100 | 100 | 60 | 100 | 100 | — | 100 | 100 | — | 100 | 90 | 100 | 100 |
| 6-15 | 63 | 100 | 100 | 70 | 70 | 100 | — | 95 | 50 | 50 | 80 | 40 | 0 | 20 |
| | 250 | 100 | 100 | 80 | 40 | 100 | — | 100 | 80 | 100 | 100 | 30 | 5 | 60 |
| 6-16 | 63 | 30 | 10 | 0 | 0 | 100 | — | 60 | 10 | — | 30 | 0 | 0 | 0 |
| | 250 | 50 | 20 | 0 | 0 | 100 | — | 90 | 30 | — | 90 | 0 | 0 | 20 |
| 6-17 | 63 | 90 | 30 | 0 | 0 | 100 | — | 70 | 10 | — | 30 | 0 | 0 | 0 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | 250 | 100 | 95 | 20 | 30 | 100 | — | 99 | 90 | — | 99 | 0 | 0 | 40 |
| 6-19 | 63 | 30 | 20 | 0 | 0 | 70 | — | 0 | 0 | 0 | 0 | 0 | 0 | 0 |
| | 250 | 70 | 50 | 0 | 0 | 90 | — | 10 | 0 | 0 | 0 | 0 | 0 | 0 |
| 6-20 | 63 | 10 | 0 | 0 | 0 | 50 | — | 0 | 0 | 0 | 0 | 0 | 0 | 0 |
| | 250 | 0 | 0 | 0 | 0 | 30 | — | 0 | 0 | 0 | 0 | 0 | 0 | 0 |
| 6-22 | 63 | 30 | 20 | 0 | 0 | 40 | — | 10 | 0 | 0 | 0 | 0 | 0 | 0 |
| | 250 | 100 | 100 | 60 | 0 | 100 | — | 50 | 0 | 10 | 20 | 0 | 0 | 10 |
| 6-23 | 63 | 50 | 0 | 0 | 0 | 30 | — | 0 | 0 | — | 0 | 0 | 0 | 0 |
| | 250 | 100 | 50 | 10 | 20 | 100 | — | 60 | 0 | — | 10 | 0 | 0 | 0 |
| 6-24 | 63 | 20 | 0 | 0 | 0 | 30 | — | 0 | 0 | — | 0 | 0 | 0 | 0 |
| | 250 | 100 | 70 | 0 | 0 | 90 | — | 40 | 0 | — | 20 | 10 | 0 | 10 |
| 7-2 | 63 | 100 | 95 | 30 | 60 | 100 | 80 | 95 | 70 | 95 | 100 | 50 | 20 | 20 |
| | 250 | 100 | 100 | 30 | 80 | 100 | 100 | 100 | 100 | 100 | 100 | 10 | 40 | 30 |
| 7-14 | 63 | 40 | 40 | 10 | 30 | 70 | — | 0 | 0 | — | 60 | 15 | 0 | 5 |
| | 250 | 80 | 60 | 50 | 20 | 100 | — | 70 | 40 | — | 70 | 10 | 0 | 20 |
| 7-15 | 63 | 80 | 40 | 0 | 0 | 100 | — | 0 | 0 | 0 | 0 | 0 | 0 | 0 |
| | 250 | 100 | 90 | 10 | 50 | 100 | — | 60 | 10 | 20 | 60 | 0 | 0 | 10 |
| 8-2 | 63 | 90 | 80 | 0 | 0 | 80 | — | 20 | 0 | 0 | 0 | 0 | 0 | 20 |
| | 250 | 100 | 100 | 90 | 0 | 100 | — | 100 | 40 | 20 | 70 | 10 | 20 | 30 |
| 8-3 | 63 | 99 | 98 | 30 | 30 | 99 | — | 95 | 0 | 20 | 30 | 0 | 10 | 0 |
| | 250 | 100 | 100 | 50 | 10 | 100 | — | 98 | 10 | 30 | 60 | 0 | 0 | 0 |
| 8-4 | 63 | 60 | 0 | 0 | 0 | 80 | — | 30 | 0 | 0 | 20 | 0 | 0 | 0 |
| | 250 | 100 | 90 | 0 | 0 | 99 | — | 70 | 0 | 20 | 20 | 0 | 0 | 20 |
| 8-5 | 63 | 40 | 0 | 0 | 0 | 0 | — | 70 | 0 | 0 | 0 | 0 | 0 | 0 |
| | 250 | 95 | 70 | 40 | 0 | 80 | — | 90 | 0 | 20 | 0 | 0 | 0 | 0 |
| 8-7 | 63 | 99 | 100 | 0 | 0 | 95 | — | 95 | 0 | 10 | 50 | 0 | 0 | 0 |
| | 250 | 100 | 100 | 0 | 0 | 100 | — | 99 | 70 | 70 | 80 | 0 | 10 | 0 |
| 8-13 | 63 | 50 | 90 | 0 | 0 | 100 | — | 20 | 0 | 0 | 0 | 0 | 0 | 10 |
| | 125 | 70 | 100 | 0 | 0 | 70 | — | 40 | 30 | 30 | 40 | 0 | 0 | 10 |
| 8-18 | 63 | 60 | 90 | 0 | 0 | 70 | — | 50 | 10 | 0 | 10 | 0 | 0 | 10 |
| | 250 | 100 | 100 | 60 | 30 | 100 | — | 100 | 90 | 50 | 80 | 0 | 10 | 30 |
| 8-30 | 63 | 100 | 70 | 20 | 20 | 100 | — | 20 | 0 | 0 | 30 | 0 | 0 | 5 |
| | 250 | 100 | 90 | 20 | 10 | 100 | — | 70 | 20 | 30 | 50 | 0 | 5 | 10 |
| 8-31 | 63 | 90 | 60 | 0 | 0 | 100 | — | 10 | 0 | 0 | 0 | 0 | 0 | 0 |
| | 250 | 100 | 95 | 20 | 30 | 100 | — | 10 | 0 | 10 | 10 | 0 | 10 | 30 |
| 8-36 | 63 | 100 | 80 | 10 | 10 | 100 | — | 0 | 0 | 0 | 0 | 0 | 0 | 20 |
| | 250 | 100 | 30 | 30 | 20 | 100 | — | 30 | 0 | 0 | 40 | 0 | 0 | 40 |
| 9-4 | 63 | 60 | 90 | 30 | 10 | 30 | — | 0 | 0 | 0 | 0 | 0 | 0 | 0 |
| | 250 | 100 | 100 | 60 | 50 | 80 | — | 70 | 10 | 30 | 60 | 50 | 0 | 10 |
| 9-14 | 63 | 40 | 20 | 0 | 0 | 80 | — | 0 | 0 | 0 | 0 | 0 | 0 | 0 |
| | 250 | 65 | 85 | 0 | 10 | 100 | — | 30 | 40 | 10 | 30 | 0 | 0 | 10 |
| 9-5 | 63 | 100 | 100 | 10 | 70 | 100 | — | 20 | 0 | 0 | 10 | 0 | 0 | 25 |
| | 250 | 100 | 100 | 80 | 100 | 100 | — | 60 | 30 | 20 | 40 | 10 | 10 | 60 |
| 9-16 | 63 | 70 | 100 | 20 | 70 | 100 | — | 39 | 0 | 10 | 10 | 40 | 0 | 80 |
| | 250 | 100 | 100 | 60 | 70 | 100 | — | 70 | 40 | 40 | 10 | 95 | 90 | 90 |
| 9-19 | 63 | 100 | 100 | 0 | 30 | 100 | — | 0 | 0 | 0 | 0 | 0 | 0 | 30 |
| | 250 | 100 | 100 | 20 | 0 | 100 | — | 60 | 0 | 20 | 80 | 20 | 0 | 50 |
| 11-6 | 63 | 100 | 95 | 20 | 0 | 100 | — | 100 | 90 | 0 | 100 | 20 | 0 | 0 |
| | 250 | 100 | 100 | 99 | 80 | 100 | — | 100 | 100 | 40 | 100 | 20 | 20 | 50 |
| 11-13 | 63 | 100 | 95 | 0 | 65 | 100 | 30 | 70 | 30 | 0 | 60 | 0 | 0 | 0 |
| | 250 | 10 | 100 | 85 | 80 | 100 | 60 | 100 | 80 | 40 | 100 | 0 | 0 | 15 |
| 12-2 | 63 | 100 | 100 | 99 | 95 | 100 | — | 95 | 40 | 90 | 95 | 90 | 40 | 50 |
| | 250 | 100 | 100 | 100 | 100 | 100 | — | 100 | 99 | 100 | 100 | 100 | 99 | 99 |
| 12-3 | 63 | 95 | 100 | 30 | 0 | 100 | — | 0 | 0 | 0 | 0 | 0 | 0 | 10 |
| | 250 | 100 | 100 | 70 | 90 | 100 | — | 30 | 0 | 0 | 30 | 20 | 0 | 20 |
| 12-5 | 63 | 30 | 70 | 0 | 0 | 90 | — | 0 | 0 | — | 0 | 0 | 0 | 0 |
| | 250 | 100 | 90 | 80 | 20 | 100 | — | 0 | 40 | — | 10 | 0 | 0 | 10 |
| 12-8 | 63 | 100 | 0 | 0 | 0 | 100 | — | 60 | 0 | 10 | 50 | 0 | 0 | 30 |
| | 250 | 100 | 100 | 20 | 40 | 100 | — | 100 | 40 | 40 | 100 | 0 | 0 | 40 |
| 13-3 | 63 | 100 | 0 | 0 | 0 | 90 | — | 10 | 0 | 0 | 0 | 0 | 0 | 0 |
| | 250 | 100 | 20 | 30 | 0 | 100 | — | 40 | 10 | 10 | 30 | 0 | 0 | 0 |
| 13-4 | 63 | 60 | 90 | 0 | 10 | 100 | — | 30 | 0 | 10 | 0 | 0 | 0 | 0 |
| | 250 | 100 | 100 | 50 | 90 | 100 | — | 90 | 30 | 40 | 90 | 35 | 15 | 30 |
| 13-5 | 63 | 30 | 0 | 0 | 0 | 20 | 0 | 30 | 0 | 0 | 0 | 0 | 0 | 0 |
| | 250 | 95 | 0 | 0 | 0 | 50 | 0 | 50 | 0 | 30 | 10 | 0 | 0 | 0 |
| 14-1 | 634 | 100 | 75 | 0 | 30 | 98 | 0 | 15 | 15 | 0 | 40 | 20 | 0 | 15 |
| | 250 | 100 | 100 | 0 | 75 | 100 | 0 | 55 | 30 | 90 | 85 | 60 | 10 | 45 |
| 14-2 | 63 | 100 | 35 | 0 | 50 | 100 | 0 | 20 | 0 | 10 | 0 | 0 | 0 | 0 |
| | 250 | 100 | 100 | 10 | 85 | 100 | 50 | 30 | 0 | 60 | 65 | 10 | 30 | 10 |
| 14-3 | 63 | 100 | 100 | 20 | 0 | 100 | 0 | 40 | 0 | 0 | 30 | 20 | 0 | 0 |
| | 250 | 100 | 100 | 80 | 50 | 100 | 65 | 80 | 40 | 60 | 90 | 90 | 90 | 50 |
| 14-4 | 63 | 90 | 50 | 20 | 0 | 60 | — | 10 | 0 | — | 20 | 0 | 0 | 0 |
| | 250 | 100 | 80 | 20 | 70 | 100 | — | 40 | 0 | — | 95 | 95 | 20 | 15 |
| 14-5 | 63 | 70 | 100 | 0 | 20 | 70 | — | 10 | 0 | — | 20 | 25 | 0 | 0 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | 250 | 100 | 100 | 10 | 30 | 100 | — | 60 | 40 | — | 95 | 20 | 70 | 20 |
| 14-6 | 63 | 100 | 30 | 30 | 10 | 20 | — | 10 | 0 | 0 | 90 | 30 | 0 | 15 |
| | 250 | 100 | 100 | 30 | 20 | 100 | — | 100 | 70 | 30 | 100 | 50 | 5 | 50 |
| 14-7 | 63 | 90 | 100 | 20 | 0 | 40 | 0 | 10 | 0 | 0 | 90 | 0 | 10 | 0 |
| | 250 | 100 | 100 | 0 | 0 | 85 | 50 | 90 | 75 | 70 | 100 | 50 | 90 | 40 |
| 14-8 | 63 | 100 | 0 | 0 | 0 | 70 | 0 | 0 | 0 | 0 | 40 | 0 | 0 | 0 |
| | 250 | 99 | 40 | 0 | 0 | 95 | 40 | 0 | 20 | 0 | 100 | 0 | 0 | 0 |
| 14-9 | 63 | 80 | 0 | 0 | 0 | 60 | 0 | 0 | 0 | 0 | 90 | 0 | 0 | 0 |
| | 250 | 100 | 90 | 0 | 0 | 90 | 0 | 20 | 70 | 30 | 100 | 0 | 75 | 5 |
| 14-10 | 63 | 100 | 0 | 0 | 0 | 0 | 50 | 0 | 0 | 0 | 0 | 0 | 0 | 20 |
| | 250 | 100 | 90 | 0 | 70 | 100 | 100 | 0 | 0 | 30 | 90 | 50 | 40 | 30 |
| 14-11 | 63 | 100 | 50 | 0 | 30 | 70 | 0 | 0 | 0 | 0 | 50 | 0 | 0 | 0 |
| | 250 | 100 | 100 | 0 | 50 | 100 | 100 | 50 | 0 | 0 | 100 | 0 | 0 | 0 |
| 14-12 | 63 | 60 | 0 | 0 | 0 | 50 | 0 | 0 | 0 | 0 | 0 | 0 | 0 | 0 |
| | 250 | 100 | 20 | 0 | 0 | 60 | 0 | 0 | 0 | 0 | 100 | 20 | 0 | 0 |
| 14-13 | 63 | 80 | 10 | 0 | 0 | 0 | 0 | 0 | 0 | 0 | 30 | 0 | 0 | 0 |
| | 250 | 100 | 80 | 0 | 0 | 70 | 30 | 10 | 0 | 0 | 100 | 10 | 5 | 0 |
| 14-14 | 63 | 100 | 0 | 0 | 0 | 60 | — | 0 | 0 | 0 | 50 | 20 | 0 | 0 |
| | 250 | 100 | 20 | 0 | 20 | 100 | — | 50 | 10 | 0 | 90 | 30 | 0 | 20 |
| 14-15 | 63 | 100 | 50 | 0 | 0 | 20 | — | 0 | 0 | 0 | 70 | 0 | 0 | 0 |
| | 250 | 100 | 100 | 40 | 20 | 95 | — | 30 | 80 | 0 | 100 | 20 | 0 | 0 |
| 14-16 | 63 | 100 | 0 | 0 | 0 | 100 | — | 0 | 0 | 0 | 50 | 0 | 0 | 0 |
| | 250 | 100 | 90 | 0 | 0 | 100 | — | 0 | 0 | 0 | 100 | 0 | 0 | 0 |
| 14-17 | 63 | 100 | 50 | 0 | 0 | 90 | — | 0 | 0 | 0 | 90 | 0 | 0 | 0 |
| | 250 | 100 | 100 | 0 | 30 | 100 | — | 80 | 50 | 30 | 100 | 0 | 40 | 0 |
| 14-18 | 63 | 100 | 40 | 0 | 0 | 100 | 0 | 0 | 0 | 0 | 0 | 0 | 0 | 0 |
| | 250 | 100 | 70 | 20 | 20 | 100 | 70 | 20 | 20 | 10 | 90 | 0 | 0 | 10 |
| 14-19 | 63 | 0 | 0 | 0 | 0 | 0 | — | 0 | 0 | 0 | 0 | 0 | 0 | 0 |
| | 250 | 90 | 50 | 0 | 0 | 80 | — | 0 | 0 | 0 | 80 | 50 | 0 | 0 |
| 14-20 | 63 | 50 | 0 | 0 | 0 | 0 | — | 0 | 0 | 0 | 0 | 0 | 0 | 0 |
| | 250 | 100 | 90 | 0 | 0 | 80 | — | 30 | 40 | 20 | 90 | 20 | 50 | 0 |
| 14-21 | 63 | 60 | 40 | 0 | 0 | 20 | 0 | 0 | 0 | 0 | 0 | 0 | 0 | 0 |
| | 250 | 95 | 100 | 10 | 0 | 75 | 40 | 0 | 20 | 35 | 70 | 70 | 70 | 20 |
| 14-22 | 63 | 100 | 0 | 0 | 0 | 20 | — | 0 | 0 | 0 | 0 | 0 | 0 | 0 |
| | 250 | 100 | 70 | 0 | 0 | 90 | — | 0 | 0 | 0 | 50 | 30 | 0 | 10 |
| 14-23 | 63 | 95 | 0 | 0 | 0 | 0 | — | 0 | 10 | 0 | 30 | 0 | 0 | 0 |
| | 250 | 100 | 80 | 0 | 30 | 90 | — | 40 | 30 | 80 | 90 | 0 | 0 | 0 |
| 14-24 | 63 | 50 | 0 | 0 | 0 | 0 | — | 0 | 0 | 0 | 20 | 0 | 0 | 0 |
| | 250 | 100 | 80 | 30 | 0 | 50 | — | 0 | 0 | 0 | 80 | 10 | 0 | 20 |
| 14-25 | 63 | 100 | 100 | 50 | 70 | 100 | — | 90 | 80 | 80 | 70 | 80 | 95 | 90 |
| | 250 | 100 | 100 | 100 | 100 | 100 | — | 100 | 100 | 100 | 100 | 100 | 110 | 100 |
| 14-26 | 63 | 100 | 80 | 0 | 0 | 70 | — | 0 | 0 | 0 | 50 | 0 | 0 | 0 |
| | 250 | 100 | 100 | 20 | 0 | 100 | — | 99 | 95 | 70 | 95 | 30 | 50 | 80 |
| 14-27 | 63 | 50 | 0 | 0 | 0 | 0 | — | 0 | 0 | 0 | 0 | 0 | 0 | 0 |
| | 250 | 100 | 30 | 0 | 0 | 90 | — | 0 | 0 | 0 | 90 | 0 | 0 | 0 |
| 14-28 | 63 | 90 | 0 | 0 | 0 | 0 | — | 0 | 0 | 0 | 0 | 0 | 0 | 0 |
| | 250 | 100 | 80 | 0 | 0 | 95 | — | 0 | 20 | 40 | 100 | 40 | 20 | 0 |
| 14-29 | 63 | 20 | 0 | 0 | 0 | 0 | — | 0 | 0 | 0 | 0 | 0 | 0 | 0 |
| | 250 | 95 | 80 | 0 | 0 | 50 | — | 0 | 0 | 0 | 50 | 20 | 10 | 20 |
| 14-30 | 63 | 70 | 0 | 0 | 0 | 0 | — | 0 | 0 | 0 | 0 | 0 | 0 | 0 |
| | 250 | 100 | 50 | 0 | 0 | 80 | — | 0 | 0 | 0 | 90 | 0 | 0 | 0 |
| 14-31 | 63 | 70 | 0 | 0 | 0 | 40 | — | 0 | 0 | 0 | 0 | 0 | 0 | 0 |
| | 250 | 100 | 70 | 0 | 50 | 50 | — | 0 | 0 | 0 | 90 | 20 | 30 | 0 |
| 14-32 | 63 | 100 | 10 | 0 | 0 | 80 | — | 0 | 0 | 0 | 20 | 0 | 0 | 0 |
| | 250 | 100 | 50 | 30 | 0 | 100 | — | 40 | 30 | 20 | 100 | 20 | 0 | 10 |
| 14-33 | 63 | 100 | 20 | 0 | 0 | 0 | — | 0 | 0 | 0 | 0 | 0 | 10 | 0 |
| | 250 | 100 | 90 | 0 | 0 | 90 | — | 50 | 0 | 30 | 99 | 20 | 20 | 10 |
| 14-34 | 63 | 100 | 100 | 20 | 10 | 95 | — | 30 | 20 | 0 | 90 | 30 | 0 | 20 |
| | 250 | 100 | 100 | 10 | 10 | 100 | — | 100 | 90 | 30 | 100 | 100 | 25 | 90 |
| 14-35 | 63 | 100 | 100 | 0 | 0 | 50 | — | 80 | 0 | 0 | 50 | 0 | 0 | 0 |
| | 250 | 100 | 100 | 0 | 0 | 100 | — | 100 | 99 | 50 | 95 | 20 | 25 | 10 |
| 14-36 | 63 | 75 | 100 | 0 | 0 | 75 | 10 | 10 | 0 | 0 | 30 | 0 | 0 | 10 |
| | 250 | 100 | 100 | 0 | 0 | 100 | 80 | 95 | 90 | 30 | 95 | 40 | 10 | 70 |
| 14-37 | 63 | 100 | 90 | 0 | 0 | 100 | — | 0 | 0 | 0 | 0 | 0 | 0 | 0 |
| | 250 | 100 | 100 | 0 | 0 | 100 | — | 95 | 99 | 0 | 100 | 0 | 0 | 80 |
| 14-38 | 63 | 99 | 40 | 0 | 0 | 90 | — | 0 | 0 | 0 | 0 | 0 | 0 | 0 |
| | 250 | 100 | 100 | 0 | 0 | 100 | — | 80 | 70 | 0 | 90 | 0 | 0 | 30 |
| 14-39 | 63 | 100 | 100 | 0 | 0 | 100 | — | 70 | 10 | 0 | 95 | 0 | 0 | 0 |
| | 250 | 100 | 100 | 20 | 0 | 100 | — | 100 | 95 | 60 | 100 | 0 | 0 | 80 |
| 14-40 | 63 | 100 | 100 | 0 | 0 | 95 | 30 | 50 | 10 | 0 | 60 | 0 | 0 | 20 |
| | 250 | 100 | 100 | 0 | 0 | 100 | 90 | 100 | 80 | 40 | 100 | 20 | 0 | 60 |
| 14-41 | 63 | 100 | 90 | 0 | 0 | 100 | — | 30 | 0 | 0 | 50 | 0 | 0 | 0 |
| | 250 | 100 | 100 | 0 | 40 | 100 | — | 100 | 80 | 0 | 100 | 50 | 0 | 50 |
| 14-42 | 63 | 95 | 80 | 0 | 0 | 90 | 0 | 30 | 0 | 0 | 0 | 0 | 0 | 10 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | 250 | 100 | 95 | 0 | 30 | 100 | 100 | 80 | 20 | 0 | 50 | 95 | 20 | 30 |
| 14-43 | 63 | 100 | 90 | 0 | 0 | 100 | 0 | 30 | 0 | 20 | 80 | 0 | 0 | 10 |
| | 250 | 100 | 100 | 0 | 0 | 100 | 100 | 95 | 80 | 30 | 100 | 70 | 20 | 40 |
| 14-44 | 63 | 70 | 80 | 0 | 0 | 70 | — | 0 | 0 | 0 | 0 | 0 | 0 | 0 |
| | 250 | 100 | 100 | 0 | 0 | 100 | | 70 | 50 | 0 | 90 | 100 | 0 | 50 |
| 14-45 | 63 | 100 | 100 | 0 | 0 | 95 | — | 0 | 0 | 0 | 30 | 0 | 0 | 10 |
| | 250 | 100 | 100 | 0 | 0 | 100 | — | 95 | 80 | 50 | 99 | 80 | 10 | 80 |
| 14-46 | 63 | 60 | 80 | 0 | 0 | 0 | 50 | 0 | 0 | 0 | 0 | 0 | 0 | 0 |
| | 250 | 95 | 100 | 0 | 0 | 90 | 100 | 0 | 0 | 0 | 0 | 30 | 0 | 30 |
| 14-47 | 63 | 100 | 100 | 0 | 0 | 100 | — | 0 | 0 | 0 | 30 | 0 | 0 | 0 |
| | 250 | 100 | 100 | 0 | 0 | 100 | — | 99 | 95 | 20 | 100 | 100 | 0 | 70 |
| 14-48 | 63 | 90 | 90 | 0 | 0 | 50 | 0 | 0 | 0 | 0 | 0 | 0 | 0 | 30 |
| | 250 | 100 | 100 | 0 | 0 | 100 | 80 | 50 | 50 | 0 | 70 | 95 | 40 | 70 |
| 14-49 | 63 | 100 | 100 | 0 | 50 | 100 | — | 50 | 0 | 20 | 50 | 0 | 10 | 40 |
| | 250 | 100 | 100 | 70 | 90 | 100 | — | 100 | 100 | 90 | 100 | 100 | 95 | 95 |
| 14-50 | 63 | 100 | 0 | 0 | 10 | 100 | — | 0 | 0 | 50 | 0 | 0 | 10 | 0 |
| | 250 | 100 | 50 | 30 | 70 | 100 | — | 50 | 30 | 95 | 40 | 0 | 90 | 0 |
| 14-51 | 63 | 100 | 10 | 0 | 0 | 90 | — | 0 | 0 | 0 | 0 | 0 | 0 | 0 |
| | 250 | 100 | 100 | 0 | 50 | 100 | — | 0 | 0 | 0 | 0 | 0 | 0 | 0 |
| 14-52 | 63 | 40 | 70 | 0 | 0 | 80 | — | 0 | 0 | 0 | 0 | 0 | 0 | 0 |
| | 250 | 90 | 100 | 0 | 30 | 100 | — | 0 | 0 | 0 | 0 | 0 | 0 | 0 |
| 14-54 | 63 | 20 | 0 | 0 | 0 | 10 | 0 | 20 | 0 | 0 | 0 | 0 | 0 | 0 |
| | 250 | 85 | 70 | 10 | 40 | 100 | 0 | 80 | 0 | 30 | 30 | 0 | 0 | 15 |
| 14-55 | 63 | 0 | 10 | 0 | 0 | 0 | 0 | 0 | 0 | 0 | 0 | 0 | 0 | 0 |
| | 250 | — | — | — | — | — | — | — | — | — | — | — | — | — |
| 14-56 | 63 | 100 | 30 | 0 | 0 | 80 | — | 20 | 0 | 0 | 30 | 0 | 0 | 10 |
| | 250 | 100 | 60 | 10 | 0 | 100 | — | 70 | 0 | 30 | 40 | 0 | 0 | 10 |
| 14-57 | 63 | 0 | 0 | 0 | 0 | 0 | — | 0 | 0 | 0 | 0 | 0 | 0 | 0 |
| | 250 | 0 | 0 | 0 | 0 | 0 | — | 0 | 0 | 0 | 20 | 0 | 0 | 0 |
| 14-59 | 63 | 0 | 0 | 0 | 0 | 40 | — | 0 | 0 | 0 | 0 | 0 | 0 | 0 |
| | 250 | 0 | 0 | 0 | 0 | 0 | — | 0 | 0 | 0 | 0 | 0 | 0 | 0 |
| 14-60 | 63 | 100 | 100 | 0 | 90 | 100 | — | 10 | 0 | 0 | 0 | 0 | 0 | 0 |
| | 250 | 100 | 100 | 0 | 100 | 100 | — | 60 | 20 | 10 | 30 | 10 | 0 | 20 |
| 14-61 | 63 | 30 | 0 | 0 | 0 | 0 | 0 | 0 | 0 | 0 | 0 | 0 | 0 | 0 |
| | 250 | 95 | 40 | 0 | 20 | 80 | 0 | 60 | 0 | 20 | 40 | 0 | 0 | 0 |
| 14-62 | 63 | 40 | 15 | 0 | 0 | 20 | 0 | 0 | 0 | 0 | 0 | 0 | 0 | 0 |
| | 250 | 100 | 95 | 0 | 0 | 80 | 30 | 60 | 20 | 60 | 50 | 0 | 5 | 15 |
| 14-63 | 63 | 99 | 70 | 0 | 0 | 80 | 0 | 30 | 0 | 0 | 70 | 0 | 0 | 0 |
| | 250 | 100 | 100 | 50 | 0 | 99 | 60 | 99 | 50 | 20 | 100 | 0 | 0 | 0 |
| 14-64 | 63 | 100 | 90 | 0 | 0 | 60 | 20 | 0 | 0 | 0 | 50 | 0 | 0 | 0 |
| | 250 | 100 | 100 | 0 | 0 | 100 | 60 | 100 | 95 | 20 | 100 | 0 | 0 | 10 |
| 14-65 | 63 | 100 | 90 | 40 | 40 | 60 | 100 | 20 | 0 | 20 | 90 | 20 | 0 | 0 |
| | 250 | 100 | 100 | 80 | 70 | 100 | 70 | 90 | 80 | 20 | 100 | 40 | 0 | 0 |
| 14-66 | 63 | 100 | 90 | 0 | 0 | 90 | 0 | 20 | 50 | 0 | 90 | 0 | 0 | 0 |
| | 250 | 100 | 100 | 0 | 60 | 100 | 0 | 100 | 100 | 30 | 100 | 0 | 0 | 20 |
| 15-1 | 63 | 100 | 100 | 100 | 100 | 100 | — | 100 | 91 | — | 100 | 95 | 95 | 90 |
| | 250 | 100 | 100 | 100 | 100 | 100 | — | 100 | 100 | — | 100 | 100 | 100 | 100 |
| 15-2 | 63 | 100 | 100 | 100 | 10 | 100 | — | 100 | 100 | 100 | 100 | 90 | 80 | 99 |
| | 250 | 100 | 100 | 100 | 100 | 100 | — | 100 | 100 | 100 | 100 | 100 | 100 | 100 |
| 15-3 | 63 | 100 | 100 | 100 | 100 | 100 | 100 | 100 | 100 | 100 | 100 | 100 | 90 | 95 |
| | 250 | 100 | 100 | 100 | 100 | 100 | 100 | 100 | 100 | 100 | 100 | 100 | 100 | 100 |
| 15-4 | 63 | 100 | 100 | 100 | 100 | 100 | — | 100 | 80 | — | 100 | 90 | 90 | 80 |
| | 250 | 100 | 100 | 100 | 100 | 100 | — | 100 | 100 | — | 100 | 100 | 100 | 100 |
| 15-5 | 63 | 100 | 100 | 100 | 100 | 100 | — | 100 | 70 | — | 100 | 90 | 80 | 70 |
| | 250 | 100 | 100 | 100 | 100 | 100 | — | 100 | 99 | — | 100 | 99 | 99 | 99 |
| 15-6 | 63 | 100 | 100 | 90 | 100 | 100 | — | 99 | 99 | 100 | 100 | 95 | 95 | 98 |
| | 250 | 100 | 100 | 100 | 100 | 100 | — | 100 | 100 | 100 | 100 | 95 | 100 | 100 |
| 15-7 | 63 | 100 | 100 | 100 | 95 | 100 | — | 100 | 80 | 95 | 90 | 95 | 85 | 90 |
| | 250 | 100 | 100 | 100 | 100 | 100 | — | 100 | 100 | 100 | 100 | 100 | 100 | 100 |
| 15-8 | 63 | 60 | 40 | 20 | 0 | 60 | — | 20 | 0 | — | 30 | 10 | 0 | 15 |
| | 250 | 100 | 100 | 80 | 70 | 100 | — | 0 | 40 | — | 100 | 80 | 90 | 90 |
| 15-9 | 63 | 100 | 100 | 90 | 99 | 100 | — | 100 | 99 | 100 | 90 | 100 | 85 | 95 |
| | 250 | 100 | 100 | 100 | 100 | 100 | — | 100 | 100 | 100 | 100 | 100 | 98 | 100 |
| 15-10 | 63 | 100 | 100 | 80 | 100 | 100 | 100 | 100 | 99 | 100 | 100 | 100 | 75 | 80 |
| | 250 | 100 | 100 | 100 | 100 | 100 | 100 | 100 | 100 | 100 | 100 | 100 | 100 | 100 |
| 15-11 | 63 | 100 | 100 | 100 | 100 | 100 | — | 100 | 100 | 100 | 100 | 99 | 100 | 100 |
| | 250 | 100 | 100 | 100 | 100 | 100 | — | 100 | 100 | 100 | 100 | 100 | 100 | 100 |
| 15-12 | 63 | 100 | 100 | 100 | 100 | 100 | — | 100 | 100 | 100 | 100 | 99 | 100 | 99 |
| | 250 | 100 | 100 | 100 | 100 | 100 | — | 100 | 100 | 100 | 100 | 100 | 100 | 100 |
| 15-13 | 46 | 100 | 100 | 100 | 100 | 100 | — | 100 | 99 | 99 | 100 | 60 | 35 | 90 |
| | 185 | 100 | 100 | 100 | 100 | 100 | — | 100 | 100 | 100 | 100 | 100 | 100 | 100 |
| 15-14 | 63 | 100 | 100 | 90 | 100 | 100 | — | 100 | 100 | 100 | 100 | 99 | 40 | 99 |
| | 250 | 100 | 100 | 100 | 100 | 100 | — | 100 | 100 | 100 | 100 | 100 | 99 | 100 |
| 15-15 | 63 | 100 | 100 | 100 | 100 | 100 | — | 100 | 100 | 100 | 100 | 100 | 95 | 95 |

TABLE XX-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | 250 | 100 | 100 | 100 | 100 | 100 | — | 100 | 100 | 100 | 100 | 100 | 100 | 100 |
| 15-16 | 63 | 100 | 100 | 90 | 90 | 100 | — | 100 | 80 | 100 | 100 | 90 | 65 | 90 |
| | 250 | 100 | 100 | 100 | 100 | 100 | — | 100 | 100 | 100 | 100 | 100 | 100 | 100 |
| 15-17 | 63 | 100 | 100 | 100 | 100 | 100 | — | 100 | 100 | 100 | 100 | 100 | 80 | 100 |
| | 250 | 100 | 100 | 100 | 100 | 100 | — | 100 | 100 | 100 | 100 | 100 | 95 | 100 |
| 15-18 | 63 | 100 | 100 | 100 | 90 | 100 | — | 95 | 75 | 75 | 100 | 75 | 80 | 90 |
| | 250 | 100 | 100 | 100 | 100 | 100 | — | 100 | 100 | 100 | 100 | 100 | 95 | 99 |
| 15-19 | 63 | 100 | 100 | 100 | 100 | 100 | — | 100 | 100 | 100 | 100 | 95 | 80 | 90 |
| | 250 | 100 | 100 | 100 | 100 | 100 | — | 100 | 100 | 100 | 100 | 100 | 100 | 100 |
| 15-20 | 63 | 100 | 100 | 60 | 80 | 100 | — | 100 | 50 | — | 100 | 80 | 65 | 70 |
| | 250 | 100 | 100 | 100 | 80 | 100 | — | 100 | 100 | — | 100 | 95 | 95 | 100 |
| 15-21 | 63 | 100 | 100 | 100 | 100 | 100 | — | 100 | 99 | 100 | 100 | 100 | 95 | 99 |
| | 250 | 100 | 100 | 100 | 100 | 100 | — | 100 | 100 | 100 | 100 | 100 | 100 | 100 |
| 15-22 | 63 | 100 | 100 | 100 | 50 | 100 | — | 90 | 60 | — | 100 | 40 | 25 | 30 |
| | 250 | 100 | 100 | 100 | 100 | 100 | — | 100 | 100 | — | 100 | 90 | 95 | 99 |
| 16-2 | 63 | 40 | 75 | 0 | 10 | 80 | — | 10 | 0 | 0 | 0 | 0 | 0 | 0 |
| | 250 | 100 | 100 | 60 | 50 | 100 | — | 60 | 10 | 30 | 50 | 15 | 0 | 0 |
| 16-6 | 63 | 70 | 90 | 50 | 50 | 90 | — | 0 | 0 | 0 | 0 | 20 | 10 | 0 |
| | 250 | 100 | 100 | 70 | 90 | 100 | — | 40 | 50 | 50 | 70 | 60 | 90 | 70 |
| 16-7 | 63 | 0 | 0 | 0 | 0 | 0 | — | 0 | 0 | 0 | 0 | 0 | 0 | 0 |
| | 250 | 50 | 0 | 0 | 0 | 0 | — | 0 | 0 | 0 | 0 | 0 | 0 | 0 |
| 17-1 | 63 | 30 | 95 | 0 | 10 | 90 | — | 50 | 0 | 0 | 20 | 10 | 0 | 10 |
| | 250 | 90 | 100 | 80 | 70 | 100 | — | 80 | 70 | 60 | 80 | 10 | 10 | 30 |
| 17-2 | 63 | 30 | 0 | 0 | 0 | 60 | — | 0 | 0 | 0 | 0 | 0 | 0 | 0 |
| | 250 | 60 | 20 | 0 | 0 | 90 | — | 0 | 0 | 0 | 0 | 0 | 0 | 0 |
| 17-4 | 63 | 30 | 0 | 0 | 0 | 20 | — | 0 | 0 | 0 | 0 | 0 | 0 | 0 |
| | 250 | 100 | 60 | 10 | 10 | 70 | — | 20 | 0 | 0 | 10 | 0 | 0 | 10 |
| 17-5 | 63 | 80 | 60 | 0 | 30 | 90 | — | 0 | 0 | 0 | 0 | 0 | 0 | 0 |
| | 250 | 100 | 100 | 30 | 35 | 100 | — | 50 | 0 | 20 | 60 | 0 | 0 | 10 |

TABLE XXI

Post-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 1-4 | 63 | 30 | 100 | 60 | 100 | 60 | 50 | — | 0 | 0 | 0 | 80 | 0 | 0 |
| | 250 | 95 | 100 | 100 | 100 | 95 | 90 | — | 40 | 70 | 50 | 100 | 20 | 35 |
| 1-5 | 63 | 0 | 10 | 0 | 0 | 0 | 0 | 0 | 0 | 0 | 0 | 10 | 0 | 0 |
| | 250 | 40 | 60 | 30 | 70 | 50 | 30 | 0 | 0 | 0 | 0 | 50 | 5 | 0 |
| 1-9 | 63 | 100 | 100 | 90 | 100 | 100 | 90 | 90 | 70 | 90 | 90 | 100 | 30 | 40 |
| 1-10 | 63 | 10 | 30 | 0 | 20 | 10 | 0 | 0 | 0 | 0 | 0 | 0 | 0 | 0 |
| | 250 | 30 | 90 | 10 | 70 | 50 | 30 | 0 | 0 | 0 | 0 | 40 | 0 | 0 |
| 1-11 | 63 | 40 | 70 | 0 | 40 | 50 | 10 | 0 | 0 | 0 | 0 | 10 | 0 | 0 |
| | 250 | 60 | 100 | 0 | 70 | 95 | 10 | 50 | 0 | 0 | 0 | 30 | 0 | 0 |
| 1-13 | 63 | 100 | 100 | 30 | 100 | 100 | 70 | 30 | 30 | 10 | 0 | 80 | 20 | 30 |
| | 250 | 100 | 100 | 70 | 100 | 100 | 85 | 90 | 70 | 90 | 75 | 100 | 80 | 80 |
| 1-15 | 63 | 0 | 30 | 0 | 0 | 0 | 0 | 0 | 0 | 0 | 0 | 0 | 0 | 0 |
| | 250 | 30 | 50 | 0 | 40 | 20 | 0 | 0 | 0 | 0 | 0 | 15 | 0 | 0 |
| 1-16 | 63 | 30 | 30 | 0 | 20 | 30 | 0 | 0 | 0 | 0 | 0 | 0 | 0 | 0 |
| | 250 | 70 | 50 | 0 | 50 | 60 | 0 | 0 | 0 | 0 | 0 | 10 | 0 | 0 |
| 1-18 | 63 | 70 | 100 | 30 | 80 | 70 | — | 70 | 0 | 50 | 50 | 50 | 0 | 0 |
| | 250 | 100 | 100 | 95 | 100 | 100 | — | 70 | 0 | 50 | 50 | 100 | 0 | 0 |
| 1-19 | 63 | 30 | 100 | 10 | 30 | 30 | — | 20 | 0 | 0 | 0 | 40 | 5 | 25 |
| | 250 | 70 | 100 | 30 | 95 | 90 | — | 95 | 80 | 70 | 10 | 95 | 45 | 80 |
| 1-20 | 63 | 90 | 100 | 0 | 100 | 90 | — | 0 | 30 | 10 | 10 | 100 | 10 | 20 |
| | 250 | 100 | 100 | 50 | 100 | 100 | — | 60 | 80 | 70 | 20 | 100 | 40 | 50 |
| 1-21 | 63 | 95 | 85 | 10 | 70 | 75 | 10 | 10 | 0 | 0 | 0 | 40 | 5 | 10 |
| | 250 | 100 | 100 | 30 | 90 | 95 | 30 | 30 | 0 | 0 | 0 | 40 | 5 | 10 |
| 1-22 | 63 | 60 | 100 | 0 | 40 | 40 | — | 0 | 0 | 0 | 0 | 30 | 5 | 10 |
| | 250 | 80 | 100 | 0 | 90 | 80 | — | 80 | 0 | 10 | 0 | 60 | 15 | 40 |
| 1-30 | 63 | 10 | 30 | 0 | 20 | 0 | 0 | 0 | 0 | 0 | 0 | 0 | 0 | 0 |
| | 250 | 30 | 100 | 30 | 100 | 60 | 70 | 0 | 0 | 0 | 0 | 20 | 10 | 20 |
| 1-31 | 63 | 10 | 20 | 0 | 10 | 0 | 0 | 0 | 0 | 0 | 0 | 0 | 0 | 0 |
| | 250 | 30 | 50 | 0 | 50 | 40 | 0 | 0 | 0 | 0 | 0 | 20 | 0 | 10 |
| 1-32 | 63 | 10 | 30 | 0 | 0 | 0 | 0 | 0 | 0 | 0 | 0 | 0 | 0 | 0 |
| | 250 | 30 | | 0 | 70 | 60 | 30 | 0 | 0 | 0 | 0 | 10 | 0 | 0 |
| 1-37 | 63 | 90 | 100 | 65 | 100 | 95 | — | 20 | 30 | 10 | 10 | 60 | 10 | 25 |
| | 250 | 100 | 100 | 90 | 100 | 100 | — | 80 | 90 | 70 | 70 | 100 | 60 | 60 |
| 1-38 | 63 | 80 | 100 | 50 | 80 | — | — | 10 | 0 | 0 | 10 | 80 | 25 | 35 |

TABLE XXI-continued

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | | Post-emerge Herbicidal Activity | | | | | | | | | | | | |
| | 250 | 100 | 100 | 90 | 100 | — | — | 80 | 80 | 80 | 80 | 100 | 70 | 70 |
| 1-51 | 63 | 70 | 60 | 40 | 40 | 30 | 70 | 0 | 0 | — | 10 | 10 | 10 | 10 |
| | 250 | 70 | 80 | 60 | 95 | 95 | 90 | 30 | 10 | — | 20 | 50 | 20 | 30 |
| 1-53 | 63 | 80 | 100 | 60 | 95 | 50 | — | 0 | 0 | 0 | 0 | 95 | 0 | 10 |
| | 250 | 100 | 100 | 95 | 100 | 100 | — | 80 | 50 | 40 | 50 | 100 | 30 | 60 |
| 1-54 | 63 | 100 | 100 | 90 | 100 | 100 | 100 | 40 | 20 | — | 40 | 99 | 50 | 40 |
| | 250 | 100 | 100 | 100 | 100 | 100 | 100 | 60 | 75 | — | 70 | 100 | 70 | 45 |
| 1-55 | 63 | 10 | 80 | 10 | 30 | 0 | 70 | 0 | 0 | 0 | 0 | 0 | 0 | 0 |
| | 250 | 10 | 90 | 20 | 95 | 20 | 50 | 40 | 0 | 0 | 30 | 20 | 10 | 0 |
| 1-59 | 63 | 95 | 100 | 40 | 100 | 100 | — | 10 | 30 | 10 | 0 | 90 | 45 | 30 |
| | 250 | 100 | 100 | 100 | 100 | 100 | — | 70 | 80 | 50 | 40 | 100 | 80 | 60 |
| 1-60 | 63 | 90 | 100 | 50 | 90 | 99 | — | 0 | 0 | 0 | 0 | 90 | 0 | 10 |
| | 250 | 100 | 100 | 90 | 100 | 100 | — | 10 | 20 | 20 | 50 | 100 | 50 | 40 |
| 1-61 | 63 | 50 | 70 | 60 | 100 | 30 | 70 | 10 | 0 | — | 10 | 20 | 10 | 10 |
| | 250 | 70 | 100 | 70 | 100 | 70 | 85 | 30 | 10 | — | 30 | 80 | 30 | 35 |
| 1-63 | 63 | 10 | 70 | 0 | 95 | 20 | 0 | 0 | 0 | 0 | 0 | 0 | 0 | 10 |
| | 250 | 10 | 100 | 0 | 90 | 50 | 50 | 20 | 30 | 0 | 0 | 80 | 0 | 40 |
| 2-1 | 63 | 50 | 100 | 50 | 100 | 95 | 30 | 0 | 0 | 0 | 0 | 90 | 10 | 30 |
| | 250 | 100 | 100 | 100 | 100 | 100 | 85 | 30 | 10 | 0 | 0 | 100 | 15 | 70 |
| 2-2 | 63 | 90 | 95 | — | 95 | 60 | 0 | 0 | 0 | 0 | 0 | 50 | 0 | 20 |
| | 250 | 100 | 100 | — | 100 | 100 | 70 | 30 | 40 | 50 | 30 | 95 | 0 | 60 |
| 2-3 | 63 | 10 | 80 | 0 | 60 | 30 | — | 0 | 0 | 0 | 0 | 70 | 0 | 0 |
| | 250 | 40 | 100 | 0 | 100 | 30 | — | 0 | 0 | 0 | 0 | 90 | 10 | 40 |
| 2-4 | 63 | 0 | 0 | 0 | 0 | 50 | — | 0 | 0 | 10 | 0 | 30 | 0 | 0 |
| | 250 | 70 | 50 | 0 | 20 | 50 | — | 0 | 0 | 10 | 0 | 30 | 0 | 0 |
| 2-5 | 63 | 20 | 90 | 10 | 50 | 40 | — | 0 | 0 | 0 | 0 | 60 | 5 | 30 |
| | 250 | 40 | 100 | 50 | 90 | 70 | — | 0 | 0 | 30 | 0 | 60 | 10 | 40 |
| 2-6 | 63 | 0 | 0 | 0 | 0 | 0 | — | 0 | 0 | 0 | 0 | 0 | 0 | 0 |
| | 250 | 10 | 70 | 0 | 30 | 30 | — | 0 | 0 | 0 | 0 | 5 | 5 | 0 |
| 2-7 | 63 | 10 | 70 | 0 | 50 | 40 | — | 0 | 0 | 0 | 0 | 70 | 0 | 40 |
| | 250 | 50 | 95 | 30 | 90 | 50 | — | 30 | 0 | 0 | 0 | 90 | 10 | 40 |
| 2-8 | 63 | 0 | 0 | 0 | 0 | 0 | — | 0 | 0 | 0 | 0 | 10 | 0 | 0 |
| | 250 | 20 | 40 | 0 | 50 | 60 | — | 0 | 0 | 0 | 0 | 10 | 0 | 0 |
| 2-10 | 63 | 0 | 95 | 0 | 60 | 50 | 0 | 0 | 0 | 0 | 0 | 20 | 5 | 0 |
| | 250 | 30 | 100 | 10 | 100 | 90 | 50 | 70 | 60 | 20 | 40 | 65 | 0 | 5 |
| 2-11 | 63 | 0 | 80 | — | 50 | 40 | — | 0 | 0 | 0 | 0 | 5 | 5 | 0 |
| | 250 | 30 | 100 | — | 60 | 65 | — | 20 | 0 | 0 | 0 | 15 | 5 | 0 |
| 2-12 | 63 | 0 | 20 | 0 | 0 | 0 | 0 | 0 | 0 | 0 | 0 | 0 | 0 | 0 |
| | 250 | 10 | 65 | 0 | 50 | 40 | 10 | 0 | 0 | 0 | 0 | 0 | 0 | 0 |
| 2-14 | 63 | 40 | 90 | 10 | 40 | 30 | — | 0 | 0 | 0 | 0 | 15 | 0 | 10 |
| | 250 | 70 | 95 | 10 | 80 | 40 | — | 0 | 0 | 0 | 0 | 20 | 10 | 30 |
| 2-15 | 63 | 0 | 70 | 10 | 40 | 40 | 10 | 0 | 0 | 0 | 0 | 10 | 0 | 0 |
| | 250 | 20 | 90 | 10 | 90 | 60 | 40 | 0 | 0 | 0 | 0 | 30 | 0 | 0 |
| 2-16 | 63 | 50 | 100 | 10 | 99 | 80 | — | 50 | 90 | 40 | 20 | 70 | 70 | 40 |
| | 250 | 100 | 100 | 80 | 100 | 100 | 100 | 100 | 100 | 95 | 60 | 100 | 90 | 45 |
| 2-18 | 63 | 0 | 0 | 0 | 0 | 0 | — | 0 | 0 | 0 | 0 | 0 | 0 | 0 |
| | 250 | 95 | 40 | 10 | 30 | 50 | — | 0 | 0 | 0 | 0 | 20 | 0 | 0 |
| 2-19 | 63 | 40 | 90 | 0 | 70 | 50 | — | 0 | 0 | 0 | 0 | 80 | 0 | 0 |
| | 250 | 75 | 100 | 10 | 100 | 50 | 30 | 30 | 0 | 0 | 0 | 100 | 0 | 20 |
| 2-23 | 63 | 70 | 100 | 95 | 100 | 70 | 90 | — | 0 | 50 | 0 | 100 | 40 | 50 |
| | 250 | 100 | 100 | 100 | 100 | 90 | 100 | — | 30 | 90 | 70 | 100 | 90 | 95 |
| 2-24 | 63 | 100 | 100 | 100 | 100 | 99 | 100 | 20 | 70 | 60 | 10 | 100 | 70 | 70 |
| | 250 | 100 | 100 | 100 | 100 | 100 | 100 | 70 | 95 | 90 | 50 | 100 | 95 | 90 |
| 2-26 | 63 | 0 | 0 | 0 | 0 | 0 | 0 | 0 | 0 | 0 | 0 | 0 | 0 | 0 |
| | 250 | 20 | 40 | 0 | 30 | 20 | 0 | 0 | 0 | 0 | 0 | 0 | 0 | 0 |
| 2-27 | 63 | 100 | 100 | 50 | 90 | 90 | 60 | — | 0 | 20 | 10 | 100 | 50 | 60 |
| | 250 | 100 | 100 | 90 | 100 | 100 | 90 | — | 80 | 85 | 70 | 100 | 95 | 95 |
| 2-28 | 63 | 100 | 100 | 30 | 60 | 60 | — | 30 | 0 | 0 | 0 | 60 | 15 | 90 |
| | 250 | 100 | 100 | 20 | 50 | 60 | — | 30 | 0 | 0 | 0 | 90 | 25 | 90 |
| 2-29 | 63 | 90 | 100 | 20 | 75 | 80 | 50 | 20 | 0 | 0 | 0 | 60 | 10 | 40 |
| | 250 | 100 | 100 | 40 | 100 | 90 | 60 | 50 | 20 | 10 | 20 | 90 | 25 | 60 |
| 2-30 | 63 | 0 | 30 | 0 | 0 | 0 | 0 | — | 0 | 0 | 0 | 0 | 0 | 0 |
| | 250 | 20 | 70 | 0 | 20 | 50 | 10 | — | 0 | 0 | 0 | 10 | 0 | 0 |
| 2-31 | 63 | 100 | 100 | — | 90 | 80 | — | 10 | 10 | 10 | 0 | 90 | 40 | 50 |
| | 250 | 90 | 100 | — | 100 | 95 | — | 20 | 40 | 30 | 20 | 95 | 60 | 70 |
| 2-32 | 63 | 100 | 100 | 80 | 100 | 95 | — | 0 | 0 | 50 | 0 | 100 | 30 | 30 |
| | 250 | 100 | 100 | 100 | 100 | 100 | — | 90 | 90 | 95 | 70 | 100 | 95 | 80 |
| 2-33 | 63 | 90 | 100 | 70 | 100 | 80 | 70 | 50 | 10 | 0 | 0 | 60 | 10 | 20 |
| | 250 | 95 | 100 | 80 | 100 | 95 | 95 | 40 | 60 | 20 | 40 | 90 | 40 | 60 |
| 2-34 | 63 | 95 | 100 | 100 | 75 | 85 | 70 | — | 0 | 40 | 10 | 90 | 60 | 65 |
| | 250 | 95 | 100 | 100 | 95 | 90 | 85 | — | 30 | 80 | 30 | 95 | 90 | 85 |
| 2-36 | 63 | 100 | 100 | 60 | 100 | 95 | 80 | 50 | 10 | 10 | 20 | 75 | 10 | 25 |
| | 250 | 100 | 100 | 60 | 100 | 100 | 95 | 60 | 0 | 10 | 20 | 100 | 20 | 40 |
| 2-37 | 63 | 0 | 0 | 0 | 0 | 0 | 0 | — | 0 | 0 | 0 | 0 | 0 | 0 |

TABLE XXI-continued

| | | Post-emerge Herbicidal Activity | | | | | | | | | | | | |
|---|---|---|---|---|---|---|---|---|---|---|---|---|---|---|
| Cmpd. no. | Rate g ai/ha | AMARE | ABUTH | CASOB | IPOHE | CHEAL | AMBEL | SETVI | ECHCG | SORHA | DIGSA | SOY | CORN | RICE |
| | 250 | 10 | 30 | 0 | 0 | 20 | 0 | — | 0 | 0 | 0 | 10 | 0 | 0 |
| 2-39 | 63 | 70 | 100 | 60 | 99 | 90 | 50 | 20 | 0 | 10 | 0 | 95 | 20 | 30 |
| | 250 | 95 | 100 | 90 | 100 | 95 | 95 | 80 | 60 | 60 | 50 | 99 | 70 | 70 |
| 2-40 | 63 | 90 | 100 | 50 | 100 | 80 | 80 | 10 | 0 | 30 | 10 | 100 | 40 | 50 |
| | 250 | 100 | 100 | 90 | 100 | 95 | 100 | 90 | 100 | 100 | 90 | 100 | 90 | 95 |
| 2-41 | 63 | 95 | 100 | 60 | 100 | 95 | 50 | 20 | 0 | 0 | 0 | 90 | 15 | 10 |
| | 250 | 100 | 100 | 95 | 100 | 100 | 95 | 30 | 30 | 70 | 20 | 100 | 80 | 70 |
| 2-42 | 63 | 95 | 100 | 65 | 100 | 90 | 70 | 50 | 30 | 10 | 0 | 100 | 10 | 60 |
| | 250 | 100 | 100 | 100 | 100 | 100 | 95 | 80 | 80 | 95 | 30 | 100 | 60 | 90 |
| 2-44 | 63 | 50 | 100 | 20 | 50 | 60 | 60 | 0 | 0 | 0 | 0 | 90 | 0 | 0 |
| | 250 | 90 | 100 | 70 | 100 | 90 | 90 | 50 | 10 | 30 | 10 | 100 | 20 | 10 |
| 2-45 | 63 | 10 | 30 | 0 | 20 | 30 | — | 0 | 0 | 0 | 0 | 10 | 0 | 0 |
| | 250 | 20 | 40 | 20 | 30 | 30 | — | 40 | 0 | 0 | 0 | 20 | 5 | 10 |
| 2-46 | 63 | 30 | 50 | 0 | 0 | 10 | — | 0 | 0 | 0 | 0 | 10 | 0 | 10 |
| | 250 | 70 | 100 | 0 | 20 | | — | 30 | 10 | 0 | 0 | 80 | 20 | 30 |
| 2-47 | 63 | 90 | 100 | 70 | 70 | 80 | 50 | 20 | 0 | 0 | 0 | 100 | 10 | 20 |
| | 250 | 100 | 100 | 100 | 100 | 100 | 90 | 30 | 10 | 0 | 0 | 100 | 15 | 45 |
| 2-48 | 63 | 95 | 100 | 50 | 100 | 95 | 85 | 20 | 0 | 30 | 0 | 100 | 50 | 80 |
| | 250 | 100 | 100 | 100 | 100 | 100 | 100 | 70 | 80 | 60 | 20 | 100 | 70 | 86 |
| 2-49 | 63 | 20 | 90 | 30 | 70 | 60 | 50 | — | 0 | 0 | 0 | 70 | 0 | 0 |
| | 250 | 40 | 100 | 50 | 70 | 60 | 40 | — | 0 | 0 | 0 | 60 | 10 | 10 |
| 2-50 | 63 | 90 | 100 | 80 | 100 | 70 | 40 | 40 | 0 | 0 | 10 | 90 | 10 | 60 |
| | 250 | 100 | 100 | 90 | 100 | 90 | 65 | 60 | 30 | 40 | 30 | 90 | 70 | 65 |
| 2-52 | 63 | 30 | 30 | 0 | 10 | 10 | 20 | 0 | 0 | 0 | 0 | 0 | 0 | 0 |
| 2-53 | 63 | 90 | 100 | 70 | 90 | 95 | 70 | 20 | 0 | 0 | 0 | 100 | 10 | 30 |
| | 250 | 100 | 100 | 100 | 100 | 100 | 90 | 40 | 70 | 50 | 20 | 100 | 70 | 70 |
| 2-54 | 63 | 100 | 100 | 90 | 100 | 100 | 90 | 10 | 20 | 50 | 10 | 100 | 80 | 90 |
| | 250 | 100 | 100 | 100 | 100 | 100 | 100 | 50 | 90 | 80 | 20 | 100 | 80 | 95 |
| 2-56 | 63 | 100 | 100 | 100 | 100 | 100 | 70 | 80 | 0 | 0 | 0 | 100 | 30 | 45 |
| | 250 | 100 | 100 | 100 | 100 | 100 | 100 | 60 | 50 | 60 | 30 | 100 | 80 | 90 |
| 2-58 | 63 | 100 | 100 | 100 | 95 | 100 | 100 | 50 | 20 | 20 | 10 | 100 | 40 | 50 |
| | 250 | 100 | 100 | 100 | 100 | 100 | 100 | 60 | 90 | 90 | 40 | 100 | 90 | 85 |
| 2-59 | 63 | 100 | 100 | 90 | 100 | 100 | 70 | 20 | 0 | 30 | 0 | 75 | 70 | 70 |
| | 250 | 100 | 100 | 100 | 100 | 100 | 100 | 20 | 30 | 65 | 30 | 90 | 80 | 80 |
| 2-61 | 63 | 100 | 100 | 100 | 100 | 100 | 100 | 60 | 40 | 20 | 20 | 100 | 35 | 60 |
| | 250 | 100 | 100 | 100 | 100 | 100 | 95 | 90 | 70 | 70 | 50 | 100 | 90 | 90 |
| 2-63 | 63 | 100 | 100 | 100 | 100 | 99 | 80 | 50 | 10 | 20 | 0 | 100 | 50 | 70 |
| | 250 | 100 | 100 | 100 | 100 | 100 | 100 | 95 | 100 | 100 | 70 | 100 | 95 | 95 |
| 2-14 | 63 | 85 | 100 | 40 | 70 | 80 | 60 | 20 | 30 | 20 | 10 | 50 | 50 | 60 |
| | 250 | 100 | 100 | 70 | 90 | 100 | 90 | 50 | 40 | 20 | 20 | 60 | 60 | 90 |
| 2-66 | 63 | 100 | 100 | 100 | 100 | 100 | 100 | 90 | 70 | 10 | 10 | 95 | 15 | 50 |
| | 250 | 100 | 100 | 70 | 90 | 100 | 75 | 80 | 50 | 50 | 20 | 90 | 70 | 90 |
| 2-67 | 63 | 100 | 100 | 100 | 99 | 100 | 100 | 20 | 0 | 0 | 0 | 100 | 20 | 70 |
| | 250 | 100 | 100 | 100 | 100 | 100 | 100 | 30 | 40 | 80 | 40 | 100 | 95 | 80 |
| 2-69 | 63 | 40 | 100 | 10 | 50 | 50 | 40 | 0 | 0 | 0 | 0 | 20 | 0 | 0 |
| | 250 | 50 | 100 | 30 | 40 | 60 | 30 | 0 | 0 | 0 | 0 | 30 | 0 | 0 |
| 2-70 | 63 | 70 | 100 | 10 | 60 | 50 | 30 | 20 | 0 | 0 | 0 | 10 | 0 | 0 |
| | 250 | 70 | 100 | 20 | 60 | 70 | 30 | 0 | 0 | 0 | 0 | 20 | 0 | 0 |
| 2-72 | 63 | 70 | 100 | 70 | 50 | 70 | 70 | — | 0 | 0 | 0 | 15 | 0 | 0 |
| | 250 | 90 | 100 | 95 | 60 | 80 | 60 | — | 0 | 0 | 0 | 30 | 10 | 20 |
| 2-73 | 63 | 100 | 100 | 60 | 100 | 70 | 100 | 50 | 30 | 10 | 30 | 95 | 25 | 20 |
| | 250 | 100 | 100 | 100 | 100 | 95 | 100 | 90 | 60 | 50 | 30 | 100 | 50 | 70 |
| 2-74 | 63 | 95 | 100 | 30 | 60 | 70 | 70 | 0 | 0 | 0 | 0 | 60 | 0 | 25 |
| | 250 | 100 | 100 | 70 | 60 | 70 | 95 | 20 | 0 | 0 | 0 | 100 | 15 | 50 |
| 2-75 | 63 | 100 | 100 | 100 | 100 | 100 | — | 30 | 10 | 20 | 0 | 100 | 10 | 70 |
| | 250 | 100 | 100 | 100 | 100 | 100 | — | 80 | 50 | 40 | 20 | 100 | 15 | 80 |
| 2-77 | 63 | 10 | 100 | 40 | 60 | 100 | — | 0 | 0 | 0 | 0 | 40 | 0 | 20 |
| | 250 | 100 | 100 | 100 | 95 | 80 | — | 0 | 0 | 0 | 0 | 90 | 10 | 40 |
| 2-78 | 63 | 100 | 100 | 70 | 80 | 100 | — | 30 | 10 | 0 | 0 | 80 | 25 | 50 |
| | 250 | 100 | 100 | 100 | 100 | 100 | — | 30 | 10 | 10 | 0 | 100 | 30 | 65 |
| 2-81 | 63 | 100 | 100 | 70 | 100 | 90 | — | 40 | 50 | 20 | 20 | 90 | 30 | 60 |
| | 250 | 100 | 100 | 100 | 100 | 100 | — | 60 | 90 | 80 | 80 | 100 | 90 | 90 |
| 2-82 | 63 | 100 | 100 | 100 | 60 | 90 | — | 40 | 20 | 0 | 0 | 60 | 10 | 50 |
| | 250 | 100 | 100 | 100 | 90 | 90 | — | 50 | 30 | 30 | 30 | 50 | 25 | 40 |
| 2-83 | 63 | 40 | 50 | 0 | 10 | 20 | — | 0 | 0 | 0 | 0 | 10 | 0 | 100 |
| | 250 | 90 | 70 | 0 | 20 | 50 | — | 0 | 0 | 0 | 0 | 10 | 0 | 0 |
| 2-84 | 63 | 80 | 30 | 20 | 30 | 30 | — | 30 | 0 | 0 | 0 | 10 | 10 | 0 |
| | 250 | 100 | 100 | 100 | 70 | 80 | — | 0 | 0 | 0 | 0 | 70 | 10 | 20 |
| 2-86 | 63 | 100 | 100 | 100 | 100 | 100 | — | 90 | 90 | 70 | 30 | 100 | 90 | 80 |
| | 250 | 100 | 100 | 100 | 100 | 100 | — | 100 | 100 | 100 | 95 | 100 | 100 | 100 |
| 2-87 | 63 | 100 | 100 | 40 | 100 | 80 | — | 30 | 10 | 10 | 10 | 95 | 30 | 40 |
| | 250 | 100 | 100 | 100 | 100 | 90 | — | 40 | 50 | 50 | 50 | 100 | 80 | 75 |
| 2-89 | 63 | 70 | 100 | 50 | 90 | 60 | — | 20 | 0 | 0 | 0 | 80 | 0 | 60 |
| | 250 | 100 | 100 | 60 | 100 | 90 | — | 20 | 10 | 10 | 0 | 99 | 0 | 70 |

TABLE XXI-continued

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | | Post-emerge Herbicidal Activity | | | | | | | | | | | | |
| 2-92 | 63 | 20 | 100 | 0 | 20 | 20 | — | 0 | 0 | 0 | 0 | 10 | 0 | 10 |
| | 250 | 50 | 100 | 30 | 100 | 80 | — | 0 | 0 | 0 | 0 | 50 | 30 | 60 |
| 2-98 | 63 | 75 | 100 | 100 | 100 | 70 | 80 | — | 0 | 0 | 0 | 100 | 20 | 40 |
| | 250 | 100 | 100 | 100 | 100 | 90 | 100 | — | 20 | 90 | 50 | 100 | 90 | 90 |
| 2-100 | 63 | 80 | 100 | 70 | 100 | 80 | 70 | 60 | 0 | 0 | 0 | 100 | 15 | 45 |
| | 250 | 100 | 100 | 60 | 100 | 80 | 90 | 70 | 30 | 60 | 20 | 100 | 80 | 70 |
| 2-102 | 63 | 0 | 0 | 0 | 0 | 0 | — | 0 | 0 | 0 | 0 | 0 | 0 | 0 |
| | 250 | 40 | 30 | 0 | 0 | 0 | — | 0 | 0 | 0 | 0 | 40 | 0 | 0 |
| 2-105 | 63 | 100 | 100 | 80 | 100 | 80 | 100 | 70 | 10 | 0 | 0 | 100 | 0 | 0 |
| | 250 | 100 | 100 | 80 | 100 | 90 | 100 | 100 | 30 | 30 | 10 | 100 | 10 | 30 |
| 2-115 | 63 | 100 | 100 | 90 | 90 | 100 | — | 0 | 10 | 0 | 20 | 50 | 5 | 20 |
| | 250 | 100 | 100 | 95 | 95 | 100 | — | 0 | 20 | 0 | 50 | 50 | 5 | 50 |
| 2-117 | 63 | 10 | 80 | 40 | 90 | — | — | 0 | 0 | 0 | 0 | 30 | 5 | 10 |
| | 250 | 70 | 100 | 95 | 100 | — | — | 0 | 0 | 0 | 0 | 90 | 20 | 40 |
| 2-118 | 63 | 30 | 60 | 0 | 50 | — | — | 0 | 0 | 0 | 0 | 40 | 10 | 10 |
| | 250 | 30 | 80 | 30 | 90 | — | — | 0 | 0 | 0 | 0 | 90 | 20 | 10 |
| 2-119 | 63 | 90 | 100 | 30 | 100 | 80 | — | 40 | 40 | 60 | 30 | 100 | 70 | 60 |
| | 250 | 100 | 100 | 60 | 100 | 100 | — | 90 | 90 | 90 | 80 | 95 | 90 | 90 |
| 2-120 | 63 | 90 | 100 | 40 | 100 | 80 | — | 20 | 40 | 40 | 10 | 70 | 50 | 50 |
| | 250 | 100 | 100 | 30 | 100 | 80 | — | 60 | 30 | 50 | 60 | 90 | 70 | 90 |
| 2-121 | 63 | 90 | 70 | 10 | 100 | 60 | — | 0 | 0 | 0 | 0 | 25 | 10 | 15 |
| | 250 | 100 | 100 | 60 | 100 | 80 | — | 20 | 0 | 10 | 10 | 60 | 20 | 25 |
| 2-122 | 63 | 100 | 100 | 100 | 100 | 100 | — | 90 | 30 | 30 | 40 | 90 | 40 | 35 |
| | 250 | 100 | 100 | 100 | 80 | 100 | — | 95 | 50 | 60 | 60 | 100 | 40 | 60 |
| 2-123 | 63 | 100 | 100 | 100 | 100 | 100 | — | 20 | 10 | 10 | 10 | 70 | 35 | 60 |
| | 250 | 100 | 100 | 100 | 100 | 100 | — | 30 | 20 | 30 | 30 | 95 | 40 | 70 |
| 2-124 | 63 | 30 | 40 | 0 | 20 | 30 | — | 0 | 0 | 0 | 0 | 15 | 0 | 0 |
| | 250 | 90 | 95 | 20 | 30 | 50 | — | 0 | 0 | 0 | 0 | 15 | 5 | 0 |
| 2-125 | 63 | 100 | 100 | 90 | 100 | 100 | — | 40 | 20 | 30 | 20 | 90 | 10 | 40 |
| | 250 | 100 | 100 | 100 | 100 | 100 | — | 60 | 40 | 40 | 40 | 100 | 20 | 70 |
| 2-126 | 63 | 80 | 90 | 60 | 80 | 80 | — | 30 | 0 | 0 | 20 | 30 | 10 | 0 |
| | 250 | 100 | 100 | 60 | 100 | 95 | — | 40 | 10 | 10 | 30 | 60 | 10 | 50 |
| 2-127 | 63 | 100 | 100 | 100 | 100 | 70 | — | 30 | 30 | 20 | 20 | 35 | 10 | 30 |
| | 250 | 100 | 100 | 60 | 95 | 100 | — | 40 | 20 | 20 | 30 | 70 | 15 | 35 |
| 2-128 | 63 | 100 | 100 | 60 | 100 | 100 | — | 50 | 10 | — | 10 | 60 | 5 | 10 |
| | 250 | 100 | 100 | 80 | 100 | 100 | — | 60 | 20 | — | 35 | 60 | 15 | — |
| 2-129 | 63 | 100 | 100 | 80 | 100 | 100 | — | 80 | 30 | — | 30 | 100 | 70 | 35 |
| | 250 | 100 | 100 | 100 | 100 | 100 | — | 90 | 50 | — | 70 | 100 | 100 | 75 |
| 2-130 | 63 | 100 | 100 | 80 | 100 | 100 | — | 60 | 50 | — | 30 | 80 | 10 | 20 |
| | 250 | 100 | 100 | 70 | 100 | 100 | — | 70 | 60 | — | 50 | 90 | 30 | 25 |
| 2-131 | 63 | 100 | 100 | 80 | 100 | 100 | — | 70 | 30 | — | 30 | 90 | 15 | 10 |
| | 250 | 100 | 100 | 100 | 100 | 100 | — | 90 | 60 | — | 70 | 100 | 70 | 75 |
| 2-132 | 63 | 100 | 100 | 100 | 100 | 100 | — | 40 | 20 | — | 10 | 80 | 60 | 50 |
| | 250 | 100 | 100 | 99 | 100 | 100 | — | 60 | 40 | — | 25 | 100 | 75 | 80 |
| 2-133 | 63 | 100 | 100 | 80 | 90 | 100 | — | 70 | 50 | — | 30 | 100 | 70 | 80 |
| | 250 | 100 | 100 | 100 | 100 | 100 | — | 75 | 85 | — | 70 | 95 | 95 | 95 |
| 2-134 | 63 | 100 | 100 | 90 | 100 | 100 | — | 20 | 10 | 10 | 0 | 70 | 10 | 50 |
| | 250 | 100 | 100 | 100 | 100 | 100 | — | 60 | 30 | 30 | 30 | 90 | 20 | 80 |
| 2-135 | 63 | 100 | 100 | 70 | 100 | 100 | — | 15 | 0 | — | 0 | 50 | 10 | 20 |
| | 250 | 100 | 100 | 100 | 95 | 100 | — | 40 | 20 | — | 10 | 90 | 25 | 40 |
| 2-136 | 63 | 100 | 100 | 60 | 80 | 95 | — | 20 | 0 | — | 0 | 70 | 15 | 5 |
| | 250 | 100 | 100 | 100 | 100 | 100 | — | 30 | 10 | — | 20 | 90 | 10 | 10 |
| 2-137 | 63 | 100 | 100 | 100 | 100 | 100 | — | 10 | 0 | — | 0 | 70 | 10 | 10 |
| | 250 | 100 | 100 | 90 | 90 | 100 | — | 30 | 30 | — | 10 | 90 | 60 | 70 |
| 2-140 | 63 | 100 | 100 | 100 | 100 | 100 | — | 40 | 30 | — | 20 | 100 | 10 | 50 |
| | 250 | 100 | 100 | 100 | 100 | 100 | — | 60 | 85 | — | 65 | 100 | 70 | 80 |
| 2-141 | 63 | 95 | 100 | 50 | 100 | 95 | — | 20 | 10 | — | 10 | 70 | 5 | 15 |
| | 250 | 95 | 100 | 95 | 95 | 100 | — | 40 | 30 | — | 30 | 70 | 10 | 65 |
| 2-142 | 63 | 0 | 0 | 0 | 0 | 20 | — | 0 | 0 | — | 0 | 15 | 10 | 10 |
| | 250 | 40 | 40 | 10 | 50 | 80 | — | 0 | 0 | — | 0 | 30 | 15 | 0 |
| 2-143 | 63 | 100 | 100 | 70 | 60 | — | — | 0 | 0 | — | 0 | 100 | 10 | 40 |
| | 250 | 100 | 100 | 100 | 100 | — | — | 40 | 30 | — | 40 | 95 | 35 | 70 |
| 2-144 | 63 | 75 | 85 | 60 | 60 | — | — | 0 | 0 | — | 0 | 40 | 40 | 15 |
| | 250 | 90 | 100 | 85 | 70 | — | — | 30 | 10 | — | 0 | 40 | 20 | 35 |
| 2-145 | 63 | 95 | 100 | 100 | 100 | — | — | 0 | 0 | 0 | 0 | 80 | 10 | 35 |
| | 250 | 100 | 100 | 100 | 100 | — | — | 40 | 20 | 10 | 10 | 95 | 20 | 60 |
| 2-146 | 63 | 30 | 70 | 20 | 40 | 30 | — | 0 | 0 | 0 | 0 | 10 | 10 | 10 |
| | 250 | 30 | 75 | 50 | 50 | 40 | — | 0 | 0 | 0 | 0 | 10 | 5 | 10 |
| 2-147 | 63 | 100 | 100 | 80 | 100 | 100 | 95 | 20 | 10 | — | 20 | 90 | 15 | 50 |
| | 250 | 100 | 100 | 95 | 100 | 100 | 100 | 40 | 50 | — | 50 | 100 | 90 | 75 |
| 2-148 | 63 | 100 | 100 | 95 | 80 | 100 | — | 50 | 50 | 0 | 40 | 80 | 25 | 0 |
| | 250 | 90 | 100 | 100 | 90 | 100 | — | 40 | 20 | 10 | 40 | 90 | 30 | 10 |
| 2-149 | 63 | 80 | 100 | 95 | 70 | 90 | — | 10 | 20 | 0 | 0 | 80 | 0 | 0 |
| | 250 | 80 | 100 | 95 | 95 | 95 | — | 20 | 50 | 0 | 20 | 90 | 15 | 10 |

TABLE XXI-continued

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | | Post-emerge Herbicidal Activity | | | | | | | | | | | | |
| 2-151 | 63 | 10 | 0 | 10 | 30 | 10 | 20 | 0 | 0 | 0 | 0 | 0 | 0 | 0 |
| | 250 | 20 | 50 | 50 | 100 | 10 | 30 | 0 | 0 | 0 | 0 | 0 | 0 | 10 |
| 2-152 | 63 | 100 | 100 | 100 | 100 | 98 | — | 30 | 30 | 20 | 20 | 60 | 15 | 40 |
| | 250 | 100 | 100 | 100 | 100 | 100 | — | 50 | 50 | 40 | 30 | 70 | 30 | 65 |
| 2-153 | 63 | 60 | 95 | 0 | 100 | 80 | — | 20 | 10 | 0 | 0 | 70 | 5 | 0 |
| | 250 | 90 | 100 | 30 | 95 | 95 | — | 30 | 20 | 20 | 10 | 50 | 5 | 10 |
| 2-154 | 63 | 100 | 100 | 50 | 100 | 100 | — | 40 | 80 | — | 10 | 90 | 10 | 65 |
| | 250 | 100 | 100 | 100 | 100 | 100 | — | 95 | 95 | — | 85 | 100 | 85 | 90 |
| 2-155 | 63 | 100 | 100 | 100 | 100 | 100 | — | 50 | 30 | 30 | 40 | 80 | 70 | 25 |
| | 125 | 100 | 100 | 100 | 100 | 100 | — | 70 | 60 | 50 | 50 | 99 | 90 | 80 |
| 2-158 | 63 | 100 | 95 | 90 | 20 | 90 | 50 | 10 | 0 | 0 | 0 | 40 | 0 | 20 |
| | 250 | 100 | 100 | 100 | 80 | 95 | 100 | 70 | 50 | 0 | 30 | 50 | 0 | 60 |
| 2-161 | 63 | 100 | 100 | 100 | 100 | 100 | 30 | 0 | 20 | 0 | 0 | 80 | 0 | 20 |
| | 250 | 100 | 100 | 100 | 100 | 100 | 100 | 20 | 60 | 30 | 50 | 80 | 20 | 70 |
| 2-163 | 63 | 100 | 99 | 90 | 98 | 100 | — | 50 | 55 | 0 | 30 | 80 | 35 | 20 |
| | 250 | 100 | 100 | 90 | 95 | 100 | — | 60 | 70 | 10 | 45 | 85 | 40 | 55 |
| 2-168 | 63 | 20 | 60 | 0 | 60 | 30 | — | 0 | 0 | 0 | 0 | 30 | 5 | 10 |
| | 250 | 50 | 100 | 80 | 100 | 50 | — | 10 | 0 | 0 | 0 | 80 | 10 | 30 |
| 2-169 | 63 | 10 | 70 | 10 | 50 | 30 | — | 0 | 0 | 0 | 0 | 70 | 10 | 10 |
| | 250 | 0 | 80 | 10 | 40 | 40 | — | 0 | 0 | 0 | 0 | 50 | 10 | 10 |
| 2-170 | 63 | 20 | 35 | 10 | 50 | 60 | — | 10 | 0 | 0 | 0 | 30 | 5 | 5 |
| | 250 | 30 | 90 | 60 | 95 | 50 | — | 20 | 20 | 10 | 30 | 90 | 15 | 10 |
| 2-171 | 63 | 30 | 60 | 30 | 60 | 40 | — | 0 | 0 | 0 | 0 | 20 | 0 | 0 |
| | 250 | 50 | 100 | 40 | 100 | 90 | — | 10 | 0 | 10 | 10 | 80 | 10 | 10 |
| 2-172 | 63 | 60 | 60 | 50 | 90 | 35 | 30 | 0 | 0 | 0 | 0 | 20 | 5 | 0 |
| | 250 | 60 | 100 | 90 | 100 | 60 | 80 | 10 | 0 | 0 | 0 | 80 | 10 | 10 |
| 2-173 | 63 | 50 | 60 | 50 | 100 | 40 | 30 | 0 | 0 | 0 | 0 | 20 | 0 | 0 |
| | 250 | 50 | 100 | 70 | 80 | 65 | 50 | 0 | 0 | 0 | 0 | 40 | 25 | 10 |
| 2-174 | 63 | 60 | 60 | 60 | 70 | 55 | — | 10 | 0 | 0 | 0 | 30 | 10 | 20 |
| | 250 | 60 | 80 | 75 | 80 | 85 | — | 10 | 0 | 0 | 10 | 80 | 25 | 20 |
| 2-175 | 63 | 100 | 100 | 100 | 100 | 100 | — | 0 | 0 | 0 | 0 | 80 | 10 | 50 |
| | 250 | 100 | 100 | 100 | 100 | 100 | — | 20 | 20 | 10 | 10 | 90 | 10 | 80 |
| 2-176 | 63 | 100 | 50 | 10 | 70 | 80 | — | 0 | 0 | 0 | 0 | 15 | 0 | 10 |
| | 250 | 100 | 90 | 30 | 95 | 90 | — | 0 | 0 | 0 | 0 | 35 | 5 | 30 |
| 2-177 | 63 | 100 | 100 | 100 | 100 | 100 | — | 45 | 20 | 30 | 30 | 95 | 15 | 50 |
| | 250 | 100 | 100 | 100 | 100 | 100 | — | 60 | 40 | 40 | 50 | 100 | 20 | 60 |
| 2-178 | 63 | 50 | 40 | 0 | 30 | 30 | — | 0 | 0 | 0 | 0 | 10 | 0 | 0 |
| | 250 | 70 | 50 | 0 | 20 | 40 | — | 0 | 0 | 0 | 0 | 15 | 0 | 0 |
| 2-179 | 63 | 100 | 100 | 80 | 80 | 80 | — | 30 | 70 | 10 | 0 | 90 | 15 | 30 |
| | 250 | 100 | 100 | 100 | 100 | 100 | — | 55 | 50 | — | 50 | 100 | 15 | 60 |
| 2-180 | 63 | 100 | 100 | 100 | 100 | 100 | — | 60 | 40 | — | 40 | 100 | 5 | 20 |
| | 250 | 100 | 100 | 100 | 100 | 100 | — | 70 | 60 | — | 40 | 100 | 20 | 65 |
| 2-181 | 63 | 100 | 100 | 100 | 100 | 100 | — | 70 | 40 | — | 30 | 90 | 10 | 15 |
| | 250 | 100 | 100 | 100 | 100 | 100 | — | 80 | 60 | — | 70 | 95 | 20 | 60 |
| 2-182 | 63 | 90 | 100 | 60 | 100 | 95 | — | 10 | 0 | — | 0 | 70 | 5 | 0 |
| | 250 | 95 | 100 | 95 | 100 | 100 | — | 80 | 30 | — | 20 | 100 | 70 | |
| 2-183 | 63 | 0 | 0 | 0 | 0 | 0 | — | 0 | 0 | — | 0 | 10 | 0 | 0 |
| | 250 | 10 | 50 | 0 | 40 | 80 | — | 0 | 0 | — | 0 | 30 | 0 | 0 |
| 2-184 | 63 | 100 | 100 | 100 | 100 | 100 | — | 60 | 40 | — | 20 | 95 | 10 | 40 |
| | 250 | 100 | 100 | 100 | 100 | 100 | — | 80 | 50 | — | 90 | 100 | 75 | 65 |
| 2-185 | 63 | 80 | 100 | 40 | 60 | 70 | — | 0 | 0 | — | 0 | 50 | 0 | 20 |
| | 250 | 100 | 100 | 60 | 80 | 100 | — | 20 | 0 | — | 10 | 75 | 5 | 35 |
| 2-187 | 63 | 99 | 100 | 70 | 100 | 100 | — | 40 | 20 | — | 10 | 100 | 15 | 50 |
| | 250 | 100 | 100 | 100 | 100 | 100 | — | 60 | 40 | — | 40 | 100 | 75 | 90 |
| 2-188 | 63 | 85 | 100 | 55 | 100 | 80 | — | 10 | 30 | — | 0 | 70 | 25 | 20 |
| | 250 | 90 | 100 | 90 | 100 | 100 | — | 20 | 40 | — | 10 | 95 | 45 | 40 |
| 2-189 | 40.5 | 100 | 85 | 40 | 60 | 100 | — | 0 | 0 | 0 | 0 | 15 | 0 | 0 |
| | 162 | 100 | 100 | 60 | 100 | 100 | — | 0 | 10 | 0 | 0 | 60 | 5 | 5 |
| 2-190 | 63 | 95 | 90 | 20 | 50 | 90 | — | 0 | 0 | 0 | 0 | 20 | 5 | 0 |
| | 250 | 99 | 90 | 80 | 90 | 100 | — | 0 | 10 | 50 | 0 | 95 | 10 | 5 |
| 2-191 | 63 | 40 | 70 | 30 | 80 | — | — | 0 | 0 | 0 | 0 | 20 | 10 | 10 |
| | 250 | 90 | 90 | 80 | 100 | — | — | 10 | 0 | 0 | 0 | 35 | 20 | 20 |
| 2-192 | 63 | 70 | 85 | 40 | 50 | 60 | — | 0 | 0 | 0 | 0 | 40 | 5 | 0 |
| | 250 | 70 | 85 | 60 | 70 | 50 | — | 0 | 0 | 0 | 0 | 70 | 15 | 20 |
| 2-194 | 63 | 99 | 95 | 50 | 95 | 90 | 95 | 20 | 0 | 0 | 0 | 50 | 5 | 30 |
| | 250 | 99 | 100 | 70 | 99 | 100 | 90 | 20 | 10 | 10 | 20 | 95 | 5 | 40 |
| 2-196 | 63 | 100 | 100 | 100 | 90 | 100 | 100 | 30 | 10 | 10 | 10 | 100 | 10 | 30 |
| | 250 | 100 | 100 | 100 | 100 | 100 | 90 | 20 | 10 | 10 | 20 | — | 15 | — |
| 2-197 | 63 | 100 | 100 | 80 | 100 | 100 | — | 10 | 0 | 0 | 10 | 70 | 10 | 20 |
| | 250 | 100 | 100 | 80 | 90 | 100 | — | 20 | 20 | 50 | 10 | 100 | 10 | 30 |
| 2-198 | 63 | 80 | 80 | 50 | 80 | 80 | — | 10 | 5 | 0 | 10 | 90 | 10 | 10 |
| | 250 | 95 | 100 | 30 | 100 | 90 | — | 10 | 5 | 50 | 10 | 95 | 40 | 30 |
| 2-199 | 63 | 95 | 100 | 100 | 100 | 100 | — | 50 | 60 | 40 | 30 | 90 | 30 | 80 |
| | 250 | 100 | 100 | 100 | 100 | 100 | — | 90 | 100 | 95 | 95 | 100 | 90 | 90 |

TABLE XXI-continued

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | | Post-emerge Herbicidal Activity | | | | | | | | | | | | |
| 2-200 | 63 | 100 | 100 | 100 | 100 | 100 | — | 30 | 0 | 0 | 0 | 80 | 10 | 10 |
| | 250 | 100 | 100 | 100 | 100 | 100 | — | 50 | 0 | 0 | 0 | 95 | 20 | 20 |
| 2-201 | 63 | 99 | 95 | 60 | 95 | 95 | — | 20 | 50 | 0 | 35 | 75 | 30 | 60 |
| | 250 | 100 | 99 | 85 | 95 | 98 | — | 30 | 60 | 0 | 45 | 85 | 35 | 65 |
| 2-202 | 63 | 100 | 100 | 100 | 100 | 100 | — | 30 | 10 | — | 0 | 90 | 15 | 20 |
| | 250 | 100 | 100 | 100 | 100 | 100 | — | 40 | 40 | — | 30 | 100 | 30 | 60 |
| 2-203 | 63 | 100 | 100 | 100 | 60 | 100 | — | 20 | 10 | 10 | 10 | 30 | 10 | 25 |
| | 250 | 100 | 100 | 100 | 95 | 100 | — | 30 | 30 | 20 | 30 | 60 | 10 | 30 |
| 2-204 | 63 | 50 | 40 | 10 | 30 | 20 | 10 | 0 | 0 | 0 | 0 | 30 | 5 | 0 |
| | 250 | 70 | 80 | 500 | 60 | 95 | 70 | 20 | 0 | 0 | 10 | 80 | 10 | 30 |
| 2-205 | 63 | 90 | 100 | 90 | 100 | 70 | 70 | 10 | 0 | 0 | 10 | 40 | 10 | 30 |
| | 250 | 40 | 100 | 100 | 70 | 70 | 100 | 10 | 0 | 0 | 10 | 30 | 20 | 30 |
| 2-206 | 63 | 20 | 50 | 50 | 70 | 50 | — | 0 | 0 | 0 | 30 | 30 | 0 | 0 |
| | 250 | 50 | 90 | 80 | 90 | 70 | — | 0 | 30 | 0 | 20 | 70 | 0 | 70 |
| 3-1 | 63 | 0 | 0 | 0 | 0 | 0 | 0 | 0 | 0 | 0 | 0 | 0 | 0 | 0 |
| | 250 | 60 | 0 | 0 | 30 | 60 | 0 | 0 | 0 | 0 | 0 | 0 | 10 | 0 |
| 3-4 | 63 | 0 | 40 | 0 | 0 | 0 | — | 0 | 0 | 0 | 0 | 10 | 0 | 0 |
| | 250 | 0 | 50 | 0 | 0 | 0 | — | 0 | 0 | 0 | 0 | 20 | 0 | 10 |
| 3-6 | 63 | 100 | 100 | 40 | 90 | 50 | — | 0 | 0 | 0 | 0 | 95 | 20 | 30 |
| | 250 | 100 | 100 | 90 | 100 | 90 | — | 40 | 20 | 20 | 10 | 100 | 70 | 70 |
| 3-26 | 63 | 50 | 60 | 20 | 60 | 50 | — | 0 | 0 | 0 | 0 | 15 | 3 | 10 |
| | 250 | 65 | 60 | 60 | 90 | 60 | — | 0 | 0 | 0 | 0 | 30 | 10 | 30 |
| 4-1 | 63 | 50 | 100 | 30 | 100 | 60 | 40 | 0 | 0 | 0 | 0 | 50 | 10 | 20 |
| | 250 | 95 | 100 | 50 | 100 | 98 | 90 | 10 | 0 | 20 | 0 | 100 | 20 | 50 |
| 4-2 | 63 | 50 | 70 | 0 | 70 | 40 | 0 | 0 | 0 | 0 | 0 | 40 | 0 | 0 |
| | 250 | 85 | 100 | 40 | 100 | 95 | 30 | 20 | 0 | 0 | 0 | 75 | 10 | 30 |
| 4-7 | 63 | 100 | 100 | 100 | 100 | 100 | — | 70 | 50 | 90 | 40 | 100 | 90 | 65 |
| | 250 | 100 | 100 | 100 | 100 | 100 | — | 100 | 100 | 90 | 90 | 100 | 100 | 90 |
| 4-23 | 63 | 100 | 100 | 80 | 100 | 80 | — | 40 | 20 | 10 | 10 | 95 | 35 | 60 |
| | 250 | 100 | 100 | 100 | 100 | 100 | — | 70 | 60 | 50 | 40 | 100 | 80 | 80 |
| 4-24 | 63 | 100 | 100 | 70 | 100 | 100 | — | 50 | — | 40 | 40 | 80 | 35 | 20 |
| | 250 | 100 | 100 | 100 | 100 | 100 | — | 80 | — | 60 | 50 | 95 | 70 | 45 |
| 4-25 | 63 | 70 | 70 | 20 | 40 | 75 | — | 20 | — | 0 | 0 | 30 | 5 | 0 |
| | 250 | 100 | 95 | 30 | 60 | 85 | — | 30 | — | 10 | 0 | 80 | 15 | 20 |
| 4-26 | 63 | 100 | 100 | 30 | 100 | 90 | — | 20 | 10 | 10 | 20 | 40 | 5 | 15 |
| | 250 | 100 | 100 | 60 | 100 | 100 | — | 60 | 50 | 50 | 50 | 80 | 20 | 45 |
| 4-27 | 63 | 60 | 70 | 20 | 70 | 60 | — | 0 | 0 | 0 | 0 | 30 | 5 | 0 |
| | 250 | 80 | 100 | 40 | 80 | 100 | — | 10 | 0 | 0 | 0 | 50 | 10 | 10 |
| 4-28 | 63 | 80 | 100 | 50 | 60 | 70 | — | 10 | 0 | 0 | 0 | 40 | 0 | 10 |
| | 250 | 100 | 100 | 50 | 80 | 90 | — | 30 | 20 | 10 | 20 | 50 | 5 | 15 |
| 4-29 | 63 | 100 | 100 | 90 | 100 | 90 | — | 80 | 70 | 60 | 50 | 100 | 80 | 60 |
| | 250 | 100 | 100 | 100 | 100 | 100 | — | 99 | 90 | 100 | 90 | 100 | 100 | 85 |
| 4-30 | 63 | 100 | 100 | 100 | 100 | 100 | — | 80 | 50 | 50 | 50 | 100 | 90 | 80 |
| | 250 | 100 | 100 | 100 | 100 | 100 | — | 100 | 90 | 100 | 85 | 100 | 99 | 85 |
| 4-31 | 63 | 100 | 100 | 10 | 100 | 100 | — | 20 | 10 | 0 | 0 | 40 | 10 | 20 |
| | 250 | 100 | 100 | 30 | 100 | 100 | — | 40 | 10 | 10 | 10 | 80 | 25 | 40 |
| 4-32 | 63 | 100 | 90 | 80 | 100 | 100 | — | 30 | 0 | 10 | 10 | 50 | 20 | 20 |
| | 250 | 100 | 100 | 80 | 100 | 100 | — | 50 | 20 | 30 | 20 | 80 | 30 | 40 |
| 4-33 | 63 | 100 | 100 | 30 | 100 | 90 | — | 30 | 10 | 0 | 10 | 70 | 15 | 30 |
| | 250 | 100 | 100 | 70 | 100 | 100 | — | 40 | 20 | 30 | 30 | 80 | 25 | 40 |
| 4-34 | 63 | 100 | 100 | 90 | 100 | 100 | — | 50 | 20 | 30 | 35 | 90 | 25 | 40 |
| | 250 | 100 | 100 | 100 | 90 | 100 | — | 75 | 50 | 30 | 60 | 95 | 50 | 80 |
| 4-36 | 63 | 100 | 100 | 100 | 100 | 100 | — | 90 | 20 | 10 | 30 | 100 | 50 | 60 |
| | 250 | 100 | 100 | 100 | 100 | 100 | — | 90 | 60 | 90 | 70 | 100 | 100 | 100 |
| 4-37 | 63 | 100 | 100 | 90 | 100 | 100 | — | 90 | 20 | 40 | 50 | 80 | 20 | 10 |
| | 250 | 100 | 100 | 100 | 100 | 100 | — | 90 | 60 | 60 | 70 | 100 | 60 | 60 |
| 4-38 | 63 | 100 | 100 | 90 | 100 | 100 | — | 60 | 50 | — | 40 | 80 | 40 | 35 |
| | 250 | 100 | 100 | 100 | 100 | 100 | — | 80 | 50 | — | 40 | 100 | 85 | 50 |
| 4-39 | 63 | 100 | 100 | 100 | 100 | 100 | — | 80 | 60 | — | 50 | 100 | 70 | 60 |
| | 250 | 100 | 100 | 100 | 100 | 100 | — | 90 | 90 | — | 80 | 100 | 100 | 60 |
| 4-40 | 63 | 100 | 100 | 100 | 100 | 100 | — | 80 | 50 | — | 40 | 90 | 30 | 40 |
| | 250 | 100 | 100 | 100 | 100 | 100 | — | 90 | 90 | — | 90 | 100 | 70 | 60 |
| 4-41 | 63 | 100 | 100 | 100 | 100 | 100 | — | 95 | 80 | — | 90 | 100 | 75 | 50 |
| | 250 | 100 | 100 | 100 | 100 | 100 | — | 95 | 90 | — | 100 | 100 | 90 | 85 |
| 4-42 | 63 | 75 | 100 | 0 | 40 | 80 | — | 0 | 0 | — | 0 | 20 | 0 | 0 |
| | 250 | 100 | 100 | 0 | 30 | 90 | — | 0 | 10 | — | 0 | 40 | 0 | 0 |
| 4-43 | 63 | 70 | 60 | 50 | 40 | 80 | — | 0 | 0 | — | 0 | 30 | 0 | 0 |
| | 250 | 100 | 100 | 60 | 40 | 90 | — | 40 | 10 | — | 0 | 40 | 10 | 0 |
| 4-44 | 63 | 100 | 100 | 100 | 100 | 100 | — | 95 | 70 | — | 70 | 100 | 90 | 70 |
| | 250 | 100 | 100 | 100 | 100 | 100 | — | 90 | 90 | — | 95 | 100 | 100 | 80 |
| 4-45 | 63 | 90 | 100 | 80 | 95 | 100 | — | 30 | 20 | — | 10 | 30 | 10 | 10 |
| | 250 | 95 | 100 | 80 | 100 | 100 | — | 60 | 20 | — | 20 | 80 | 20 | 20 |
| 4-46 | 63 | 100 | 95 | 80 | 100 | 90 | — | 10 | 20 | — | 0 | 50 | 10 | 10 |
| | 250 | 100 | 90 | 95 | 90 | 100 | — | 10 | 30 | — | 20 | 100 | 80 | 70 |

TABLE XXI-continued

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | | Post-emerge Herbicidal Activity | | | | | | | | | | | | |
| 4-47 | 63 | 75 | 100 | 100 | 85 | 100 | — | 40 | 30 | — | 40 | 90 | 30 | 30 |
| | 250 | 95 | 10 | 100 | 100 | 100 | — | 60 | 50 | — | 30 | 95 | 65 | 60 |
| 4-48 | 63 | 100 | 100 | 95 | 100 | 100 | — | 30 | 20 | — | 20 | 95 | 90 | 80 |
| | 250 | 100 | 100 | 100 | 100 | 100 | — | 40 | 80 | — | 40 | 100 | 90 | 80 |
| 4-49 | 63 | 100 | 100 | 80 | 80 | 100 | — | 30 | 10 | 0 | 10 | 40 | 20 | 10 |
| | 250 | 100 | 100 | 100 | 100 | 100 | — | 30 | 10 | 10 | 10 | 90 | 80 | 70 |
| 4-50 | 63 | 30 | 60 | 0 | 30 | 40 | — | 0 | 0 | 0 | 0 | 15 | 0 | 0 |
| | 250 | 70 | 95 | 20 | 90 | 95 | — | 0 | 0 | 0 | 0 | 20 | 10 | 0 |
| 4-53 | 63 | 70 | 100 | 30 | 100 | 60 | — | 10 | 0 | 0 | 0 | 60 | 5 | 30 |
| | 250 | 100 | 100 | 90 | 100 | 90 | — | 70 | 60 | 40 | 40 | 90 | 70 | 65 |
| 4-54 | 63 | 100 | 100 | 90 | 100 | 100 | — | 80 | 70 | 40 | 30 | 70 | 40 | 90 |
| | 250 | 100 | 100 | 100 | 100 | 100 | — | 90 | 80 | 70 | 60 | 100 | 75 | 100 |
| 4-55 | 63 | 50 | 100 | 20 | 40 | 50 | — | 10 | 0 | 0 | 0 | 30 | 10 | 0 |
| | 250 | 80 | 100 | 40 | 85 | 90 | — | 40 | 20 | 10 | 10 | 60 | 5 | 35 |
| 4-56 | 63 | 100 | 100 | 100 | 100 | 100 | — | 90 | 50 | 40 | 20 | 100 | 80 | 65 |
| | 250 | 100 | 100 | 100 | 100 | 100 | — | 100 | 90 | 90 | 70 | 100 | 100 | 85 |
| 4-57 | 63 | 100 | 100 | 60 | 100 | 95 | — | 50 | 30 | 30 | 10 | 95 | 40 | 50 |
| | 250 | 100 | 100 | 100 | 100 | 100 | — | 90 | 40 | 50 | 60 | 100 | 90 | 80 |
| 4-58 | 63 | 100 | 100 | 90 | 100 | 100 | — | 50 | 30 | 30 | 20 | 100 | 30 | 60 |
| | 250 | 100 | 100 | 100 | 100 | 100 | — | 90 | 40 | 50 | 60 | 100 | 70 | 75 |
| 4-59 | 63 | 90 | 100 | 30 | 100 | 100 | — | 0 | 0 | 0 | 0 | 60 | 5 | 50 |
| | 250 | 100 | 100 | 60 | 100 | 100 | — | 30 | 20 | 30 | 20 | 90 | 25 | 60 |
| 4-60 | 63 | 100 | 100 | 60 | 100 | 100 | — | 65 | 60 | 50 | 40 | 90 | 25 | 50 |
| | 250 | 100 | 100 | 100 | 100 | 100 | — | 90 | 50 | 50 | 60 | 100 | 55 | 70 |
| 4-61 | 63 | 100 | 100 | 100 | 100 | 100 | — | 70 | 40 | 50 | 50 | 100 | 50 | 40 |
| | 250 | 100 | 100 | 100 | 100 | 100 | — | 80 | 60 | 70 | 70 | 95 | 70 | 80 |
| 4-62 | 63 | 100 | 100 | 90 | 100 | 100 | — | 60 | 20 | 30 | 10 | 100 | 30 | 30 |
| | 250 | 100 | 100 | 100 | 100 | 100 | — | 80 | 40 | 30 | 50 | 90 | 45 | 30 |
| 4-63 | 63 | 100 | 100 | 60 | 100 | 80 | — | 0 | 0 | 0 | 0 | 90 | 10 | 10 |
| | 250 | 100 | 100 | 100 | 100 | 100 | — | 30 | 20 | 10 | 10 | 100 | 30 | 60 |
| 4-64 | 63 | 100 | 100 | 60 | 100 | 100 | — | 50 | 20 | 10 | 10 | 100 | 30 | 15 |
| | 250 | 100 | 100 | 100 | 100 | 100 | — | 80 | 30 | 30 | 30 | 90 | 40 | 50 |
| 4-65 | 63 | 100 | 100 | 100 | 100 | 100 | — | 100 | 60 | 70 | 60 | 100 | 80 | 70 |
| | 250 | 100 | 100 | 100 | 100 | 100 | — | 100 | 70 | 80 | 80 | 100 | 90 | 80 |
| 4-66 | 63 | 80 | 100 | 20 | 100 | 80 | — | 10 | 0 | 0 | 10 | 40 | 15 | 30 |
| | 250 | 100 | 100 | 90 | 100 | 100 | — | 60 | 40 | 50 | 50 | 80 | 60 | 70 |
| 4-67 | 63 | 100 | 100 | 100 | 100 | 100 | — | 90 | 40 | — | 70 | 100 | 55 | 50 |
| | 250 | 100 | 100 | 100 | 100 | 100 | — | 90 | 70 | — | 80 | 100 | 70 | 70 |
| 4-68 | 63 | 100 | 100 | 100 | 100 | 100 | — | 100 | 90 | — | 75 | 100 | 95 | 60 |
| | 250 | 100 | 100 | 100 | 100 | 100 | — | 100 | 98 | — | 90 | 100 | 100 | 80 |
| 4-69 | 63 | 100 | 100 | 40 | 70 | 90 | — | 40 | 20 | — | 20 | 40 | 5 | 0 |
| | 250 | 100 | 100 | 70 | 100 | 100 | — | 80 | 40 | — | 50 | 80 | 35 | 40 |
| 4-70 | 63 | 90 | 100 | 60 | 100 | 90 | — | 60 | 40 | — | 30 | 100 | 40 | 30 |
| | 250 | 100 | 100 | 90 | 100 | 100 | — | 95 | 80 | — | 70 | 100 | 90 | 70 |
| 5-17 | 63 | 0 | 90 | 0 | 30 | 20 | — | 0 | 0 | 0 | 0 | 15 | 0 | 10 |
| | 250 | 30 | 100 | 30 | 40 | 60 | — | 80 | 20 | 10 | 0 | 70 | 10 | 50 |
| 5-18 | 63 | 0 | 70 | 0 | 0 | 10 | — | 0 | 0 | 0 | 0 | 10 | 0 | 20 |
| | 250 | 10 | 70 | 0 | 0 | 10 | — | 0 | 0 | 0 | 0 | 20 | 0 | 20 |
| 5-26 | 63 | 100 | 100 | 90 | 90 | 100 | — | 40 | 20 | — | 20 | 70 | 10 | 50 |
| | 250 | 90 | 100 | 100 | 70 | 100 | — | 70 | 60 | — | 30 | 80 | 5 | 60 |
| 5-28 | 63 | 100 | 100 | 90 | 100 | 100 | — | 10 | 0 | — | 10 | 60 | 25 | 60 |
| | 250 | 100 | 100 | 100 | 100 | 100 | — | 30 | 50 | — | 30 | 90 | 70 | 70 |
| 6-13 | 63 | 70 | 100 | 0 | 50 | 85 | — | 50 | 0 | 0 | 20 | 30 | 15 | 10 |
| | 250 | 90 | 90 | 30 | 60 | 90 | — | 90 | 30 | 10 | 30 | 45 | 20 | 30 |
| 6-14 | 63 | 80 | 100 | 60 | 100 | 100 | — | 90 | 20 | 30 | 60 | 100 | 60 | 60 |
| | 250 | 100 | 100 | 90 | 100 | 100 | — | 100 | 90 | 90 | 90 | 100 | 100 | 90 |
| 6-15 | 63 | 100 | 100 | 100 | 100 | 100 | — | 50 | 40 | — | 30 | 90 | 5 | 60 |
| | 250 | 100 | 100 | 100 | 100 | 100 | — | 85 | 70 | — | 60 | 90 | 25 | 90 |
| 6-16 | 63 | 100 | 100 | 80 | 100 | 100 | — | 30 | 20 | — | 20 | 40 | 20 | 20 |
| | 250 | 90 | 100 | 60 | 75 | 100 | — | 60 | 40 | — | 30 | 70 | 35 | 70 |
| 6-17 | 63 | 60 | 90 | 50 | 50 | 90 | — | 0 | 0 | — | 0 | 20 | 5 | 0 |
| | 250 | 70 | 100 | 70 | 70 | 90 | — | 30 | 30 | — | 20 | 20 | 15 | 10 |
| 6-19 | 63 | 0 | 0 | 0 | 0 | 0 | — | 0 | 0 | 0 | 0 | 0 | 0 | 0 |
| | 250 | 30 | 50 | 0 | 30 | 60 | — | 0 | 0 | 0 | 0 | 10 | 0 | 0 |
| 6-20 | 63 | 0 | 0 | 0 | 0 | 0 | — | 0 | 0 | 0 | 0 | 0 | 0 | 0 |
| | 250 | 60 | 50 | 0 | 40 | 60 | — | 0 | 0 | 0 | 0 | 10 | 0 | 0 |
| 6-22 | 63 | 70 | 60 | 0 | 20 | 50 | — | 0 | 0 | 0 | 0 | 30 | 0 | 0 |
| | 250 | 100 | 80 | 0 | 70 | 70 | — | 0 | 0 | 0 | 0 | 30 | 0 | 30 |
| 6-23 | 63 | 20 | 40 | 0 | 10 | 20 | — | 0 | 0 | 0 | 0 | 10 | 0 | 0 |
| | 250 | 85 | 55 | 10 | 30 | 70 | — | 30 | 0 | 0 | 10 | 30 | 15 | 15 |
| 6-24 | 63 | 0 | 20 | 0 | 0 | 30 | — | 0 | 0 | 0 | 0 | 10 | 0 | 0 |
| | 250 | 80 | 95 | 10 | 60 | 90 | — | 40 | 0 | 0 | 0 | 20 | 0 | 0 |
| 7-2 | 63 | 100 | 100 | — | 80 | 95 | 0 | 20 | 30 | 20 | 20 | 40 | 10 | 30 |
| | 250 | 100 | 100 | — | 100 | 100 | 10 | 50 | 90 | 40 | 70 | 80 | 10 | 20 |

TABLE XXI-continued

| | | Post-emerge Herbicidal Activity | | | | | | | | | | | | |
|---|---|---|---|---|---|---|---|---|---|---|---|---|---|---|
| Cmpd. no. | Rate g ai/ha | AMARE | ABUTH | CASOB | IPOHE | CHEAL | AMBEL | SETVI | ECHCG | SORHA | DIGSA | SOY | CORN | RICE |
| 7-14 | 63 | — | — | — | — | — | — | — | — | — | — | — | — | — |
| | 250 | 70 | 95 | 60 | 100 | 90 | — | 20 | 10 | — | 10 | 40 | 25 | 15 |
| 7-15 | 63 | 100 | 100 | 40 | 70 | 100 | — | 10 | 0 | 0 | 0 | 30 | 10 | 0 |
| | 250 | 100 | 99 | 80 | 70 | 100 | — | 10 | 10 | 0 | 0 | 30 | 10 | 30 |
| 8-2 | 63 | 95 | 100 | 50 | 50 | 40 | 30 | 40 | 20 | 10 | 30 | 40 | 10 | 20 |
| | 250 | 100 | 100 | 30 | 90 | 80 | 90 | 60 | 30 | 0 | 30 | 10 | 20 | 15 |
| 8-3 | 63 | 90 | 90 | 0 | 40 | 70 | — | 0 | 0 | 0 | 0 | 20 | 0 | 20 |
| | 250 | 100 | 100 | 50 | 60 | 90 | — | 70 | 0 | 20 | 0 | 30 | 0 | 80 |
| 8-4 | 63 | 70 | 60 | 0 | 0 | 70 | — | 0 | 0 | 0 | 0 | 30 | 0 | 50 |
| | 250 | 90 | 80 | 10 | 20 | 90 | — | 30 | 0 | 0 | 0 | 50 | 0 | 50 |
| 8-5 | 63 | 40 | 70 | 0 | 0 | 70 | — | 0 | 0 | 0 | 0 | 20 | 0 | 40 |
| | 250 | 100 | 90 | 10 | 40 | 70 | — | 20 | 0 | 0 | 0 | 50 | 0 | 50 |
| 8-7 | 63 | 95 | 95 | 0 | 10 | 95 | — | 0 | 0 | 0 | 0 | 50 | 10 | 0 |
| | 250 | 100 | 100 | 90 | 70 | 99 | — | 90 | 20 | 0 | 10 | 90 | 10 | 90 |
| 8-13 | 63 | 100 | 100 | 30 | 50 | 90 | — | 30 | 20 | 10 | 20 | 30 | 10 | 30 |
| | 125 | 100 | 100 | 50 | 60 | 90 | — | 30 | 40 | 20 | 10 | 60 | 40 | 70 |
| 8-18 | 63 | 100 | 100 | 30 | 50 | 70 | — | 30 | 10 | 10 | 10 | 30 | 5 | 50 |
| | 250 | 100 | 100 | 40 | 60 | 80 | — | 30 | 30 | 30 | 20 | 70 | 30 | 60 |
| 8-30 | 63 | 100 | 100 | 80 | 100 | 100 | — | 40 | 30 | 30 | 20 | 90 | 10 | 40 |
| | 250 | 100 | 100 | 100 | 100 | 100 | — | 70 | 70 | 50 | 40 | 95 | 15 | 35 |
| 8-31 | 63 | 100 | 100 | 60 | 100 | 100 | — | 20 | — | 10 | 10 | 80 | 10 | 45 |
| | 250 | 100 | 100 | 80 | 100 | 100 | — | 20 | — | 30 | 30 | 90 | 10 | 30 |
| 8-36 | 63 | 95 | 100 | 70 | 100 | 95 | — | 10 | 0 | 0 | 10 | 30 | 10 | 10 |
| | 250 | 90 | 100 | 95 | 85 | 100 | — | 10 | 20 | 10 | 5 | 40 | 15 | 20 |
| 9 4 | 63 | 50 | 50 | 20 | 45 | 70 | — | 20 | — | 0 | 0 | 40 | 5 | 10 |
| | 250 | 80 | 100 | 60 | 100 | 85 | — | 30 | — | 10 | 0 | 90 | 10 | 40 |
| 9-14 | 63 | 85 | 100 | 40 | 80 | 95 | — | 10 | 0 | — | 0 | 60 | 15 | 0 |
| | 250 | 100 | 100 | 40 | 90 | 100 | — | 20 | 10 | — | 10 | 90 | 50 | 40 |
| 9-15 | 63 | 100 | 100 | 100 | 100 | 100 | — | 10 | 0 | 0 | 0 | 100 | 5 | 40 |
| | 250 | 100 | 100 | 100 | 100 | 100 | — | 35 | 10 | 10 | 20 | 100 | 10 | 70 |
| 9-16 | 63 | 30 | 100 | 50 | 90 | 65 | — | 0 | 0 | 0 | 10 | 90 | 5 | 30 |
| | 250 | 75 | 100 | 85 | 100 | 80 | — | 20 | 10 | 0 | 0 | 100 | 65 | 70 |
| 9-19 | 63 | 80 | 100 | 80 | 75 | 100 | — | 10 | 0 | 0 | 0 | 60 | 10 | 15 |
| | 250 | 98 | 100 | 95 | 90 | 100 | — | 20 | 10 | 0 | 10 | 80 | 10 | 25 |
| 11-6 | 63 | 100 | 100 | 100 | 70 | 80 | 100 | 10 | 50 | 0 | 0 | 10 | 0 | 20 |
| | 250 | 100 | 100 | 100 | 100 | 100 | 100 | 50 | 80 | 0 | 0 | 40 | 20 | 60 |
| 11-13 | 63 | 100 | 95 | 85 | 98 | 100 | — | 55 | 65 | 0 | 40 | 65 | 45 | 45 |
| | 250 | 100 | 100 | 85 | 98 | 100 | — | 40 | 55 | 15 | 60 | 85 | 45 | 65 |
| 12-2 | 63 | 30 | 100 | 50 | 90 | 100 | — | 0 | 30 | 10 | 0 | 60 | 10 | 20 |
| | 250 | 100 | 100 | 95 | 100 | 100 | — | 50 | 80 | 90 | 70 | 100 | 100 | 80 |
| 12-3 | 63 | 95 | 90 | 20 | 50 | 90 | — | 0 | 0 | 0 | 0 | 20 | 5 | 0 |
| | 250 | 99 | 90 | 80 | 90 | 100 | — | 0 | 10 | 50 | 0 | 95 | 10 | 5 |
| 12-5 | 63 | 70 | 100 | 40 | 100 | 100 | — | 20 | 10 | — | 0 | 40 | 25 | 20 |
| | 250 | 85 | 100 | 60 | 99 | 99 | — | 10 | 10 | — | 10 | 30 | 20 | 15 |
| 12-8 | 63 | 80 | 100 | 50 | 90 | 95 | — | 20 | 10 | 0 | 10 | 40 | 5 | 20 |
| | 250 | 90 | 100 | 70 | 80 | 99 | — | 25 | 10 | 10 | 0 | 80 | 10 | 15 |
| 13-3 | 63 | 90 | 100 | 90 | 75 | 100 | — | 10 | 0 | — | 0 | 30 | 10 | 25 |
| | 250 | 90 | 90 | 100 | 70 | 100 | — | 30 | 20 | — | 10 | 40 | 10 | 20 |
| 13-4 | 63 | 100 | 100 | 95 | 85 | 95 | — | 20 | 10 | — | 0 | 70 | 5 | 30 |
| | 250 | 95 | 100 | 100 | 85 | 100 | — | 40 | 30 | — | 10 | 90 | 5 | 50 |
| 13-5 | 63 | 70 | 70 | 40 | 50 | 95 | — | 0 | 0 | 0 | 0 | 10 | 7 | 10 |
| | 250 | 75 | 70 | 30 | 60 | 90 | — | 10 | 0 | 0 | 20 | 25 | 15 | 20 |
| 14-1 | 63 | 100 | 85 | 55 | 85 | 80 | — | 40 | 85 | 25 | 80 | 100 | 85 | 40 |
| | 250 | 100 | 98 | 70 | 100 | 98 | — | 70 | 95 | 75 | 95 | 100 | 100 | 80 |
| 14-2 | 63 | 100 | 80 | 50 | 75 | 95 | — | 30 | 0 | 0 | 20 | 35 | 35 | 25 |
| | 250 | 100 | 100 | 60 | 100 | 95 | — | 20 | 45 | 30 | 40 | 40 | 45 | 30 |
| 14-3 | 63 | 95 | 100 | 10 | 50 | 90 | — | 30 | 99 | 80 | 99 | 100 | 100 | 5 |
| | 250 | 100 | 100 | 75 | 100 | 100 | — | 70 | 100 | 70 | 100 | 100 | 100 | 80 |
| 14-4 | 63 | 100 | 80 | 50 | 50 | 100 | — | 30 | 85 | — | 75 | 100 | 70 | 15 |
| | 250 | 100 | 100 | 100 | 60 | 100 | — | 65 | 99 | — | 95 | 100 | 80 | 40 |
| 14-5 | 63 | 100 | 100 | 10 | 30 | 100 | — | 60 | 40 | — | 95 | 20 | 70 | 20 |
| | 250 | 100 | 100 | 50 | 100 | 100 | — | 95 | 100 | — | 100 | 95 | 100 | 30 |
| 14-6 | 63 | 95 | 90 | 50 | 70 | 80 | 40 | 30 | 99 | 50 | 50 | 100 | 50 | 0 |
| | 250 | 100 | 100 | 100 | 100 | 100 | 80 | 80 | 100 | 65 | 75 | 100 | 60 | 35 |
| 14-7 | 63 | 95 | 50 | 0 | 20 | 90 | 50 | 60 | 100 | 70 | 80 | 85 | 95 | 10 |
| | 250 | 100 | 100 | 20 | 60 | 99 | 90 | 85 | 100 | 90 | 100 | 99 | 100 | 25 |
| 14-8 | 63 | 90 | 60 | 30 | 30 | 70 | 10 | 10 | 95 | — | 40 | 95 | 40 | 5 |
| | 250 | 100 | 100 | 80 | 95 | 99 | 50 | 40 | 99 | — | 85 | 100 | 88 | 30 |
| 14-9 | 63 | 90 | 70 | 0 | 0 | 60 | 10 | 30 | 98 | — | 75 | 80 | 70 | 5 |
| | 250 | 99 | 100 | 0 | 80 | 99 | 70 | 60 | 100 | — | 75 | 90 | 99 | 20 |
| 14-10 | 63 | 90 | 80 | 80 | 70 | 90 | — | 50 | 95 | 20 | 10 | 100 | 20 | 0 |
| | 250 | 100 | 100 | 90 | 80 | 100 | — | 90 | 100 | 50 | 100 | 100 | 60 | 20 |
| 14-11 | 63 | 95 | 80 | 50 | 90 | 50 | — | 80 | 100 | 50 | 99 | 60 | 100 | 10 |
| | 250 | 100 | 100 | 70 | 100 | 100 | — | 100 | 100 | 99 | 100 | 100 | 100 | 20 |

TABLE XXI-continued

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | | Post-emerge Herbicidal Activity | | | | | | | | | | | | |
| 14-12 | 63 | 85 | 10 | 20 | 40 | 90 | 80 | 30 | 98 | — | 50 | 95 | 30 | 0 |
| | 250 | 90 | 85 | 80 | 70 | 99 | 80 | 40 | 99 | — | 60 | 100 | 85 | 10 |
| 14-13 | 63 | 90 | 30 | 0 | 40 | 60 | 30 | 20 | 100 | — | 65 | 75 | 55 | 0 |
| | 250 | 100 | 80 | 20 | 60 | 100 | 40 | 40 | 99 | — | 90 | 98 | 100 | 15 |
| 14-14 | 63 | 50 | 50 | 0 | 30 | 50 | 70 | 50 | 100 | 0 | 90 | 100 | 10 | 0 |
| | 250 | 100 | 100 | 60 | 50 | 90 | 70 | 70 | 100 | 20 | 100 | 100 | 50 | 30 |
| 14-15 | 63 | 100 | 60 | 0 | 50 | 50 | 20 | 70 | 100 | 50 | 95 | 40 | 20 | 0 |
| | 250 | 100 | 90 | 50 | 90 | 100 | 100 | 80 | 100 | 40 | 100 | 100 | 60 | 0 |
| 14-16 | 63 | 60 | 60 | 20 | 40 | 95 | — | 0 | 95 | 0 | 90 | 100 | 0 | 0 |
| | 250 | 100 | 100 | 40 | 50 | 100 | — | 30 | 100 | 30 | 100 | 100 | 70 | 10 |
| 14-17 | 63 | 100 | 100 | 20 | 20 | 90 | — | 20 | 100 | 50 | 100 | 80 | 70 | 0 |
| | 250 | 100 | 100 | 30 | 70 | 100 | — | 70 | 100 | 90 | 100 | 100 | 95 | 0 |
| 14-18 | 63 | 100 | 30 | 20 | 30 | 99 | 0 | 10 | 99 | 10 | 20 | 10 | 20 | 10 |
| | 250 | 100 | 60 | 60 | 60 | 100 | 10 | 20 | 100 | 30 | 60 | 40 | 50 | 25 |
| 14-19 | 63 | 90 | 60 | 40 | 30 | 90 | — | 0 | 100 | 0 | 100 | 100 | 0 | 0 |
| | 250 | 100 | 100 | 70 | 90 | 100 | — | 30 | 100 | 0 | 100 | 100 | 40 | 20 |
| 14-20 | 63 | 95 | 99 | 0 | 50 | 80 | — | 0 | 100 | 10 | 100 | 70 | 0 | 0 |
| | 250 | 100 | 100 | 50 | 70 | 100 | — | 50 | 100 | 90 | 100 | 100 | 80 | 10 |
| 14-21 | 63 | 90 | 100 | 30 | 40 | 70 | 50 | 10 | 99 | 10 | 70 | 95 | 50 | 10 |
| | 250 | 100 | 95 | 60 | 50 | 95 | 95 | 40 | 100 | 70 | 98 | 100 | 100 | 45 |
| 14-22 | 63 | 50 | 30 | 0 | 10 | 50 | 100 | 30 | 100 | 40 | 80 | 95 | 10 | 0 |
| | 250 | 100 | 100 | 50 | 80 | 90 | 100 | 60 | 100 | 60 | 95 | 100 | 50 | 10 |
| 14-23 | 63 | 50 | 50 | 20 | 80 | 50 | 50 | 60 | 100 | 40 | 50 | 100 | 0 | 0 |
| | 250 | 100 | 90 | 70 | 95 | 80 | 40 | 70 | 100 | 50 | 95 | 100 | 40 | 20 |
| 14-24 | 63 | 40 | 70 | 0 | 20 | 80 | 50 | 0 | 100 | 0 | 95 | 30 | 10 | 10 |
| | 250 | 90 | 100 | 0 | 40 | 90 | 50 | 50 | 100 | 50 | 100 | 100 | 20 | 50 |
| 14-25 | 63 | 95 | 100 | 50 | 70 | 80 | 100 | 50 | 100 | 40 | 95 | 100 | 100 | 10 |
| | 250 | 100 | 100 | 80 | 100 | 100 | 100 | 80 | 100 | 95 | 100 | 100 | 100 | 50 |
| 14-26 | 63 | 90 | 70 | 50 | 20 | 60 | 100 | 0 | 100 | 30 | 100 | 100 | 40 | 10 |
| | 250 | 100 | 100 | 90 | 100 | 100 | 100 | 0 | 100 | 70 | 100 | 100 | 100 | 10 |
| 14-27 | 63 | 50 | 70 | 50 | 70 | 90 | — | 0 | 99 | 0 | 70 | 95 | 5 | 0 |
| | 250 | 90 | 80 | 30 | 50 | 100 | — | 20 | 100 | 10 | 95 | 100 | 10 | 0 |
| 14-28 | 63 | 90 | 100 | 30 | 50 | 95 | — | 0 | 100 | 0 | 20 | 80 | 10 | 0 |
| | 250 | 100 | 100 | 30 | 70 | 100 | — | 30 | 100 | 50 | 50 | 100 | 70 | 40 |
| 14-29 | 63 | 90 | 50 | 0 | 80 | 30 | 100 | 20 | 100 | 50 | 70 | 100 | 15 | 0 |
| | 250 | 100 | 100 | 40 | 80 | 60 | 100 | 70 | 100 | 70 | 95 | 100 | 50 | 10 |
| 14-30 | 63 | 70 | 60 | 20 | 0 | 50 | — | 0 | 100 | 0 | 60 | 100 | 10 | 0 |
| | 250 | 100 | 100 | 60 | 50 | 100 | — | 30 | 100 | 50 | 100 | 100 | 20 | 0 |
| 14-31 | 63 | 90 | 90 | 50 | 10 | 70 | — | 0 | 100 | 0 | 95 | 50 | 10 | 0 |
| | 250 | 100 | 100 | 50 | 70 | 90 | — | 50 | 100 | 20 | 100 | 100 | 50 | 0 |
| 14-32 | 63 | 95 | 90 | 20 | 0 | 0 | 40 | 40 | 100 | 0 | 70 | 70 | 0 | 0 |
| | 250 | 100 | 95 | 40 | 20 | 80 | 40 | 70 | 100 | 10 | 90 | 100 | 0 | 0 |
| 14-33 | 63 | 100 | 90 | 0 | 20 | 20 | 0 | 40 | 100 | 10 | 70 | 10 | 10 | 0 |
| | 250 | 100 | 100 | 0 | 20 | 70 | 100 | 90 | 100 | 95 | 100 | 70 | 95 | 0 |
| 14-34 | 63 | 100 | 99 | 40 | 60 | 100 | 40 | 100 | 100 | 60 | 70 | 99 | 80 | 25 |
| | 250 | 100 | 100 | 100 | 90 | 100 | 100 | 100 | 100 | 80 | 99 | 100 | 100 | 70 |
| 14-35 | 63 | 100 | 95 | 0 | 70 | 100 | 100 | 50 | 100 | 30 | 50 | 100 | 100 | 80 |
| | 250 | 100 | 100 | 90 | 100 | 100 | 100 | 95 | 100 | 70 | 95 | 100 | 100 | 100 |
| 14-36 | 63 | 100 | 95 | 20 | 30 | 99 | 100 | 85 | 99 | 20 | 40 | 95 | 95 | 35 |
| | 250 | 100 | 100 | 40 | 70 | 100 | 95 | 99 | 100 | 40 | 65 | 100 | 95 | 60 |
| 14-37 | 63 | 100 | 100 | 20 | 30 | 100 | 100 | 90 | 100 | 0 | 80 | 90 | 20 | 70 |
| | 250 | 100 | 100 | 50 | 100 | 100 | 100 | 100 | 100 | 30 | 100 | 100 | 95 | 100 |
| 14-38 | 63 | 100 | 100 | 0 | 70 | 100 | — | 90 | 100 | 0 | 95 | 0 | 50 | 0 |
| | 250 | 100 | 100 | 0 | 70 | 100 | — | 100 | 100 | 30 | 100 | 20 | 100 | 40 |
| 14-39 | 63 | 100 | 99 | 60 | 20 | 100 | 50 | 95 | 100 | 30 | 60 | 90 | 30 | 90 |
| | 250 | 100 | 100 | 100 | 50 | 100 | 50 | 100 | 100 | 40 | 100 | 100 | 50 | 100 |
| 14-40 | 63 | 100 | 90 | 20 | 30 | 100 | 90 | 85 | 100 | 20 | 20 | 50 | 35 | 15 |
| | 250 | 100 | 100 | 60 | 60 | 100 | 100 | 99 | 100 | 20 | 40 | 95 | 70 | 75 |
| 14-41 | 63 | 100 | 100 | 0 | 30 | 100 | — | 90 | 100 | 40 | 100 | 100 | 100 | 20 |
| | 250 | 100 | 100 | 0 | 50 | 100 | — | 100 | 100 | 70 | 100 | 100 | 100 | 95 |
| 14-42 | 63 | 100 | 100 | 60 | 100 | 100 | — | 100 | 100 | 60 | 95 | 100 | 100 | 95 |
| | 250 | 100 | 100 | 90 | 100 | 100 | — | 100 | 100 | 95 | 100 | 100 | 100 | 100 |
| 14-43 | 63 | 100 | 100 | 40 | 95 | 100 | — | 90 | 100 | 80 | 80 | 100 | 95 | 95 |
| | 250 | 100 | 100 | 90 | 100 | 100 | — | 100 | 100 | 95 | 100 | 100 | 100 | 100 |
| 14-44 | 63 | 100 | 100 | 0 | 50 | 100 | — | 100 | 100 | 30 | 100 | 100 | 100 | 90 |
| | 250 | 100 | 100 | 0 | 90 | 100 | — | 100 | 100 | 80 | 100 | 100 | 100 | 100 |
| 14-45 | 63 | 100 | 100 | 30 | 100 | 100 | 100 | 70 | 100 | 70 | 90 | 90 | 70 | 70 |
| | 250 | 100 | 100 | 30 | 100 | 100 | 100 | 95 | 100 | 90 | 100 | 100 | 100 | 100 |
| 14-46 | 63 | 95 | 100 | 60 | 100 | 100 | — | 90 | 100 | 80 | 80 | 100 | 95 | 60 |
| | 250 | 100 | 100 | 90 | 100 | 100 | — | 100 | 100 | 90 | 100 | 100 | 100 | 100 |
| 14-47 | 63 | 100 | 100 | 0 | 80 | 100 | 100 | 90 | 100 | 70 | 95 | 100 | 40 | 100 |
| | 250 | 100 | 100 | 70 | 100 | 100 | 100 | 100 | 100 | 80 | 100 | 100 | 100 | 100 |
| 14-48 | 63 | 100 | 100 | 0 | 0 | 100 | 80 | 50 | 50 | 0 | 70 | 95 | 40 | 70 |
| | 250 | 100 | 100 | 100 | 100 | 100 | — | 100 | 100 | 90 | 90 | 100 | 100 | 100 |

TABLE XXI-continued

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | | Post-emerge Herbicidal Activity | | | | | | | | | | | | |
| 14-49 | 63 | 100 | 100 | 70 | 100 | 100 | 100 | 50 | 100 | 70 | 70 | 95 | 80 | 50 |
| | 250 | 100 | 100 | 95 | 100 | 100 | 100 | 100 | 100 | 95 | 95 | 100 | 100 | 95 |
| 14-50 | 63 | 100 | 30 | 90 | 0 | 50 | — | 0 | 0 | 0 | 0 | 0 | 10 | 30 |
| | 250 | 100 | 50 | 100 | 0 | 100 | — | 0 | 0 | 0 | 50 | 20 | 30 | 50 |
| 14-51 | 63 | 0 | 0 | 0 | 0 | 0 | 0 | 0 | 10 | 0 | 0 | 0 | 0 | 0 |
| | 250 | 0 | 50 | 0 | 30 | 10 | 20 | 0 | 20 | 0 | 0 | 30 | 0 | 0 |
| 14-52 | 63 | 20 | 90 | 0 | 100 | — | — | 0 | 0 | 0 | 0 | 0 | 0 | 0 |
| | 250 | 50 | 100 | 70 | 100 | — | — | 0 | 10 | 0 | 0 | 100 | 10 | 0 |
| 14-54 | 63 | 40 | 60 | 0 | 30 | 20 | — | 10 | 30 | 0 | 0 | 30 | 5 | 10 |
| | 250 | 50 | 80 | 30 | 80 | 60 | — | 10 | 30 | 0 | 10 | 35 | 15 | 10 |
| 14-55 | 63 | 30 | 70 | 10 | 70 | 30 | — | 0 | 10 | 0 | 0 | 10 | 5 | 20 |
| | 250 | — | — | — | — | — | — | — | — | — | — | — | — | — |
| 14-56 | 63 | 100 | 70 | 30 | 100 | 99 | 90 | 30 | 20 | 30 | 10 | 40 | 10 | 0 |
| | 250 | 100 | 100 | 40 | 100 | 100 | 80 | 70 | 80 | 70 | 50 | 50 | 30 | 25 |
| 14-59 | 63 | 20 | 50 | 0 | 30 | 10 | — | 0 | 0 | 0 | 0 | 0 | 0 | 0 |
| | 250 | 20 | 30 | 10 | 30 | 10 | — | 0 | 0 | 0 | 0 | 10 | 0 | 0 |
| 14-60 | 63 | 70 | 100 | 40 | 100 | 99 | — | 20 | 50 | 20 | 10 | 100 | 0 | 10 |
| | 250 | 100 | 100 | 70 | 100 | 100 | — | 30 | 75 | 50 | 60 | 100 | 60 | 20 |
| 14-61 | 63 | 20 | 30 | 0 | 20 | 40 | — | 0 | 0 | 0 | 0 | 0 | 0 | 0 |
| | 250 | 60 | 60 | 30 | 50 | 75 | — | 20 | 60 | 20 | 70 | 40 | 70 | 30 |
| 14-62 | 63 | 30 | 40 | 0 | 30 | 10 | 40 | 0 | 0 | — | 0 | 15 | 5 | 0 |
| | 250 | 50 | 60 | 30 | 50 | 20 | 30 | 0 | 0 | — | 0 | 15 | 5 | 5 |
| 14-63 | 63 | 95 | 90 | 95 | 70 | 80 | 20 | 50 | 100 | — | 40 | 95 | 35 | 5 |
| | 250 | 100 | 100 | 100 | 70 | 100 | 50 | 70 | 99 | — | 90 | 100 | 80 | 15 |
| 14-44 | 63 | 100 | 100 | 10 | 30 | 70 | 30 | 30 | 100 | — | 40 | 90 | 99 | 5 |
| | 250 | 100 | 100 | 20 | 80 | 99 | 40 | 70 | 100 | — | 99 | 90 | 100 | 0 |
| 14-65 | 63 | 100 | 100 | 90 | 50 | 90 | — | 100 | 100 | 30 | 99 | 100 | 0 | 0 |
| | 250 | 100 | 100 | 100 | 70 | 100 | — | 100 | 100 | 60 | 100 | 100 | 50 | 10 |
| 14-66 | 63 | 95 | 100 | 80 | 70 | 80 | — | 95 | 100 | 60 | 100 | 80 | 90 | 0 |
| | 250 | 100 | 100 | 90 | 90 | 99 | — | 100 | 100 | 80 | 100 | 99 | 100 | 10 |
| 15-1 | 63 | 100 | 100 | 100 | 100 | 100 | — | 80 | 80 | — | 90 | 100 | 80 | 75 |
| | 250 | 100 | 100 | 100 | 100 | 100 | — | 100 | 99 | — | 100 | 100 | 95 | 95 |
| 15-2 | 63 | 20 | 80 | 10 | 90 | — | — | 0 | 0 | 0 | 0 | 40 | 15 | 50 |
| | 250 | 95 | 100 | 75 | 100 | — | — | 80 | 90 | 70 | 80 | 100 | 80 | 75 |
| 15-3 | 63 | 95 | 100 | 70 | 95 | 95 | — | 30 | 10 | 0 | 20 | 90 | 25 | 50 |
| | 250 | 100 | 100 | 100 | 100 | 100 | — | 80 | 90 | 90 | 80 | 100 | 80 | 90 |
| 15-4 | 63 | 70 | 100 | 50 | 100 | 100 | — | 50 | 40 | — | 30 | 90 | 50 | 70 |
| | 250 | 100 | 100 | 80 | 100 | 100 | — | 80 | 90 | — | 70 | 100 | 90 | 95 |
| 15-5 | 63 | 70 | 100 | 40 | 90 | 100 | — | 40 | 40 | — | 30 | 100 | 70 | 60 |
| | 250 | 100 | 100 | 80 | 100 | 100 | — | 80 | 90 | — | 70 | 100 | 90 | 90 |
| 15-6 | 63 | 50 | 100 | 30 | 50 | — | — | 30 | 20 | — | 0 | 60 | 25 | 60 |
| | 250 | 85 | 100 | 70 | 100 | — | — | 75 | 95 | — | 90 | 100 | 80 | 95 |
| 15-7 | 63 | 100 | 100 | 60 | 100 | 100 | — | 30 | 40 | — | 20 | 90 | 60 | 50 |
| | 250 | 100 | 100 | 100 | 100 | 100 | — | 90 | 95 | — | 75 | 100 | 80 | 90 |
| 15-8 | 63 | 20 | 70 | 0 | 50 | 95 | — | 0 | 0 | — | 0 | 60 | 0 | 10 |
| | 250 | 60 | 100 | 40 | 90 | 90 | — | 30 | 20 | — | 0 | 90 | 55 | 60 |
| 15-9 | 63 | 10 | 80 | 10 | 100 | — | — | 0 | 0 | — | 0 | 40 | 30 | 50 |
| | 250 | 95 | 100 | 60 | 85 | — | — | 80 | 90 | — | 80 | 95 | 70 | 90 |
| 15-10 | 63 | 100 | 100 | 100 | 100 | 100 | — | 30 | 10 | 30 | 60 | 95 | 45 | 50 |
| | 250 | 100 | 100 | 100 | 100 | 100 | — | 75 | 80 | 70 | 90 | 95 | 65 | 80 |
| 15-11 | 63 | 95 | 100 | 90 | 100 | 100 | — | 40 | 50 | 50 | 50 | 95 | 45 | 65 |
| | 250 | 100 | 100 | 100 | 100 | 100 | — | 80 | 99 | 99 | 95 | 100 | 85 | 99 |
| 15-12 | 63 | 95 | 100 | 90 | 100 | 100 | — | 70 | 70 | 80 | 95 | 100 | 80 | 80 |
| | 250 | 100 | 100 | 100 | 100 | 100 | — | 100 | 100 | 99 | 100 | 100 | 95 | 99 |
| 15-13 | 63 | 80 | 100 | 60 | 100 | 95 | — | 20 | 20 | 10 | 10 | 95 | 15 | 60 |
| | 250 | 95 | 100 | 100 | 100 | 100 | — | 60 | 85 | 70 | 70 | 100 | 50 | 90 |
| 15-14 | 63 | 100 | 100 | 80 | 100 | 100 | — | 20 | 20 | 20 | 20 | 100 | 20 | 40 |
| | 250 | 100 | 100 | 100 | 100 | 100 | — | 55 | 90 | 70 | 60 | 100 | 65 | 50 |
| 15-15 | 63 | 100 | 100 | 80 | 90 | 100 | — | 40 | 30 | 30 | 40 | 95 | 45 | 70 |
| | 250 | 100 | 100 | 100 | 100 | 100 | — | 95 | 100 | 99 | 100 | 100 | 90 | 95 |
| 15-16 | 63 | 80 | 100 | 80 | 100 | 100 | — | 30 | 10 | 10 | 20 | 95 | 15 | 40 |
| | 250 | 100 | 100 | 100 | 100 | 100 | — | 60 | 90 | 70 | 80 | 100 | 45 | 80 |
| 15-17 | 63 | 90 | 100 | 80 | 100 | — | — | 40 | 50 | 20 | 40 | 90 | 35 | 75 |
| | 250 | 100 | 100 | 100 | 100 | — | — | 90 | 99 | 95 | 99 | 100 | 80 | 90 |
| 15-18 | 63 | 100 | 100 | 40 | 90 | 100 | — | 20 | 10 | 0 | 10 | 90 | 20 | 30 |
| | 250 | 100 | 100 | 100 | 100 | 100 | — | 80 | 95 | 99 | 100 | 100 | 80 | 85 |
| 15-19 | 63 | 100 | 100 | 75 | 100 | 100 | — | 40 | 50 | 40 | 50 | 90 | 35 | 65 |
| | 250 | 100 | 100 | 100 | 100 | 100 | — | 100 | 100 | 100 | 100 | 100 | 85 | 90 |
| 15-20 | 63 | 100 | 100 | 80 | 100 | 100 | — | 80 | 50 | — | 30 | 95 | 40 | 35 |
| | 250 | 100 | 100 | 100 | 100 | 100 | — | 100 | 100 | — | 90 | 100 | 84 | 80 |
| 15-21 | 63 | 95 | 100 | 100 | 100 | 100 | — | 50 | 60 | 40 | 30 | 90 | 30 | 80 |
| | 250 | 100 | 100 | 100 | 100 | 100 | — | 90 | 100 | 95 | 95 | 100 | 90 | 90 |
| 15-22 | 63 | 100 | 100 | 70 | 100 | 100 | — | 40 | 40 | — | 30 | 90 | 30 | 50 |
| | 250 | 100 | 100 | 100 | 100 | 100 | — | 95 | 100 | — | 90 | 100 | 90 | 90 |

TABLE XXI-continued

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| | | Post-emerge Herbicidal Activity | | | | | | | | | | | | |
| 16-2 | 63 | 60 | 40 | 0 | 0 | 30 | — | 0 | 0 | 0 | 0 | 10 | 0 | 0 |
| | 250 | 60 | 70 | 10 | 0 | 70 | — | 0 | 0 | 0 | 0 | 40 | 10 | 20 |
| 16-4 | 63 | 0 | 0 | 0 | 0 | 0 | — | 0 | 0 | 0 | 0 | 0 | 0 | 0 |
| | 250 | 0 | 0 | 0 | 0 | 0 | — | 0 | 0 | 0 | 0 | 0 | 0 | 0 |
| 16-1 | 63 | 70 | 70 | 0 | 30 | 0 | — | 0 | 0 | 20 | 20 | 0 | 0 | 0 |
| | 250 | 70 | 100 | 0 | 70 | 70 | — | 0 | 0 | 40 | 80 | 0 | 0 | 10 |
| 16-7 | 63 | 0 | 0 | 0 | 0 | 0 | — | 0 | 0 | 0 | 0 | 0 | 0 | 0 |
| | 250 | 0 | 0 | 30 | 30 | 0 | — | 0 | 0 | 0 | 0 | 0 | 0 | 0 |
| 17-1 | 63 | 10 | 70 | 20 | 80 | 30 | — | 0 | 0 | 0 | 0 | 10 | 0 | 0 |
| | 250 | 30 | 70 | 10 | 80 | 60 | — | 0 | 0 | 0 | 0 | 30 | 5 | 0 |
| 17-2 | 63 | 0 | 0 | 0 | 0 | 0 | — | 0 | 0 | 0 | 0 | 0 | 0 | 0 |
| | 250 | 30 | 50 | 10 | 20 | 40 | — | 0 | 0 | 0 | 0 | 10 | 0 | 0 |
| 17-4 | 63 | 20 | 35 | 10 | 20 | 20 | — | 0 | 0 | 0 | 0 | 10 | 0 | 0 |
| | 250 | 70 | 70 | 20 | 80 | 40 | — | 0 | 0 | 0 | 0 | 15 | 0 | 0 |
| 17-5 | 63 | 10 | 50 | 10 | 30 | 40 | — | 0 | 0 | 0 | 0 | 20 | 0 | 0 |
| | 250 | 40 | 80 | 20 | 70 | 80 | — | 0 | 0 | 0 | 0 | 35 | 10 | 0 |

What is claimed is:

1. A compound represented by the formula I or its salts

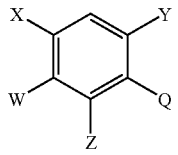

I wherein X is hydrogen, halogen, nitro, amino, NHR, $N(R)_2$, amide, [thioatnide]*thioamide*, cyano, alkylcarbonyl, alkoxycarbonyl, alkylsulfonamnde, unsubstituted or substituted alkyl, haloalkyl, alkoxy, haloalkoxy, alkoxycarbonylalkoxy, benzyloxy, amyloxy, or heteroaryloxy;

Y is hydrogen, halogen, or nitro;

W is hydrogen, OR, SR, NHR, $N(R)_2$, $CH_2R$, $CH(R)_2$, $C(R)_3$, halogen, nitro, or cyano, where multiple R groups represent any possible combination of substituents described by R; R is hydrogen, alkyl, alkenyl, alkynyl, cycloalkyl, aryl, heteroaryl, alkoxy, cycloalkyloxy, aryloxy, heteroaryloxy, alkylsulfonyl, benzyl, alkylcarbonyl, alkenylcarbonyl, alkynylcarbonyl, arylcarbonyl, heteroarylcarbonyl, alkoxycarbonyl, aryloxycarbonyl, or heteroaryloxycarbonyl, where any of these groups may be unsubstituted or substituted with any of the functional groups represented by one or more of the following: halogen, cyano, nitro, amino, carboxyl, alkyl, haloalkyl, alkylsilyl, alkylcarbonyl, haloalkylcarbonyl, alkoxy, [alkoxybarbonyl]*alkoxycarbonyl*, haloalkoxy, haloalkoxycarbonyl, alkylsulfonyl, haloalkylsulfonyl, aryl, heteroaryl, or cycloalkyl;

Q is heterocycle:

Q is a heterocycle:

Q1

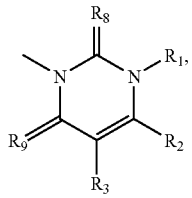

Q12

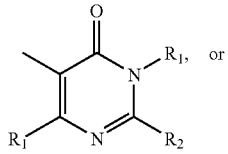

Q13

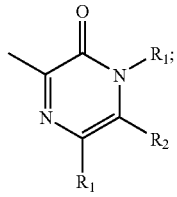

wherein $R_1$ is hydrogen, alkyl, haloalkyl, alkenyl, alkynyl, amino, alkoxyalkyl, acetyl, alkoxycarbonylamino, alkylcarbonylamino, or alkoxycarbonyl;

$R_2$ is alkyl or haloalkyl;

$R_1$ and $R_2$ could combine to form a five- or six-membered heterocyclic ring;

$R_3$ is hydrogen, halogen, nitro, amino, alkylamino, haloalkylamino, cyano, or amide;

$R_8$ and $R_9$ are independently oxygen, or sulfur;

Q6, Q7, and Q10 may optionally be unsaturated containing one or two double bonds in the 6-membered ring;

Z is amino, hydroxyl, thiol, formyl, carboxyl, cyano, alkylcarbonyl, arylcarbonyl, azido, or one of the following:

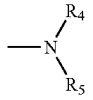

wherein $R_4$ is alkyl, alkenyl, alkynyl, amino, cycloalkyl, heterocycloalkyl, alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heteroarylcarbonyl, alkoxycarbonyl, alkylthiocarbonyl, cycloalkyloxycarbonyl, aryloxycarbonyl, [arylthiocarbonyl,] aryl-thiocarbonyl, heteroaryloxycarbonyl, aminocarbonyl, alkylaminocarbonyl, arylaminocarbonyl, heteroarylaminocarbonyl, alkoxycarbonylcarbonyl or arylcarbonylcarbonyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, alkyklcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl or methylenedioxy, wherein the alkyl moiety or aryl moiety may be substituted with halogen, cyano, nitro, alkyl, alkoxy, haloalkyl, haloalkoxy, alkoxycarbonyl, aryl, or heterocycloalkyl; and $R_5$ is hydrogen or any one of the groups represented by $R_4$; or $R_4$ and $R_5$ could combine to form a 4–8 membered heterocyclic ring;

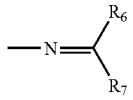

wherein $R_6$ represents alkyl, haloalkyl, dialkylamino, unsubstituted or substituted aryl and heteroaryl; and $R_7$ represents hydrogen, halogen or any of the groups represented by $R_6$;

—$OR_4$,

—$SR_4$,

—$CH_2R_{10}$,

—$CH(R_{10})_2$,

—$C(R_{10})_3$, or

—$CH{=}CHR_{10}$ wherein $R_{10}$ is carboxyl, alkyl, alkenyl, alkynyl, amino, cycloalkyl, heterocycloalkyl, alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heteroarylcarbonyl, alkoxycarbonyl, alkyithiocarbonyl, cycloalkyloxycarbonyl, aryloxycarbonyl, arylthio-carbonyl, aryl-thiocarbonyl, heteroaryloxycarbonyl, aminocarbonyl, alkylaminocarbonyl, arylaminocarbonyl, heteroarylaminocarbonyl, alkoxycarbonylcarbonyl or arylcarbonylcarbonyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl or methylenedioxy, wherein the alkyl moiety or aryl moiety may be substituted with halogen, cyano, nitro, alkyl, alkoxy, haloalkyl, haloalkoxy, alkoxycarbonyl, cycloalkyl, aryl, or heterocycloalkyl;

provided that (1) Z is not alkyl, alkoxy, haloalkyl, haloalkoxy, alkylthio, haloalkythio, alkenyl, haloalkenyl, amino, monoalkylamino, dialkylamino, alkoxyalkoxy alkoxyalkoxy, hydroxyl, alkynyloxy or cyano, when Q is Q1 and $R_2$ is haloalkyl.

2. The compound according to claim 1 wherein Z is represented by the following:

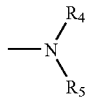

wherein $R_4$ and $R_5$ are the same as defined in claim 1; or —$CH_2R_{10}$, wherein $R_{10}$ is the same as defined in claim 1.

3. The compound according to claims 1 or 2 wherein X is halogen or cyano;

Y is halogen;

W is OR;

R is alkyl, alkenyl, or alkynyl, where any of these groups may be unsubstituted or substituted with any of the functional groups represented by one or more of the following: halogen, cyano, nitro, amino, or carboxyl.

4. The compound according to claim 1 wherein Q is

Q1

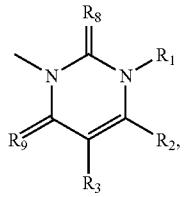

wherein $R_1$ is alkyl, amino, or haloalkyl;

$R_2$ is haloalkyl;

$R_3$ is hydrogen;

$R_8$ and $R_9$ are independently oxygen, or sulfur.

5. The compound according to claim 1 wherein X is a halogen;

Y is fluorine;

W is OR; R is alkyl, alkenyl, or alkynyl, where any of these groups may be unsubstituted or substituted with halogen or cyano;

Q is

Q1

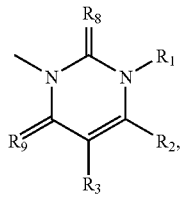

wherein $R_1$ is alkyl, amino, or haloalkyl;

$R_2$ is haloalkyl;

$R_3$ is hydrogen;

$R_8$ $R_9$ are independently oxygen, or sulfur;

Z is represented by the following:

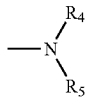

wherein $R_4$ is alkylcarbonyl, alkenylcarbonyl, alkynylcarbonyl, cycloalkylcarbonyl, arylcarbonyl, heteroarylcarbonyl, alkoxycarbonyl, alkylthiocarbonyl, cycloalkyloxycarbonyl, aryloxycarbonyl, [arylthiocarbonyl,] aryl-thiocarbonyl, heteroaryloxycarbonyl, aminocarbonyl, alkylaminocarbonyl, arylaminocarbonyl, heteroarylaminocarbonyl, alkoxycarbonylcarbonyl, or arylcarbonylcarbonyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl, or methylenedioxy, wherein the alkyl moiety or aryl moiety may be substituted with halogen, cyano, nitro, alkyl, alkoxy, haloalkyl, haloalkoxy, alkoxycarbonyl, aryl, or [heterocyclcoalkyl] *heterocycloalkyl*; and $R_5$ is hydrogen;

or —$CH_2R_{10}$, wherein $R_{10}$ is carboxyl, alkyl, alkenyl, or alkynyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl, or methylenedioxy, wherein [teh] *the* alkyl moiety or aryl moiety may be substituted with halogen, cyano, nitro, alkyl, alkoxy, haloalkyl, haloalkoxy, alkoxycarbonyl, cycloalkyl, aryl, or heterocycloalkyl.

6. A compound selected from the group consisting of 3-(2-amino-4-chloro-6-fluoro-3-methoxyphenyl)-1-methyl-6-trifluoromethyl-2,4(1H,3H)pyrimidinedione; [and 3-(2-amino-4-chloro-6-fluoro-3-methoxyphenyl)-1-amino-6-trifluoromethyl-2,4(1H,3H)-pyrimidinedione] *3-(2-amino-4-chloro-3-methoxyphenyl)-1-amino-6-trifluoromethyl-2,4(1H,3H)-pyrimidinedione;*

*3-(2-amino-4-chloro-6-fluro-3-methylphenyl)-1-methyl-6-trifluoromethyl-2,4(1H,3H)-pyrimidinedione; and 3-(2-amino-4-chloro-3-difluoromethoxy-6-fluorophenyl)-1methyl-6-trifluoromethyl-2,4(1H,3H)-pyrimidinedione.*

7. A herbicidal composition, characterized in that it contains at least one compound according to claim 1 *or 6* and an agricultural adjuvant.

8. A process for preparing a compound represented by the formula I-1 or its salts:

I-1

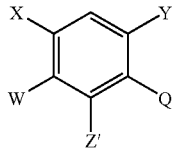

wherein X is hydrogen, halogen, nitro, amino, NHR, $N(R)_2$, [ainide]*amide*, thioamide, cyano, alkylcarbonyl, alkoxycarbonyl, alkylsulfonamide, unsubstituted or substituted alkyl, haloalkyl, alkoxy, haloalkoxy, alkoxycarbonylalkoxy, [benzloxy]*benzyloxy*, aryloxy or heteroaryloxy;

Y is hydrogen, halogen, or nitro;

W is hydrogen, OR, SR, NH, $N(R)_2$, $CH_2R$, $CH(R)_2$, $C(R)_3$, halogen, nitro, or cyano, where multiple R groups represent any possible combination of substituents described by R; R is hydrogen, alkyl, alkenyl, alkynyl, cycloalkyl, aryl, heteroaryl, alkoxy, cycloalkyloxy, aryloxy, heteroaryloxy, alkylsulfonyl, benzyl, alkylcarbonyl, alkenylcarbonyl, alkynylcarbonyl, arylcarbonyl, heteroarylcarbonyl, alkoxycarbonyl, aryloxycarbonyl, or heteroaryloxycarbonyl, where any of these groups may be unsubstituted or substituted with any of the functional groups represented by one or more of the following: halogen, cyano, nitro, amino, carboxyl, alkyl, haloalkyl, alkylsilyl, alkylcarbonyl, haloalkylcarbonyl, alkoxy, alkoxycarbonyl, haloalkoxy, haloalkoxycarbonyl, alkylsulfonyl, haloalkylsulfonyl, aryl, heteroaryl, or cycloalkyl;

Q is a heterocycle:

Q1

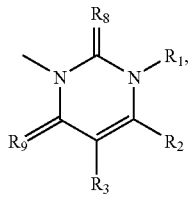

Q12

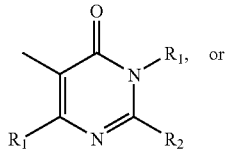

or

Q13

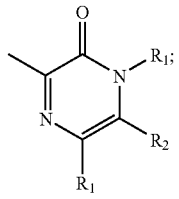

wherein $R_1$ is hydrogen, alkyl, haloalkyl, alkenyl, alkynyl, amino, alkoxyalkyl, acetyl, alkoxycarbonylamino, alkylcarbonylamino, or alkoxycarbonyl;

$R_2$ is alkyl or haloalkyl;

$R_1$ and $R_2$ could combine to form a five- or six-membered heterocyclic ring;

$R_3$ is hydrogen, halogen, nitro, amino, alkylamino, haloalkylamino, cyano, or amide;

$R_8$ and $R_9$ are independently oxygen, or sulfur;

Q6, Q7, and Q10 may optionally be unsaturated containing one or two double bonds in the 6-membered ring;

Z' is one of the following:

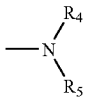

wherein $R_4$ is alkyl, alkenyl, alkynyl, amino, cycloalkyl, heterocycloalkyl, alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heteroarylcarbonyl, alkoxycarbonyl, alkylthiocarbonyl, cycloalkyloxycarbonyl, aryloxycarbonyl, [arylthio-carbonyl,] arylthiocarbonyl, heteroaryloxycarbonyl, aminocarbonyl, alkylaminocarbonyl, arylaminocarbonyl, heteroarylaminocarbonyl, alkoxycarbonylcarbonyl, or arylcarbonylcarbonyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, alkyklcarbonyl, alkylcarbonyloxy, alkoxy, alkoxycarbonyl, alkylthio, alkyithiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl, or methylenedioxy, wherein the alkyl moiety or aryl moiety may be substituted with halogen, cyano, nitro, alkyl, alkoxy, haloalkyl, haloalkoxy, alkoxycarbonyl, aryl, or heterocycloalkyl; and $R_5$ is hydrogen or any one of the groups represented by $R_4$; or $R_4$ and $R_5$ could combine to form a 4–8 membered heterocyclic ring;

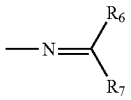

wherein $R_6$ represents alkyl, [haloallcyl] *haloalkyl*, dialkylamino, unsubstituted or substituted aryl and heteroaryl; and $R_7$ represents hydrogen, halogen or any of the groups represented by $R_6$;

—$CH_2R_{10}$,

—$CH(R_{10})_2$,

—$C(R_{10})_3$, or

—CH═$CHR_{10}$ wherein $R_{10}$ is carboxyl, alkyl, alkenyl, alkynyl, amino, cycloalkyl, heterocycloalkyl, [25] alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heteroarylcarbonyl, alkoxycarbonyl, alkyithiocarbonyl, cycloalkyloxycarbonyl, aryloxycarbonyl, [arylthio-carbonyl,] arylthiocarbonyl, heteroaryloxycarbonyl, aminocarbonyl, alkylaminocarbonyl, arylaminocarbonyl, heteroarylaminocarbonyl, alkoxycarbonylcarbonyl or arylcarbonylcarbonyl, where any of these groups may be unsubstituted or substituted with any of the functional groups represented by one or more of the following: halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl or methylenedioxy, wherein the alkyl moiety or aryl moiety may be substituted with halogen, cyano, nitro, alkyl, alkoxy, haloalkyl, haloalkoxy, alkoxycarbonyl, cycloalkyl, aryl, or heterocycloalkyl;

provided that [(1)] Z' is not alkyl, haloalkyl, alkenyl, haloalkenyl, monoalkylamino, or dialkylamino, when Q is Q1 and $R_2$ is haloalkyl, which comprises of reacting a compound represented by the formula II:

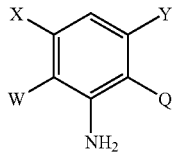

II with a compound selected from the group consisting of an alkyl halide, alkyl acid halide, aryl acid halide, alkyl acid anhydride, aryl acid anhydride, alkylhaloformate, alkyl isocyanate, aryl isocyanate, alkyl dihalide, aliphatic aldehyde, aliphatic ketone, aromatic aldehyde, and aromatic ketone.

9. A compound represented by the formula III:

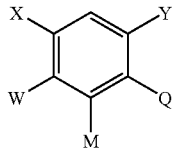

III wherein X is hydrogen, halogen, nitro, amino, NHR, $N(R)_2$, amide, thioamide, cyano, alkylcarbonyl, alkoxycarbonyl, alkylsulfonamide, unsubstituted or substituted alkyl, haloalkyl, alkoxy, haloalkoxy,alkoxycarbonylalkoxy, benzyloxy, aryloxy, or heteroaryloxy;

Y is hydrogen, halogen, or nitro;

W is hydrogen, OR, SR, NHR, $N(R)_2$, $CH_2R$, $CH(R)_2$, $C(R)_3$, halogen, nitro, or cyano, where multiple R groups represent any possible combination of substituents described by R; R is hydrogen, alkyl, alkenyl, alkynyl, cycloalkyl, aryl, heteroaryl, alkoxy, cycloalkyloxy, aryloxy, heteroaryloxy, alkylsulfonyl, benzyl, alkylcarbonyl, alkenylcarbonyl, alkynylcarbonyl, arylcarbonyl, heteroarylcarbonyl, alkoxycarbonyl, aryloxycarbonyl, or heteroaryloxycarbonyl, where any of these groups may be unsubstituted or substituted with any of the functional groups represented by one or more of the following: halogen, cyano, nitro, amino, carboxyl, alkyl, haloalkyl, alkylsilyl, alkylcarbonyl, haloalkylcarbonyl, alkoxy, alkoxycarbonyl, haloalkoxy, haloalkoxycarbonyl, alkylsulfonyl, haloalkylsulfonyl, aryl, heteroaryl, or cycloalkyl;

Q is a heterocycle:

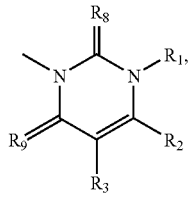

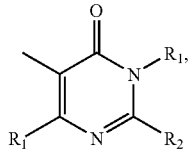

or

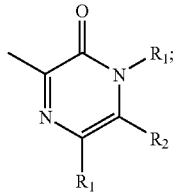

wherein $R_1$ is hydrogen, alkyl, haloalkyl, alkenyl, alkynyl, amino, alkoxyalkyl, acetyl, alkoxycarbonylamino, alkylcarbonylamino, or alkoxycarbonyl;

Q1

$R_2$ is alkyl or haloalkyl;

$R_1$ and $R_2$ could combine to form a five- or six-membered heterocyclic ring;

$R_3$ is hydrogen, halogen, nitro, amino, alkylamino, haloalkylamino, cyano, or amide;

Q12

$R_8$ and $R_9$ are independently oxygen or sulfur;

M is nitro,

*provided that 1-methyl-6-trifluoromethyl-3-(4-bromo-2-fluoro-5-hydroxy-6-nitrophenyl)-2,4(1H,3H)-pyrimidinedione and 1-methyl-6-trifluoromethyl-3-(4-chloro-2-fluoro-5-hydroxy-6-nitrophenyl)-2,4(1H,3H)-pyrimidinedione are excluded.*

Q13

10. A method for controlling undesired vegetation which comprises applying to a locus to be protected a herbicidally effective amount of a compound of claim 1 *or 6*.

11. The method of claim 10 wherein the locus to be protected is a cereal crop field.

12. The method of claim 11 wherein the compound [of claim 1] is applied to soil as a preemergent herbicide.

13. The method of claim 11 wherein the compound [of claim 1] is applied to plant foliage.

14. A method to defoliate potato and cotton using a compound of claim 1 *or 6*.

* * * * *